United States Patent [19]
Fujii

[11] Patent Number: 4,864,021
[45] Date of Patent: Sep. 5, 1989

[54] 5-FLUOROURACIL DERIVATIVES

[75] Inventor: Setsuro Fujii, Kyoto, Japan

[73] Assignee: Otsuka Pharmaceutical Co., Ltd., Osaka, Japan

[21] Appl. No.: 903,824

[22] Filed: Sep. 3, 1986

Related U.S. Application Data

[63] Continuation-in-part of Ser. No. 793,056, Oct. 30, 1985, abandoned.

[30] Foreign Application Priority Data

| Oct. 30, 1984 | [JP] | Japan | 59-229938 |
|---|---|---|---|
| Nov. 30, 1984 | [JP] | Japan | 59-254587 |
| Jan. 17, 1985 | [JP] | Japan | 60-7190 |
| Mar. 25, 1985 | [JP] | Japan | 60-59788 |
| May 9, 1985 | [JP] | Japan | 60-98295 |
| Aug. 30, 1985 | [JP] | Japan | 60-192582 |
| Sep. 3, 1985 | [JP] | Japan | 60-195223 |
| Jul. 25, 1986 | [JP] | Japan | 61-176464 |
| Jul. 30, 1986 | [JP] | Japan | 61-181027 |

[51] Int. Cl.$^4$ .................... C07H 19/00
[52] U.S. Cl. ........................ 536/23
[58] Field of Search .................... 536/23

[56] References Cited

U.S. PATENT DOCUMENTS 4,124,765  11/1978  Kurono et al. .

FOREIGN PATENT DOCUMENTS

| 4967/85 | 10/1985 | Denmark . | |
|---|---|---|---|
| 0009882 | 4/1980 | European Pat. Off. . | |
| 0129984 | 1/1985 | European Pat. Off. . | |
| 180897 | 5/1986 | European Pat. Off. . | |
| 2658672 | 6/1978 | Fed. Rep. of Germany | 536/23 |
| 2428052 | 1/1980 | France . | |
| 59-29699 | 2/1984 | Japan . | |
| 3242/86 | 10/1985 | Rep. of Korea . | |
| 549011 | 10/1985 | Spain . | |
| 74104810 | 10/1985 | Taiwan . | |
| 2066812 | 7/1981 | United Kingdom . | |
| 2072164 | 9/1981 | United Kingdom . | |

OTHER PUBLICATIONS

European Search Rpt. EP 85 11 3724 and attachment.
Chemical Abstracts, vol. 101, 1984, p. 657, Abstract 55487, dated 2/16/84.

*Primary Examiner*—Johnnie R. Brown
*Assistant Examiner*—James O. Wilson
*Attorney, Agent, or Firm*—Armstrong, Nikaido, Marmelstein, Kubovcik & Murray

[57]  ABSTRACT

An anticancer compound is disclosed which is represented by the formula

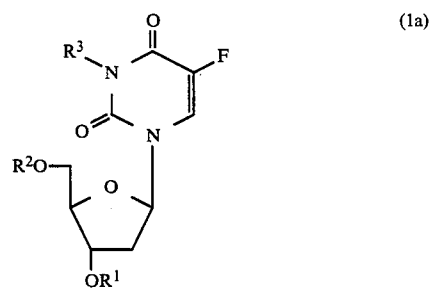

(1a)

wherein one of $R^1$ and $R^2$ is a phenyl-lower alkyl optionally having a substituent, phenyl-lower alkenyl or naphthyl-lower alkyl, the other of $R^1$ and $R^2$ is hydrogen or acyl, and $R^3$ is hydrogen, acyl or tetrahydrofuranyl, or represented by the formula

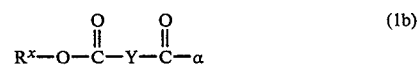

(1b)

wherein $R^x$ is an optionally substituted pyridyl, Y is arylene and α is a known 5-fluorouracil derivative residue which can be converted to 5-fluorouracil in vivo and which is linked to the carbonyl by an ester or amide linkage.

20 Claims, No Drawings

5-FLUOROURACIL DERIVATIVES

This application is a continuation-in-part of application Ser. No. 793,056 filed Oct. 30, 1985, now abandoned.

This invention relates to novel 5-fluorouracil derivatives, process for preparinng the same and pharmaceutical compositions containing the same.

The 5-fluorouracil derivatives of the invention are novel compounds undisclosed in literature and having antitumor action.

The inventor has carried out research in an attempt to improve the antitumore action of known 5-fluorouracils, 2'-deoxy-5-fluorouridines and related compounds and to render them less toxic, and consequently succeeded in synthesizing a class of novel 5-fluorouracil derivatives and 5-fluorouridine derivatives which are substituted at 3'- or 5'-position with phenyl-lower alkyloxy group optionally having specific substituent(s) and related compounds. The inventor has also found that the compounds thus prepared have an excellent antitumor action and are very useful as antitumor agents.

The present invention provides a compound selected from the group consisting of (a) a compound represented by the formula

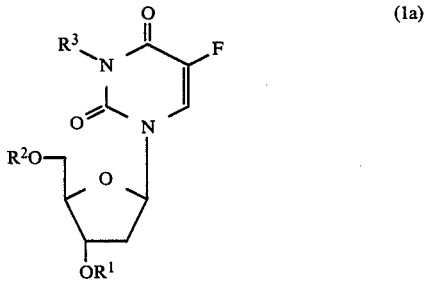

(1a)

wherein one of $R^1$ and $R^2$ is phenyl-lower alkyl group optionally having substituent selected from the group consisting of lower alkyl group, lower alkoxy group, halogen atom, carboxyl group, lower alkoxycarbonyl group and di(lower alkyl)amino group on the phenyl ring, phenyl-lower alkyl group having lower alkylenedioxy or phenyl group as the substituent on the phenyl ring, phenyl-lower alkenyl group or naphthyl-lower alkyl group, the other of $R^1$ and $R^2$ is hydrogen atom or acyl group, and $R^3$ is hydrogen atom, acyl group or tetrahydrofuranyl group; and (b) a compound represented by the formula

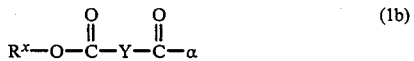

(1b)

wherein $R^x$ is a pyridyl group optionally having 1 to 4 substituents selected from the group consisting of hydroxy group, oxo group, halogen atom, amino group, carboxyl group, cyano group, nitro group, carbamoyl group, lower alkylcarbamoyl group, carboxy-lower alkylcarbamoyl group, phenyl-carbamoyl optionally substituted with 1 to 3 substituents selected from the group consisting of halogen atom, lower alkoxy group and lower alkyl group on the phenyl ring, lower alkoxycarbonyl-lower alkylcarbamoyl group, lower alkyl group, lower alkenyl group, lower alkoxycarbonyl group, tetrahydrofuranyl group, tetrahydropyranyl group, lower alkoxy-lower alkyl group, lower alkylthio-lower alkyl group, phenyl-lower alkoxy-lower alkyl group, phthalidyl group and acyloxy group, Y is arylene group, and $\alpha$ is a known 5-fluorouracil derivative residue which can be converted to 5-fluorouracil in vivo and which is linked by an ester or amide linkage to the carbonyl group to which the substituent $\alpha$ is attached.

Throughout the specification, the terms "lower alkyl" and "lower alkoxy" used as such or as contained in various functinal groups are intended to exemplify $C_1$–$C_6$ straight or branched chain alkyl groups such as methyl, ethyl, propyl, isopropyl, butyl, tert-butyl, pentyl, hexyl, etc; and $C_1$–$C_6$ straight or branched chain alkoxy groups, such as methoxy, ethoxy, propoxy, isopropoxy, butoxy, tert-butoxy, pentyloxy, hexyloxy, etc., respectively. Further throughout the specification, the term "halogen" used as it is or as contained in various functional groups is intended to exemplify fluorine, chlorine, bromine, iodine, etc. Also throughout the specification, the term "lower alkylenedioxy" used as such or as contained in various functional groups is meant to exemplify $C_1$–$C_4$ alkylenedioxy groups such as methylenedioxy, ethylenedioxy, trimethylenedioxy, tetramethylenedioxy, etc.

With respect to the substituents for substituted phenyl-lower alkyl groups, examples of lower alkyl groups include $C_1$–$C_6$ straight or branched chain alkyl groups such as methyl, ethyl, propyl, isopropyl, butyl, tert-butyl, pentyl, hexyl, etc; examples of lower alkoxy groups are $C_1$–$C_6$ straight or branched chain alkoxy groups, such as methoxy, ethoxy, propoxy, isopropoxy, butoxy, tert-butoxy, pentyloxy, hexyloxy, etc; examples of halogen atoms are fluorine, chlorine, bromine and iodine; examples of lower alkoxycarbonyl groups are $C_2$–$C_7$ straight or branched chain alkoxycarbonyl groups such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, etc. Examples of phenyl-lower alkyl groups optionally substituted with the above substituents or with carboxy or di(lower alkyl)amino group on the phenyl ring are phenylalkyl groups in which the phenyl group optionally substituted with one to three of the above substituents is linked with $C_1$–$C_6$ alkylene group such as methylene ethylene, trimethylene, 1-methylethylene, tetramethylene, 2-methyltrimethylene, pentamethylene, hexamethylene, etc. Examples thereof are follows.

benzyl, 2-methylbenzyl, 3-methylbenzyl, 4-methylbenzyl, 2-ethylbenzyl, 3-ethylbenzyl, 4-ethylbenzyl, 2-propylbenzyl, 3-propylbenzyl, 4-propylbenzyl, 2-butylbenzyl, 3-butylbenzyl, 4-butylbenzyl, 2-tert-butylbenzyl, 3-tert-butylbenzyl, 4-tert-butylbenzyl, 2-pentylbenzyl, 3-pentylbenzyl, 4-pentylbenzyl, 2-hexylbenzyl, 3-hexylbenzyl, 4-hexylbenzyl, 2,3-dimethylbenzyl, 2,4-dimethylbenzyl, 2,5-dimethylbenzyl, 2,6-dimethylbenzyl, 3,4-dimethylbenzyl, 3,5-dimthylbenzyl, 2,3,4-trimethylbenzyl, 2,4,5-trimethylbenzyl, 2,3,5-trimethylbenzyl, 2,4,6trimethylbenzyl, 3,4,5-trimethylbenzyl, 2,3-diethylbenzyl, 2,4-diethylbenzyl, 2,5-diethylbenzyl, 2,6-diethylbenzyl, 2,4,6-triethylbenzyl, 2,4-diproopylbenzyl, 3,4,5-triethylbenzyl, 3-methyl-4-ethylbenzyl, 1-phenylethyl, 2-phenylethyl, 2-phenyl-1-methyl-ethyl, 1-(2-methylphenyl)ethyl, 2-(2-methylphenyl)ethyl, 2-(3-methylphenyl)ethyl, 2-(4-methylphenyl)ethyl, 1-(2,4-dimethylphenyl)ethyl, 2-(2,4-dimethylphenyl)ethyl, 1-(2,4,6-trimethylphenyl)ethyl, 2-(2,4,6-trimethylphenyl- )ethyl, 3-phenylpropyl, 3-(4-methylphenyl)propyl, 4-phenylbutyl, 4-(2-methylphenyl)butyl, 5-phenylpentyl, 5-(3-methylphenyl)pentyl, 6-phenylhexyl, 6-(4-methylphenyl)hexyl, 2-methoxybenzyl, 3-methoxybenzyl, 4-methoxybenzyl, 2,3-dimethoxybenzyl, 2,4-dimethoxybenzyl, 2,5-dimethoxybenzyl, 3-methoxy-4-ethoxybenzyl, 2,6-dimethoxybenzyl, 3,4-dimethoxybenzyl, 3,5-dimethoxybenzyl, 2,3,4-trimethoxybenzyl, 2,4,5-trimethoxybenzyl, 2,3,5-trimethoxybenzyl, 2,4,6-trimethoxybenzyl, 3,4,5-trimethoxybenzyl, 2-ethoxybenzyl, 4-propoxybenzyl, 3-butoxybenzyl, 2-tert-butoxybenzyl, 3-pentyloxybenzyl, 4-hexyloxybenzyl, 2,3-diethoxybenzyl, 1-(4-methoxyphenyl)ethyl, 2-(3,4-dimethoxyphenyl)ethyl, 3-(4-methoxyphenyl)propyl, 4-(2-methoxyphenyl)butyl, 5-(4-methoxyphenyl)pentyl, 6-(4-methoxyphenyl)hexyl, 6-(3,4,5-tripentyloxyphenyl)hexyl, 2-fluorobenzyl, 3-fluorobenzyl, 4-fluorobenzyl, 2,3-difluorobenzyl, 2,4-difluorobenzyl, 2,5-difluorobenzyl, 2-fluoro-3-chlorobenzyl, 2-fluoro-3-bromobenzyl, 2,6-difluorobenzyl, 2,3,4-trifluorobenzyl, 2,4,5-trifluorobenzyl, 2,3,5-trifluorobenzyl, 2,4,6-trifluorobenzyl, 3,4,5-trifluorobenzyl, 1-(2-fluorophenyl)ethyl, 2-(2-fluorophenyl)ethyl, 3-(3-fluorophenyl)propyl, 4-(2-fluorophenyl)butyl, 5-(2-fluorophenyl)pentyl, 6-(3-fluorophenyl)hexyl, 2-bromobenzyl, 3-bromobenzyl, 4-bromobenzyl, 2,3-dibromobenzyl, 2-bromo-3-fluorobenzyl, 2-fluoro-4-bromobenzyl, 2,4-dibromobenzyl, 2,5-dibromobenzyl, 2,6-dibromobenzyl, 2,3,4-tribromobenzyl, 2,4,5-tribromobenzyl, 2,3,5-tribromobenzyl, 2,4,6-tribromobenzyl, 3,4,5-tribromobenzyl, 1-(2-bromophenyl)ethyl, 2-(2-bromophenyl)ethyl, 3-(2-bromophenyl)propyl, 4-(3-bromophenyl)butyl, 5-(2-bromophenyl)pentyl, 6-(4-bromophenyl)hexyl, 2-chlorobenzyl, 3-chlorobenzyl, 4-chlorobenzyl, 2,3-dichlorobenzyl, 2,4-dichlorobenzyl, 2,5-dichlorobenzyl, 2,6-dichlorobenzyl, 2-bromo-4-chlorobenzyl, 2-fluoro-4-chlorobenzyl, 2,3,4-trichlorobenzyl, 2,4,5-trichlorobenzyl, 2,3,5-trichlorobenzyl, 2,4,6-trichlorobenzyl, 3,4,5-trichlorobenzyl, 1-(4-chlorophenyl)ethyl, 2-(4-chlorophenyl)ethyl, 3-(2-chlorophenyl)propyl, 4-(4-chlorophenyl)butyl, 5-(3-chlorophenyl)pentyl, 6-(4-chlorophenyl)hexyl, 2-(3,4-dichlorophenyl)ethyl, 2-iodobenzyl, 3-iodobenzyl, 4-iodobenzyl, 3,4-diiodobenzyl, 3,4,5-triiodobenzyl, 2-(3-iodophenyl)ethyl, 6-(2-iodophenyl)hexyl, 2-carboxybenzyl, 3-carboxybenzyl, 4-carboxybenzyl, 2,3-dicarboxybenzyl, 2,4-dicarboxybenzyl, 2,5-dicarboxybenzyl, 2,6-dicarboxybenzyl, 3,4-dicarboxybenzyl, 3,5-dicarboxybenzyl, 2,3,4-tricarboxybenzyl, 2,4,6-tricarboxybenzyl, 3,4,5-tricarboxybenzyl, 1-(4-carboxyphenyl)ethyl, 2-(4-carboxyphenyl)ethyl, 2-(2,6-dicarboxyphenyl)ethyl, 3-(3-carboxyphenyl)propyl, 5-(2,4,6-tricarboxyphenyl)pentyl, 6-(4-carboxyphenyl)hexyl, 6-(3,5-dicarboxyphenyl)hexyl, 4-methoxycarbonylbenzyl, 3-methoxycarbonylbenzyl, 2-methoxycarbonylbenzyl, 4-ethoxycarbonylbenzyl, 3-ethoxycarbonylbenzyl, 2-ethoxycarbonylbenzyl, 4-propoxycarbonylbenzyl, 4-butyoxycarbonylbenzyl, 4-pentyloxycarbonylbenzyl, 4-hexyloxycarbonylbenzyl, 3,4-dimethoxycarbonylbenzyl, 2,4-dimethoxycarbonylbenzyl, 3,5-dimethoxycarbonylbenzyl, 2,3,4-trimethoxycarbonylbenzyl, 3,4,5-trimethoxycarbonylbenzyl, 2-(4-methoxycarbonylphenyl)ethyl, 6-(4-methoxycarbonylphenyl)hexyl, 2-(N,N-dimethylamino)benzyl, 3-(N,N-dimethylamino)benzyl, 4-(N,N-dimethylamino)benzyl, 4-(N-methyl, N-ethylamino)benzyl, 2,4-di(N,N-dimethylamino)benzyl, 2,4,6-tri(N,N-dimethylamino)benzyl, etc.

Examples of phenyl-lower alkyl groups having lower alkylenedioxy or phenyl group as the substituent and represented by $R^1$ and $R^2$ in the formula (1a) are phenyl-alkyl groups in which phenyl group substituted with $C_1-C_4$ alkylenedioxy or phenyl group is linked with $C_1-C_6$ alkylene group, such as 2,3-methylenedioxybenzyl, 3,4-methylenedioxybenzyl, 2,3-ethylenedioxybenzyl, 3,4-ethylenedioxybenzyl, 3,4-trimethylenedioxybenzyl, 3,4-tetramethylenedioxybenzyl, 1-(3,4-methylenedioxyphenyl)ethyl, 2-(3,4-methylenedioxyphenyl)ethyl, 3-(3,4-methylenedioxyphenyl)propyl, 4-(3,4-methylenedioxyphenyl)butyl, 5-(3,4-methylenedioxyphenyl)pentyl, 6-(3,4-methylenedioxyphenyl)hexyl, 3-(3,4-trimethylenedioxyphenyl)propyl, 2-phenylbenzyl, 3-phenylbenzyl, 4-phenylbenzyl, 2-(3-phenylphenyl)ethyl, 1-(4-phenylphenyl)ethyl, 2-(4-phenylphenyl)ethyl, 3-(4-phenylphenyl)propyl, 4-(4-phenylphenyl)butyl, 5-(4-phenylphenyl)pentyl, 6-(4-phenylphenyl)hexyl, etc.

Examples of phenyl-lower alkenyl groups represented by $R^1$ and $R^2$ are phenyl-$C_2-C_6$ alkenyl groups such as 2-phenylethylenyl, 3-phenyl-1-propenyl, 3-phenyl-2-propenyl, 4-phenyl-1-butenyl, 4-phenyl-2-butenyl, 4-phenyl-3-butenyl, 5-phenyl-4-pentenyl, 6-phenyl-5-hexenyl, etc.

Examples of naphthyl lower alkyl groups represented by $R^1$ and $R^2$ are naphthyl-$C_1-C_6$ alkyl groups such as α-naphthylmethyl, β-naphthylmethyl, 2-(α-nephthyl)ethyl, 3-(β-naphthyl)propyl, 4-(α-naphthyl)butyl, 5-(β-naphthyl)pentyl, 6-(α-naphthyl)hexyl, 3-(α-naphthyl)-2-methylpropyl, 1-(α-naphthyl)ethyl, etc.

Examples of acyl groups disclosed in the specification and claims and especially represented by $R^1$, $R^2$ and $R^3$ are various and include the following:

(i) $C_1-C_{20}$ alkanoyl groups optionally substituted with the substituents selected from the group consisting of halogen atom, hydroxy group, lower alkoxy group, aryloxy group, substituted or unsubstituted aryl group, phenyl-lower alkoxycarbonyl group and lower alkyl-carbamoyl group.

(ii) arylcarbonyl groups optionally substituted with lower alkylenedioxy group or with 1 to 3 substituents selected from the group consisting of halogen atom, lower alkyl group, lower alkoxy group, carboxy group, lower alkoxycarbonyl group, nitro group, cyano group, phenyl-lower alkoxycarbonyl group, hydroxy group, guanidyl group, phenyl-lower alkoxy group, amino group and amino group substituted with lower alkyl group.

(iii) 5- or 6-membered unsaturated hetero ring-carbonyl groups having nitrogen atom, sulfur atom or oxygen atom as the hetero atom.

(iv) carbonic acid ester residue such as aryloxycarbonyl groups, straight or branched-chain or cyclic alkoxycarbonyl groups.

(v) substituted or unsubstituted cycloalkylcarbonyl groups.

(vi) lower alkenyl (or lower alkynyl)carbonyl groups.

(vii) lower alkenyl (or lower alkynyl)oxycarbonyl groups.

(viii) pyridyloxycarbonylarylenecarbonyl groups represented by the formula

(Y)

wherein $R^x$ is pyridyl groups optionally substituted with 1 to 4 substituents selected from the group consisting of hydroxy group, oxo group, halogen atom, amino group, carboxy group, cyano group, nitro group, carbamoyl group, lower alkyl carbamoyl group, carboxy-lower alkylcarbamoyl group, lower alkoxycarbonyl-lower alkylcarbamoyl group, phenyl carbamoyl group optionally substituted with 1 to 3 substituents selected from the group consisting of halogen atom, lower alkoxy group and lower alkyl group on the phenyl ring, lower alkyl group, lower alkenyl group, lower alkoxycarbonyl group, tetrahydrofuranyl group, tetrahydropyranyl group, lower alkoxy-lower alkyl group, lower alkylthio-lower alkyl group, phenyl-lower alkoxy-lower alkyl group, phthalidyl group and acyloxy group having acyl as represented by $R^1$, $R^2$ and $R^3$, preferably acyl exemplified in the foregoing items (i) to (vii) in the acyl moiety, and Y is arylene group.

Examples of the acyl groups included in the items (i) to (viii) are as follows.

(i) $C_1$-$C_{20}$ alkanoyl groups optionally substituted with the substituents selected from the group consisting of halogen atom, hydroxy group, lower alkoxy group, aryloxy group, substituted or unsubstituted aryl group, phenyl-lower alkoxycarbonyl group and lower alkylcarbamoyl group.

$C_1$-$C_{20}$ unsubstituted alkanoyl groups such as formyl, acetyl, propionyl, butyryl, isobutyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, ocatadecanoyl, nonadecanoyl, eicosanoyl, etc; $C_2$-$C_6$ alkanoyl groups substituted with 1 to 3 halogen atoms such as monochloroacetyl, monobromoacetyl, dichloroacetyl, trichloroacetyl, 3-chloropropionyl, 4-chlorobutyryl, 5-chloropentanoyl, 6-chlorohexanoyl, etc; $C_2$-$C_6$ alkanoyl groups substituted with hydroxy group such as hydroxyacetyl, 3-hydroxypropionyl, 5-hydroxypentanoyl, 4-hydroxybutanoyl, 6-hydroxyhexanoyl, etc; $C_2$-$C_6$ alkanoyl groups substituted with $C_1$-$C_6$ alkoxy group such as methoxyacetyl, ethoxyacetyl, 3-propoxypropionyl, 6-hexyloxyhexanoyl, 3-methoxypropionyl, etc; $C_2$-$C_6$ alkanoyl groups substituted with phenoxy or naphthyloxy group such as phenoxyacetyl, 2-phenoxypropionyl, 3-phenoxypropionyl, 4-phenoxybutyryl, 5-phenoxypentanoyl, 6-pheenoxyhexanoyl, α-naphthyloxyacetyl, etc; $C_2$-$C_6$ alkanoyl groups substituted with aryl group optionally substituted with 1 to 3 substituents selected from the group consisting of halogen atom, lower alkyl group, lower alkoxy group, carboxy group, lower alkoxycarbonyl group, nitro group and cyano group on the aryl ring (phenyl ring, naphthyl ring, etc.), such as α-phenylacetyl, 2-phenylpropionyl, 3-phenylpropionyl, 4-phenylbutyryl, 5-phenylpentanoyl, 6-phenylhexanoyl, α-(2-chlorophenyl)acetyl, α-(4-methylphenyl)acetyl, α-(3,4,5-trimethoxyphenyl)acetyl, α-(3,4-dimethoxyphenyl)acetyl, 6-(4-carboxyphenyl)hexanoyl, 4-(4-ethoxycarbonylphenyl)pentanoyl, α-(4-nitrophenyl)acetyl, α-(4-cyanophenyl)acetyl, α-naphthylacetyl, β-naphthylacetyl, etc; $C_1$-$C_{20}$ alkanoyl groups substituted with phenyl-$C_2$-$C_7$ lower alkoxycarbonyl group such as α-benzyloxycarbonylacetyl, 2-benzyloxycarbonylpropionyl, 3-benzyloxycarbonylpropionyl, 4-benzyloxycarbonylbutyryl, 5-benzyloxycarbonylpentanoyl, 6-benzyloxycarbonylhexanoyl, 3-(α-phenethyloxycarbonyl)propionyl, 3-(β-phenethyloxycarbonyl)propionyl, 5-(benzyloxycarbonyl)hexanoyl, 7-(benzyloxycarbonyl)heptanoyl, 8-(α-phenethyloxycarbonyl)octanoyl, 9-(β-phenethyloxycarbonyl)nonanoyl, 10-(benzyloxycarbonyl)decanoyl, 11-(β-phenethyloxycarbonyl)tridecanoyl, 15-(benzyloxycarbonyl)pentadecanoyl, 17-(benzyloxycarbonyl)heptadecanoyl, 20-(benzyloxycarbonyl)eicosanoyl, etc; $C_1$-$C_{20}$ alkanoyl groups substituted with $C_2$-$C_7$ lower alkylcarbamoyl group such as methylcarbamoylacetyl, ethylcarbamoylacetyl, propylcarbamoylacetyl, butylcarbamoylacetyl, tert-butylcarbamoylacetyl, pentylcarbamoylacetyl, hexylcarbamoylacetyl, methylcarbamoylpropionyl, ethylcarbamoylbutyryl, propylcarbamoylpentanoyl, ethylcarbamoylhexanoyl, ethylcarbamoylheptanoyl, methylcarbamoyloctanoyl, ethylcarbamoylnonanoyl, methylcarbamoyldecanoyl, methylcarbamoytridecanoyl, ethylcarbamoylpentadecanoyl, methylcarbamoylheptadecanoyl, methylcarbamoyleicosaonyl, etc;

(ii) aryl-carbonyl groups optionally substituted with lower alkylenedioxy group or with 1 to 3 substituents selected from the group consisting of halogen atom, lower alkyl group, lower alkoxy group, carboxy group, lower alkoxycarbonyl group, nitro group, cyano group, phenyl-lower alkoxycarboxy group, hydroxy group, guanidyl group, phenyl-lower alkoxy group, amino group and amino group substituted with lower alkyl group on the aryl ring.

aryl-carbonyl groups such as phenylcarbonyl, naphthylcarbonyl, etc. optionally substituted with lower alkylenedioxy group or with 1 to 3 substituents selected from the group consisting of halogen atom, lower alkyl group, lower alkoxy group, carboxy group, lower alkoxycarbonyl groups, nitro group, cyano group, phenyl-lower alkoxycarbonyl group, hydroxy group, guanidyl group, phenyl-lower alkoxy group, amino group and amino group substituted with lower alkyl group, such as benzoyl, α-naphthylcarbonyl, β-naphthylcarbonyl, 2-methylbenzoyl, 3-methylbenzoyl, 4-methylbenzoyl, 2,4-dimethylbenzoyl, 3,4,5-trimethylbenzoyl, 4-ethylbenzoyl, 2-methoxybenzoyl, 3-methoxybenzoyl, 4-methoxybenzoyl, 2,4-dimethoxybenzoyl, 3,4,5-trimethoxybenzoyl, 4-ethoxybenzoyl, 2-methoxy-4-ethoxybenzoyl, 2-propoxybenzoyl, 3-propoxybenzoyl, 4-propoxybenzoyl, 2,4-dipropoxybenzoyl, 3,4,5-tripropoxybenzoyl, 2-carboxybenzoyl, 3-carboxybenzoyl, 4-carboxybenzoyl, 2-chlorobenzoyl, 3-chlorobenzoyl, 4-chlorobenzoyl, 2,3-dichlorobenzoyl, 2,4,6-trichlorobenzoyl, 2-bromobenzoyl, 4-fluorobenzoyl, 2-methoxycarbonylbenzoyl, 3-methoxycarbonylbenzoyl, 4-methoxycarbonylbenzoyl, 2-ethoxycarbonylbenzoyl, 3-ethoxycarbonylbenzoyl, 4-ethoxycarbonylbenzoyl, 2-propoxycarbonylbenzoyl, 3-propoxycarbonylbenzoyl, 4-propoxycarbonylbenzoyl, 2-isopropoxycarbonylbenzoyl, 3-isopropoxycarbonylbenzoyl, 4-isopropoxycarbonylbenzoyl, 2-butoxycarbonylbenzoyl, 3-butoxycarbonylbenzoyl, 4-butoxycarbonylbenzoyl, 2-tert-butoxycarbonylbenzoyl, 3-tert-butoxycarbonylbenzoyl, 4-tert-butoxycarbonylbenzoyl, 2-pentyloxycarbonylbenzoyl, 3-pentyloxycarbonylbenzoyl, 4-pentyloxycarbonylbenzoyl, 2-hexyloxycarbonylbenzoyl, 3-hexyloxycarbonylbenzoyl, 4-hexyloxycarbonylbenzoyl, 3,5-dimethoxycarbonylbenzoyl, 3,4,5-trimethoxycarbonylbenzoyl, β-methyl-α-naphthylcarbonyl, α-methoxy-β-naphthylcarbonyl, β-chloro-α-naphthylcarbonyl, 2-cyanobenzoyl, 4-cyanobenzoyl, 2-nitrobenzoyl, 4-nitrobenzoyl, 2-benzyloxycarbonylbenzoyl, 3-benzyloxycarbonylbenzoyl, 4-benzyloxycarbonylbenzoyl, 3-(α-phenethyloxycarbonyl)benzoyl, 4-(β-phenethyloxycarbonyl)benzoyl, 4-(3-phenylpropoxycarbonyl)benzoyl, 4-(6-phenylhexyloxycarbonyl)benzoyl, 2-hydroxybenzoyl, 3-hydroxybenzoyl, 2,3-dihydroxybenzoyl, 3,4-dihydroxybenzoyl, 3,4,5-trihydroxybenzoyl, 4-hydroxybenzoyl, 2-guanidylbenzoyl, 3-guanidylbenzoyl, 4-guanidylbenzoyl, 2-(benzyloxy)benzoyl, 3-(benzyloxy)benzoyl, 4-(benzyloxy)benzoyl, 2-(α-phenethyloxy)benzoyl, 3-(α-phenethyloxy)benzoyl, 4-(α-phenethyloxy)benzoyl, 2-(β-phenethyloxy)benzoyl, 3-(β-phenethyloxy)benzoyl, 4-(β-phenethyloxy)benzoyl, 4-(3-phenylpropoxy)benzoyl, 4-(4-phenylbutoxy)benzoyl, 4-(5-phenylpentyloxy)benzoyl, 4-(6-phenylhexyloxy)benzoyl, 2-aminobenzoyl, 3-aminobenzoyl, 4-aminobenzoyl, 2-methylaminobenzoyl, 3-methylaminobenzoyl, 4-methylaminobenzoyl, 2-ethylaminobenzoyl, 3-propylaminobenzoyl, 4-butylaminobenzoyl, 3-pentylaminobenzoyl, 4-hexylaminobenzoyl, 2-(N,N-dimethylamino)benzoyl, 3-(N,N-dimethylamino)benzoyl, 4-(N,N-dimethylamino)benzoyl, 3-(N-methyl-N-ethylamino)benzoyl, 4-(N,N-diethylamino)benzoyl, 3-(N,N-dipropylamino)benzoyl, 4-(N,N-dibutylamino)benzoyl, 4-(N,N-dipentylamino)benzoyl, 4-(N,N-dihexylamino)benzoyl, 3-benzyloxycarbonyl-1-naphthylcarbonyl, 6-(β-phenethyloxycarbonyl)-1-naphthylcarbonyl, 4-benzyloxycarbonyl-2-naphthylcarbonyl, 5-(α-phenethyloxycarbonyl)-2-naphthylcarbonyl, 2-hydroxy-1-naphthylcarbonyl, 3-hydroxy-1-naphthylcarbonyl, 4-hydroxy-1-naphthylcarbonyl, 5-hydroxy-1-naphthylcarbonyl, 6-hydroxy-1-naphthylcarbonyl, 7-hydroxy-1-naphtylcarbonyl, 8-hydroxy-1-naphthylcarbonyl, 1-hydroxy-2-naphthylcarbonyl, 4-hydroxy-2-naphthylcarbonyl, 5-hydroxy-2-naphthylcarbonyl, 7-hydroxy-2-napthylcarbonyl, 2-guanidyl-1-napthylcarbonyl, 3-guanidyl-1-naphthylcarbonyl, 5-guanidyl-1-naphthylcarbonyl, 6-guanidyl-1-naphthylcarbonyl, 8-guanidyl-1-naphthylcarbonyl, 1-guanidyl-2-naphthylcarbonyl, 4-guanidyl-2-naphthylcarbonyl, 6-guanidyl-2-naphthylcarbonyl, 8-guanidyl-2-naphthylcarbonyl, 2-amino-1-naphthylcarbonyl, 3-amino-1-naphthylcarbonyl, 4-amino-1-naphthylcarbonyl, 6-amino-1-naphthylcarbonyl, 4-amino-2-naphthylcarbonyl, 5-amino-1-naphthylcarbonyl, 7-amino-2-naphthylcarbonyl, 8-amino-2-naphthylcarbonyl, 3-(N,N-dimethylamino)-2-naphthylcarbonyl, 4-(N-methyl-N-ethylamino)-1-naphthylcarbonyl, 6-(N,N-dimethylamino)-1-naphthylcarbonyl, 7-(N-methyl-N-ethylamino)-2-naphthylcarbonyl, 8-(N-methyl-N-ethylamino)-1-naphthylcarbonyl, 3,4-methylenedioxybenzoyl, 3,4-ethylenedioxybenzoyl, 2,3-methylenedioxybenzoyl, etc.

(iii) 5- or 6-membered unsaturated hetero ring-carbonyl groups having nitrogen atom, sulfur atom or oxygen atom as the hetero atom.

thienylcarbonyl, furanylcarbonyl, thiazolylcarbonyl, quinolylcarbonyl, pyrazinylcarbonyl, pyridylcarbonyl, etc., such as 2-thienylcarbonyl, 3-thientylcarbonyl, 2-furanylcarbonyl, 3-furanylcarbonyl, 4-thiazolylcarbonyl, 2-quinolylcarbonyl, 2-pyrazinylcarbonyl, 2-pyridylcarbonyl, 3-pyridylcarbonyl, 4-pyridylcarbonyl, etc.

(iv) carbonic acid ester residue such as aryloxycarbonyl groups, straight or branched-chain or cyclic alkoxycarbonyl groups.

aryloxycarbonyl groups optionally substituted with 1 to 3 substituents selected from the group consisting of halogen atom, lower alkyl group and lower alkoxy group on the aryl ring (phenyl ring, naphthyl ring, etc.), such as phenoxycarbonyl, α-naphthyloxycarbonyl, β-naphthyloxycarbonyl, 2-methylphenoxycarbonyl, 3-methylphenoxycarbonyl, 4-methylphenoxycarbonyl, 2,4-dimethylphenoxycarbonyl, 3,4,5-trimethylphenoxycarbonyl, 4-ethylphenoxycarbonyl, 2-methoxyphenoxycarbonyl, 3-methoxyphenoxycarbonyl, 4-methoxyphenoxycarbonyl, 2,4-dimethoxyphenoxycarbonyl, 3,4,5-trimethoxyphenoxycarbonyl, 4-ethoxyphenoxycarbonyl, 2-propoxyphenoxycarbonyl, 3-propoxyphenoxycarbonyl, 4-propoxyphenoxycarbonyl, 2,4-dipropoxyphenoxycarbonyl, 3,4,5-tripropoxyphenoxycarbonyl, 2-chlorophenoxycarbonyl, 3-chlorophenoxycarbonyl, 4-chlorophenoxycarbonyl, 2,3-dichlorophenoxycarbonyl, 2,4,6-trichlorophenoxycarbonyl, 2-bromophenoxycarbonyl, 4-fluorophenoxycarbonyl, β-methyl-α-naphthyloxycarbonyl, α-methoxy-β-naphthyloxycarbonyl, β-chloro-α-naphthyloxycarbonyl etc; straight or branched-chain or cyclic alkoxycarbonyl groups having 1 to 8 carbon atoms in the alkoxy moiety, such as methoxycarbonyl, ethoxycarbonyl, propoxycarbonyl, isopropoxycarbonyl, tert-butoxycarbonyl, butoxycarbonyl, pentyloxycarbonyl, hexyloxycarbonyl, cyclopropoxycarbonyl, cyclobutyloxycarbonyl, cyclopentyloxycarbonyl, cyclohexyloxycarbonyl, cycloheptyloxycarbonyl, cyclooctyloxycarbonyl, etc.

(v) substituted or unsubstituted cycloalkyl carbonyl groups.

cycloalkylcarbonyl groups optionally substituted with halogen atom, hydroxy group, lower alkoxy group or lower alkyl group and having 3 to 8 carbon atoms in the cycloalkyl ring, such as cyclopropylcarbonyl, cyclobutylcarbonyl, cyclopentylcarbonyl, cyclohexylcarbonyl, cycloheptylcarbonyl, cyclooctylcarbonyl, 2-chlorocyclohexylcarbonyl, 3-hydroxycyclopentylcarbonyl, 3-methylcyclohexylcarbonyl, 4-methoxycyclohexylcarbonyl, etc.

(vi) lower alkenyl (or lower alkynyl)carbonyl groups.

carbonyl groups having $C_2$–$C_6$ alkenyl or alkynyl group, such as vinylcarbonyl, allylcarbonyl, 2-butenylcarbonyl, 3-butenylcarbonyl, 1-methylallylcarbonyl, 2-pentenylcarbonyl, 3-hexenylcarbonyl, ethynylcarbonyl, propynylcarbonyl, 2-butynylcarbonyl, 1-methyl-3-pentynylcarbonyl, 4-hexynylcarbonyl, etc.

(vii) lower alkenyl (or lower alkynyl)oxycarbonyl groups.

carbonyl groups having $C_2$–$C_6$ alkenyloxy or alkynyloxy group, such as vinyloxycarbonyl, allyloxycarbonyl, 2-butenyloxycarbonyl, 3-butenyloxycarbonyl, 2-hexenyloxycarbonyl, 1-methylallyloxycarbonyl, 2-pentenyloxycarbonyl, 3-hexenyloxycarbonyl, ethynyloxycarbonyl, propynyloxycarbonyl, 2-butynyloxycarbonyl, 1-methyl-3-pentynyloxycarbonyl, 4-hexynyloxycarbonyl, etc.

(viii) pyridyloxycarbonylarylenecarbonyl group represented by the formula (Y)

The substituents on the substituted pyridyl group represented by $R^x$ are exemplified below.

Examples of lower alkylcarbamoyl groups are alkylcarbamoyl groups having one or two $C_1$–$C_6$ alkyl groups such as N-methylcarbamoyl, N-ethylcarbamoyl, N-propylcarbamoyl, N-isopropylcarbamoyl, N-butylcarbamoyl, N-tert-butylcarbamoyl, N-pentylcarbamoyl, N-hexylcarbamoyl, N,N-dimethylcarbamoyl, N,N-diethylcarbamoyl, N,N-dipropylcarbamoyl, N-isopropyl-N-methylcarbamoyl, N-ethyl-N-methylcarbamoyl, N-methyl-N-pentyl-carbamoyl, N-propyl-N-pentylcarbamoyl, N,N-dipentylcarbamoyl, N-ethyl-N-hexylcarbamoyl, N-hexyl-N-pentylcarbamoyl, N,N-dihexylcarbamoyl and the like.

Examples of phenylcarbamoyl groups optionally having 1 to 3 substituents selected from the group consisting of halogen, lower alkyl and lower alkoxy on the phenyl ring are carbamoyl groups having one or two phenyl groups which may optionally have 1 to 3 substituents selected from the group consisting of halogen, $C_1$–$C_6$ alkoxy and $C_1$–$C_6$ alkyl on the phenyl ring such as N-(2-chlorophenyl)carbamoyl, N-(3,5-dichloro)-phenylcarbamoyl, N-(3-methoxyphenyl)carbamoyl, N-(4-propoxyphenyl)carbamoyl, N-(2-methylphenyl)-carbamoyl, N-(4-ethylphenyl)carbamoyl, N-(3-isopropylphenyl)carbamoyl, N-(4-hexylphenyl)carbamoyl, N-phenylcarbamoyl, N,N-diphenylcarbamoyl and the like.

Examples of lower alkenyl groups are $C_2$–$C_6$ alkenyl groups such as vinyl, allyl, 2-butenyl, 3-butenyl, 1-methylallyl, 2-pentenyl, 2-hexenyl and the like.

Examples of lower alkoxycarbonyl groups are carbonyl groups having $C_1$–$C_6$ alkoxy group such as methoxycarbonyl, ethoxycarbonyl, propoxycarbonyl, isopropoxycarbonyl, tert-butoxycarbonyl, butoxycarbonyl, pentyloxycarbonyl, hexyloxycarbonyl and the like.

Examples of tetrahydrofuranyl groups are 2-tetrahydrofuranyl, 3-tetrahydrofuranyl and the like.

Examples of lower alkoxy-lower alkyl groups are alkoxyalkyl groups in which the alkoxy moiety and alkyl moiety each have 1 to 6 carbon atoms, such as methoxymethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl, 2-pentyloxyethyl, 2-hexyloxyethyl and the like.

Examples of phenyl-lower alkoxy-lower alkyl groups are alkoxyalkyl groups which is substituted with phenyl group and in which the alkoxy moiety and alkyl moiety each have 1 to 6 carbon atoms, such as benzyloxymethyl, 2-benzyloxyethyl, 5-(2-phenylpentyloxy)pentyl, 6-benzyloxyhexyl, 4-hexyloxyhexyl, phenylmethoxymethyl, 2-phenylethoxymethyl, 2-(phenylmethoxy)ethyl, 2-(phenylmethoxy)propyl, 4-(phenylmethoxy)-butyl, 5-(phenylmethoxy)pentyl, 6-(phenylmethoxy)-hexyl, 2-(2-phenylethoxy)ethyl, 2-(4-phenylbutoxy)ethyl, 4-(4-phenylbutoxy)butyl, 6-phenylmethoxyhexyl and the like.

Examples of lower alkoxycarbonyl-lower alkylcarbamoyl groups are carbamoyl groups substituted with one alkoxycarbonylalkyl group in which the alkoxy moiety and the alkyl moiety each have 1 to 6 carbon atoms, such as methoxycarbonylmethylcarbamoyl, 3-methoxycarbonylpropylcarbamoyl, ethoxycarbonylmethylcarbamoyl, propoxycarbonylmethylcarbamoyl, isopropoxycarbonylmethylcarbamoyl, butoxycarbonylmethylcarbamoyl, tert-butoxycarbonylmethylcarbamoyl, pentyloxycarbonylmethylcarbamoyl, hexyloxycarbonylmethylcarbamoyl, 2-methoxycarbonylethylcarbamoyl, 2-methoxycarbonyl-1-methyl-ethylcarbamoyl, 4-methoxycarbonylbutylcarbamoyl, 2-methoxycarbonyl-1,1-dimethylethylcarbamoyl, 5-methoxycarbonylpentylcarbamoyl, 6-methoxycarbonylhexylcarbamoyl, 2-ethoxycarbonylethylcarbamoyl, 4-ethoxycarbonylbutylcarbamoyl, 6-propoxycarbonylhexylcarbamoyl, 5-isopropoxycarbonylpentylcarbamoyl, 1,1-dimethyl-2-butoxycarbonylethylcarbamoyl, 2-methyl-3-tert-butoxycarbonylpropylcarbamoyl, 2-pentyloxycarbonylethylcarbamoyl, hexyloxycarbonylethylcarbamoyl and the like.

Examples of carboxy-lower alkylcarbamoyl groups are carboxy-$C_1$–$C_6$ alkylcarbamoyl groups, such as N-(carboxymethyl)carbamoyl, N-(2-carboxyethyl)carbamoyl, N-(3-carboxypropyl)carbamoyl, N-(2-methyl-2-carboxyethyl)carbamoyl, N-(4-carboxybutyl)carbamoyl, N-(2-methyl-3-carboxypropyl)carbamoyl, N-(2,2-dimethyl-2-carboxyethyl)carbamoyl, N-(5-carboxypentyl)carbamoyl, N-(6-carboxyhexyl)carbamoyl and the like.

Examples of tetrahydropyranyl groups are 2-tetrahydropyranyl, 3-tetrahydropyranyl, 4-tetrahydropyranyl and the like.

Examples of lower alkylthio-lower alkyl groups are $C_1$–$C_6$ alkylthio-$C_1$–$C_6$ alkyl groups, such as methylthiomethyl, ethylthiomethyl, propylthiomethyl, butylthiomethyl, tert-butylthiomethyl, pentylthiomethyl, hexylthiomethyl, methylthioethyl, methylthiopropyl, methylthiobutyl, methylthiopentyl, methylthiohexyl, ethylthioethyl, ethylthiobutyl, propylthiohexyl and the like.

The pyridine ring is preferably substituted at any of the 2- to 6-positions with one to four of the substituents selected from the group consisting of the hydroxy, halogen, amino, carboxyl, cyano, nitro, oxo, lower alkyl, lower alkenyl, lower alkoxycarbonyl, carbamoyl and acyloxy among the substituents exemplified above, or preferably substituted at the 1-position with the carbamoyl, lower alkylcarbamoyl, phenylcarbamoyl optionally having 1 to 3 substituents selected from the group consisting of halogen, lower alkoxy and lower alkyl on the phenyl ring, tetrahydrofuranyl, phthalidyl, lower alkoxy-lower alkyl, phenyl-lower alkoxy-lower alkyl or lower alkoxycarbonyl-lower alkylcarbamoyl group among the substituents exemplified above.

Preferable examples of the group of the formula (Y) are those represented by the formula

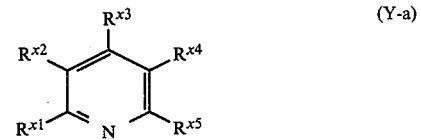

(Y-a)

wherein $R^{x1}$ is hydroxy or acyloxy; $R^{x2}$ and $R^{x4}$ are each hydrogen, halogen, amino, carboxyl, carbamoyl, cyano, nitro, lower alkyl, lower alkeny or lower alkoxycarbonyl; $R^{x3}$ and $R^{x5}$ are each hydrogen, hydroxy or acyloxy; when at least one of $R^{x1}$, $R^{x3}$ and $R^{x5}$ is free hydroxy, the structure of 1-position on the pyridine ring can be

due to the keto-enol tautomerism, said hydrogen attached to nitrogen being optionally substituted with a substituent selected from the group consisting of lower alkyl, tetrahydrofuranyl, tetrahydropyranyl, lower alkoxy-lower alkyl, phthalidyl, carbamoyl, lower alkoxycarbonyl-lower alkylcarbamoyl, phenyl-lower alkoxy-lower alkyl, phenylcarbamoyl which may have 1 to 3 substituents selected from the group consisting of halogen, lower alkoxy and lower alkyl on the phenyl ring, lower alkylcarbamoyl, carboxy-lower alkylcarbamoyl, lower alkylthio-lower alkyl and lower alkenyl, provided that at least one of $R^{x1}$, $R^{x3}$ and $R^{x5}$ represents hydroxy group and that the hydrogen of one hydroxyl group represented by $R^{x1}$, $R^{x3}$ or $R^{x5}$ is substituted with a group

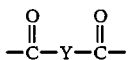

wherein Y is as defined above.

More preferable groups of the formula (Y) are those represented by the formula (Y-a) wherein $R^{x4}$ is halogen, amino, carboxyl, carbamoyl, cyano, nitro, lower alkyl, lower alkenyl or lower alkoxycarbonyl.

The most preferable groups of the formula (Y) are those represented by the formula (Y-a) wherein $R^{x4}$ is halogen or cyano.

Examples of the pyridyl groups represented by $R^x$ and optionally having the above various substituents are as follows.

2-pyridyl, 3-pyridyl, 4-pyridyl, 2-hydroxy-3-pyridyl, 2-hydroxy-4-pyridyl, 2-hydroxy-5-pyridyl, 2-hydroxy-6-pyridyl, 2-hydroxy-5-chloro-3-pyridyl, 2-hydroxy-5-chloro-4-pyridyl, 4-hydroxy-5-chloro-2-pyridyl, 2-hydroxy-5-chloro-6-pyridyl, 2-hydroxy-5-fluoro-4-pyridyl, 4-hydroxy-5-fluoro-2-pyridyl, 2-hydroxy-5-fluoro-6-pyridyl, 2-hydroxy-5-bromo-4-pyridyl, 4-hydroxy-5-bromo-2-pyridyl, 2-hydroxy-5-bromo-6-pyridyl, 2-hydroxy-5-iodo-4-pyridyl, 4-hydroxy-5-iodo-2-pyridyl, 2-hydroxy-5-iodo-6-pyridyl, 2-hydroxy-3-bromo-4-pyridyl, 4-hydroxy-3-bromo-2-pyridyl, 2-hydroxy-3-chloro-4-pyridyl, 4-hydroxy-3-chloro-2-pyridyl, 2-hydroxy-3-chloro-6-pyridyl, 2-hydroxy-4-chloro-6-pyridyl, 1-(2-tetrahydrofuranyl)-1,2-dihydro-2-oxo-3-pyridyl, 1-(2-tetrahydrofuranyl)-1,2-dihydro-2-oxo-4-pyridyl, 1-(2-tetrahydrofuranyl)-1,2-dihydro-2-oxo-5-pyridyl, 1-(2-tetrahydrofuranyl)-1,2-dihydro-2-oxo-6-pyridyl, 1-(3-tetrahydrofuranyl)-1,2-dihydro-2-oxo-4-pyridyl, 1-(2-tetrahydrofuranyl)-1,2-dihydro-2-oxo-5-chloro-4-pyridyl, 1-(2-tetrahydrofuranyl)-1,2-dihydro-2-oxo-5-chloro-6-pyridyl, 1-(2-tetrahydrofuranyl)-1,2-dihydro-2-oxo-5-fluoro-4-pyridyl, 1-(2-tetrahydrofuranyl)-1,2-dihydro-2-oxo-5-bromo-4-pyridyl, 1-(2-tetrahydrofuranyl)-1,2-dihydro-2-oxo-5-iodo-4-pyridyl, 1-(3-tetrahydrofuranyl)-1,2-dihydro-2-oxo-5-chloro-4-pyridyl, 1-(2-tetrahydrofuranyl)-1,2-dihydro-2-oxo-3-chloro-4-pyridyl, 1-ethoxymethyl-1,2-dihydro-2-oxo-3-pyridyl, 1-ethoxymethyl-1,2-dihydro-2-oxo-4-pyridyl, 1-ethoxymethyl-1,2-dihydro-2-oxo-5-pyridyl, 1-ethoxymethyl-1,2-dihydro-2-oxo-6-pyridyl, 1-methoxymethyl-1,2-dihydro-2-oxo-4-pyridyl, 1-(2-methoxyethyl)-1,2-dihydro-2-oxo-4-pyridyl, 1-ethoxymethyl-1,2-dihydro-2-oxo-5-chloro-3-pyridyl, 1-ethoxymethyl-1,2-dihydro-2-oxo-5-chloro-4-pyridyl, 1-ethoxymethyl-1,2-dihydro-2-oxo-5-chloro-6-pyridyl, 1-ethoxymethyl-1,2-dihydro-2-oxo-5-fluoro-4-pyridyl, 1-ethoxymethyl-1,2-dihydro-2-oxo-5-bromo-4-pyridyl, 1-ethoxymethyl-1,2-dihydro-2-oxo-5-iodo-4-pyridyl, 1-methoxymethyl-1,2-dihydro-2-oxo-5-chloro-4-pyridyl, 1-(2-methoxyethyl)-1,2-dihydro-2-oxo-5-chloro-4-pyridyl, 1-(2-ethoxymethyl)-1,2-dihydro-2-oxo-3-chloro-4-pyridyl, 2-acetyloxy-5-chloro-4-pyridyl, 2-acetyloxy-5-fluoro-4-pyridyl, 2-acetyloxy-5-bromo-4-pyridyl, 2-acetyloxy-5-iodo-4-pyridyl, 2-acetyloxy-5-methyl-4-pyridyl, 2-acetyloxy-5-cyano-4-pyridyl, 2-acetyloxy-5-nitro-4-pyridyl, 2-acetyloxy-5-carboxy-4-pyridyl, 2-propanoyloxy-5-chloro-4-pyridyl, 2-butanoyloxy-5-chloro-4-pyridyl, 2-isobutanoyloxy-5-chloro-4-pyridyl, 2-pentanoyloxy-5-chloro-4-pyridyl, 2-hexanoyloxy-5-chloro-4-pyridyl, 3-acetyloxy-5-chloro-4-pyridyl, 2-acetyloxy-3-chloro-4-pyridyl, 4-acetyloxy-5-chloro-2-pyridyl, 4-acetyloxy-5-fluoro-2-pyridyl, 4-acetyloxy-5-bromo-2-pyridyl, 4-acetyloxy-5-iodo-2-pyridyl, 4-acetyloxy-5-methyl-2-pyridyl, 4-acetyloxy-5-cyano-2-pyridyl, 4-acetyloxy-5-nitro-2-pyridyl, 4-acetyloxy-5-carboxy-2-pyridyl, 6-acetyloxy-5-chloro-2-pyridyl, 4-propanoyloxy-5-chloro-2-pyridyl, 4-butanoyloxy-5-chloro-2-pyridyl, 4-isobutanoyloxy-5-chloro-2-pyridyl, 4-pentanoyloxy-5-chloro-2-pyridyl, 4-hexanoyloxy-5-chloro-2-pyridyl, 4-acetyloxy-3-chloro-2-pyridyl, 3-acetyloxy-5-chloro-2-pyridyl, 2-acetyloxy-4-pyridyl, 2-propanoyloxy-4-pyridyl, 2-hexanoyloxy-4-pyridyl, 4-acetyloxy-2-pyridyl, 4-propanoyloxy-2-pyridyl, 4-hexanoyloxy-2-pyridyl, 2-methoxycarbonyloxy-5-chloro-4-pyridyl, 2-methoxycarbonyloxy-6-chloro-4-pyridyl, 2-ethoxycarbonyloxy-3-chloro-4-pyridyl, 2-ethoxycarbonyloxy-5-chloro-4-pyridyl, 2-ethoxycarbonyloxy-5-fluoro-4-pyridyl, 2-ethoxycarbonyloxy-5-bromo-4-pyridyl, 2-ethoxycarbonyloxy-6-chloro-4-pyridyl, 2-ethoxycarbonyloxy-5-chloro-3-pyridyl, 2-ethoxycarbonyloxy-5-chloro-6-pyridyl, 2-propoxycarbonyloxy-5-chloro-4-pyridyl, 2-hexyloxycarbonyloxy-5-chloro-4-pyridyl, 2-benzoyloxy-4-pyridyl, 3-benzoyloxy-4-pyridyl, 4-benzoyloxy-2-pyridyl, 3-benzoyloxy-2-pyridyl, 2-(2-methylbenzoyl)oxy-4-pyridyl, 2-(3-methylbenzoyl)oxy-4-pyridyl, 2-(4-methylbenzoyl)oxy-4-pyridyl, 2-(4-ethylbenzoyl)oxy-4-pyridyl, 2-(2-chlorobenzoyl)oxy-4-pyridyl, 2-(3-chlorobenzoyl)oxy-4-pyridyl, 2-(4-chlorobenzoyl)oxy-4-pyridyl, 2-(4-fluorobenzoyl)oxy-4-pyridyl, 2-(4-tert-butylbenzoyl)oxy-4-pyridyl, 2-(4-hexylbenzoyl)oxy-4-pyridyl, 4-(2-methylbenzoyl)oxy-2-pyridyl, 4-(4-ethylbenzoyl)oxy-2-pyridyl, 4-(3-chlorobenzoyl)oxy-2-pyridyl, 4-(4-fluorobenzoyl)oxy-2-pyridyl, 4-(4-tert-butylbenzoyl)oxy-2-pyridyl, 2-benzoyloxy-5-chloro-4-pyridyl, 2-benzoyloxy-5-fluoro-4-pyridyl, 2-benzoyloxy-5-bromo-4-pyridyl, 2-benzoyloxy-5-iodo-4-pyridyl, 2-benzoyloxy-5-methyl-4-pyridyl, 2-benzoyloxy-5-cyano-4-pyridyl, 2-benzoyloxy-5-nitro-4-pyridyl, 2-benzoyloxy-5-carboxy-4-pyridyl, 3-benzoyloxy-5-chloro-4-pyridyl, 2-benzoyloxy-3-chloro-4-pyridyl, 2-(2-methylbenzoyl)oxy-5-chloro-4-pyridyl, 2-(3-methylbenzoyl)oxy-5-chloro-4-pyridyl, 2-(4-methylbenzoyl)oxy-5-chloro-4-pyridyl, 2-(3,4,5-trimethylbenzoyl)oxy-5-chloro-4-pyridyl, 2-(4-ethylbenzoyl)oxy-5-chloro-4-pyridyl, 2-(4-tert-butylbenzoyl)oxy-5-fluoro-4-pyridyl, 2-(4-hexylbenzoyl)oxy-5-bromo-4-pyridyl, 2-(2-chlorobenzoyl)oxy-5-chloro-4-pyridyl, 2-(3-chlorobenzoyl)oxy-5-chloro-4-pyridyl, 2-(4-chlorobenzoyl)oxy-5-chloro-4-pyridyl, 2-(4-fluorobenzoyl)oxy-5-chloro-4-pyridyl, 2-(2,4-dichlorobenzoyl)oxy-5-chloro-4-pyridyl, 2-(3,4,5-trichlorobenzoyl)oxy-5-chloro-4-pyridyl, 2-(2-methoxybenzoyl)oxy-5-chloro-4-pyridyl, 2-(3-methoxybenzoyl)oxy-5-chloro-4-pyridyl, 2-(4-methoxybenzoyl)oxy-5-chloro-4-pyridyl, 2-(3,4,5-trimethoxybenzoyl)oxy-5-chloro-4-pyridyl, 4-benzoyloxy-5-chloro-2-pyridyl, 4-benzoyloxy-5-fluoro-2-pyridyl, 4-benzoyloxy-5-bromo-2-pyridyl, 4-benzoyloxy-5-iodo-2-pyridyl, 4-benzoyloxy-5-methyl-2-pyridyl, 4-benzoyloxy-5-cyano-2-pyridyl, 4-benzoyloxy-5-nitro-2-pyridyl, 4-benzoyloxy-5-carboxy-2-pyridyl, 3-benzoyloxy-5-chloro-2-pyridyl, 6-benzoyloxy-5-chloro-2-pyridyl, 6-(2,4-dichlorobenzoyloxy)-3-cyano-2-pyridyl, 6-(3,4,5-trimethoxybenzyloxy)-3-cyano-2-pyridyl, 6-(4-fluorobenzoyloxy)-3-chloro-2-pyridyl, 6-benzoyloxy-3-cyano-2-pyridyl, 4-(4-methylbenzoyl)oxy-5-chloro-2-pyridyl, 4-(2,4-dimethylbenzoyl)oxy-5-chloro-2-pyridyl, 4-

(3,4,5-trimethylbenzoyl)oxy-5-chloro-2-pyridyl, 4-(2-chlorobenzoyl)oxy-5-chloro-2-pyridyl, 4-(2,4-dichlorobenzoyl)oxy-5-chloro-2-pyridyl, 4-(4-methoxybenzoyl)oxy-5-chloro-2-pyridyl, 1-phthalidyl-1,2-dihydro-2-oxo-3-pyridyl, 1-phthalidyl-1,2-dihydro-2-oxo-4-pyridyl, 1-phthalidyl-1,2-dihydro-2-oxo-5-pyridyl, 1-phthalidyl-1,2-dihydro-2-oxo-6-pyridyl, 1-carbomethoxymethylcarbamoyl-1,2-dihydro-2-oxo-3-pyridyl, 1-carbomethoxymethylcarbamoyl-1,2-dihydro-2-oxo-4-pyridyl, 1-carbomethoxymethylcarbamoyl-1,2-dihydro-2-oxo-5-pyridyl, 1-carbomethoxymethylcarbamoyl-1,2-dihydro-2-oxo-6-pyridyl, 1-carboethoxymethylcarbamoyl-1,2-dihydro-2-oxo-4-pyridyl, 2-hydroxy-5-methyl-3-pyridyl, 2-hydroxy-5-methyl-4-pyridyl, 2-hydroxy-5-methyl-6-pyridyl, 2-hydroxy-5-ethyl-4-pyridyl, 2-hydroxy-3-methyl-4-pyridyl, 2-hydroxy-3-cyano-4-pyridyl, 2-hydroxy-3-cyano-5-pyridyl, 2-hydroxy-3-cyano-6-pyridyl, 2-hydroxy-5-cyano-6-pyridyl, 2-hydroxy-3-nitro-4-pyridyl, 2-hydroxy-3-nitro-5-pyridyl, 2-hydroxy-5-nitro-6-pyridyl, 2-hydroxy-6-nitro-4-pyridyl, 2-hydroxy-5-carboxy-3-pyridyl, 2-hydroxy-5-carboxy-4-pyridyl, 2-hydroxy-5-carboxy-6-pyridyl, 2-hydroxy-3-carboxy-4-pyridyl, 2-hydroxy-5-ethoxycarbonyl-3-pyridyl, 2-hydroxy-5-ethoxycarbonyl-4-pyridyl, 2-hydroxy-5-ethoxycarbonyl-6-pyridyl, 2-hydroxy-3-ethoxycarbonyl-4-pyridyl, 2-hydroxy-3,5-dichloro-4-pyridyl, 2-hydroxy-3,5-dichloro-6-pyridyl, 2-hydroxy-3,5-dibromo-4-pyridyl, 2-hydroxy-3,5-dibromo-6-pyridyl, 2-hydroxy-3-amino-4-pyridyl, 2-hydroxy-3-amino-5-pyridyl, 2-hydroxy-3-amino-6-pyridyl, 2-hydroxy-3-carbamoyl-4-pyridyl, 2-hydroxy-3-carbamoyl-5-pyridyl, 2-hydroxy-3-carbamoyl-6-pyridyl, 2,4-dihydroxy-6-pyridyl, 2,6-dihydroxy-4-pyridyl, 1,2-dihydro-2-oxo-4-pyridyl, 1,6-dihydro-6-oxo-2-pyridyl, 1-(benzyloxymethyl)-5-chloro-1,2-dihydro-2-oxo-4-pyridyl, 1-(benzyloxymethyl)-5-fluoro-1,2-dihydro-2-oxo-6-pyridyl, 1-(β-phenethyloxymethyl)-5-bromo-1,2-dihydro-2-oxo-4-pyridyl, 1-(2-benzyloxyethyl)-5-chloro-1,2-dihydro-2-oxo-4-pyridyl, 5-chloro-4-[p-(N,N-dimethylamino)benzoyloxy]-2-pyridyl, 5-bromo-4-[p-(N,N-dimethylamino)benzoyloxy]-2-pyridyl, 5-chloro-4-[p-(N,N-dimethylamino)benzoyloxy]-3-pyridyl, 5-chloro-4-[p-(N-methyl,N-ethylamino)benzoyloxy]-2-pyridyl, 5-fluoro-4-[o-(N,N-dimethylamino)benzoyloxy]-2-pyridyl, 5-fluoro-4-hexanoyloxy-2-pyridyl, 5-bromo-4-hexanoyloxy-2-pyridyl, 5-iodo-4-hexanoyloxy-2-pyridyl, 5-fluoro-4-octadecanoyloxy-2-pyridyl, 5-chloro-4-octadecanoyloxy-2-pyridyl, 5-bromo-4-octadecanoyloxy-2-pyridyl, 5-iodo-4-octadecanoyloxy-2-pyridyl, 5-fluoro-4-(2-furoyloxy)-2-pyridyl, 5-chloro-4-(2-furoyloxy)-2-pyridyl, 5-bromo-4-(2-furoyloxy)-2-pyridyl, 5-iodo-4-(2-furoyloxy)-2-pyridyl, 5-chloro-4-(3-furoyloxy)-2-pyridyl, 5-bromo-4-(3-furoyloxy)-2-pyridyl, 5-fluoro-4-(2-thenoyloxy)-2-pyridyl, 5-chloro-4-(2-thenoyloxy)-2-pyridyl, 5-bromo-4-(2-thenoyloxy)-2-pyridyl, 5-iodo-4-(2-thenoyloxy)-2-pyridyl, 5-chloro-4-(3-thenoyloxy)-2-pyridyl, 5-iodo-4-(3-thenoyloxy)-2-pyridyl, 4-(1-naphthoyloxy)-2-pyridyl, 4-(2-naphthoyloxy)-2-pyridyl, 5-(1-naphthoyloxy)-2-pyridyl, 5-(2-naphthoyloxy)-2-pyridyl, 6-(2-naphthoyloxy)-2-pyridyl, 3-cyano-6-(2-thenoyloxy)-2-pyridyl, 3-cyano-6-(3-thenoyloxy)-2-pyridyl, 4-cyano-6-(2-thenoyloxy)-2-pyridyl, 3-cyano-6-(2-furoyloxy)-2-pyridyl and the like.

Arylene groups represented by Y in the pyridyloxycarbonyl-arylene carbonyl group of the formula (Y) include those formed from aromatic hydrocarbons or 5- or 6-membered aromatic heterocycles containing one or two heteroatoms which are the same or different and which is or are selected from the group consisting of nitrogen and oxygen by removing two hydrogen atoms each bonded to the two different carbon atoms. Examples of such arylene groups are phenylene groups such as 1,2-phenylene, 1,3-phenylene, 1,4-phenylene and the like; naphthylene groups such as b 1,2-naphthylene, 1,3-naphthylene, 1,4-naphthylene, 1,5-naphthylene, 1,6-naphthylene, 1,7-naphthylene, 1,8-naphthylene and the like; pyridinediyl groups such as 2,4-pyridinediyl, 2,5-pyridinediyl, 2,6-pyridinediyl, 3,4-pyridinediyl, 3,5-pyridinediyl and the like; pyrazinediyl groups such as 2,3-pyrazinediyl, 2,6-pyrazinediyl, 2,5-pyrazinediyl, and the like; furandiyl groups such as 2,3-furandiyl, 3,4-furandiyl, 2,5-furandiyl, and the like; 4-pyridon-1-lower alkyl-diyl groups such as 4-pyridon-1-methyl-2,3-diyl, 4-pyridon-1-methyl-2,5-diyl, 4-pyridon-1-methyl-2,6-diyl and the like.

With respect to the formula (1b), the group

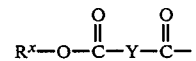

is the same as defined above concerning the acyl group (Y) under the item (viii).

Of the group

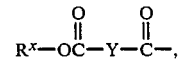

preferable are groups represented by the formula

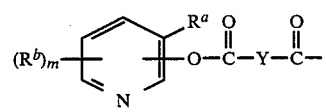

(1b-a)

wherein Y is as defined above, $R^a$ is hydrogen, halogen, amino, carboxyl, cyano, nitro, lower alkyl, lower alkenyl or lower alkoxycarbonyl group, $R^b$ is hydroxy or acyloxy and m is an integer of 1 or 2, with the proviso that the group

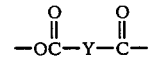

is attached to the 2-, 4- or 6-position of the pyridine ring and $R^b$ is attached to a remaining 2-, 4- or 6-position of the pyridine ring.

With the group of the formula (1b-a), $R^a$ preferably represents cyano and $R^b$ preferably represents benzoyloxy group optionally substituted with 1 to 3 halogen atoms. The substituent α is not particularly limited and include any of known 5-fluorouracil derivative groups so far as it can be converted to 5-fluorouracil in vivo and so far as it can form an ester or amide linkage when taken together with the carbonyl group to which this substituent α is attached. For example, suitable 5-fluorouracil derivative groups include those formed from the 5-fluorouracil derivatives represented by the formulas (1-1a), (1-1b) and (1-1c).

(a) A compound of the formula

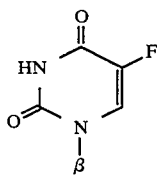
(1-1a)

wherein β represents hydrogen atom, tetrahydrofuranyl, lower alkylcarbamoyl, phthalidyl, lower alkoxy-lower alkyl or lower alkanoyloxy-lower alkoxycarbonyl group β preferably represents lower alkoxy-lower alkyl alkyl group.

The compound of the formula (1-1a) is disclosed in J. Med. Chem. 25, 1219, 1982, Cancer Chemother. Pharmacol., 1, 203-208, 1978 and Japanese Unexamined Patent Publication No. 37787/1975.

With respect to the formula (1-1a),

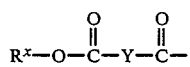

group can be linked by an amide linkage to the 3- or 1-position of the 5-fluorouracil ring.

(b) A compound of the formula

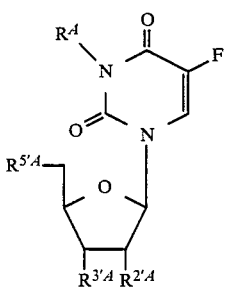
(1-1b)

wherein $R^A$ represents hydrogen atom or benzoyl group substituted with lower alkylenedioxy or lower alkoxy group on the phenyl ring, $R^{2'A}$ represents hydrogen atom, hydroxy or lower alkanoyloxy group, $R^{3'A}$ represents hydroxy or lower alkanoyloxy group, phenoxycarbonyloxy group substituted with lower alkoxy group on the phenyl ring, or phenyl-lower alkyloxy group optionally having 1 to 3 substituents selected from the group consisting of lower alkyl, lower alkoxy and halogen on the phenyl ring, and $R^{5'A}$ represents hydrogen, hydroxy, lower alkyl, lower alkanoyloxy group, phenoxycarbonyloxy group substituted with lower alkoxy group on the phenyl ring, or phenyl-lower alkyloxy group optionally having 1 to 3 substituents selected from the group consisting of lower alkyl, lower alkoxy and halogen on the phenyl ring, except for a compound wherein $R^{2'A}$ is hydrogen, one of $R^{3'A}$ and $R^{5'A}$ is phenyl-lower alkyloxy group optionally having 1 to 3 substituents selected from the group consisting of lower alkyl, lower alkoxy and halogen on the phenyl ring, and the other of $R^{3'A}$ and $R^{5'A}$ is lower alkanoyloxy group or hydroxy group.

The compound of the formula (1-1b) is disclosed in J. Med. Chem, 22, 1330, 1979, Japanese Unexamined Patent Publications No. 118800/1984 and No. 126221/1985.

With respect to the formula (1-1b),

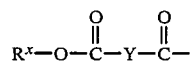

group can be linked by an amide linkage to the 3-position of the 5-fluorouracil ring or by an ester linkage with the hydroxy group of the ribofuranoside moiety.

(c) A compound of the formula

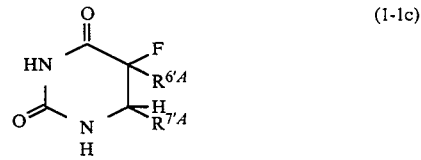
(1-1c)

wherein $R^{6'A}$ represents lower alkoxycarbonyl group, $R^{7'A}$ represents lower alkoxy group or group $$-O-N=CH-\langle\text{furyl}\rangle.$$

The compound of the formula (1-1c) is disclosed in EPC application published under the publication No. 99091.

With respect to the formula (1-1c),

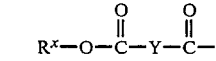

group can be linked by an amide linkage to the 1- or 3-position of the 5-fluorouracil ring.

With respect to the compounds of the formula (1-1a), (1-1b) and (1-1c), the groups represented by β, $R^A$, $R^{2'A}$, $R^{3'A}$, $R^{5'A}$, $R^{6'A}$ and $R^{7'A}$ are exemplified below.

Examples of lower alkylcarbamoyl groups are alkylcarbamoyl groups having one or two $C_1$-$C_6$ alkyl groups such as N-methylcarbamoyl, N-ethylcarbamoyl, N-propylcarbamoyl, N-isopropylcarbamoyl, N-butylcarbamoyl, N-tert-butylcarbamoyl, N-pentylcarbamoyl, N-hexylcarbamoyl, N,N-dimethylcarbamoyl, N,N-diethylcarbamoyl, N,N-dipropylcarbamoyl, N-isopropyl-N-methylcarbamoyl, N-ethyl-N-methylcarbamoyl, N-methyl-N-pentyl-carbamoyl, N-propyl-N-pentylcarbamoyl, N,N-dipentylcarbamoyl, N-ethyl-N-hexylcarbamoyl, N-hexyl-N-pentylcarbamoyl, N,N-dihexylcarbamoyl and the like.

Examples of lower alkoxy-lower alkyl groups are alkoxyalkyl groups in which the alkoxy moiety and alkyl moiety each have 1 to 6 carbon atoms, such as methoxymethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl, 2-pentyloxyethyl, 2-hexyloxyethyl and the like.

Examples of lower alkanoyloxy-lower alkoxycarbonyl groups are alkanoyloxy-alkoxycarbonyl groups in which the alkanoyl moiety and alkoxy moiety each have 1 to 6 carbon atoms, such as acetyloxymethoxycarbonyl, 4-(formyloxy)butoxycarbonyl, 6-(propionyloxy)hexyloxycarbonyl, 5-(isobutyryloxy)pentyloxycarbonyl, 6-(hexanoyloxy)hexyloxycarbonyl, 2-(hexanoyloxy)ethoxycarbonyl, 2-(acetyloxy)ethoxycarbonyl, acetyloxymethoxycarbonyl and the like.

Examples of benzoyl groups substituted with lower alkylenedioxy or lower alkoxy group on the phenyl ring are $C_1$-$C_4$ alkylenedioxybenzoyl groups such as 3,4-methylenedioxybenzoyl, 3,4-ethylenedioxybenzoyl, 2,3-methylenedioxybenzoyl and the like, and 2-methoxybenzoyl, 3-methoxybenzoyl, 4-methoxybenzoyl, 4-ethoxybenzoyl, 2-propoxybenzoyl, 3-propoxybenzoyl, 4-propoxybenzoyl, and the like.

Examples of lower alkanoyloxy groups are $C_1$-$C_6$ straight or branched chains alkanoyloxy groups such as formyloxy, acetyloxy, propionyloxy, butyryloxy, isobutyryloxy, pentanoyloxy, hexanoyloxy and the like.

Examples of phenoxycarbonyloxy groups substituted with lower alkoxy group on the phenyl ring are 2-methoxyphenoxycarbonyloxy, 3-methoxyphenoxycarbonyloxy, 4-methoxyphenoxycarbonyloxy, 4-ethoxyphenoxycarbonyloxy, 2-propoxyphenoxycarbonyloxy, 3-propoxyphenoxycarbonyloxy, 4-propoxyphenoxycarbonyloxy and the like.

Examples of phenyl-lower alkyl groups which constitute phenyl-lower alkoxy groups optionally having 1 to 3 substituents selected from the group consisting of lower alkyl, lower alkoxy and halogen on the phenyl ring are phenylalkyl groups in which phenyl group optionally substituted with one to three of the above substituents is linked with $C_1$-$C_6$ alkylene group, such as benzyl, 2-methylbenzyl, 3-methylbenzyl, 4-methylbenzyl, 2-ethylbenzyl, 3-ethylbenzyl, 4-ethylbenzyl, 2-propylbenzyl, 3-propylbenzyl, 4-propylbenzyl, 2-butylbenzyl, 3-butylbenzyl, 4-butylbenzyl, 2-tert-butylbenzyl, 3-tert-butylbenzyl, 4-tert-butylbenzyl, 2-pentylbenzyl, 3-pentylbenzyl, 4-pentylbenzyl, 2-hexylbenzyl, 3-hexylbenzyl, 4-hexylbenzyl, 2,3-dimethylbenzyl, 2,4-dimethylbenzyl, 2,5-dimethylbenzyl, 2,6-dimethylbenzyl, 3,4-dimethylbenzyl, 3,5-dimethylbenzyl, 2,3,4-trimethylbenzyl, 2,4,5-trimethylbenzyl, 2,3,5-trimethylbenzyl, 2,4,6-trimethylbenzyl, 3,4,5-trimethylbenzyl, 2,3-diethylbenzyl, 2,4-diethylbenzyl, 2,5-diethylbenzyl, 2,6-diethylbenzyl, 2,4,6-triethylbenzyl, 2,4-dipropylbenzyl, 3,4,5-triethylbenzyl, 3-methyl-4-ethylbenzyl, 1-phenylethyl, 2-phenylethyl, 2-phenyl-1-methyl-ethyl, 1-(2-methylphenyl)ethyl, 2-(2-methylphenyl)ethyl, 2-(3-methylphenyl)ethyl, 2-(4-methylphenyl)ethyl, 1-(2,4-dimethylphenyl)ethyl, 2-(2,4-dimethylphenyl)ethyl, 1-(2,4,6-trimethylphenyl)ethyl, 2-(2,4,6-trimethylphenyl)ethyl, 3-phenylpropyl, 3-(4-methylphenyl)propyl, 4-phenylbutyl, 4-(2-methylphenyl)butyl, 5-phenylpentyl, 5-(3-methylphenyl)pentyl, 6-phenylhexyl, 6-(4-methylphenyl)hexyl, 2-methoxybenzyl, 3-methoxybenzyl, 4-methoxybenzyl, 2,3-dimethoxybenzyl, 2,4-dimethoxybenzyl, 2,5-dimethoxybenzyl, 3-methoxy-4-ethoxybenzyl, 2,6-dimethoxybenzyl, 3,4-dimethoxybenzyl, 3,5-dimethoxybenzyl, 2,3,4-trimethoxybenzyl, 2,4,5-trimethoxybenzyl, 2,3,5-trimethoxybenzyl, 2,4,6-trimethoxybenzyl, 3,4,5-trimethoxybenzyl, 2-ethoxybenzyl, 4-propoxybenzyl, 3-butoxybenzyl, 2-tert-butoxybenzyl, 3-pentyloxybenzyl, 4-hexyloxybenzyl, 2,3-diethoxybenzyl, 1-(4-methoxyphenyl)ethyl, 2-(3,4-dimethoxyphenyl)ethyl, 3-(4-methoxyphenyl)propyl, 4-(2-methoxyphenyl)butyl, 5-(4-methoxyphenyl)pentyl, 6-(4-methoxyphenyl)hexyl, 6-(3,4,5-tripentyloxyphenyl)hexyl, 2-fluorobenzyl, 3-fluorobenzyl, 4-fluorobenzyl, 2,3-difluorobenzyl, 2,4-difluorobenzyl, 2,5-difluorobenzyl, 2-fluoro-3-chlorobenzyl, 2-fluoro-3-bromobenzyl, 2,6-difluorobenzyl, 2,3,4-trifluorobenzyl, 2,4,5-trifluorobenzyl, 2,3,5-trifluorobenzyl, 2,4,6-trifluorobenzyl, 3,4,5-trifluorobenzyl, 1-(2-fluorophenyl)ethyl, 2-(2-fluorophenyl)ethyl, 3-(3-fluorophenyl)propyl, 4-(2-fluorophenyl)butyl, 5-(2-fluorophenyl)pentyl, 6-(3-fluorophenyl)hexyl, 2-bromobenzyl, 3-bromobenzyl, 4-bromobenzyl, 2,3-dibromobenzyl, 2-bromo-3-fluorobenzyl, 2-fluoro-4-bromobenzyl, 2,4-dibromobenzyl, 2,5-dibromobenzyl, 2,6-dibromobenzyl, 2,3,4-tribromobenzyl, 2,4,5-tribromobenzyl, 2,3,5-tribromobenzyl, 2,4,6-tribromobenzyl, 3,4,5-tribromobenzyl, 1-(2-bromophenyl)ethyl, 2-(2-bromophenyl)ethyl, 3-(2-bromophenyl)propyl, 4-(3-bromophenyl)butyl, 5-(2-bromophenyl)pentyl, 6-(4-bromophenyl)hexyl, 2-chlorobenzyl, 3-chlorobenzyl, 4-chlorobenzyl, 2,3-dichlorobenzyl, 2,4-dichlorobenzyl, 2,5-dichlorobenzyl, 2,6-dichlorobenzyl, 2-bromo-4-chlorobenzyl, 2-fluoro-4-chlorobenzyl, 2,3,4-trichlorobenzyl, 2,4,5-trichlorobenzyl, 2,3,5-trichlorobenzyl, 2,4,6-trichlorobenzyl, 3,4,5-trichlorobenzyl, 1-(4-chlorophenyl)ethyl, 2-(4-chlorophenyl)ethyl, 3-(2-chlorophenyl)propyl, 4-(4-chlorophenyl)butyl, 5-(3-chlorophenyl)pentyl, 6-(4-chlorophenyl)hexyl, 2-(3,4-dichlorophenyl)ethyl, 2-iodobenzyl, 3-iodobenzyl, 4-iodobenzyl, 3,4-diiodobenzyl, 3,4,5-triiodobenzyl, 2-(3-iodophenyl)ethyl, 6-(2-iodophenyl)hexyl and the like.

Examples of lower alkoxycarbonyl groups are carbonyl groups having $C_1$-$C_6$ alkoxy group such as methoxycarbonyl, ethoxycarbonyl, propoxycarbonyl, isopropoxycarbonyl, tert-butoxycarbonyl, butoxycarbonyl, pentyloxycarbonyl, hexyloxycarbonyl and the like.

Of the compounds of the formula (1b) of the invention, especially preferable are those represented by the formula

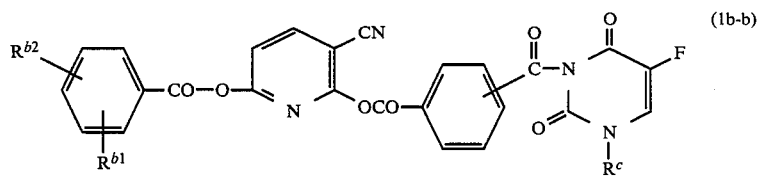

wherein $R^{b1}$ and $R^{b2}$ are the same or different and represent a hydrogen or halogen atom and $R^c$ represents lower alkoxy-lower alkyl.

The compounds of the formula (1b-b) are especially preferable since they can be readily absorbed, can exhibit a sustained effect, are stable, exhibit little or no gastrointestinal toxicity such as diarrhea, emesia or gastrointestinal bleeding, have a wide safety margin (i.e., great difference between the dose at which anticancer activity is exhibited and the dose at which side effects such as toxicity are caused), and have high therapeutic indices.

Representative of the compounds of this invention represented by the formula (1b) are as follows: 5-fluoro-3-[3-(4-pentanoyloxy-2-pyridyloxycarbonyl)benzoyl]-1-(2-tetrahydrofuranyl)uracil, 3-[3-(4-ethoxycarbonyloxy-2-pyridyloxycarbonyl)benzoyl]-5-fluoro-1-(2-tetrahydrofuranyl)uracil, 5-fluoro-3-[3-[2-(2-methylbenzoyloxy)-4-pyridyloxycarbonyl]benzoyl]-1-(2-tetrahydrofuranyl)uracil, 3-[3-(2-benzoyloxy-4-pyridyloxycarbonyl)benzoyl]-5-fluoro-1-(2-tetrahydrofuranyl)uracil, 5-fluoro-3-[3-[4-(2-naphthoyloxy)-2-pyridyloxycarbonyl]benzoyl]-1-(2-tetrahydrofuranyl)uracil, 5-fluoro-3-[3-(4-phenylacetyloxy-2-pyridyloxycarbonyl)benzoyl]-1-(2-tetrahydrofuranyl)uracil, 3-[3-(1,2-dihydro-2-oxo-4-pyridyloxycarbonyl)benzoyl]-5-fluoro-1-(2-tetrahydrofuranyl)uracil, 3-[3-(1-ethoxymethyl-1,2-dihydro-2-oxo-4-pyridyloxycarbonyl)benzoyl]-5-fluoro-1-(2-tetrahydrofuranyl)uracil, 3-[3-(1-N-ethylcarbamoyl-1,2-dihydro-2-oxo-4-pyridyloxycarbonyl)benzoyl]-5-fluoro-1-(2-tetrahydrofuranyl)uracil, 5-fluoro-3-[4-[4-(3-pyridylcarbonyloxy)-2-pyridyloxycarbonyl]benzoyl]-1-(2-tetrahydrofuranyl)uracil, 5-fluoro-3-[3-[4-(2-tethenoyloxy)-2-pyridyloxycarbonyl]benzoyl]-1-(2-tetrahydrofuranyl)uracil, 3-[3-[4-(2-furoyloxy)-2-pyridyloxycarbonyl]benzoyl]-5-fluoro-1-(2-tetrahydrofuranyl)uracil, 3-[3-(4-benzoyloxy-5-bromo-2-pyridyloxycarbonyl)benzoyl]-5-fluoro-1-(2-tetrahydrofuranyl)uracil, 3-[3-(4-benzoyloxy-5-cyano-2-pyridyloxycarbonyl)benzoyl]-5-fluoro-1-(2-tetrahydrofuranyl)uracil, 3-[3-(4-benzoyloxy-5-nitro-2-pyridyloxycarbonyl)benzoyl]-5-fluoro-1-(2-tetrahydrofuranyl)uracil, 3-[3-(4-acetoxy-5-chloro-2-pyridyloxycarbonyl)benzoyl]-5-fluoro-1-(2-tetrahydrofuranyl)uracil, 3-[3-(2-acetoxy-5-chloro-4-pyridyloxycarbonyl)benzoyl]-5-fluoro-1-(2-tetrahydrofuranyl)uracil, 3-[3-(4-benzoyloxy-5-chloro-2-pyridyloxycrbonyl)benzoyl]-5-fluoro-1-(2-tetrahydrofuranyl)uracil, 3-[3-(2-benzoyloxy-5-chloro-4-pyridyloxycarbonyl)benzoyl]-5-fluoro-1-(2-tetrahydrofuranyl)uracil, 3-[3-[4-(2-chloro-3-methylbenzoyloxy)-2-pyridyloxycarbonyl)benzoyl]-5-fluoro-1-(2-tetrahydrofuranyl)uracil, 5-fluoro-3-[3-[4-(4-methoxybenzoyloxy)-5-chloro-2-pyridyloxycarbonyl]benzoyl]-1-(2-tetrahydrofuranyl)uracil, 5-fluoro-3-[3-[4-phenolcarbonyloxy-5-chloro-2-pyridyloxycarbonyl]benzoyl]-1-(2-tetrahydrofuranyl)uracil, 5-fluoro-3-[3-[4-(3,4,5-trimethoxybenzoyloxy)-5-chloro-2-pyridyloxycarbonyl]benzoyl]-1-(2-tetrahydrofuranyl)uracil, 3-[3-[5-chloro-4-(4-dimethylaminobenzoyloxy)-2-pyridyloxycarbonyl]benzoyl]-5-fluoro-1-(2-tetrahydrofuranyl)uracil, 3-[3-(5-chloro-4-octadecanoyloxy-2-pyridyloxycarbonyl)benzoyl]-5-fluoro-1-(2-tetrahydrofuranyl)uracil, 3-[3-(1-benzyloxymethyl-5-chloro-1,2-dihydro-2-oxo-4-pyridyloxycarbonyl)benzoyl]-5-fluoro-1-(2-tetrahydrofuranyl)uracil, 3-[3-[5-chloro-1,2-dihydro-2-oxo-1-(2-tetrahydrofuranyl)-4-pyridyloxycarbonyl)benzoyl]-5-fluoro-1-(2-tetrahydrofuranyl)uracil, 3-[3-(1-ethoxymethyl-1,2-dihydro-2-oxo-4-pyridyloxycarbonyl)benzoyl]-5-fluoro-1-(2-tetrahydrofuranyl)uracil, 3-[3-(5-chloro-4-hydroxy-2-pyridyloxycarbonyl)benzoyl]-5-fluoro-1-(2-tetrahydrofuranyl)uracil, 3-[3-(1,2-dihydro-2-oxo-6-pyridyloxycarbonyl)benzoyl]-5-fluoro-1-(2-tetrahydrofuranyl)uracil, 3-[3-[3-chloro-6-(4-fluorobenzoyloxy)-2-pyridyloxycarbonyl]benzoyl]-5-fluoro-1-(2-tetrahydrofuranyl)uracil, 3-[3-[3-carbamoyl-6-(4-methoxybenzoyloxy)-2-pyridyloxycarbonyl]benzoyl]-5-fluoro-1-(2-tetrahydrofuranyl)uracil, 3-[3-(4-amino-3-cyano-6-benzoyloxy-2-pyridyloxycarbonyl)benzoyl]-5-fluoro-1-(2-tetrahydrofuranyl)uracil, 3-[3-(6-benzoyloxy-3-cyano-2-pyridyloxycarbonyl)benzoyl]-5-fluoro-1-(2-tetrahydrofuranyl)uracil, 3-[3-[3-cyano-6-(3,4,5-trimethoxybenzoyloxy)-2-pyridyloxycarbonyl]benzoyl]-5-fluoro-1-(2-tetrahydrofuranyl)uracil, 3-[3-(3-cyano-6-nicotinoyloxy-2-pyridyloxycarbonyl)benzoyl]-5-fluoro-1-(2-tetrahydrofuranyl)uracil, 3-[3-[3-cyano-6-(2-furoyloxy)-2-pyridyloxycarbonyl]benzoyl]-5-fluoro-1-(2-tetrahydrofuranyl)uracil, 3-[3-[3-cyano-6-(2-thenoyloxy)-2-pyridyloxycarbonyl]benzoyl]-5-fluoro-1-(2-tetrahydrofuranyl)uracil, 3-[3-[3-cyano-6-(2,4-dichlorobenzoyloxy)-2-pyridyloxycarbonyl]benzoyl]-5-fluoro-1-(2-tetrahydrofuranyl)uracil, 3-[3-(3-cyano-6-acetoxy-2-pyridyloxycarbonyl)benzoyl]-5-fluoro-1-(2-tetrahydrofuranyl)uracil, 3-[3-[3-cyano-6-octadecanoyloxy)-2-pyridyloxycarbonyl]benzoyl]-5-fluoro-1-(2-tetrahydrofuranyl)uracil, 3-[3-(6-benzoyloxy-3-cyano-2-pyridyloxycarbonyl)benzoyl]-5-fluoro-1-(N-hexylcarbamoyl)uracil, 3-[3-[3-cyano-6-(2-furoyloxy)-2-pyridyloxycarbonyl]benzoyl]-5-fluoro-1-(N-hexylcarbamoyl)uracil, 3-[3-(4-acetoxy-5-chloro-2-pyridyloxycarbonyl)benzoyl]-5-fluoro-1-(N-hexylcarbamoyl)uracil, 3-[3-(4-benzoyloxy-5-chloro-2-pyridyloxycarbonyl)benzoyl]-5-fluoro-1-(N-hexylcarbamoyl)uracil, 3-[3-(2-benzoyloxy-5-chloro-4-pyridyloxycarbonyl)benzoyl]-5-fluoro-1-(N-hexylcarbamoyl)uracil, 3-[3-(5-chloro-4-hydroxy-2-pyridyloxycarbonyl)benzoyl]-5-fluoro-1-(N-hexylcarbamoyl)uracil, 3-[3-[3-chloro-6-(4-fluorobenzoyloxy)-2-pyridyloxycarbonyl]benzoyl]-5-fluoro-1-(3-phthalidyl)uracil, 3-[3-(4-amino-6-benzoyloxy-3-cyano-2-pyridyloxycarbonyl)benzoyl]-5-fluoro-1-(3-phthalidyl)uracil, 3-[3-(6-benzoyloxy-3-cyano-2-pyridyloxycarbonyl)benzoyl]-5-fluoro-1-(3-phthalidyl)uracil, 3-[3-[3-cyano-6-(3,4,5-trimethoxybenzoyloxy)-2-pyridyloxycarbonyl]benzoyl]-5-fluoro-1-(3-phthalidyl)uracil, 3-[3-[3-cyano-6-(2,4-dichlorobenzoyloxy)-2-pyridyloxycarbonyl]benzoyl]-5-fluoro-1-(3-phthalidyl)uracil, 3-[3-(4-acetoxy-5-chloro-2-pyridyloxycarbonyl)benzoyl]-5-fluoro-1-(3-phthalidyl)uracil, 3-[3-(4-benzoyloxy-5-chloro-2-pyridyloxycarbonyl)benzoyl]-5-fluoro-1-(3-phthalidyl)uracil, 3-[3-(2-benzoyloxy-5-chloro-4-pyridyloxycarbonyl)benzoyl]-5-fluoro-1-(3-phthalidyl)uracil, 3-[3-[5-chloro-1,2-dihydro-2-oxo-1-(2-tetrahydrofuranyl)-4-pyridyloxycarbonyl]benzoyl]-5-fluoro-1-(3-phthalidyl)uracil, 1-acetoxymethoxycarbonyl-3-[3-[3-carbamoyl-6-(4-methoxybenzoyloxy)-2-pyridyloxycarbonyl]benzoyl]-5-fluorouracil, 1-acetoxymethoxycarbonyl-3-[3-(6-benzoyloxy-3-cyano-2-pyridyloxycarbonyl)benzoyl]-5-fluorouracil 1-acetoxymethoxycarbonyl-3-[3-(3-cyano-6-nicotinoyloxy-2-pyridyloxycarbonyl)benzoyl]-5-fluorouracil, 1-acetoxymethoxycarbonyl-3-[3-(3-cyano-6-(2-thenoyloxy)-2-pyridyloxycarbonyl]benzoyl]-5-fluorouracil, 1-acetoxymethoxycarbonyl-3-[3-(4-benzoyloxy-5-chloro-2-pyridyloxycarbonyl)benzoyl]-5-fluorouracil, 1-acetoxymethoxycarbonyl-3-[3-(2-benzoyloxy-5-chloro-4-pyridyloxycarbonyl)benzoyl]-5-fluorouracil, 1-acetoxymethoxycarbonyl-3-[3-[5-chloro-4-(3,4,5-trimethoxybenzoyloxy)-2-pyridyloxycarbonyl]benzoyl]-5-fluorouracil, 3-[3-[3-chloro-6-(4-fluorobenzoyloxy)-2-pyridyloxycarbonyl]benzoyl]-5,6-dihydro-5-ethoxycarbonyl-5-fluoro-6-furfurylideneaminooxyuracil, 3-[3-(6-benzoyloxy-3-cyano-2-pyridyloxycarbonyl)benzoyl]-5,6-dihydro-5-ethoxycarbonyl-5-fluoro-6-furfurylideneaminooxyuracil, 3-[3-[3-cyano-6-(3,4,5-trimethoxybenzoyloxy)-2-pyridyloxycarbonyl]benzoyl]-5,6-dihydro-5-ethoxycarbonyl-5-fluoro-6-furfurylideneaminooxyuracil, 3-[3-(6-acetoxy-3-cyano-2-pyridyloxycarbonyl)benzoyl]-5,6-dihydro-5-ethoxycarbonyl-5-fluoro-6-furfurylideneaminooxyuracil, 3-[3-(3-cyano-6-octadecanoyloxy-2-pyridyloxycarbonyl)benzoyl]-5,6-dihydro-5-ethoxycarbonyl-5-fluoro-6-furfurylideneaminooxyuracil, 3-[3-(4-acetoxy-5-chloro-2-pyridyloxycarbonyl)benzoyl]-5,6-dihydro-5-ethoxycarbonyl-5-fluoro-6-furfurylideneaminooxyuracil, 3-[3-(4-benzoyloxy-5-chloro-2-pyridyloxycarbonyl)benzoyl]-

5,6-dihydro-5-ethoxycarbonyl-5-fluoro-6-furfurylideneaminooxyuracil, 3-[3-(2-benzoyloxy-5-chloro-4-pyridyloxycarbonyl)benzoyl]-5,6-dihydro-5-ethoxycarbonyl-5-fluoro-6-furfurylideneaminooxycuracil, 3-[3-(4-acetoxy-5-chloro-2-pyridyloxycarbonyl)benzoyl]-1-ethoxymethyl-5-fluorouracil, 3-[3-(4-benzoyloxy-5-chloro-2-pyridyloxycarbonyl)benzoyl]-1-ethoxymethyl-5-fluorouracil, 3-[3-(2-benzoyloxy-5-chloro-4-pyridyloxycarbonyl)benzoyl]-1-ethoxymethyl-5-flurouracil, 3-[3-[4-(2-chloro-3-methylbenzoyloxy)-2-pyridyloxycarbonyl]benzoyl]-1-ethoxymethyl-5-fluorouracil, 3-[3-[5-chloro-4-(3,4,5-trimethoxybenzoyloxy)-2-pyridyloxycarbonyl]benzoyl]-1-ethoxymethyl-5-fluorouracil, 3-[3-(4-benzoyloxy-5-chloro-2-pyridyloxycarbonyl)benzoyl]-5-fluorouracil, 3-[3-(2-benzoyloxy-5-chloro-4-pyridyloxycarbonyl)benzoyl]-5-fluorouracil, 3-[3-(1,2-dihydro-2-oxo-6-pyridyloxycarbonyl)benzoyl]-5-fluorouracil, 3-[3-[3-carbamoyl-6-(4-methoxybenzoyloxy)-2-pyridyloxycarbonyl]benzoyl]-5'-deoxy-2',3'-di-O-acetyl-5-fluorouridine, 3-[3-(6-benzoyloxy-3-cyano-2-pyridyloxycarbonyl)benzoyl]-5'-deoxy-2',3'-di-O-acetyl-5-fluorouridine, 3-[3-[3-cyano-6-(2-furoyloxy)-2-pyridyloxycarbonyl]benzoyl]-5'-deoxy-2',3'-di-O-acetyl-5-fluorouridine, 3-[3-(4-acetoxy-5-chloro-2-pyridyloxycarbonyl)benzoyl]-5'-deoxy-2',3'-di-O-acetyl-5-fluorouridine, 3-[3-(2-acetoxy-5-chloro-4-pyridyloxycarbonyl)benzoyl]-5'-deoxy-2',3'-di-O-acetyl-5-fluorouridine, 3-[3-(4-benzoyloxy-5-chloro-2-pyridyloxycarbonyl)benzoyl]-5'-deoxy-2',3'-di-O-acetyl-5-fluorouridine, 3-[3-(2-benzoyloxy-5-chloro-4-pyridyloxycarbonyl)benzoyl]-5'-deoxy-2',3'-di-O-acetyl-5-fluorouridine, 3-[3-[5-chloro-4-(4-methoxybenzoyloxy)-2-pyridyloxycarbonyl]benzoyl]-5'-deoxy-2',3'-di-O-acetyl-5-fluorouridine, 3-[3-(4-benzoyloxy-5-chloro-2-pyridyloxycarbonyl)benzoyl]-2'-deoxy-3',5'-di-O-benzyl-5-fluorouridine, 3-[3-(4-benzoyloxy-5-chloro-2-pyridyloxycarbonyl)benzoyl]-2'-deoxy-3',5'-di-O-(4-chlorobenzyl)-5-fluorouridine, 3-[3-(2-benzoyloxy-5-chloro-4-pyridyloxycarbonyl)benzoyl]-2'-deoxy-3',5'-di-O-benzyl-5-fluorouridine, 3-[3-(2-benzoyloxy-5-chloro-4-pyridyloxycarbonyl)benzoyl]-2'-deoxy-3',5'-di-O-(4-chlorobenzyl)-5-fluorouridine, 3-[3-(4-benzoyloxy-5-chloro-2-pyridyloxycarbonyl)benzoyl]-5-fluoro-2',3',5'-tri-O-acetyluridine, 3-[3-(2-benzoyloxy-5-chloro-4-pyridyloxycarbonyl)benzoyl]-5-fluoro-2',3',5'-tri-O-acetyluridine, 3-[3-[5-chloro-1,2-dihydro-2-oxo-1-(2-tetrahydrofuranyl)-4-pyridyloxycarbonyl]benzoyl]-5-fluoro-2',3',5'-tri-O-acetyluridine, 3-[3-(4-acetoxy-5-chloro-2-pyridyloxycarbonyl)benzoyl]-2'-deoxy-3',5'-di-O-acetyl-5-fluorouridine, 3-[3-(4-benzoyloxy-5-chloro-2-pyridyloxycarbonyl)benzoyl]-2'-deoxy-3',5'-di-O-acetyl-5-fluorouridine, 3-[3-(2-benzoyloxy-5-chloro-4-pyridyloxycarbonyl)benzoyl]-2'-deoxy-3',5'-di-O-acetyl-5-fluorouridine, 3-[3-[5-chloro-4-(4-methoxybenzoyloxy)-2-pyridyloxycarbonyl]benzoyl]-2'-deoxy-3',5'-di-O-acetyl-5-fluorouridine, 3-[3-(5-chloro-4-hydroxy-2-pyridyloxycarbonyl)benzoyl]-2'-deoxy-3',5'-di-O-acetyl-5-fluorouridine, 3-[3-(4-benzoyloxy-5-chloro-2-pyridyloxycarbonyl)benzoyl]-5-fluorouracil, 3-[3-(2-benzoyloxy-5-chloro-4-pyridyloxycarbonyl)benzoyl]-5-fluorouracil, 3-[3-(1,2-dihydro-2-oxo-6-pyridyloxycarbonyl)benzoyl]-5-fluorouracil, 1-[3-(4-benzoyloxy-5-chloro-2-pyridyloxycarbonyl)benzoyl]-5-fluorouracil, 1-[3-(6-benzoyloxy-3-cyano-2-pyridyloxycarbonyl)benzoyl]-5-fluorouracil, 3-[4-(1,2-dihydro-2-oxo-4-pyridyloxycarbonyl)benzoyl]-5-fluoro-1-(2-tetrahydrofuranyl)uracil, 3-[4-(6-benzoyloxy-3-cyano-2-pyridyloxycarbonyl)benzoyl]-5-fluoro-1-(2-tetrahydrofuranyl)uracil, 3-[4-(2-benzoyloxy-5-chloro-4-pyridyloxycarbonyl)benzoyl]-5-fluoro-1-(3-phthalidyl)uracil, 3-[4-(4-acetoxy-5-chloro-2-pyridyloxycarbonyl)benzoyl]-5-fluoro-1-(3-phthalidyl)uracil, 3-[4-(4-benzoyloxy-5-chloro-2-pyridyloxycarbonyl)benzoyl]-5-fluoro-2',3',5'-tri-O-acetyluridine, 3-[4-(6-benzoyloxy-3-cyano-2-pyridyloxycarbonyl)-3-furoyl]-5-fluoro-1-(2-tetrahydrofuranyl)uracil, 3-[4-(6-benzoyloxy-3-cyano-2-pyridyloxycarbonyl)-3-furoyl]-2'-deoxy-3',5'-di-O-acetyl-5-fluorouridine, 3-[4-(4-benzoyloxy-5-chloro-2-pyridyloxycarbonyl)-3-furoyl]-5-fluoro-2',3',5'-tri-O-acetyluridine, 3-[4-(2-benzoyloxy-5-chloro-4-pyridyloxycarbonyl)-3-furoyl]-5-fluoro-1-(2-tetrahydrofuranyl)uracil, 3-[4-(4-acetoxy-5-chloro-2-pyridyloxycarbonyl)-3-furoyl]-5-fluoro-2',3',5'-tri-O-acetyluridine, 3-[5-(6-benzoyloxy-3-cyano-2-pyridyloxycarbonyl)-3-nicotinoyl]-5-fluoro-1-(2-tetrahydrofuranyl)uracil, 3-[5-(6-benzoyloxy-3-cyano-2-pyridyloxycarbonyl)-3-nicotinoyl]-5'-deoxy-2',3'-di-O-acetyl-5-fluorouridine, 1-[5-(6-benzoyloxy-3-cyano-2-pyridyloxycarbonyl)-3-nicotinoyl]-5-fluorouracil, 3-[5-(4-benzoyloxy-5-chloro-2-pyridyloxycarbonyl)-3-nicotinoyl]-5'-deoxy-2',3'-di-O-acetyl-5-fluorouridine, 3-[5-(2-benzoyloxy-5-chloro-4-pyridyloxycarbonyl)-3-nicotinoyl]-5-fluoro-1-(2-tetrahydrofuranyl)uracil, 3-[4-(6-benzoyloxy-3-cyano-2-pyridyloxycarbonyl)-2-naphthoyl]-5-fluoro-1-(2-tetrahydrofuranyl)uracil, 3-[4-(2-benzoyloxy-5-chloro-4-pyridyloxycarbonyl)-2-naphthoyl]-1-ethoxymethyl-5-fluorouracil, 1-[3-(4-acetoxy-5-chloro-2-pyridyloxycarbonyl)-1-naphthoyl]-5-fluorouracil, 3-[6-(6-benzoyloxy-3-cyano-2-pyridyloxycarbonyl)-1-methyl-4-pyridone-2-ylcarbonyl]-5-fluorouracil, 3-[6-(1-benzyloxymethyl-5-chloro-1,2-dihydro-2-oxo-4-pyridyloxycarbonyl)-1-methyl-4-pyridone-2-ylcarbonyl]-5-fluoro-1-(2-tetrahydrofuranyl)uracil, 3-[6-(2-benzoyloxy-4-pyridyloxycarbonyl)pyrazine-2-ylcarbonyl]-2'-deoxy-3',5'-di-O-acetyl-5-fluorouridine, 3-[3-(3-cyano-6-benzoyloxy-4-pyridyloxycarbonyl)benzoyl]-1-ethoxymethyl-5-fluorouracil, 3-[3-[3-cyano-6-(2,4,6-trichlorobenzoyloxy)-2-pyridyloxycarbonyl]benzoyl]-1-ethoxymethyl-5-fluorouracil, 3-[3-[3-cyano-6-benzoyloxy-2-pyridyloxycarbonyl]benzoyl]-1-methoxymethyl-5-fluorouracil, 3-[3-(3-cyano-6-benzoyloxy-4-pyridyloxycarbonyl)benzoyl]-1-methoxymethyl-5-fluorouracil, 3-[3-(3-cyano-6-benzoyloxy-2-pyridyloxycarbonyl)benzoyl]-1-ethoxymethyl-5-fluorouracil, 3-[3-[3-cyano-6-(4-chlorobenzoyloxy)-2-pyridyloxycarbonyl]benzoyl]-1-ethoxymethyl-5-fluorouracil, 3-[3-[3-cyano-6-(2,4-dichlorobenzoyloxy)-2-pyridyloxycarbonyl]benzoyl]-1-ethoxymethyl-5-fluorouracil, 3-[4-(3-cyano-6-benzoyloxy-2-pyridyloxycarbonyl)benzoyl]-1-ethoxymethyl-5-fluorouracil, 3-[4-(3-cyano-6-furoyloxy-2-pyridyloxycarbonyl)-3-furoyl]-1-(2-tetrahydrofuranyl)-5-fluorouracil, 3-[4-(4-acetoxy-5-chloro-2-pyridyloxycarbonyl)-3-furoyl]-1-(2-tetrahydrofuranyl)-5-fluorouracil, 3-[4-(3-cyano-6-thenoyloxy-2-pyridyloxycarbonyl)-3-furoyl]-1-(2-tetrahydrofuranyl)-5-fluorouracil, 3-[3-(5-cyano-6-hydroxy-2-pyridyloxycarbonyl)benzoyl]-1-ethoxymethyl-5-fluorouracil.

The compounds of the invention having the substituent of the formula (Y) include keto-enol tautomers. This invention includes these tautomers.

The compounds of the present invention can be prepared by the processes represented by the following reaction schemes (a) to (d).

Reaction scheme (a)

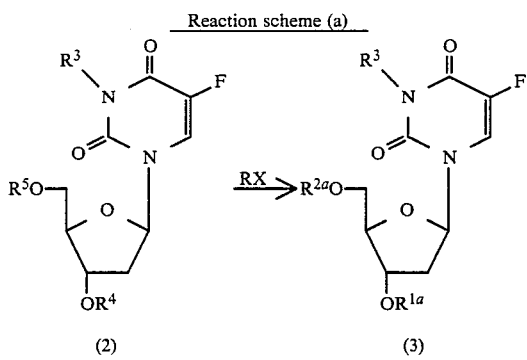

(2)     (3)

wherein $R^3$ is as defined above, one of $R^4$ and $R^5$ is a hydrogen atom and the other is a hydrogen atom, acyl or protective group, R is phenyl-lower alkyl which may have substituent selected from the group consisting of lower alkyl, lower alkoxy, halogen atom, carboxyl, lower alkoxycarbonyl and di(lower alkyl)amino group on the phenyl ring, phenyl-lower alkyl having lower alkylenedioxy or phenyl as the substituent, phenyl-lower alkenyl or naphthyl-lower alkyl, one of $R^{1a}$ and $R^{2a}$ is a hydrogen atom or acyl and the other is the same group as R, and X is a halogen atom.

The protective groups represented by $R^4$ or $R^5$ include the following groups.

(A) Triaryl-substituted methyl groups represented by the formula

    (A)

wherein Ar is aryl. Exemplary of such a group is a methyl group substituted with three aryl groups such as phenyls which may have halogen atom, nitro, lower alkyl or lower alkoxy as the substituent.

(B) Cyclic ether residue groups represented by the formula

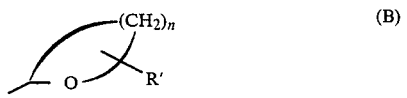    (B)

wherein R' is lower alkyl, and n is 2 or 3. Examples of such groups are 2-tetrahydrofuranyl and 2-tetrahydropyranyl.

(C) Lower alkoxymethyl groups such as methoxymethyl, ethoxymethyl and hexyloxymethyl.

(D) Tri(lower alkyl)silyl groups such as trimethylsilyl and t-butyldimethylsilyl.

The present reaction is conducted by reacting a compound of the formula (2) (hereinafter referred to as "compound (2)") with a phenyl-lower alkyl halide, phenyl-lower alkenyl halide or naphthyl-lower alkyl halide (RX) to substitute the desired group R for the hydrogen atom of the hydroxyl group at the 3'- or 5'-position of the compound (2), followed by a reaction for removing the protective group or acyl when required, to obtain a compound (3).

The reaction for introducing the group R is conducted under the usual reaction conditions for removing a hydrogen halide. The hydrogen halide removing agent to be used can be any of various basic compounds which are generally used for such reactions. Examples of useful compounds are sodium hydroxide, potassium hydroxide, sodium carbonate, potassium carbonate, sodium hydrogencarbonate, potassium hydrogencarbonate, alkali metals such as sodium and potassium, alkali metal hydrides such as sodium hydride and potassium hydride, etc.

The reaction can be conducted in the presence of a solvent or in the absence thereof. Examples of useful solvents are usual inert solvents such as water, ethers such as tetrahydrofuran (THF) and dioxane, aromatic hydrocarbons such as benzene, toluene, xylene and chlorobenzene, ketones such as acetone and methyl ethyl ketone, nitriles such as acetonitrile and propionitrile, etc.

While the ratio of the compound (2) to the phenyl-lower alkyl halide, phenyl-lower alkenyl halide or naphthyl-lower alkyl halide is not limited specifically but is widely variable, usually at least about 1 mole, preferably 1 to 5 moles, of the latter is used per mole of the former. The reaction temperature is not limited specifically either but is widely variable. It is, however, usually 0° to 100° C., preferably room temperature to 80° C. The reaction is carried usually for about 30 minutes to about 64 hours, preferably about 1 to about 5 hours.

When the compound obtained by the above reaction has a protective group at the 3'- or 5'-position, the desired compound (3) can be obtained by subsequently subjecting the product to a reaction for removing the protective group. This reaction is carried out usually in a solvent, using a suitable amount of a catalyst which is commonly used for acid hydrolysis reactions. Examples of suitable catalysts are inorganic acids such as hydrochloric acid, sulfuric acid and perchloric acid, and organic acids including lower alkanoic acids such as formic acid, acetic acid and propionic acid, benzoic acid, organosulfonic acids such as methanesulfonic acid, ethanesulfonic acid, benzenesulfonic acid and 4-methylbenzenesulfonic acid. Examples of useful solvents are usual inert solvents including water, lower alcohols such as methanol, ethanol and isopropanol, ketones such as acetone and methyl ethyl ketone, ethers such as diethyl ether, THF and dioxane, aromatic hydrocarbons such as benzene, toluene, xylene and chlorobenzene, lower alkanoic acids such as acetic acid and propionic acid, and mixtures of such solvents. The reaction temperature is not limited specifically but is suitably determined from a wide range. Usually it is 0° to 100° C., preferably room temperature to about 80° C. The reaction takes about 3 minutes to about 20 hours. The acid is usually used in a catalytic amount to an excessive amount, preferably in an excessive amount.

When the compound (3) prepared by the process of the scheme (a) has acyl at least at one of the 3-, 3'- and 5'-positions, the compound is subjected to a hydrolysis reaction, whereby one or all of the acyl groups can be converted to hydrogen. The hydrolysis reaction is carried out under the usual conditions for acid or alkali hydrolysis. The catalyst to be used for this reaction can be any one of those which are commonly used for acid or alkali hydrolysis. Typical of these catalysts are basic compounds such as sodium hydroxide, potassium hydroxide and barium hydroxide, and inorganic acids such as hydrochloric acid, sulfuric acid and nitric acid. The amount of catalyst to be used is not limited specifically but is suitably variable over a wide range. Generally, the reaction proceeds advantageously in a solvent. A wide variety of usual inert solvents are usable for this purpose. Examples of useful solvents are water, lower alcohols such as ethanol, methanol and isopropanol, ketones such as acetone and methyl ethyl ketone, and mixtures of such solvents. The reaction temperature is not limited specifically but is suitably determined from a wide range. It is usually 0° to 100° C., preferably room temperature to about 80° C. The reaction takes about 30 minutes to about 10 hours.

Reaction scheme (b)

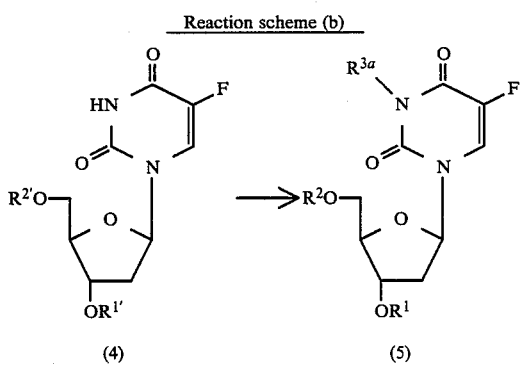

wherein one of $R^{1'}$ and $R^{2'}$ is the same as the group R defined above, the other is a hydrogen atom, acyl or a protective group, $R^{3a}$ is acyl, and $R^1$ and $R^2$ are as defined above.

The present reaction, wherein acyl is introduced into the 3-position of the pyrimidine moiety (acylation), can be conducted by a usual process, e.g., the acid halide process. With the acid halide process, an acyl halide ($R^{3a}X$) is caused to act on the compound (4) in a suitable solvent in the presence of an acid scavenger to give the desired compound (5). Examples of useful acid scavengers are sodium hydrogen carbonate, sodium carbonate, potassium carbonate, pyridine, triethylamine, etc. Examples of useful solvents are benzene, chloroform, methylene chloride, carbon tetrachloride, dioxane, tetrahydrofuran, etc. The acyl halide is used in an amount of at least about one mole, preferably about 1 to about 3 moles, per mole of the compound (4). The reaction temperature is usually −30° to 100° C., preferably room temperature to about 80° C. The reaction takes about 20 minutes to about 20 hours.

When the compound (4) to be reacted has a free hydroxyl group at its 3′- or 5′-position, acylation takes place also at such position simultaneously with acylation at the 3-position. Accordingly, it is desirable to protect the hydroxyl group at the 3′- or 5′-position before acylation and to remove the protective group after the acylation. The reaction for introducing the protective group will be described later. The reaction to remove the protective group can be carried out by the same method as already described for the reaction scheme (a).

Reaction scheme (c)

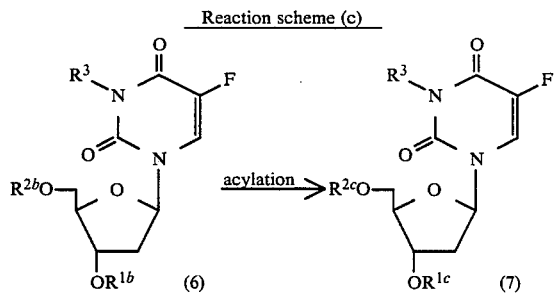

wherein one of $R^{1b}$ and $R^{2b}$ is a hydrogen atom, the other is the same as the group R defined above, one of $R^{1c}$ and $R^{2c}$ is acyl, the other is the same as the group R defined above, and $R^3$ is as defined above.

This reaction acylates the free hydroxyl group at the 3′- or 5′-position of the compound (6) to afford a compound (7). For the acylation reaction, any of usual acylation processes are usable, such as the acid halide process, acid anhydride process, mixed acid anhydride process, N,N-dicyclohexylcarbodiimide process (DCC process), etc., among which the acid anhydride process and acid halide process are advantageous.

The acid anhydride process is conducted by heating the compound (6) with an acid anhydride in a suitable solvent. The acid anhydride to be used is the anhydride of an acid corresponding to the acyl group to be introduced into the 3′- or 5′-position. Examples of such anhydrides are acetic anhydride, propionic anhydride, butyric anhydride, benzoic anhydride, etc. These acid anhydrides are used in an amount of at least one mole, preferably about 1 to about 3 moles, per mole of the compound (6). Examples of useful solvents are various inert solvents including pyridine, hydrocarbon halides such as chloroform and dichloromethane, ethers such as dioxane and THF, aromatic hydrocarbons such as benzene and toluene, dimethylformamide (DMF), dimethyl sulfoxide (DMSO), acetonitrile, etc. The reaction temperature is usually about −30° C. to about 100° C., preferably room temperature to about 80° C. The reaction takes about 20 minutes to about 20 hours. The reaction can be carried out advantageously in the presence of a basic compound. Examples of useful basic compounds are organic bases such as pyridine, triethylamine, N,N-dimethylaniline and like tertiary amines, and inorganic basic compounds such as sodium hydrogencarbonate, potassium carbonate and sodium acetate.

The acid halide process is practiced by causing an acyl halide ($R^{3a}X$) to act on the compound (6) in a suitable solvent in the presence of an acid scavenger, in the same manner as described for the reaction scheme (b).

When the reagent, i.e., the acid halide is used in an amount of at least two moles per mole of the starting compound for the processes of the reaction schemes (b) and (c), the reaction may give an O- and N-acylated compound wherein the 3′- or 5′-position and the 3-position are acylated at the same time, in addition to an O-acylated compound wherein the 3′- or 5′-position is acylated and an N-acylated compound wherein the 3-position is acylated. The O- and N-acylated compound can be easily separated from the O-acylated compound or N-acylated compound.

Reaction scheme (d)

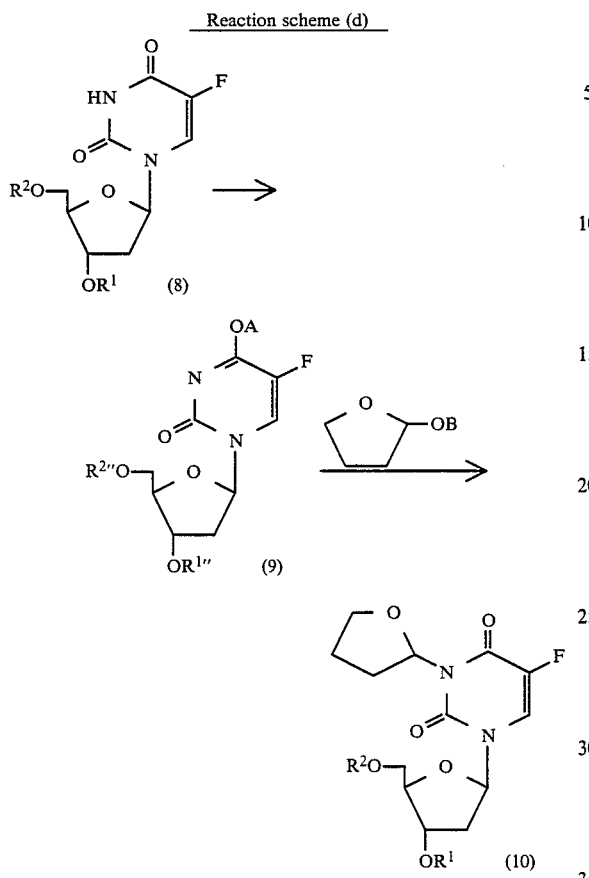

compound (10) is obtained. This reaction is carried out in the same manner as the reaction already stated for the reaction scheme (a) for the removal of the protective group.

In this way, the compound of the present invention is obtained. The compound is isolated and purified easily by a usual method, such as reprecipitation, recrystallization, silica gel chromatography, ion exchange chromatography, gel chromatography, affinity chromatography or the like.

The starting materials to be used for the processes of the reaction schemes (a) to (d) can be prepared, for example, by the processes represented by the following reaction schemes (e) to (g).

Reaction scheme (e)

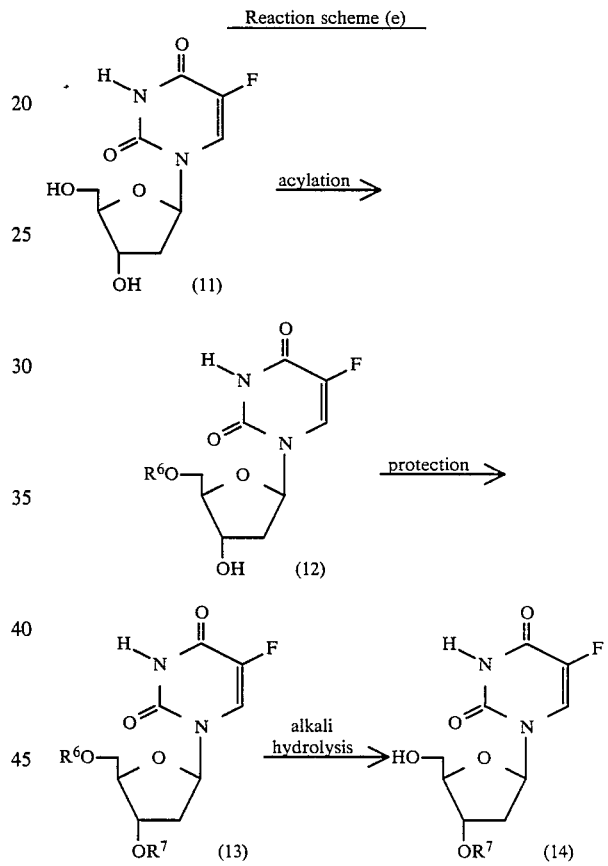

wherein $R^1$ and $R^2$ are as defined above, A is tri(lower alkyl)silyl, B is lower alkanoyl such as $C_1$-$C_6$ alkanoyl, one of $R^{1''}$ and $R^{2''}$ is the same as the group R defined above and the other is the same as the group A or acyl.

According to the above scheme, bis-N,O-tri(lower alkyl)silylacetamide is reacted with a compound (8) (trialkylsilylation) to obtain a compound (9), which is then reacted with 2-lower alkanoyloxytetrahydrofuran (tetrahydrofuranylation) to give a compound (10).

The trialkylsilylation reaction is conducted in a suitable inert solvent at about 0° to about 100° C., preferably at room temperature to 50° C. for 30 minutes to 6 hours. Examples of suitable solvents are ethers such as dioxane and THF, aromatic hydrocarbons such as benzene and toluene, DMF, DMSO, acetonitrile, etc. The bis-N,O-tri(lower alkyl)silylacetamide is used in an amount of at least one equivalent, preferably 1 to 2 equivalents, per functional group to be reacted therewith.

The subsequent tetrahydrofuranylation reaction is carried out in a solvent as exemplified above at about 0° to about 100° C., preferably at room temperature to 50° C. for 30 minutes to 6 hours. 2-Lower alkanoyloxytetrahydrofuran is used in an amount of at least one mole, preferably 1 to 2 moles, per mole of the compound (9). This reaction proceeds advantageously when the reaction system contains a Lewis acid, such as stannic chloride (SnCl$_4$), aluminum chloride or zinc chloride, usually in an amount of at least 0.1 mole based on the compound (9). When the compound (9) used for the tetrahydrofuranylation reaction contains tri(lower alkyl)silyl as $R^{1''}$ or $R^{2''}$, the product is subsequently subjected to a reaction to remove this group, whereby the desired wherein $R^6$ is acyl, and $R^7$ is a protective group.

The acylation of the compound (11) is conducted in the same manner as the acylation of the compound (6) shown in the reaction scheme (c). More preferably, the acylation is conducted by reacting the compound (11) with an acid anhydride, corresponding to the acyl to be introduced into the 5'-position, in an amount of about 1 to about 1.5 moles per mole of the compound (11) at a temperature of about −30° C. to about 80° C. for about 1 to about 6 hours in the same inert solvent as used for the acid anhydride process shown by the scheme (c).

The above reaction gives as the main product a compound (12) wherein the 5'-position is acylated and also as a secondary product a compound wherein the 3'-position is acylated.

The compound (12) resulting from the reaction is then subjected to a reaction to protect the hydroxyl group at the 3'-position. By this reaction, the protective group mentioned with respect to the reaction scheme (a) is introduced into the 3'-position of the compound (12). Useful reagents for introducing the protective group are triaryl-substituted methyl halides for giving a protective group represented by the formula (A), unsaturated cyclic ethers represented by the formula

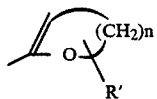
(B')

wherein R' and n are the same as those in the formula (B) for giving a protective group represented by the formula (B), lower alkoxymethyl halides and tri(lower alkyl)silyl halides.

The protective group-introducing reaction wherein such a halide is used is conducted in the same manner as the hydrogen halide removing reaction shown in the reaction scheme (a). However, it is desirable that the reaction is used in an amount of 1 to 2 moles, preferably 1 to 1.5 moles, per mole of the compound (12), and that the reaction temperature is −30° C. to 80° C.

The protective group-introducing reaction wherein an unsaturated cyclic ether of the formula (B') is used is conducted in the presence of an acid catalyst in an aprotic inert solvent such as THF, dioxane or acetonitrile. Examples of useful acid catalysts are hydrohalogenic acids such as hydrogen bromide and hydrogen chloride, and Lewis acids such as aluminum chloride, boron fluoride and zinc chloride. The reaction is conducted using 1 to 1.5 moles of the reagent per mole of the compound (12) at −30° C. to 60° C. for about 2 to about 5 hours.

The reaction to remove the acyl from the 5'-position of the resulting product (13) is conducted under the conditions of alkali hydrolysis, i.e. under the same conditions as the hydrolysis reaction for the reaction scheme (a) wherein a basic compound is used.

Reaction scheme (f)

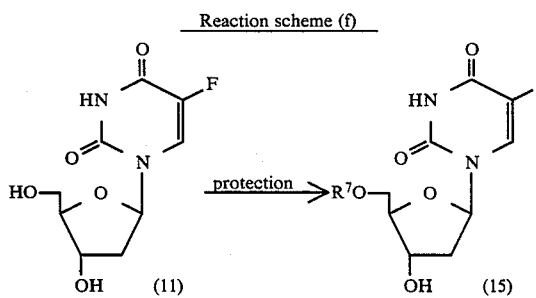

wherein R⁷ is as defined above.

This reaction introduces a protective group directly into the compound (11), giving a compound (15) having the protective group at the 5'-position. The reaction is conducted under the same conditions as in the reaction scheme (e).

The processes of the schemes (e) and (f) afford starting compounds having an acyl group or protective group at the 3'- or 5'-position.

Reaction scheme (g)

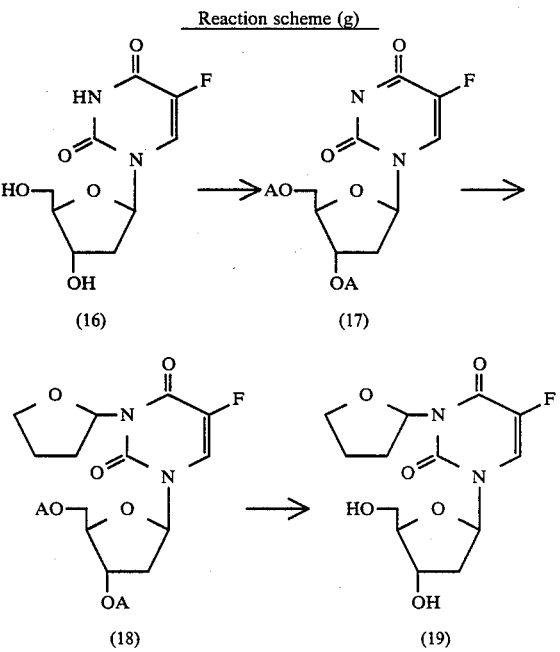

wherein A is as defined above.

The trialkylsilylation of the compound (16) is conducted in the same manner as that of the compound (8) shown in the reaction scheme (d) except that at least 3 moles of bis-O,N-tri(lower alkyl)silylacetamide is used per mole of the compound (16).

The tetrahydrofuranylation of the 3-position of the resulting compound (17) and the subsequent reaction for removing the lower alkylsilyl group from the 3'- and 5'-positions of the compound (18) are conducted in the same manner as the corresponding reactions shown in the reaction scheme (d). Consequently a compound (19) is obtained which has tetrahydrofuranyl at the 3-position. When subjected to the reaction of the scheme (e) or (f), the compound (19) provides a starting compound having tetrahydrofuranyl at the 3-position and further having an acyl group or protective group at the 3'- or 5'-position.

The starting compound obtained by the processes of the reaction schemes are usable directly as such or after isolation from the reaction system by a usual method.

When the acyl of the formula (Y) is to be introduced by the acylation reaction described, the acyl halide material can be prepared by the process of the following reaction scheme (h).

Reaction scheme (h)

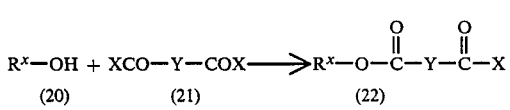

wherein $R^x$, Y and X are as defined above.

The above reaction can be conducted in the same manner as the acid halide process described for the reaction scheme (c).

The compounds of the present invention can be prepared also by the processes of the following reaction schemes (i) to (o).

Reaction scheme (i)
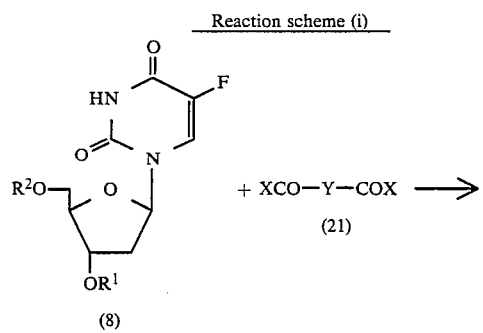
Reaction scheme (j)
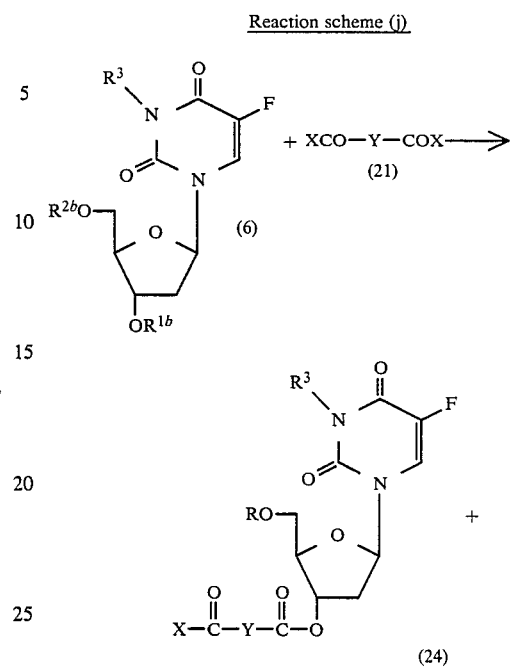
wherein $R^1$, $R^2$, X and Y are as defined above.
The above reaction can be conducted in the same manner as the acid halide process described for the reaction scheme (b).
wherein R, $R^{1b}$, $R^{2b}$, $R^3$, X and Y are as defined above.
The above reaction can be conducted in the same manner as is the case with the scheme (i).
Reaction scheme (k)
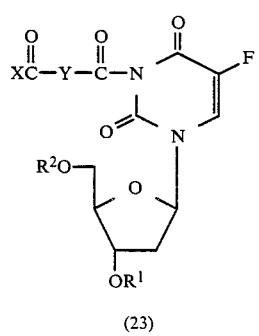
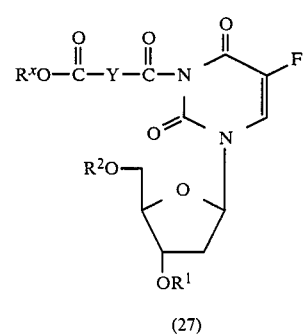

Reaction scheme (k)

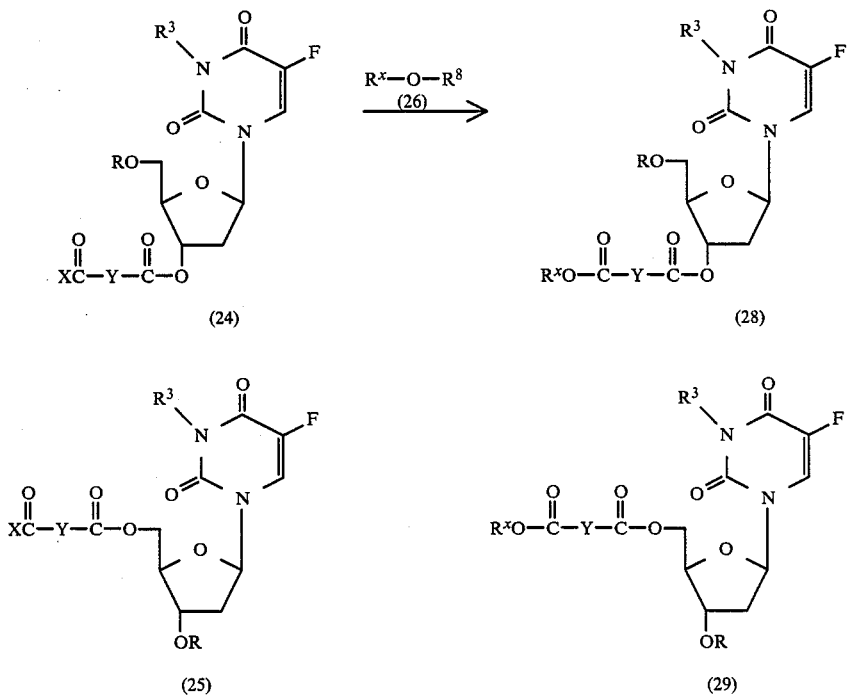

wherein $R^1$, $R^2$, $R^3$, X, Y, R and $R^x$ are as defined above, and $R^8$ is a hydrogen atom or tri(lower alkyl)silyl group.

According to the above scheme, one of the acid halides (23), (24) and (25) obtained by the processes of the schemes (i) and (j) is reacted with a compound (26) for acylation. When the compound (26) used is one wherein $R^8$ is hydrogen, the reaction can be carried out in the same manner as in the scheme (c).

Further when the compound (26) used is one wherein $R^8$ is tri(lower alkyl)silyl group, the reaction is conducted using a solvent, which will not adversely affect the reaction, in a dry state, preferably in an anhydrous state. Examples of preferred solvents are halogenated hydrocarbon such as dichloromethane and chloroform, aromatic hydrocarbons such as benzene and toluene, and aprotic solvents such as dioxane, acetonitrile, acetone and tetrahydrofuran. Usually, at least about one mole, preferably 1 to 3 moles, of the compound (26) is used per mole of the acid halide (23), (24) or (25). The reaction is conducted at about 0° to about 100° C., preferably room temperature to about 80° C., for 1 to 6 hours, preferably about 2 hours. When $R^8$ is hydrogen, it is desirable to use a base, such as triethylamine, trimethylamine, dimethylaniline or pyridine, for the reaction. Further if $R^8$ is tri(lower alkyl)silyl, it is desirable to use a Lewis acid such as stannic chloride, zinc chloride or aluminum chloride.

The compounds (26) to be used for the present reaction are generally those known but include some novel compounds. Such compounds can be easily prepared by the following process. The compound substituted with 2-tetrahydrofuranyl at the 1-position of the pyridine ring can be prepared from a corresponding known pyridine derivative having a hydrogen atom at the 1-position, by adding hexamethyldisilazane to the derivative, refluxing the mixture for about 2 to about 20 hours, thereafter removing the excess of the silazane from the reaction mixture, dissolving the residue in halogenated hydrocarbon such as dichloromethane and chloroform or in an aprotic solvent such as dioxane and acetonitrile adding to the solution 2-acetoxytetrahydrofuran in an amount of at least about one mole to 2 moles per mole of the pyridine derivative and a Lewis acid such as stannic chloride, zinc chloride or aluminum chloride, and reacting the mixture at about 0° to about 100° C., preferably around room temperature for about 1 to about 10 hours. When 2-acetoxytetrahydrofuran used for the reaction is replaced by an aroyl halide, lower alkanoyl halide, aroyloxycarbonyl halide, lower alkoxycarbonyl halide 2-halogenophthalide allyl halide, phenyl-lower alkoxy-lower alkyl halide or lower alkoxy-lower alkyl halide, the compound obtained has the substituent of aroyloxy group, lower alkanoyloxy group, aroyloxycarbonyloxy group or lower alkoxycarbonyloxy group at the 2 and/or 4 position(s) of the pyridine ring, or of phthalidyl group, allyl group, phenyl-lower alkoxy-lower alkyl group or lower alkoxy-lower alkyl group at the 1-position of the pyridine ring. Further the compound substituted with N-(lower alkoxycarbonyl lower alkyl)aminocarbonyl at the 1-position of the pyridine ring can be prepared from a corresponding pyridine derivative having a hydrogen atom at the 1-position, by adding to the derivative with at least about one mole of a lower alkoxycarbonyl-lower alkyl-isocyanate per mole of the derivative in a solvent such as dioxane, dichloromethane, chloroform, acetonitrile, acetone or pyridine, and subjecting the mixture to reaction at about 0° to about 100° C. for about 10 minutes to about 1 hour, preferably about 30 minutes.

Reaction scheme (l)

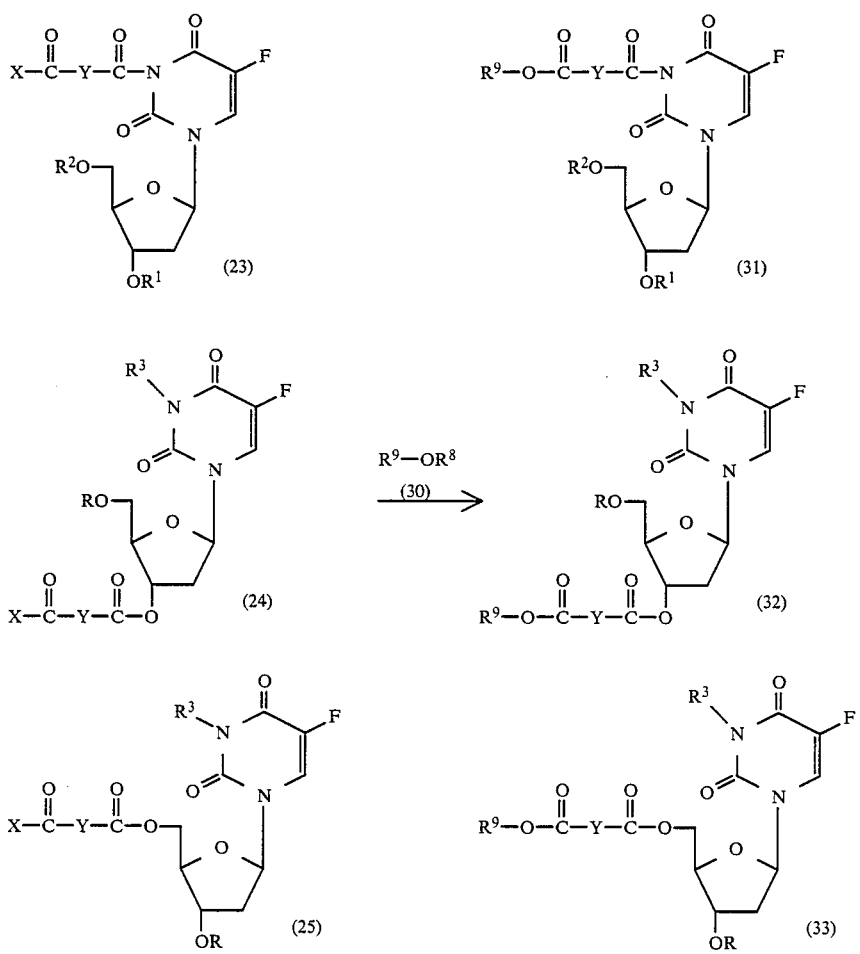

wherein $R^1$, $R^2$, $R^3$, $R^8$, X, Y and R are as defined above, and $R^9$ is lower alkyl.

According to the above scheme, a compound (30) is reacted with one of the acid halides (23), (24) and (25) obtained from the processes of the schemes (i) and (j). The reaction is conducted under the same conditions as in the reaction scheme (k).

Reaction scheme (m)

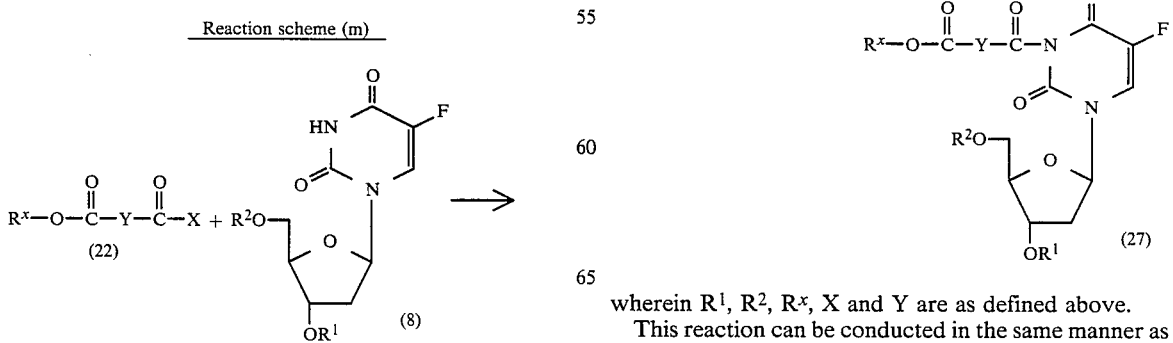

wherein $R^1$, $R^2$, $R^x$, X and Y are as defined above.

This reaction can be conducted in the same manner as in the reaction of the scheme (i).

Reaction scheme (n)

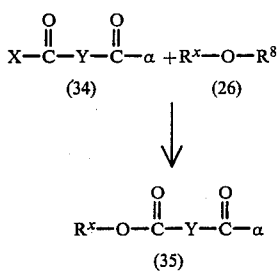

wherein $R^8$, $\alpha$, $R^x$, X and Y are as defined above.

This reaction can be carried out in the same manner as the reaction of the scheme (k). Reaction scheme (o)

Reaction shceme (o)

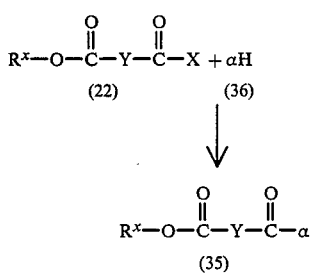

wherein $R^x$, $\alpha$, X and Y are as defined above.

This reaction can be carried out in the same manner as the reaction of the scheme (i).

The compounds (1a) and (1b) of the present invention have an outstanding anticancer effect and are low in toxicity. For example, they are reduced in side effects such as loss of body weight. The present compounds are therefore very useful as antitumor agents for curing cancers in man and animals.

Our research has revealed that the anticancer effect of the present compounds (1) can be further enhanced when they are used in combination with a pyridine derivative represented by the formula (X) below.

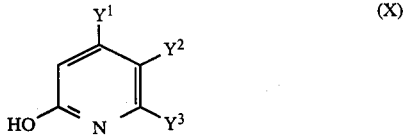

wherein one of $Y^1$ and $Y^3$ is a hydrogen atom, the other is hydroxyl, $Y^2$ is a hydrogen atom, halogen atom, lower alkyl, cyano or nitro, and the hydroxyl group(s) at the 2-, 4- and/or 6-position(s) may be an acylated one.

Some of the compounds of the formula (X) are known. The others can be easily prepared by a known process (Triv. Chem. Rec. 73, 704 (1954)). The acylation of the hydroxyl group(s) at the 2-, 4- and/or 6-position(s) can be conducted in the same manner as in reaction scheme (b) or (c).

The desired products of the present invention are used in the form of generally acceptable pharmaceutical compositions which are prepared by using diluents and excipients such as fillers, bulking agents, binders, wetting agents, disintegrating agents, surfactants, lubricants and the like. Administration unit forms of these pharmaceutical compositions of the present invention can be varied and selected so as to meet various therapeutical purposes. Typical forms of the pharmaceutical compositions can be exemplified such as tablets, pills, powders, liquids, suspensions, emulsions, granules, capsules, suppositories, injections (liquids, suspensions and others), ointments and the like.

In shaping into the form of tablets, those known as the carriers in this field can widely be applied for example, excipients such as lactose, purified sugar, sodium chloride, glucose, urea, starch, calcium carbonate, kaolin, crystalline cellulose, silicic acid and others; binders such as water, ethanol, propanol, simple syrup, a glucose solution, starch solution, gelatin solution, carboxymethyl cellulose, shellac, methyl cellulose, potassium phaphate, polyvinylpyrrolidone and others; disintegrating agents such as dried starch, sodium alginate, agar-agar powder, laminaran powder, sodium hydrogen carbonate, calcium carbonate, a fatty acid ester of polyoxyethylene sorbitan, sodium laurylsulfate, monoglyceride of stearic acid, starch, lactose and others; disintegration inhibitors such as purified sugar, stearing cacao butter, hydrogenated oils and others; absorption accelerators such as quaternary ammonium base, sodium laurylsulfate and others; wetting agents such as glycerin, starch and others; adsorption accelerators such as starch, lactose, kaolin, bentonite, colloidal silicic acid and others; and lubricants such as purified talc powder, stearic acid salts, boric acid powder, polyethylene glycol and others can be exemplified. If necessary, the tablets can further be coated with usual coating film to make them into coated tablets, for example sugar-coated tablets, gelatin film-coated tablets, enteric film-coated tablets, film-coated tablets, or double-layered tablets, multiple-layered tablets and others. In shaping into the form of pills, those known as the carriers in this field can widely be applied for example, excipients such as glucose, lactose, starch, cacao butter, hydrogenated vegetable oils, kaolin, talc and others; binders such as powdered gum arabi, powdered tragacanth gum, gelatin, ethanol and others; disintegrating agent such as laminaran, agar-agar powder and others. In shaping into the form of suppositories, those known in this field can widely be applied for example, polyethylene glycol, cacao butter, a higher alcohol, an ester of a higher alcohol, gelatin, semi-synthesized glyceride and others. Capsules are prepared in a conventional manner by admixing the compound of the invention with the foregoing various carrier and encapsulating the mixture into hard-gelatin capsules, soft-gelatin capsules, etc. In case of preparing injections, solutions, emulsions and suspensions being prepared are sterilized, and they are preferably isotonic to the blood. In preparing into the form of solutions emulsions and suspensions, those known as the diluents in this field can widely be applied, for example water, ethanol, propylene glycol, ethoxylated isostearyl alcohol, polyoxylated isostearyl alcohol, a polyoxyethylene sorbitan fatty acid ester and others. In case of preparing isotonic solutions, sufficient amount of sodium chloride, glucose or glycerin may be added to make the solution to be isotonic to the blood. The pharmaceutical compositions for injection preparation may further be contain usual dissolving agents, buffer solutions, analgesic agents or the like if necessary. The pharmaceutical composition of the present invention may also contain coloring agents, preservatives, perfumes, seasoning agents, sweetening agents and others, as well as contain other medicines, if necessary. In shaping into the form of pastes, creams and gels, diluents such as white vaseline, paraffins, glycerine, cellulose derivatives, polyethylene glycols, silicones, bentonite and the like can be used.

The amount of the desired product according to the present invention to be contained as the active ingredient in the pharmaceutical composition is not specifically restricted and can be selected from a wide range, generally 1 to 70% by weight, may be used.

Administration method of the above-mentioned pharmaceutical composition is not specifically restricted and can be administered through a suitable method for the respective types of administration forms, depending upon age of the patient, distinction of the sex and other conditions, conditions of the patient and others. For example, tablets, pills, liquids, suspensions, emulsions, granules and capsules are administered orally; injections are administered intraveneously singly or as a mixture with usual injectable transfusions such as a glucose solution, an amino acids solutions, and others; and if necessary the injections are administered singly intramuscularly, intracutaneously, subcutaneously or intraperitoneally; and the suppositories are administered into rectum.

The dosage of the desired products of the present invention may suitably be selected depending upon the method for administration, age of the patient, distinction of sex and other conditions, and conditions of the symptoms, and generally the pharmaceutical compositions of the invention can be administered in an amount of about 0.5 to about 20 mg/kg of the body weight/day, calculated as the compound of the invention (active ingredient), in 1 to 4 divided doses.

The present invention will be described in greater detail with reference to the following reference examples, examples, pharmaceutical tests and preparation examples.

In connection with the NMR data in the reference examples and examples, the numerals used as a subscript at the right of the symbol "C", "H" or "N" are used to refer to the position in the compound. Thus the term "$C_6$—H", for example, refers to the hydrogen bonded to the carbon atom at the 6-position. Similarly the term "$C_{3'.4'.5'}$—H", for example, denotes the hydrogens bonded to the carbon atoms at the 3'-, 4'- and 5'-positions. Also the term "$H_1$", for example, refers to the hydrogen bonded to the carbon atom at the 1-position. The term "$N_3$—H", for example, refers to the hydrogen bonded to the nitrogen atom at the 3-position of the 5-fluorouracil ring.

REFERENCE EXAMPLE 1

Preparation of 2'-deoxy-5'-O-trityl-5-fluorouridine

A 9.00 g quantity of sodium chloride was added to a solution of 5.00 g of 2'-deoxy-5-fluorouridine in pyridine at room temperature with stirring, and the solution was stirred for 15 hours. The solvent was distilled off and the residue was dissolved in ethyl acetate. The solution was washed three times with a saturated aqueous solution of sodium chloride. The ethyl acetate layer was dried on sodium sulfate and concentrated. The residue was applied to a silica gel column to conduct gradient elution using chloroform and methanol (up to 2%)-chloroform mixtures, giving 6.80 g of 2'-deoxy-5'-O-trityl-5-fluorouridine in a yield of 69%.

REFERENCE EXAMPLE 2

Preparation of 2'-deoxy-5-fluoro-3-(2-tetrahydrofuranyl)uridine

A 16.5 g quantity of N,O-bis(trimethylsilyl) acetamide was added to a suspension of 5.00 g of 2'-deoxy-5-fluorouridine in 50 ml of dry dichloromethane at room temperature with stirring, and the mixture was stirred for four hours. Then a solution of 4.00 g of 2-acetoxytetrahydrofuran and 1.17 ml of stannic chloride in 10 ml of dry dichloromethane was added and the mixture was stirred for 1.5 hours. Then 8.0 ml of triethylamine was added to neutralize the mixture and the mixture was washed with water. The dichloromethane layer was concentrated and the residue was dissolved in 100 ml of methanol. A 3 ml quantity of acetic acid was added thereto and the mixture was left to stand at 40° C. for 3 hours. The solvent was distilled off and the residue was applied to a silica gel column to conduct gradient elution using chloroform and methanol (up to 4%)-chloroform mixtures, giving 5.25 g of 2'-deoxy-5-fluoro-3-(2-tetrahydrofuranyl)uridine as an oil in a yield of 81.7%.

$^1$H-NMR (CDCl$_3$)δ: 8.06 (1H, d, J=6 Hz, $C_6$—H) 6.53 (1H, bt, J=6 Hz,

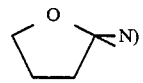

6.23 (1H, bt, J=6 Hz, $C_{1'}$—H) 4.45–3.75 (8H, m, $C_{3'.4'.5'}$—H, $C_{3'.5'}$—OH,

2.29–2.16 (6H, m, $C_{2'}$—H,

REFERENCE EXAMPLE 3

Preparation of 5-chloro-4-hydroxy-1-(2-tetrahydrofuranyl)-2(1H)-pyridone

A 10 ml quantity of hexamethyldisilazane was added to 1.00 g of 5-chloro-4-hydroxy-2(1H)-pyridone, and the mixture was refluxed for 6 hours. Then excess hexamethyldisilazane was distilled off and the oily residue was dissolved in 50 ml of dichloromethane. To the solution was added 1.00 g of 2-acetoxytetrahydrofuran and 0.1 ml of stannic chloride and the mixture was stirred overnight at room temperature. The reaction mixture was neutralized with triethylamine, and the solvent was distilled off. Methanol was added to the residue and the mixture was stirred at room temperature for 2 hours. The solvent was distilled off and the residue was placed on a silica gel column and eluted with 2% methanol-chloroform, giving 1.07 g of the title compound in a yield of 73.5%.

M.p. 170°–173° C.

¹H-NMR (DMSO-d₆)δ: 11.6 (1H, bs, OH) 7.59 (1H, s, C₆—H) 6.09–5.99 (1H, q,

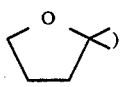

5.76 (1H, s, C₃—H) 4.39–3.73 (2H, m,

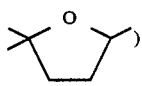

2.42–1.82 (4H, m,

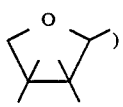

REFERENCE EXAMPLE 4

Preparation of 5-chloro-1-ethoxymethyl-4-hydroxy-2(1H)-pyridone

Following the general procedure of Reference Example 3 and using chloromethyl ethyl ester in place of the 2-acetoxytetrahydrofuran, 5-chloro-1-ethoxymethyl-4-hydroxy-2(1H)-pyridone was prepared in a yield of 39%.

M.p. 217°–219° C.

¹H-NMR (DMSO-d₆)δ: 11.63 (1H, bs, OH) 7.87 (1H, s, C₆—H) 5.75 (1H, s, C₃—H) 5.16 (2H, s, N—CH₂—O—) 3.49 (2H, q, J=7 Hz, —OCH₂ CH₃) 1.09 (3H, t, J=7 Hz, —OCH₂ CH₃).

REFERENCE EXAMPLE 5

Preparation of 2-benzoyloxy-5-chloro-4-hydroxypyridine

The title compound was prepared in a yield of 51% by following the general procedure of Reference Example 3 and using benzoyl chloride in place of the 2-acetoxytetrahydrofuran. The title compound softens at 184° C.

¹H-NMR (DMSO-d₆)δ: 8.27 (1H, s, C₆—H) 8.16–8.07 (2H, m,

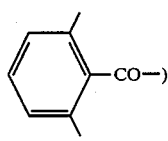

7.78–7.51 (3H, m,

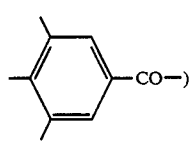

6.91 (1H, s, C₃—H).

REFERENCE EXAMPLE 6

Preparation of 4-hydroxy-1-(3-phthalidyl)-2(1H)-pyridone

A 10 ml quantity of hexamethyldisilazane was added to 1.00 g of 4-hydroxy-2(1H)-pyridone and the mixture was refluxed for 6 hours. Then the reaction mixture was concentrated under reduced pressure and the concentrate was dissolved in 20 ml of acetonitrile. To this solution was added 2.29 g of 3-bromophthalide and the mixture was stirred overnight at room temperature. Methanol was added to the reaction mixture and the resulting mixture was stirred at room temperature for 15 minutes. Then the reaction mixture was concentrated under reduced pressure, and the concentrate was applied to a silica gel column and eluted with 1% methanol-chloroform, giving 0.62 g of the title compound in a yield of 30%.

M.p. 239°–241° C.

¹H-NMR (DMSO-d₆)δ: 11.05 (1H, bs, OH) 8.29–7.52 (5H, m,

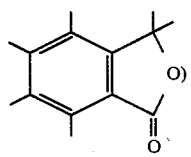

6.99 (1H, d, J=8 Hz, C₆—H) 5.88 (1H, dd, J₃.₅=2 Hz, J₅.₆=8 Hz, C₅—H) 5.65 (1H, d, J=2 Hz, C₃—H).

REFERENCE EXAMPLE 7

Preparation of 1-carbomethoxymethylcarbamoyl-4-hydroxy-2(1H)-pyridone

A 2.49 g quantity of carbomethoxymethylisocyanate was added to a suspension of 2.00 g of 4-hydroxy-2(1H)-pyridone in 60 ml of dioxane, and the mixture was stirred at 90° C. for 30 minutes. The solvent was distilled off, and ether was added to the residue. The precipitate thus formed was filtered, giving 2.20 g of the title compound in a yield of 54%.

M.p. 124°–126° C.

¹H-NMR (DMSO-d₆)δ: 11.52 (1H, bs, OH) 10.82 (1H, t, J=6 Hz, —CONHCH₂—) 8.20 (1H, d, J=8 Hz, C₆—H) 6.17 (1H, dd, J₅.₆=8 Hz, J₃.₅=2 Hz, C₅—H) 5.74 (1H, d, J=2 Hz, C₃—H) 4.15 (2H, d, J=6 Hz, —CONHCH₂—) 3.68 (3H, s, —COOCH₃).

REFERENCE EXAMPLE 8

Preparation of 1-benzyloxymethyl-5-chloro-4-hydroxy-2(1H)-pyridone

Following the general procedure of Reference Example 3 and using benzyloxymethyl chloride in place of 2-acetoxytetrahydrofuran and also using acetonitrile as the solvent in place of dichloromethane, the title compound was prepared in a yield of 57%.

M.p. 165°–167° C.

¹H-NMR (DMSO-d₆)δ: 11.65 (1H, bs, OH) 7.92 (1H, s, C₆—H) 7.31 (5H, s, phenyl—H) 5.77 (1H, s, C₃—H) 5.27 (2H, s, —NCH₂O—) 4.55 (2H, s,

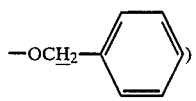

REFERENCE EXAMPLE 9

Preparation of 2,4-bis(trimethylsilyloxy)-5-chloropyridine

A 50 ml quantity of hexamethyldisilazane was addd to 9.6 g of 5-chloro-4-hydroxy-2(1H)-pyridone, and the mixture was stirred overnight on an oil bath at 140° C. The insolubles were removed by filtration, and the filtrate was distilled under reduced pressure, giving 14.4 g of the title compound boiling at 120° C./7 mm Hg. Yield 75%.

REFERENCE EXAMPLE 10

Preparation of 2-acetoxy-5-chloro-4-hydroxy-2(1H)-pyridone

A 2.09 ml quantity of acetyl bromide and 0.10 ml of stannic chloride were added to a solution of 5.00 g of 2,4-bis(trimethylsilyloxy)-5-chloropyridine in 250 ml of dry dichloromethane, and the mixture was stirred at room temperature for 3.5 hours. The reaction mixture was neutralized with triethylamine, and the solvent was distilled off. The residue was applied to a silica gel column and eluted with 40% ethyl acetate-benzene as an eluent, giving 2.07 g of the title compound in a yield of 64%.

M.p. 270°–272° C.

$^1$H-NMR (DMSO-d$_6$)δ: 11.90 (1H, bs, OH) 8.20 (1H, s, C$_6$—H) 6.69 (1H, s, C$_3$—H) 2.27 (3H, s, COCH$_3$).

EXAMPLE 1

Preparation of 5'-O-benzyl-2'-deoxy-5-fluorouridine ($R^1=R^3=H$, $R^2=C_6H_5CH_2$)

To a solution of 1.00 g of 5'-O-acetyl-2'-deoxy-5-fluoro-3'-O-trityluridine in 30 ml of methanol was added 1N aqueous solution of sodium hydroxide, and the mixture was stirred at room temperature for 4 hours. The reaction mixture was neutralized with acetic acid and concentrated. The concentrate was washed with petroleum ether, dried, and dissolved in a mixture of 20 ml of benzene and 20 ml of dioxane. To the solution were added 0.27 ml of benzyl bromide and 0.15 g of potassium hydroxide powder, and the mixture was refluxed overnight. The solvent was distilled off and the residue was dissolved in 50 ml of 80% acetic acid, and the solution was left to stand at 80° C. for 4 hours. The solvent was distilled off, and the residue was placed on a silica gel column to conduct a gradient elution using chloroform and mixtures of methanol (up to 2%) and chloroform. The fractions corresponding to 5'-O-benzyl-2'-deoxy-5-fluorouridine were collected and concentrated. The concentrate was recrystallized from ethanol, giving 0.33 g of the title compound in a yield of 52%.

M.p.129°–130° C.

Elementary Analysis: for C$_{16}$H$_{17}$FN$_2$O$_5$: Calcd. (%): C 57.14; H 5.09; N 8.33. Found (%): C 57.14; H 5.35; N 8.34.

$^1$H-NMR (DMSO-d$_6$)δ: 11.76 (1H, bs, —NH—, disappeared by addition of D$_2$O) 7.95 (1H, d, J=7 Hz, C$_6$—H) 7.34 (5H, s, phenyl-H) 6.15 (1H, t, J=7 Hz, C$_{1'}$—H) 5.33 (1H, bs, 3'—OH, disappeared by addition of D$_2$O) 4.55 (2H, s,

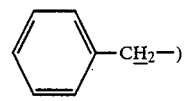

4.34–4.16 (1H, m, C$_{3'}$—H) 4.00–3.89 (1H, m, C$_{4'}$—H) 3.69–3.63 (2H, m, C$_{5'}$—H) 2.14 (2H, t, J=6 Hz, C$_{2'}$—H).

EXAMPLE 2

Preparation of 3'-O-benzyl-2'-deoxy-5-fluorouridine ($R^2=R^3=H$, $R^1=C_6H_5CH_2$)

To a mixture of 50 ml of benzene and 50 ml of dioxane were added 1.00 g of 2'-deoxy-5-fluoro-5'-O-trityluridine, 0.30 ml of benzyl bromide and 0.23 g of potassium hydroxide powder, and the mixture was refluxed for 25 hours. The insolubles were removed by filtration and the filtrate was concentrated and the concentrate was dissolved in 5 ml of 80% acetic acid. The solution was left to stand at 80° C. for 2 hours. The solvent was distilled off and the residue was placed on a silica gel column to conduct a gradient elution using chloroform and mixtures of methanol (up to 2%) and chloroform. The fractions corresponding to 3'-O-benzyl-2'-deoxy-5-fluorouridine were collected and concentrated. The concentrate was recrystallized from ethanol, giving 0.14 g of the title compound in a yield of 20%.

M.p. 138°–139° C.

Elementary Analysis: for C$_{16}$H$_{17}$FN$_2$O$_5$: Calcd. (%): C 57.14; H 5.09; N 8.33. Found: (%): C 57.16; H 5.30; N 8.13.

$^1$H-NMR (DMSO-d$_6$)δ: 11.82 (1H, bs, —NH—, disappeared by addition of D$_2$O) 8.21 (1H, d, J=7 Hz, C$_6$—H) 7.35 (5H, s, phenyl—H) 6.16 (1H, t, J=6 Hz, C$_{1'}$—H) 5.22 (1H, bs, 5'—OH, disappeared by addition of D$_2$O) 4.54 (2H, s,

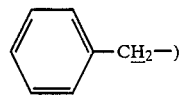

4.24–4.19 (1H, m, C$_{3'}$—H) 4.09–4.06 (1H, m, C$_{4'}$—H) 3.65–3.53 (2H, m, C$_{5'}$—H) 2.51–2.16 (2H, m, C$_{2'}$—H)

EXAMPLE 3

Preparation of 2'-deoxy-5-fluoro-3'-O-(3,4-methylenedioxybenzyl)uridine ($R^2=R^3=H$, $R^1=$3,4-methylenedioxybenzyl)

The title compound was prepared in a yield of 23% in the same manner as in Example 2 except that acetonitrile was used as the reaction solvent in place of the dioxane.

M.p. 186°–188° C.

Elementary Analysis: for C$_{17}$H$_{17}$FN$_2$O$_7$.0.5H$_2$O: Calcd. (%): C 52.44; H 4.66; N 7.19. Found (%): C 52.60; H 4.62; N 7.03.

$^1$H-NMR(CDCl$_3$)δ: 11.80 (1H, d, J=5 Hz, —NH—, disappeared by addition of D$_2$O) 8.18 (1H, d, J=7 Hz, C$_6$—H) 6.90–6.85 (3H, m, phenyl—H) 6.11 (1H, t, J=6 Hz, C$_{1'}$—H) 5.99 (2H, s, —O—CH$_2$—O—) 5.17 (1H, t, J=5 Hz, 5'—OH, disappeared by addition of D$_2$O) 4.42 (2H, s,

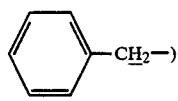

4.18–4.00 (2H, m, $C_{3'}.C_{4'}$—H) 3.64–3.61 (2H, m, $C_{5'}$—H) 2.30–2.20 (2H, m, $C_{2'}$—H).

EXAMPLES 4 AND 5

Preparation of 3'-O-benzyl-2'-deoxy-5-fluorouridine ($R^2=R^3=H$, $R^1=C_6H_5CH_2$, Example 4) and 5'-O-benzyl-2'-deoxy-5-fluorouridine ($R^1=R^3=H$, $R^2=C_6H_5CH_2$, Example 5)

A 11.4 g quantity of potassium hydroxide was dissolved in a mixture of 350 ml of water and 100 ml of dioxane. To the mixture were added 10.0 g of 2'-deoxy-5-fluorouridine and 3.0 ml of benzyl bromide at room temperature with stirring. Then, every 24 hours, 100 ml of 5% aqueous solution of potassium hydroxide and 3.0 ml of benzyl bromide were added three times to the mixture. Then, the resulting mixture was stirred overnight. The reaction mixture was washed twice with 200 ml of ether, and the aqueous layer was neutralized with 6N-HCl and concentrated to about 200 ml. The concentrate was adjusted to a pH of about 3 to 4 with 6N-HCl and extracted twice with 100 ml of ethyl acetate. The ethyl acetate layer was separated, dried on anhydrous sodium sulfate and concentrated. The oily residue was placed on a silica gel column to conduct a gradient elution using chloroform and mixtures of methanol (up to 2%) and chloroform. The fractions corresponding to 3'-O-benzyl-2'-deoxy-5-fluorouridine were collected and concentrated. The concentrate was recrystallized from ethanol, giving 3.57 g of the desired compound in a yield of 26.1%.

M.p. 138°–139° C.

Elementary Analysis: for $C_{16}H_{17}FN_2O_5$: Calcd. (%): C 57.14; H 5.09; N 8.33. Found (%): C 57.12; H 5.28; N 8.24.

Then the fractions corresponding to 5'-O-benzyl-2'-deoxy-5-fluorouridine were collected and concentrated. The concentrate was recrystallized from ethanol, giving 0.40 g of the desired compound in a yield of 2.9%.

M.p. 129°–130° C.

Elementary Analysis: for $C_{16}H_{17}FN_2O_5$: Calcd. (%): C 57.14; H 5.09; N 8.33. Found (%): C 57.29; H 5.30; N 8.26.

EXAMPLES 6–17

The general procedures of Examples 4 and 5 were followed, thereby giving the following compounds.

Example 6

3'-O-(2-fluorobenzyl)-2'-deoxy-5-fluorouridine ($R^2=R^3=H$, $R^1=$2-fluorobenzyl)

Yield 34%.
M.p. 121°–123° C.
$^1$H-NMR(DMSO-d$_6$)δ: 11.82 (1H, bs, —NH—, disappeared by addition of D$_2$O) 8.21 (1H, d, J=7 Hz, $C_6$—H) 7.67–7.19 (4H, m, phenyl—H) 6.15 (1H, t, J=6 Hz, $C_{1'}$—H) 5.26 (1H, bs, 5'—OH, disappeared by addition of D$_2$O) 4.60 (2H, s,

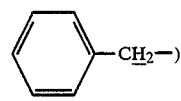

4.28–4.05 (2H, m, $C_{3'}.C_{4'}$—H) 3.77–3.67 (2H, m, $C_{5'}$—H) 2.41–2.18 (2H, m, $C_{2'}$—H).

Example 7

5'-O-(2-fluorobenzyl)-2'-deoxy-5-fluorouridine ($R^1=R^3=H$, $R^2=$2-fluorobenzyl)

Yield 5.2%.
M.p.-(oily).
$^1$H-NMR(DMSO-d$_6$)δ: 11.7 (1H, bs, —NH—, disappeared by addition of D$_2$O) 7.92 (1H, d, J=7 Hz, $C_6$—H) 7.52–7.07 (4H, m, phenyl—H) 6.20 (1H, t, J=6 Hz, $C_{1'}$—H) 4.62 (2H, s,

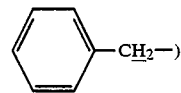

4.44–3.97 (2H, m, $C_{3'}.C_{4'}$—H) 3.84–3.57 (2H, m, $C_{5'}$—H) 2.21–2.08 (2H, m, $C_{2'}$—H).

Example 8

3'-O-(3-fluorobenzyl)-2'-deoxy-5-fluorouridine ($R^2=R^3=H$, $R^1=$3-fluorobenzyl)

Yield 27%.
M.p. 113°–115° C.
$^1$H-NMR(DMSO-d$_6$)δ: 11.81 (1H, bs, —NH—, disappeared by addition of D$_2$O) 8.21 (1H, d, J=7 Hz, $C_6$—H) 7.46–7.01 (4H, m, phenyl—H) 6.17 (1H, t, J=6 Hz, $C_{1'}$—H) 5.22 (1H, bt, J=5 Hz, 5'—OH, disappeared by addition of D$_2$O) 4.58 (2H, s,

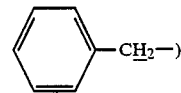

4.31–4.06 (2H, m, $C_{3'.4'}$—H) 3.74–3.59 (2H, m, $C_{5'}$—H) 2.38–2.03 (2H, m, $C_{2'}$—H).

Example 9

5'-O-(3-fluorobenzyl)-2'-deoxy-5-fluorouridine ($R^1=R^3=H$, $R^2=$3-fluorobenzyl)

Yield 5.9%.
M.p.-(oily).
$^1$H-NMR(CDCl$_3$)δ: 10.4 (1H, bs, —NH—, disappeared by addition of D$_2$O) 7.92 (1H, d, J=7 Hz, $C_6$—H) 7.41—6.77 (4H, m, phenyl—H) 6.28 (1H, bs, $C_{1'}$—H) 4.63–3.51 (6H, m, $C_{3'.4'.5'}$—H,

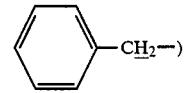

2.49–1.93 (2H, m, $C_{2'}$—H).

Example 10

3'-O-(2-bromobenzyl)-2'-deoxy-5-fluorouridine
($R^2=R^3=H$, $R^1=$2-bromobenzyl)

Yield 33%.
M.p. 122°–124° C.
$^1$H-NMR(DMSO-$d_6$)δ: 11.81 (1H, bs, —NH—, disappeared by addition of $D_2O$) 8.20 (1H, d, J=7 Hz, $C_6$—H) 7.67–7.32 (4H, m, phenyl—H) 6.15 (1H, t, J=6 Hz, $C_{1'}$—H) 5.21 (1H, t, J=5 Hz, 5'—OH, disappeared by addition of $D_2O$) 4.57 (2H, s,

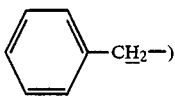

4.25–4.05 (2H, m, $C_{3'.4'}$—H) 3.70–3.52 (2H, m, $C_{5'}$—H) 2.40–1.94 (2H, m, $C_{2'}$—H).

Example 11

5'-O-(2-bromobenzyl)-2'-deoxy-5-fluorouridine
($R^1=R^3=H$, $R^2=$2-bromobenzyl)

Yield 5%
M.p.-(oily)
$^1$H-NMR(DMSO-$d_6$)δ: 11.78 (1H, bs, —NH—, disappeared by addition of $D_2O$) 7.91 (1H, d, J=7 Hz, $C_6$-H) 7.69–7.32 (4H, m, phenyl—H) 6.15 (1H, t, J=6 Hz, $C_{1'}$—H) B 5.35 (1H, t, J=7 Hz, 5'—OH, disappeared by addition of $D_2O$) 4.60 (2H, s,

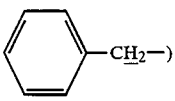

4.31–3.42 (4H, m, $C_{3'.4'.5'}$—H) 2.20–2.09 (2H, m, $C_{2'}$—H).

Example 12

3'-O-(3-bromobenzyl)-2'-deoxy-5-fluorouridine
($R^2=R^3=H$, $R^1=$3-bromobenzyl)

Yield 19%.
M.p. 166°–168° C.
$^1$H-NMR(DMSO-$d_6$)δ: 11.80 (1H, bs, —NH—, disappeared by addition of $D_2O$) 8.18 (1H, d, J=7 Hz, $C_6$—H) 7.69–7.31 (4H, m, phenyl—H) 6.15 (1H, t, J=6 Hz, $C_{1'}$—H) 5.19 (1H, t, J=5 Hz, 5'—OH, disappeared by addition of $D_2O$) 4.54 (2H, s,

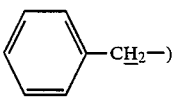

4.23–4.03 (2H, m, $C_{3'.4'}$—H) 3.71–3.57 (2H, m, $C_{5'}$—H) 2.34–2.21 (2H, m, $C_{2'}$—H).

Example 13

5'-O-(3-bromobenzyl)-2'-deoxy-5-fluorouridine
($R^1=R^3=H$, $R^2=$3-bromobenzyl)

Yield 3%
M.p.-(oily)
$^1$H-NMR(DMSO-$d_6$)δ: 11.90 (1H, bs, —NH—, disappeared by addition of $D_2O$) 8.00 (1H, d, J=7 Hz, $C_6$—H) 7.67–7.34 (4H, m, phenyl—H) 6.12 (1H, t, J=6 Hz, $C_{1'}$—H) 5.46 (1H, bs, 3'—OH, disappeared by addition of $D_2O$) 4.54 (2H, s,

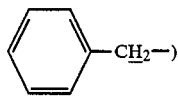

4.30–3.90 (2H, m, $C_{3'.4'}$—H) 3.74–3.68 (2H, m, $C_{5'}$—H) 2.13 (2H, t, J=6 Hz, $C_{2'}$—H).

Example 14

3'-O-(4-bromobenzyl)-2'-deoxy-5-fluorouridine
($R^2=R^3=H$, $R^1=$4-bromobenzyl)

Yield 12%.
M.p. 214°–217° C.
$^1$H-NMR(DMSO-$d_6$)δ: 11.80 (1H, bs, —NH—, disappeared by addition of $D_2O$) 8.18 (1H, d, J=7 Hz, $C_6$—H) 7.55 and 7.30 (each 2H, d, J=8 Hz, phenyl—H) 6.11 (1H, t, J=6 Hz, $C_{1'}$—H) 5.19 (1H, t, J=5 Hz, 5'—OH, disappeared by addition of $D_2O$) 4.51 (2H, s,

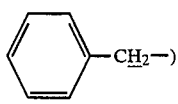

4.23–4.02 (2H, m, $C_{3'.4'}$—H) 3.73–3.60 (2H, m, $C_{5'}$—H) 2.36–2.07 (2H, m, $C_{2'}$—H).

Example 15

3'-O-(4-t-butylbenzyl)-2'-deoxy-5-fluorouridine
($R^2=R^3=H$, $R^1=$4-t-butylbenzyl)

Yield 17%.
M.p.-(powder).
$^1$H-NMR(DMSO-$d_6$)δ: 11.80 (1H, bs, —NH—, disappeared by addition of $D_2O$) 8.18 (1H, d, J=7 Hz, $C_6$—H) 7.48 and 7.30 (each 2H, d, J=8 Hz, phenyl—H) 6.12 (1H, t, J=6 Hz, $C_{1'}$—H) 5.18 (1H, t, J=5 Hz, 5'—OH, disappeared by addition of $D_2O$) 4.48 (2H, s,

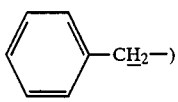

4.30–4.04 (2H, m, $C_{3'.4'}$—H) 3.76–3.60 (2H, m, $C_{5'}$—H) 2.24–2.08 (2H, m, $C_{2'}$—H) 1.27 (9H, s, $CH_3 \times 3$).

Example 16

5'-O-(4-t-butylbenzyl)-2'-deoxy-5-fluorouridine
($R^1=R^3=H$, $R^2=$4-t-butylbenzyl)

Yield 2%.
M.p.-(oily).
$^1$H-NMR(DMSO-$d_6$)δ: 11.80 (1H, bs, —NH—, disappeared by addition of $D_2O$) 7.94 (1H, d, J=7 Hz, $C_6$—H) 7.34 and 7.16 (each 2H, d, J=8 Hz, phenyl—H) 6.14 (1H, t, J=6 Hz, $C_1$—H) 5.31 (1H, bs, 3+-OH, disappeared by addition of $D_2O$) 4.51 (2H, s,

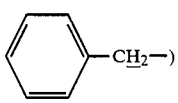

4.28-3.94 (2H, m, C$_{3'\cdot 4'}$—H) 3.74-3.64 (2H, m, C$_{5'}$—H) 2.13 (2H, t, J=6 Hz, C$_{2'}$—H) 1.27 (9H, s, CH$_3\times$3).

Example 17

3'-O-(4-phenylbenzyl)-2'-deoxy-5-fluorouridine (R$^2$=R$^3$=H, R$^1$=4-phenylbenzyl)

Yield 12%.

M.p. 207°-209° C.

$^1$H-NMR (DMSO-d$_6$)δ: 11.90 (1H, bs, —NH—, disappeared by addition of D$_2$O) 8.19 (1H, d, J=7 Hz, C$_6$—H) 7.69-7.39 (9H, m, phenyl—H) 6.15 (1H, t, J=6 Hz, C$_{1'}$—H) 5.25 (1H, t, J=5 Hz, 5'—OH, disappeared by addition of D$_2$O) 4.58 (2H, s,

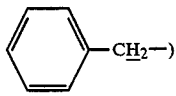

4.29-4.07 (2H, m, C$_{3'\cdot 4'}$—H) 3.83-3.63 (2H, m, C$_{5'}$—H) 2.26-2.06 (2H, m, C$_{2'}$—H).

EXAMPLES 18 AND 19

Preparation of 3+-O-(4-chlorobenzyl)-2'-deoxy-5-fluorouridine (R$^2$=R$^3$=H, R$^1$=4-chlorobenzyl, Example 18) and 5'-O-(4-chlorobenzyl)-2'-deoxy-5-fluorouridine (R$^1$=R$^3$=H, R$^2$=4-chlorobenzyl, Example 19)

A 4.0 g quantity of potassium hydroxide was dissolved in a mixture of 150 ml of water and 40 ml of dioxane. To the mixture were added 2.00 g of 2'-deoxy-5-fluorouridine and 5.5 g of 4-chlorobenzyl chloride at room temperature with stirring. Two days later, the same subsequent procedure as in Examples 4 and 5 were conducted and the resulting residue was placed on a silica gel column to conduct a gradient elution using chloroform and mixtures of methanol (up to 2%) and chloroform. The fractions corresponding to 3'-O-(4-chlorobenzyl)-2'-deoxy-5-fluorouridine were collected and concentrated, giving 0.50 g of the desired compound in a yield of 17%.

M.p. 196°-198° C.

$^1$H-NMR(DMSO-d$_6$)δ: 11.81 (1H, bs, —NH—, disappeared by addition of D$_2$O) 8.20 (1H, d, J=7 Hz, C$_6$—H) 7.38 (4H, s, phenyl—H) 6.14 (1H, t, J=7 Hz, C$_{1'}$—H) 5.21 (1H, bt, J=5 Hz, 5'—OH, disappeared by addition of D$_2$O) 4.53 (2H, s,

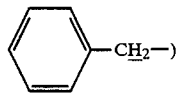

4.23-4.14 (1H, m, C$_{3'}$—H) 4.10-4.03 (1H, m, C$_{4'}$—H) 3.71-3.58 (2H, m, C$_{5'}$—H) 2.41-2.02 (2H, m, C$_{2'}$—H).

Elementary Analysis: for C$_{16}$H$_{16}$ClFN$_2$O$_5$: Calcd. (%): C 51.83; H 4.35; N 7.56. Found (%): C 51.82; H 4.60; N 7.41.

Then the fractions corresponding to 5'-O-(4-chlorobenzyl)-2'-deoxy-5-fluorouridine were collected and concentrated, giving 0.12 g of the desired compound in a yield of 4.0% as a powder.

$^1$H-NMR(DMSO-d$_6$)δ: 11.79 (1H, bs, —NH—, disappeared by addition of D$_2$O) 7.91 (1H, d, J=7 Hz, C$_6$—H) 7.38 (4H, s, phenyl—H) 6.13 (1H, t, J=6 Hz, C$_{1'}$—H) 5.33 (1H, bs, 3'-OH, disappeared by addition of D$_2$O) 4.53 (2H, s,

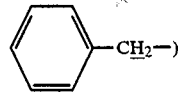

4.38-4.21 (1H, m, C$_{3'}$—H) 4.04-3.82 (1H, m, C$_{4'}$—H) 3.78-3.74 (2H, m, C$_{5'}$—H) 2.25-1.98 (2H, m, C$_{2'}$—H).

Elementary Analysis: for C$_{16}$H$_{16}$ClFN$_2$O$_5$: Calcd. (%): C 51.83; H 4.35; N 7.56. Found (%): C 51.73; H 4.80; N 7.97.

EXAMPLES 20-22

The general procedures of Examples 18 and 19 were followed, thereby giving the following compounds.

Example 20

3'-O-(2,4-dichlorobenzyl)-2'-deoxy-5-fluorouridine (R$^2$=R$^3$=H, R$^1$=2,4-dichlorobenzyl)

Yield 14%.

M.p. 88°-90° C.

$^1$H-NMR(DMSO-d$_6$)δ: 11.82 (1H, bs, —NH—, disappeared by addition of D$_2$O) 8.20 (1H, d, J=7 Hz, C$_6$—H) 7.60-7.37 (3H, m, phenyl—H) 6.14 (1H, t, J=6 Hz, C$_{1'}$—H) B 5.21 (1H, t, J=5 Hz, 5'—OH, disappeared by addition of D$_2$O) 4.59 (2H, s,

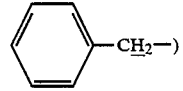

4.28-4.03 (2H, m, C$_{3'\cdot 4'}$—H) 3.69-3.60 (2H, m, C$_{5'}$—H) 2.37-2.19 (2H, m, C$_{2'}$—H).

Example 21

5'-O-(2,4-dichlorobenzyl)-2'-deoxy-5-fluorouridine (R$^1$=R$^3$=H, R$^2$=2,4-dichlorobenzyl)

Yield 3.3%

M.p. 109°-111° C.

$^1$H-NMR(DMSO-d$_6$)δ: 11.77 (1H, bs, —NH—, disappeared by addition of D$_2$O) 7.89 (1H, d, J=7 Hz, C$_6$—H) 7.60-7.36 (3H, m, phenyl—H) 6.14 (1H, t, J=6 Hz, C$_{1'}$—H) 5.33 (1H, bs, 3'—OH, disappeared by addition of D$_2$O) 4.61 (2H, s,

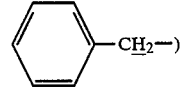

4.36-3.83 (2H, m, C$_{3'\cdot 4'}$—H) 3.74-3.60 (2H, m, C$_{5'}$—H) 2.14 (2H, t, J=6 Hz, C$_{2'}$—H).

EXAMPLE 22

3'-O-(4-methoxybenzyl)-2'-deoxy-5-fluorouridine (R$^2$=R$^3$=H, R$^1$=4-methoxybenzyl)

Yield 8.1%.

M.p. 164°-166° C.

$^1$H-NMR(DMSO-d$_6$)δ: 11.81 (1H, bs, —NH—, disappeared by addition of D$_2$O) 8.19 (1H, d, J=7 Hz, C$_6$—H) 7.27 and 6.91 (each 2H, d, J=8 Hz, phenyl—H)

6.12 (1H, t, J=6 Hz, $C_{1'}$—H) 5.19 (1H, bt, J=5 Hz, 5'—OH, disappeared by addition of $D_2O$) 4.45 (2H, s,

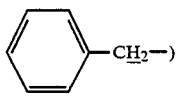

4.19–4.02 (2H, m, $C_{3'.4'}$—H) 3.70–3.50 (2H, m, $C_{5'}$—H) 2.31–2.13 (2H, m, $C_{2'}$—H).

EXAMPLE 23

Preparation of 2'-deoxy-5-fluoro-3'-(2-methylbenzyl)uridine ($R^2=R^3=H$, $R^1=$2-methylbenzyl)

A 1.14 g quantity of potassium hydroxide was dissolved in a mixture of 33 ml of water and 16 ml of acetonitrile. To the solution were added 1.00 g of 2'-deoxy-5-fluorouridine and 1.50 g of 2-methylbenzyl bromide at room temperature with stirring. Then the same subsequent procedures as in Examples 4 and 5 were conducted, giving 0.29 g of the title compound in a yield of 20%.

M.p. 114°–116° C.

$^1$H-NMR(DMSO-$d_6$)δ: 11.79 (1H, bs, —NH—, disappeared by addition of $D_2O$) 8.19 (1H, d, J=7 Hz, $C_6$—H) 7.30–7.17 (4H, m, phenyl—H) 6.11 (1H, t, J=6 Hz, $C_{1'}$—H) 5.19 (1H, t, J=5 Hz, 5'—OH, disappeared by addition of $D_2O$) 4.45 (2H, s,

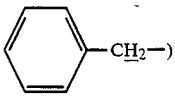

4.22–4.02 (2H, m, $C_{3'.C_{4'}}$—H) 3.66–3.62 (2H, m, $C_{5'}$—H) 2.29–2.21 (5H, m, $C_{2'}$—H and $CH_3$).

Elementary Analysis: for $C_{17}H_{19}FN_2O_5$: Calcd. (%): C 58.28; H, 5.46; N 7.99 Found (%): C 58.12; H 5.64; N 8.01.

EXAMPLES 24 AND 25

The general procedure of Example 23 was followed, thereby giving the following compounds.

EXAMPLE 24

3'-O-(3-methylbenzyl)-2'-deoxy-5-fluorouridine ($R^2=R^3=H$, $R^1=$3-methylbenzyl)

Yield 23%

M.p. 129°–131° C.

$^1$H-NMR(DMSO-$d_6$)δ: 11.80 (1H, bs, —NH—, disappeared by addition of $D_2O$) 8.19 (1H, d, J=7 Hz, $C_6$—H) 7.15 (4H, s, phenyl—H) 6.12 (1H, t, J=6 Hz, $C_{1'}$—H) 5.18 (1H, t, J=5 Hz, 5'—OH, disappeared by addition of $D_2O$) 4.49 (2H, s,

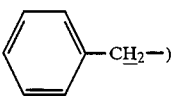

4.21–4.02 (2H, m, $C_{3'.4'}$—H) 3.66–3.61 (2H, m, $C_{5'}$—H) 2.31–2.22 (5H, m, $C_{2'}$—H and $CH_3$).

EXAMPLE 25

3'-O-(4-methylbenzyl)-2'-deoxy-5-fluorouridine ($R^2=R^3=H$, $R^1=$4-methylbenzyl)

Yield 21%

M.p. 178°–180° C.

$^1$H-NMR(DMSO-$d_6$)δ: 11.81 (1H, bs, —NH—, disappeared by addition of $D_2O$) 8.18 (1H, d, J=7 Hz, $C_6$—H) 7.30–7.13 (4H, m, phenyl—H) 6.12 (1H, t, J=6 Hz, $C_{1'}$—H) 5.17 (1H, t, J=5 Hz, 5'—OH, disappeared by addition of $D_2O$) 4.20–4.01 (2H, m, $C_{3'.C_{4'}}$—H) 3.65–3.60 (2H, m, $C_{5'}$—H) 2.29–2.12 (5H, m, $C_{2'}$—H and $CH_3$).

EXAMPLE 26

Preparation of 3'-O-benzyl-2'-deoxy-5-fluoro-5'-O-nicotinoyluridine ($R^1=C_6H_5CH_2$, $R^3=H$, $R^2=$3-pyridinecarbonyl)

A 0.21 g quantity of nicotinoyl chloride (hydrochloride) was added to a solution of 0.20 g of 3'-O-benzyl-2'-deoxy-5-fluorouridine in 10 ml of pyridine, and the mixture was left to stand at 80° C. for 3 hours. The solvent was distilled off and the residue was dissolved in 30 ml of ethyl acetate. The solution was washed twice with 20 ml of water. The ethyl acetate layer was dried on anhydrous sodium sulfate and concentrated. The concentrate was placed on a silica gel column and eluted with chloroform, giving 0.18 g of the title compound in a yield of 69%.

M.p. 130°–132° C.

$^1$H-NMR(CDCl$_3$)δ: 11.14 (1H, bs, —NH—, disappeared by addition of $D_2O$) 9.22 (1H, s,

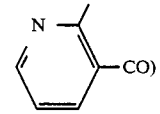

8.81 (1H, d, J=4 Hz,

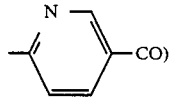

8.24 (1H, d, J=8 Hz,

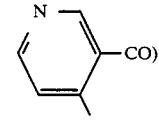

7.53–7.28 (7H, m,

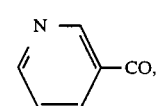

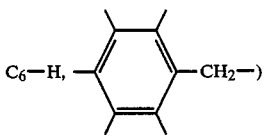

6.22 (1H, t, J=6 Hz, $C_{1'}$—H) 4.71-4.21 (6H, m,

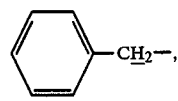

$C_{3',4',5'}$—H) 2.75-2.04 (2H, m, $C_{2'}$—H).

Elementary Analysis: for $C_{22}H_{20}FN_3O_6$: Calcd. (%): C 59.86; H 4.57; N 9.52. Found (%): C 60.01; H 4.56; N 9.58.

EXAMPLES 27-38

The general procedure of Example 26 was followed, thereby giving the following compounds.

Example 27

3'-O-benzyl-5'-O-benzoyl-2'-deoxy-5-fluorouridine ($R^1=C_6H_5CH_2$, $R^2=C_6H_5CO$, $R^3=H$)

Yield 75%.
M.p. 125°-127° C.
$^1$H-NMR(DMSO-$d_6$)$\delta$: 11.94 (1H, bs, —NH—, disappeared by addition of $D_2O$) 8.00-7.41 (6H, m,

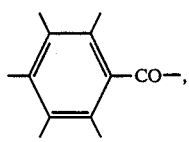

$C_6$—H) 7.33 (5H, s,

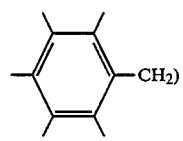

6.17 (1H, t, J=6 Hz, $C_{1'}$—H) 4.59 (6H, m,

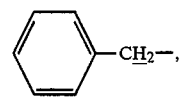

$C_{3',4',5'}$—H) 2.40-2.27 (2H, m, $C_{2'}$—H).

Example 28

3'-O-benzyl-5'-O-phenoxycarbonyl-2'-deoxy-5-fluorouridine ($R^1=C_6H_5CH_2$, $R^2=C_6H_5OCO$—, $R^3=H$)

Yield 38%.
M.p.-(oily).
$^1$H-NMR(DMSO-$d_6$)$\delta$: 12.00 (1H, bs, —NH—, disappeared by addition of $D_2O$) 7.95 (1H, d, J=7 Hz, $C_6$—H) 7.55-7.16 (10H, m, phenyl—H) 6.17 (1H, t, J=6 Hz, $C_{1'}$—H) 4.56-4.21 (6H, m,

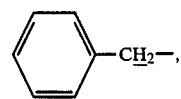

$C_{3',4',5'}$—H) 2.39-2.28 (2H, m, $C_{2'}$—H).

Example 29

3'-O-benzyl-5'-O-n-hexanoyl-2'-deoxy-5-fluorouridine ($R^1=C_6H_5CH_2$, $R^2=CH_3(CH_2)_4CO$, $R^3=H$)

Yield 51%.
M.p.-(oily).
$^1$H-NMR(DMSO-$d_6$)$\delta$: 11.94 (1H, bs, —NH—, disappeared by addition of $D_2O$) 7.90 (1H, d, J=7 Hz, $C_6$—H) 7.33 (5H, s, phenyl—H) 6.19 (1H, t, J=6 Hz, $C_{1'}$—H) 4.54 (2H, s,

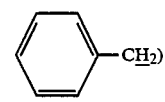

4.29-4.12 (4H, m, $C_{3',4',5'}$—H) 2.38-2.23 (4H, m, $C_{2'}$—H, —$CH_2CO$—) 1.61-1.15 (6H, m, $CH_3(CH_2)_3CH_2CO$—) 0.84 (3H, t, J=6 Hz, $CH_3CH_2$—)

Example 30

3'-O-benzyl-5'-O-benzyl-carbonyl-2'-deoxy-5-fluorouridine ($R^1=C_6H_5CH_2$, $R^2=C_6H_5CH_2CO$, $R^3=H$)

Yield 42%.
M.p.-(oily).
$^1$H-NMR(CDCl$_3$)$\delta$: 10.06 (1H, bs, —NH—, disappeared by addition of $D_2O$) 7.42-7.23 (11H, m, phenyl-H, $C_6$—H) 6.15 (1H, t, J=6 Hz, $C_{1'}$—H) 4.43 (2H, s,

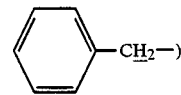

4.33-4.11 (3H, m, $C_{3',5'}$—H) 3.96-3.83 (1H, m, $C_{4'}$—H) 3.64 (2H, s,

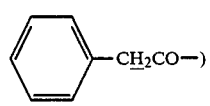

2.47-2.27, 1.65-1.49 (2H, m, $C_{2'}$—H).

EXAMPLE 31

3'-O-benzyl-5'-O-ethoxycarbonyl-2'-deoxy-5-fluorouridine ($R^1=C_6H_5CH_2$, $R^2=CH_3CH_2OCO$, $R^3=H$)

Yield 37%
M.p.-(oily)
$^1$H-NMR(CDCl$_3$)$\delta$: 10.18 (1H, bs, —NH—, disappeared by addition of $D_2O$) 7.68 (1H, d, J=6 Hz, $C_6$—H) 7.32 (5H, s, phenyl—H) 6.31 (1H, t, J=6 Hz, $C_{1'}$—H) 4.40 (2H, s,

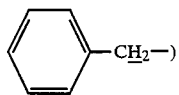

4.37–4.10 (6H, m, $C_{3',4',5'}$—H, $OCH_2CH_3$) 2.67–2.42, 2.23–1.92 (2H, m, $C_{2'}$—H) 1.30 (3H, t, J=7 Hz, —$OCH_2\underline{C}H_3$).

EXAMPLE 32

3'-O-benzyl-5'-O-(3-methylbenzoyl)-2'-deoxy-5-fluorouridine ($R^1=C_6H_5CH_2$, $R^2$=3-methylbenzoyl, $R^3$=H)

Yield 67%
M.p. 131°–133° C.
$^1$H-NMR(CDCl$_3$)δ: 9.61 (1H, bs, —NH—, disappeared by addition of D$_2$O) 7.78–7.73 (2H, m,

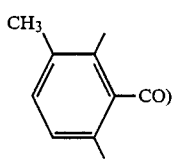

7.60 (1H, d, J=6 Hz, $C_6$—H) 7.38–7.22 (7H, m,

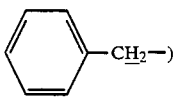

6.25 (1H, t, J=6 Hz, $C_{1'}$—H) 4.55–4.35 (5H, m, $C_{3',5'}$—H,

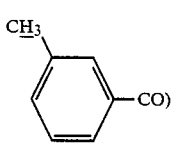

4.28–4.18 (1H, m, $C_{4'}$—H) 2.73–2.47, 2.16–1.87 (2H, m, $C_{2'}$—H) 2.38 (3H, s,

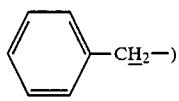

Example 33

3'-O-benzyl-5'-O-(4-n-propoxybenzoyl)-2'-deoxy-5-fluorouridine ($R^1=C_6H_5CH_2$, $R^2$=4-n-propoxybenzoyl, $R^3$=H)

Yield 78%.
M.p.-(oily).
$^1$H-NMR(CDCl$_3$)δ: 9.27 (1H, bs, —NH—, disappeared by addition of D$_2$O) 7.91 (2H, d, J=9 Hz, CO

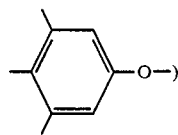

7.62 (1H, d, J=6 Hz, $C_6$—H) 7.32 (5H, s,

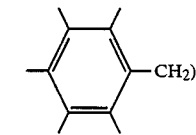

6.91 (2H, d, J=9 Hz,

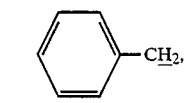

6.25 (1H, t, J=6 Hz, $C_{1'}$—H) 4.55–4.52 (4H, m,

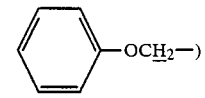

$C_{5'}$—H) 4.45–4.39 (1H, m, $C_{3'}$—H) 4.29–4.15 (1H, m, $C_{4'}$—H) 3.97 (2H, t, J=7 Hz, —$CH_2O$—) 2.74–2.52, 2.16–1.64 (4H, m, $CH_3\underline{C}H_2CH_2$—O—, $C_{2'}$—H) 1.04 (3H, t, J=7 Hz, $C\underline{H}_3CH_2$—).

EXAMPLE 34

3'-O-benzyl-5'-O-phenoxymethylcarbonyl-2'-deoxy-5-fluorouridine ($R^1=C_6H_5CH_2$, $R^2$=phenoxymethylcarbonyl, $R^3$=H)

Yield 90%
M.p.-(oily)
$^1$H-NMR(CDCl$_3$)δ: 10.03 (1H, bs, —NH—, disappeared by addition of D$_2$O) 7.58 (1H, d, J=6 Hz, $C_6$—H) 7.35–6.77 (10H, m, phenyl—H) 6.22 (1H, t, J=6 Hz, $C_{1'}$—H) 4.65 (2H, s,

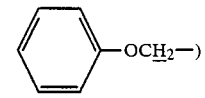

4.42–4.23 (5H, m, $C_{3',5'}$—H,

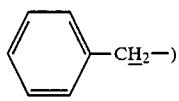

3.97–3.84 (1H, m, $C_{4'}$—H) 2.49–2.23, 1.96–1.65 (1H, m, $C_{2'}$—H)

Example 35

3'-O-benzyl-5'-O-α-naphthylcarbonyl-2'-deoxy-5-fluorouridine ($R^1=C_6H_5CH_2$, $R^2=$α-naphthylcarbonyl, $R^3=H$)

Yield 48%.
M.p. 158°–160° C.
$^1$H-NMR(CDCl$_3$)δ: 9.20 (1H, bs, —NH—, disappeared by addition of D$_2$O) 8.87–8.73 (1H, m, —CO—[naphthyl])

8.10–7.38 (12H, m, C$_6$—H,

[mesityl-CH$_2$, CO—naphthyl])

6.25 (1H, t, J=6 Hz, C$_{1'}$—H) 4.68–4.56 (4H, m, C$_{5'}$—H,

[phenyl-CH$_2$—])

4.45–4.38 (1H, m, C$_{3'}$—H) 4.32–4.18 (1H, m, C$_{4'}$—H) 2.70–2.43, 2.17–1.86 (2H, m, C$_{2'}$—H).

EXAMPLE 36

3'-O-(4-chlorobenzoyl)-5'-O-benzyl-2'-deoxy-5-fluorouridine ($R^1=$4-chlorobenzoyl, $R^2=C_6H_5CH_2$, $R_3=H$)

Yield 57%.
M.p. 215°–217° C.
$^1$H-NMR(DMSO-d$_6$)δ: 11.83 (1H, bs, —NH—, disappeared by addition of D$_2$O) 8.06–7.97 (3H, m, C$_6$—H,

[CO—C$_6$H$_3$(CH$_3$)—Cl])

7.61 (2H, d, J=8 Hz,

[CO—C$_6$H$_3$(CH$_3$)—Cl])

7.35 (5H, s,

[mesityl-CH$_2$—])

6.27 (1H, t, J=6 Hz, C$_{1'}$—H) 5.54–5.47 (1H, m, C$_{3'}$—H) 4.60 (2H, s,

[phenyl-CH$_2$—])

4.42–4.32 (1H, m, C$_{4'}$—H) 3.80–3.71 (2H, m, C$_{5'}$—H) 2.52–2.38 (2H, m, C$_{2'}$—H).

EXAMPLE 37

3'-O-benzyl-5'-O-(3,4,5-trimethoxybenzoyl)-2'-deoxy-5-fluorouridine ($R^1=C_6H_5CH_2$, $R^2=$3,4,5-trimethoxybenzoyl, $R^3=H$)

Yield 63%.
$^1$H-NMR(DMSO-d$_6$)δ: 11.87 (1H, s, —NH—, disappeared by addition of D$_2$O) 7.93 (1H, d, J=7 Hz, C$_6$—H) 7.33 (5H, s,

[mesityl-CH$_2$—])

7.25 (2H, s,

[3,4,5-trimethoxybenzoyl CO—])

6.17 (1H, t, J=7 Hz, C$_{1'}$—H) 4.61–4.35 (6H, m, C$_{3',4',5'}$—H,

[phenyl-CH$_2$—])

3.82, 3.77 (total 9H, each s,

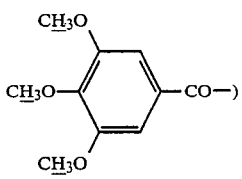

2.54–2.39 (2H, m, C$_{2'}$—H).

Example 38

3'-O-(4-chlorobenzyl)-5'-O-acetyl-2'-deoxy-5-fluorouridine (R$^1$=4-chlorobenzyl, R$^2$=CH$_3$CO, R$^3$=H)

Yield 90%.

$^1$H-NMR(CDCl$_3$)δ: 7.67 (1H, d, J=6 Hz, C$_6$—H) 7.28 (5H, s, phenyl-H) 6.22 (1H, t, J=6 Hz, C$_{1'}$—H) 4.50 (2H, s,

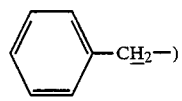

4.40–4.11 (4H, m, C$_{3'.4'.5'}$—H) 2.71–2.46, 2.28–1.93 (5H, m, C$_{2'}$—H, CH$_3$CO—).

EXAMPLE 39

Preparation of
3'-O-benzyl-2'-deoxy-5-fluoro-3-phenoxycarbonyluridine (R$^1$=C$_6$H$_5$CH$_2$, R$^2$=H, R$^3$=phenoxycarbonyl)

To a solution of 0.50 g of 3'-O-benzyl-2'-deoxy-5-fluorouridine in 20 ml of dioxane were added 0.38 ml of trimethylchlorosilane and 1.04 ml of triethylamine, and the mixture was stirred at room temperature for 2 hours. Then, the resulting mixture was left to stand at 60° C. for 30 minutes. To the reaction mixture were added 0.40 g of phenoxycarbonylchloride and 1.00 ml of triethylamine, and the mixture was left to stand at 60° C. for 3 hours. The solvent was distilled off and the residue was dissolved in 50 ml of ethyl acetate. Then, the solution was washed with saturated aqueous solution of sodium chloride. The ethyl acetate layer was separated and concentrated. The residue was dissolved in 30 ml of methanol and 0.5 ml of acetic acid was added thereto. The mixture was left to stand overnight and the resulting mixture was concentrated. The residue was applied to a silica gel column to conduct gradient elution using chloroform and mixtures of methanol (up to 2%) and chloroform, giving 0.58 g of the title compound in a yield of 86%.

M.p. 110°–112° C.

$^1$H-NMR(CDCl$_3$)δ: 8.16 (1H, d, J=7 Hz, C$_6$—H) 7.34–7.22 (10H, m, phenyl—H) 6.27 (1H, t, J=6 Hz, C$_{1'}$—H) 4.49 (2H, s,

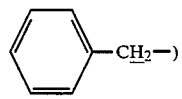

4.26–4.17 (2H, m, C$_{3'.4'}$—H) 3.95–3.60 (2H, m, C$_{5'}$—H) 2.63–1.98 (2H, m, C$_{2'}$—H).

Elementary Analysis: for C$_{23}$H$_{21}$FN$_2$O$_7$: Calcd. (%) C 60.53; H 4.64; N 6.14. Found (%) C 60.60; H 4.72; N 6.08.

EXAMPLE 40

The general procedure of Example 39 was followed, thereby giving the following compound.

3'-O-benzyl-2'-deoxy-3-(4-propoxybenzoyl)-5-fluorouridine (R$^1$=C$_6$H$_5$CH$_2$, R$^2$=H, R$^3$=4-propoxybenzoyl)

Yield 65%

M.p.-(glassy powder)

$^1$H-NMR(CDCl$_3$)δ: 8.19 (1H, d, J=7 Hz, C$_6$—H) 7.85 (2H, d, J=9 Hz,

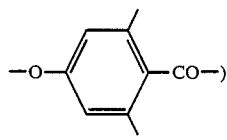

7.27 (5H, s,

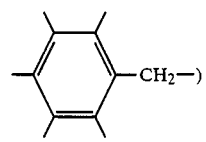

6.90 (2H, d, J=9 Hz,

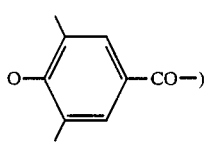

6.25 (1H, t, J=6 Hz, C$_{1'}$—H) 4.44 (2H, s,

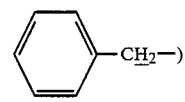

4.20–3.55 (6H, m, C$_{3'.4'.5'}$—H, —CH$_2$CH$_2$O—) 2.57–1.58 (4H, m, C$_{2'}$—H, CH$_3$CH$_2$CH$_2$O—) 0.99 (3H, t, J=7 Hz, CH$_3$CH$_2$—).

EXAMPLE 41

Preparation of
3'-O-benzyl-2'-deoxy-3-benzoyl-5-fluorouridine
(R$^1$=C$_6$H$_5$CH$_2$, R$^2$—H, R$^3$=C$_6$H$_5$CO)

To a solution of 0.50 g of 3'-O-benzyl-2'-deoxy-5-fluorouridine in 20 ml of dioxane were added 0.75 ml of trimethylchlorosilane and 2.00 ml of triethylamine, and the mixture was stirred at room temperature for 2 hours. Then, the resulting mixture was left to stand at 60° C. for 30 minutes. To the reaction mixture was added 0.42 g of benzoyl bromide and 1.00 ml of triethylamine, and the mixture was left to stand at 60° C. for 1 hour. The solvent was distilled off and the residue was dissolved in 50 ml of ethyl acetate. Then, the solution was washed with saturated aqueous solution of sodium chloride. The ethyl acetate layer was separated and concentrated. The residue was dissolved in 30 ml of methanol and 0.5 ml of acetic acid was added thereto. The mixture was left to stand overnight. The solvent was distilled off and the residue was applied to a silica gel column to conduct gradient elution using chloroform and mixtures of methanol (up to 2%) and chloroform, giving 0.35 g of the title compound as a powder in a yield of 54%.

M.p.-(glassy powder).

$^1$H-NMR (CDCl$_3$)δ: 8.19 (1H, d, J=7 Hz, C$_6$—H), 7.94–7.85 (2H, m,

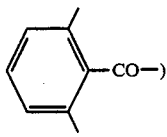

7.64–7.21 (8H, m,

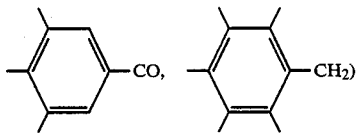

6.24 (1H, J=6 Hz, C$_{1'}$—H) 4.46 (2H, s,

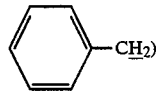

4.24–4.12 (2H, m, C$_{3'.4'}$—H) 3.92–3.56 (2H, m, C$_{5'}$—H) 2.60–1.96 (2H, m, C$_{2'}$—H).

EXAMPLE 42

Preparation of
5'-O-acetyl-3'-O-benzyl-3-benzoyl-2'-deoxy-5-fluorouridine (R$^1$=C$_6$H$_5$CH$_2$, R$^2$=CH$_3$CO, R$^3$=C$_6$H$_5$CO)

To a solution of 0.20 g of 5'-O-acetyl-3'-O-benzyl-2'-deoxy-5-fluorouridine in 10 ml of dioxane were added 0.29 g of benzoyl chloride and 0.73 ml of triethylamine, and the mixture was left to stand at 80° C. for 2 hours. The solvent was distilled off and the residue was dissolved in 50 ml of ethyl acetate. The solution was washed with water. The ethyl acetate layer was dried on anhydrous sodium sulfate and concentrated. The concentrate was placed on a silica gel column and eluted with chloroform, giving 0.2 g of the title compound as an oil in a yield of 78%.

$^1$H-NMR(CDCl$_3$)δ: 7.95–7.27 (11H, m, phenyl—H, C$_6$—H) 6.20 (1H, t, J=6 Hz, C$_{1'}$—H) 4.45 (2H, s,

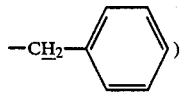

4.23∝4.08 (4H, m, C$_{3'.4'.5'}$—H) 2.60–2.05 (5H, m, C$_{2'}$—H, COCH$_3$).

Elementary Analysis: for C$_{25}$H$_{23}$FN$_2$O$_7$: Calcd. (%) C 62.24; H 4.80; N 5.81. Found (%) C 62.34; H 5.06; N 5.77.

EXAMPLES 43–53

The general procedure of Example 42 was followed, thereby giving the following compounds.

EXAMPLE 43

3'-O-benzyl-5'-O-acetyl-2'-deoxy-3-(4-propoxybenzoyl)-5-fluorouridine (R$^1$=C$_6$H$_5$CH$_2$, R$^2$—CH$_3$CO, R$^3$=4-propoxybenzoyl)

Yield 38%.
M.p.-(oily).
$^1$H-NMR(CDCl$_3$)δ: 7.85 (2H, d, J=9 Hz,

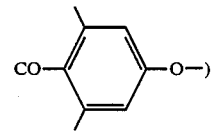

7.75 (1H, d, J=7 Hz, C$_6$—H) 7.30 (5H, s,

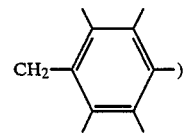

6.92 (2H, d, J=9 Hz,

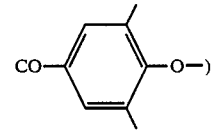

6.20 (1H, t, J=6 Hz, C$_{1'}$—H) 4.45 (2H, s,

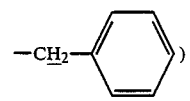

4.23–4.08 (4H, m, C$_{3'.4'.5'}$—H) 3.96 (2H, t, J=6 Hz, —OCH$_2$CH$_2$CH$_3$) 2.70–1.68 (7H, m, C$_{2'}$—H, COCH$_3$, —OCH$_2$CH$_2$CH$_3$) 1.01 (3H, t, J=7 Hz, —O(CH$_2$)$_2$CH$_3$).

Example 44

3'-O-benzyl-5'-O-acetyl-2'-deoxy-3-(4-chlorobenzoyl)-5-fluorouridine (R$^1$=C$_6$H$_5$CH$_2$, R$^2$=CH$_3$CO, R$^3$=4-chlorobenzoyl)

Yield 73%
M.p.-(oily)
$^1$H-NMR (CDCl$_3$)δ: 7.84 (2H, d, J=9 Hz),

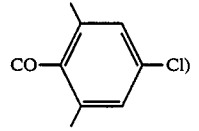

7.78 (1H, d, J=6 Hz, C$_6$—H) 7.44 (2H, d, J=9 Hz,

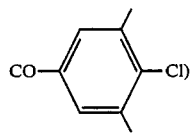

7.30 (5H, s,

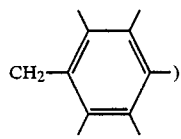

6.20 (1H, t, J=6 Hz, C$_{1'}$—H) 4.51 (2H, d, J=1 Hz,

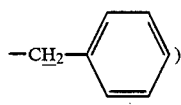

4.28–4.08 (4H, m, C$_{3'.4'.5'}$—H) 2.70–2.43, 2.25–2.03 (5H, m, C$_{2'}$—H, COCH$_3$).

Example 45

3'-O-benzyl-5'-O-acetyl-2'-deoxy-3-(2-methylbenzoyl)-5-fluorouridine (R$^1$=C$_6$H$_5$CH$_2$, R$^2$=CH$_3$CO, R$^3$=2-methylbenzoyl)

Yield 44%

M.p.-(oily)

$^1$H-NMR(CDCl$_3$)δ: 7.62–7.32 (10H, m, C$_6$—H, phenyl—H) 6.19 (1H, t, J=7 Hz, C$_{1'}$—H) 4.47 (2H, d, J=1 Hz,

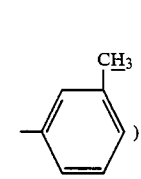

4.25–4.07 (4H, m, C$_{3'.4'.5'}$—H)
2.67–2.00 (8H, m, C$_{2'}$—H, COCH$_3$,

Example 46

3'-O-benzyl-5'-O-acetyl-2'-deoxy-3-(3-methylbenzoyl)-5-fluorouridine (R$^1$=C$_6$H$_5$CH$_2$, R$^2$=CH$_3$CO, R$^3$=3-methylbenzoyl)

Yield 68%.

M.p.-(oily).

$^1$H-NMR(CDCl$_3$)δ: 7.81–7.65 (3H, m, c$_6$—H,

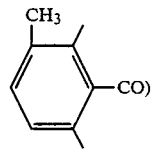

7.47–7.16 (7H, m,

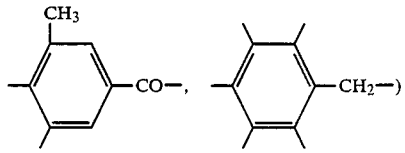

6.20 (1H, t, J=6 Hz, C$_{1'}$—H) 4.46 (2H, s,

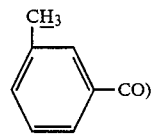

4.25–4.08 (4H, m, C$_{3'.4'.5'}$—H) 2.67–2.00 (8H, m, C$_{2'}$—H, COCH$_3$,

Example 47

3'-O-benzyl-5'-acetyl-2'-deoxy-3-(4-methylbenzoyl)-5-fluorouridine (R$^1$=C$_6$H$_5$CH$_2$, R$^2$=CH$_3$CO, R$^3$=4-methylbenzoyl)

Yield 84%.

M.p.-(oily).

$^1$H-NMR(CDCl$_3$)δ: 7.79 (2H, d, J=8 Hz,

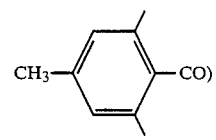

7.78 (1H, d, J=7 Hz, C$_6$—H) 7.27 (5H, s,

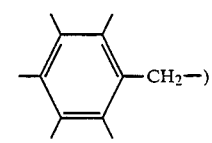

7.22 (2H, d, J=8 Hz,

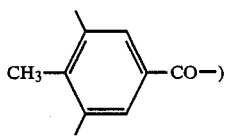

6.20 (1H, t, J=6 Hz, C$_{1'}$—H) 4.45 (2H, s,

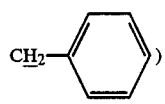

4.24–4.08 (4H, m, C$_{3'.4'.5'}$—H) 2.60–2.05 (8H, m, C$_{2'}$—H, COCH$_3$,

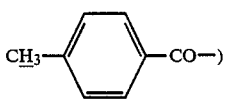

Example 48

3'-O-benzyl-5'-O-acetyl-2'-deoxy-3-(4-methoxybenzoyl)-5-fluorouridine (R$^1$=C$_6$H$_5$CH$_2$, R$^2$=CH$_3$CO, R$^3$=4-methoxybenzoyl Yield 70%.
M.p.-(powder).
$^1$H-NMR(CDCl$_3$)δ: 7.85 (2H, d, J=8 Hz,

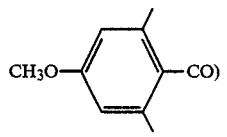

7.77 (1H, d, J=7 Hz, C$_6$—H) 7.28 (5H, s,

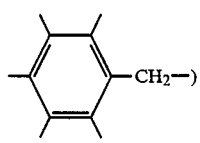

6.91 (2H, d, J=8 Hz,

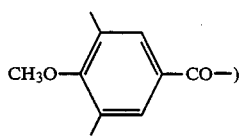

6.21 (1H, t, J=6 Hz, C$_{1'}$—H) 4.47 (2H, s,

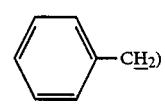

4.25–4.09 (4H, m, C$_{3'.4'.5'}$—H) 3.80 (3H, s, CH$_3$O—) 2.49–2.07 (5H, m, C$_{2'}$—H, COCH$_3$).

Example 49

3'-O-benzyl-5'-O-benzoyl-2'-deoxy-3-benzoyl-5-fluorouridine (R$^1$=C$_6$H$_5$CH$_2$, R$^2$=R$^3$=C$_6$H$_5$CO)

Yield 94%
M.p.-(oily).
$^1$H-NMR(CDCl$_3$)δ: 8.03–7.32 (16H, m, phenyl—H, C$_6$—H) 6.20 (1H, t, J=6 Hz, C$_{1'}$—H) 4.48–4.16 (6H, m, C$_{3'.4'.5'}$—H,

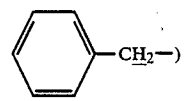

2.70–2.42, 2.25–1.95 (2H, m, C$_{2'}$—H).

Example 50

3'-O-benzyl-5'-O-phenoxycarbonyl-2'-deoxy-3-phenoxycarbonyl-5-fluorouridine (R$^1$=C$_6$H$_5$CH$_2$, R$^2$=R$^3$=phenoxycarbonyl)

Yield 48%.
M.p.-(oily).
$^1$H-NMR(DMSO-d$_6$)δ: 8.21 (1H, d, J=7 Hz, C$_6$—H) 7.57–7.16 (15H, m, phenyl—H) 6.20 (1H, t, J=7 Hz, C$_{1'}$—H) 4.59–4.28 (6H, m, C$_{3'.4'.5'}$—H,

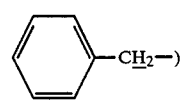

2.54–2.38 (2H, m, C$_{2'}$—H).

Example 51

3'-O-benzyl-5'-O-α-naphthylcarbonyl-2'-deoxy-3-α-naphthylcarbonyl-5-fluorouridine (R$^1$=C$_6$H$_5$CH$_2$, R$^2$=R$^3$=α-naphthylcarbonyl)

Yield 29%.
M.p.-(oily).
$^1$H-NMR(CDCl$_3$)δ: 9.11–8.79 (2H, m,

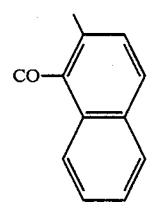

×2) 8.11–7.19 (13H, m,

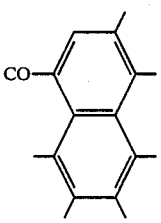

×2, C$_6$—H) 6.20 (1H, t, J=7 Hz, C$_{1'}$—H) 4.71–4.10 (6H, m, C$_{3'.4'.5'}$—H,

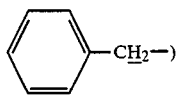

2.64–2.36, 2.15–1.85 (2H, m, C$_{2'}$—H).

Example 52

3'-O-benzyl-5'-O-(3-methoxybenzoyl)-2'-deoxy-3-(3-methylbenzoyl)-5-fluorouridine (R$^1$=C$_6$H$_5$CH$_2$, R$^2$=R$^3$=3-methylbenzoyl)

Yield 18%
M.p.-(oily)
$^1$H-NMR(CDCl$_3$)δ: 7.81–7.62 (5H, m,

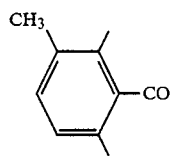

×2, C$_6$—H) 7.43–7.24 (9H, m,

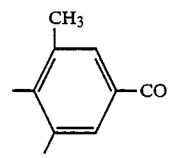

×2,

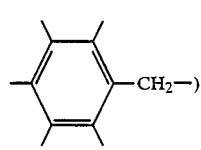

6.23 (1H, t, J=6 Hz, C$_{1'}$—H) 4.60–4.20 (6H, m, C$_{3'.4'.5'}$—H,

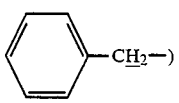

2.78–2.50, 2.24–1.93 (2H, m, C$_{2'}$—H) 2.39, 2.37 (each s, 3H,

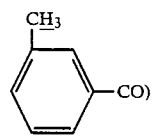

Example 53

3'-O-benzyl-5'-O-acetyl-2'-deoxy-3-hexanoyl-5-fluorouridine (R$^1$=C$_6$H$_5$CH$_2$, R$^2$=CH$_3$CO, R$^3$=hexanoyl)

Yield 48%
M.p.-(oily)

$^1$H-NMR(CDCl$_3$)δ: 7.66 (1H, d, J=6 Hz, C$_6$—H) 7.32 (5H, s, phenyl—H) 6.20 (1H, t, J=6 Hz, C$_{1'}$—H) 4.54 (2H, s,

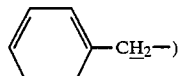

4.38–4.07 (4H, m, C$_{3'.4'.5'}$—H) 2.82 (2H, t, J=9 Hz, —CH$_2$—CO—) 2.59–2.44, 2.22–2.02 (5H, m, C$_{2'}$—H and CH$_3$CO—) 1.92–1.67 (2H, m, —CH$_2$CH$_2$CO—) 1.56–1.22 (4H, m, CH$_3$CH$_2$CH$_2$CH$_2$CH$_2$CO—) 0.90 (3H, t, J=5 Hz, CH$_3$CH$_2$)

EXAMPLE 54

Preparation of
3'-O-benzyl-5'-O-acetyl-2'-deoxy-5-fluorouridine
(R$^1$=C$_6$H$_5$CH$_2$, R$^2$=CH$_3$CO, R$^3$=H)

A 3.33 ml quantity of acetic anhydride was added to a solution of 3.95 g of 3'-O-benzyl-2'-deoxy-5-fluorouridine in 30 ml of pyridine, and the mixture was left to stand at 40° C. overnight. The solvent was distilled off and the residue was dissolved in 30 ml of ethyl acetate. The solution was washed twice with 15 ml of water. The ethyl acetate layer was dried on anhydrous sodium sulfate and concentrated. The concentrate was placed on a silica gel column and eluted with chloroform, giving 3.62 g of the title compound in a yield of 81.5%.
M.p. 87°–88° C.
$^1$H-NMR(DMSO-d$_6$)δ: 11.86 (1H, d, J=4 Hz, —NH—, disappeared by addition of D$_2$O) 7.93 (1H, d, J=7 Hz, C$_6$—H) 7.35 (5H, s, phenyl—H) 6.15 (1H, t, J=6 Hz, C$_{1'}$—H) 4.55 (2H, s,

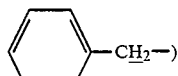

4.32–4.20 (4H, m, C$_{3'.4'.5'}$—H) 2.39–2.28 (2H, t, J=6 Hz, C$_{2'}$—H) 2.04 (3H, s, COCH$_3$).

Elementary Analysis: for C$_{18}$H$_{19}$FN$_2$O$_6$: Calcd. (%) C 57.14; H 5.06; N 7.40. Found (%) C 56.99; H 5.22; N 7.37.

EXAMPLE 55

Preparation of
3'-O-acetyl-5'-O-benzyl-2'-deoxy-5-fluorouridine
(R$^1$=CH$_3$CO, R$^2$=C$_6$H$_5$CH$_2$, R$^3$=H)

Following the general procedure of Example 54 and using 1.00 g of 5'-O-benzyl-2'-deoxy-5-fluorouridine, 1.00 g of the title compound was prepared in a yield of 88.9%.
M.p. 114°–116° C.
$^1$H-NMR(DMSO-d$_6$)δ: 11.85 (1H, bs, —NH—, disappeared by addition of D$_2$O) 7.95 (1H, d, J=7 Hz, C$_6$—H) 7.34 (5H, s, phenyl—H) 6.17 (1H, t, J=6 Hz, C$_{1'}$—H) 5.25–5.23 (1H, m, C$_{3'}$—H) 4.57 (2H, s,

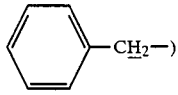

4.32–4.20 (1H, m, C$_{4'}$—H) 3.84–3.73 (2H, m, C$_{5'}$—H) 2.37–2.25 (2H, m, C$_{2'}$—H) 2.06 (3H, s, COCH$_3$).

Elementary Analysis: for $C_{18}H_{19}FN_2O_6$: Calcd. (%) C 57.14; H 5.06; N 7.40. Found (%) C 56.91; H 5.32; N 7.25.

EXAMPLE 56

Preparation of 3'-O-benzyl-5'-O-chloroacetyl-2'-deoxy-5-fluorouridine ($R^1=C_6H_5CH_2$, $R^2=CH_2Cl-CO$, $R^3-H$)

Chloroacetic anhydride was added to a solution of 0.20 g of 3'-O-benzyl-2'-deoxy-5-fluorouridine in 10 ml of pyridine, and the mixture was left to stand at room temperature overnight. Then the same subsequent procedures as in Example 54 were conducted, giving 0.11 g of the title compound as an oil in a yield of 45%.

$^1$H-NMR (CDCl$_3$)δ: 10.22 (1H, bs, —NH—, disappeared by addition of D$_2$O) 7.60 (1H, d, J=6 Hz, C$_6$—H) 7.32 (5H, s, phenyl—H) 6.23 (1H, t, J=6 Hz, C$_{1'}$—H) 4.53 (2H, d, J=3 Hz,

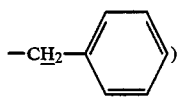

4.45–4.08 (6H, m, C$_{3',4',5'}$—H, ClCH$_2$CO—) 2.69–2.06 (2H, m, C$_{2'}$—H)

Elementary Analysis: for $C_{18}H_{18}ClFN_2O_6$: Calcd. (%) C 52.37; H 4.39; N 6.79. Found (%) C 52.43; H 4.63; N 6.80.

EXAMPLE 57

Preparation of 3'-O-benzyl-2'-deoxy-3-(2-tetrahydrofuranyl)-5-fluorouridine ($R^1=C_6H_5CH_2$, $R^2=H$, $R^3=$2-tetrahydrofuranyl)

Following the general procedure of Reference Example 2 and using 0.40 g of 3'-O-benzyl-2'-deoxy-5-fluorouridine, 0.37 g of the title compound was prepared as an oil in a yield of 77%.

$^1$H-NMR (CDCl$_3$)δ: 8.01 (1H, d, J=6 Hz, C$_6$—H) 7.30 (5H, s, phenyl—H) 6.58 (1H, bt, J=6 Hz,

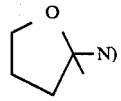

6.26 (1H, bt, J=6 Hz, C$_{1'}$—H) 4.51 (2H, s,

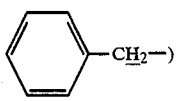

4.39–3.50 (7H, m, C$_{3',4',5'}$—H, C$_{6'}$—OH,

2.60–1.86 (6H, m, C$_{2'}$—H,

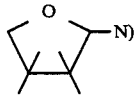

Elementary Analysis: for $C_{20}H_{23}FN_2O_6$: Calcd (%) C 59.11; H, 5.70; N 6.80. Found (%) C 59.02; H, 6.11; N 6.78.

EXAMPLE 58

Preparation of 5'-O-acetyl-3'-O-benzyl-2'-deoxy-5-fluoro-3-[3-(2-hydroxy-4-pyridyloxycarbonyl)benzoyl]uridine To a solution of 3.00 g of 5'-O-acetyl-3'-O-benzyl-2'-deoxy-5-fluorouridine in 100 ml of dry dioxane were added 2.40 g of isophthaloyl chloride and 8.5 ml of triethylamine, and the mixture was refluxed for 2 hours. Then, to the reaction mixture were added a suspension of 1.77 g of 4-hydroxy-2(1H)-pyridone and 9.60 ml of triethylamine in 100 ml of dry dioxane, and the mixture was refluxed for 2 hours. The insolubles were removed by filtration and the filtrate was concentrated. The residue was dissolved in 100 ml of ethyl acetate, and the solution was washed twice with 30 ml of saturated aqueous solution of sodium chloride. The ethyl acetate layer was dried on anhydrous sodium sulfate and concentrated. The residue was placed on a silica gel column to conduct a gradient elution using chloroform and mixtures of methanol (up to 2%) and chloroform. The fractions corresponding to the title compound were collected and concentrated to dryness, giving 1.48 g of the title compound as a powder in a yield of 30%.

$^1$H-NMR (CDCl$_3$)δ:

8.62–7.31 (11H, m, phenyl—H, C$_6$—H and C$_6$—H of the pyridine ring) 6.50 (1H, d, J=2 Hz, C$_3$—H of the pyridine ring) 6.31 (1H, dd, J$_{5-6}$=7 Hz, J$_{3-5}$=2 Hz, C$_5$—H of the pyridine ring) 6.23 (1H, coalesced in part with the signal of C$_5$—H of the pyridine ring, C$_{1'}$—H) 4.52 (2H, d,

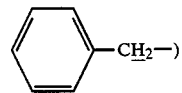

4.30–4.13 (4H, m, C$_{3',4',5'}$—H) 2.53–2.06 (5H, m, C$_{2'}$—H and COCH$_3$).

EXAMPLE 59

Preparation of 5'-O-acetyl-3'-O-benzyl-3-[3-(5-chloro-4-hydroxy-2-pyridyloxycarbonyl)benzoyl]-2'-deoxy-5-fluorouridine To a solution of 1.00 g of 5'-O-acetyl-3'-O-benzyl-2'-deoxy-5-fluorouridine in 50 ml of dry dioxane were added 0.80 g of isophthaloyl chloride and 2.95 ml of triethylamine, and the mixture was reflux for 2 hours. The insolubles were removed by filtration and the filtrate was concentrated. The residue was dissolved in 50 ml of dry dichloromethane. To the solution was added 1.35 g of 2,4-bis(trimethylsilyloxy)-5-chloropyridine, and the mixture was stirred at room temperature overnight. The solvent was distilled off and the residue was dissolved in 50 ml of ethyl acetate. The solution was washed three times with saturated aqueous solution of hydrogencarbonate and washed three times with saturated aqueous solution of sodium chloride. The ethyl acetate layer was dried on anhydrous sodium sulfate and concentrated. The residue was placed on a silica gel column to conduct a gradient elution using chloroform and mixtures of methanol (up to 1%) and chloroform. The fractions corresponding to the title compound were collected and concentrated to dryness, giving 0.30 g of the title compound in a yield of 17% as a powder.

$^1$H-NMR (CDCl$_3$)δ: 8.61–7.31 (11H, m, phenyl—H, C$_6$—H and C$_6$—H of the pyridine ring) 6.82 (1H, s, C$_3$—H of the pyridine ring) 6.19 (1H, t, J=6 Hz, C$_{1'}$—H) 4.52 (2H, d,

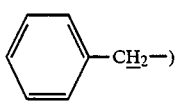

4.29–3.95 (4H, m, C$_{3'.4'.5'}$—H) 2.74–2.10 (5H, m, C$_{2'}$—H and COC$\underline{H}_3$).

EXAMPLE 60

Preparation of 5′-O-acetyl-3′-O-benzyl-2′-deoxy-3-[3-(1,2-dihydro-2-oxo-1-(2-tetrahydrofuranyl)-4-pyridyloxycarbonyl)benzoyl]-5-fluorouridine Following the general procedure of Example 58 and using 4-hydroxy-1-(2-tetrahydrofuranyl)-2(1H)-pyridone in place of the 4-hydroxy-2(1H)-pyridone, the title compound was prepared as a powder in a yield of 41%.

$^1$H-NMR (CDCl$_3$)δ: 8.61–7.65 (5H, m,

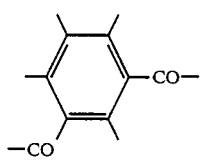

and C$_6$—H) 7.53 (1H, d, J=8 Hz, C$_6$—H of the pyridine ring) 7.29 (5H, s,

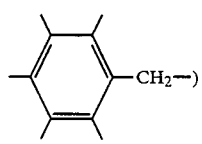

6.40 (1H, d, J=2 Hz, C$_3$—H of the pyridine ring) 6.27–6.12 (3H, m, C$_{1'}$—H,

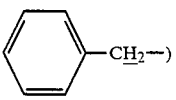

and C$_5$—H of the pyridine ring) 4.50 (2H, s,

4.27–3.92 (6H, m, C$_{3'.4'.5'}$—H and

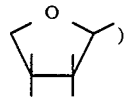

2.50–1.98 (9H, m, C$_{2'}$—H, COC$\underline{H}_3$ and

EXAMPLE 61

Preparation of 5′-O-acetyl-3′-O-benzyl-3-[3-(5-chloro-1,2-dihydro-2-oxo-1-(2-tetrahydrofuranyl)-4-pyridyloxycarbonyl)benzoyl]-2′-deoxy-5-fluorouridine Following the general procedure of Example 58 and using 3-chloro-4-hydroxy-1-(2-tetrahydrofuranyl)-2(1H)-pyridone in place of 4-hydroxy-2(1H)-pyridone, the title compound was prepared as a powder in a yield of 72%.

$^1$H-NMR (CDCl$_3$)δ: 8.93–7.58 (6H, m, C$_6$—H, C$_6$—H of the pyridine ring and

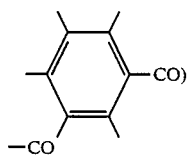

7.21 (5H, s,

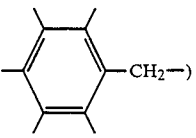

6.58 (1H, s, C$_3$—H of the pyridine ring) 6.20–6.08 (2H, m, C$_{1'}$—H and

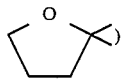

4.50 (2H, s,

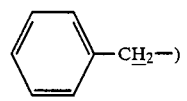

4.36–3.97 (6H, m, C$_{3'.4'.5'}$—H and

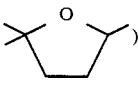

2.55–1.92 (9H, m, C$_{2'}$—H, COC$\underline{H}_3$ and

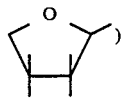

EXAMPLE 62

Preparation of
5′-O-acetyl-3′-O-benzyl-2′-deoxy-5-fluoro-3-[3-(1,2-dihydro-1-ethoxymethyl-2-oxo-4-pyridyloxycarbonyl)-benzoyl]uridine Following the general procedure of Example 58 and using 1-ethoxymethyl-4-hydroxy-2(1H)-pyridone in place of 4-hydroxy-2(1H)-pyridone, the title compound was prepared in a yield of 32% as a powder.

$^1$H-NMR (CDCl$_3$)δ: 8.70–7.31 (11H, m, phenyl—H, C$_6$—H and C$_6$—H of the pyridine ring) 6.47 (1H, bs, C$_3$—H of the pyridine ring) 6.20–6.10 (2H, m, C$_{1'}$—H and C$_5$—H of the pyridine ring) 5.36 (2H, s, N—C$\underline{H}$$_2$OC$_2$H$_5$) 4.52–4.00 (6H, m, C$_{3'.4'.5'}$—H and

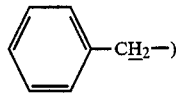

3.63 (2H, q, J=7 Hz, —OC$\underline{H}$$_2$CH$_3$) 2.80–1.90 (5H, m, C$_{2'}$—H and COC$\underline{H}$$_3$) 1.22 (3H, t, J=7 Hz, —OCH$_2$C$\underline{H}$$_3$).

EXAMPLE 63

Preparation of
5′-O-acetyl-3′-O-benzyl-3-[3-(5-chloro-1,2-dihydro-1-ethoxymethyl-2-oxo-4-pyridyloxycarbonyl)benzoyl]-2′-deoxy-5-fluorouridine Following the general procedure of Example 58 and using 5-chloro-1-ethoxymethyl-4-hydroxy-2(1H)-pyridone in place of 4-hydroxy-2(1H)-pyridone, the title compound was prepared in a yield of 20% as a powder.

$^1$H-NMR (CDCl$_3$)δ: 8.66–7.68 (5H, m, C$_6$—H and

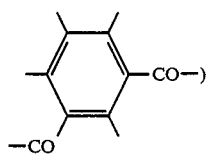

7.59 (1H, s, C$_6$—H of the pyridine ring) 7.30 (5H, s,

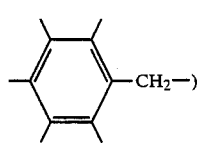

6.64 (1H, s, C$_3$—H of the pyridine ring) 6.21 (1H, t, J=6 Hz, C$_{1'}$—H) 5.31 (2H, s, N—C$\underline{H}$$_2$OC$_2$H$_5$) 4.50 (2H, s,

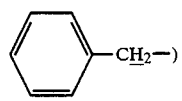

4.28–4.06 (4H, m, C$_{3'.4'.5'}$—H) 3.63 (2H, q, J=7 Hz, —OC$\underline{H}$$_2$CH$_3$) 2.58–2.02 (5H, m, C$_{2'}$—H and COC$\underline{H}$$_3$) 1.22 (3H, t, J=7 Hz, —OCH$_2$C$\underline{H}$$_3$).

EXAMPLE 64

Preparation of
5′-O-acetyl-3-[3-(2-benzoyloxy-5-chloro-4-pyridyloxycarbonyl)benzoyl]-3′-O-benzyl-2′-deoxy-5-fluorouridine Following the general procedure of Example 58 and using 2-benzoyloxy-5-chloro-4-hydroxypyridine in place of 4-hydroxy-2(1H)-pyridone, the title compound was prepared in a yield of 27% as a powder.

$^1$H-NMR (CDCl$_3$)δ: 8.68–7.41 (12H, m, C$_6$—H, C$_{3.6}$—H of the pyridine ring,

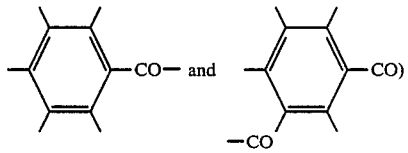

7.28 (5H, s,

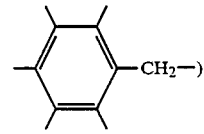

6.20 (1H, t, J=6 Hz, C$_{1'}$—H) 4.49 (2H, s,

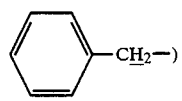

4.27–4.04 (4H, m, C$_{3'.4'.5'}$—H) 2.70–2.07 (5H, m, C$_{2'}$—H and COC$\underline{H}$$_3$).

EXAMPLE 65

Preparation of
5′-O-acetyl-3′-O-benzyl-2′-deoxy-3-[3-(1,2-dihydro-1-carbomethoxymethylcarbamoyl-2-oxo-4-pyridyloxycarbonyl)benzoyl]-5-fluorouridine The general procedure of Example 58 was followed using 4-hydroxy-1-carbomethoxymethylcarbamoyl-2(1H)-pyridone in place of the 4-hydroxy-2(1H)-pyridone, thereby giving the title compound as a powder in a yield of 5.7%.

$^1$H-NMR CDCl$_3$)δ: 10.86 (1H, t, J=6 Hz, —CONHCH$_2$—) 8.61–7.60 (6H, m, C$_6$—H,

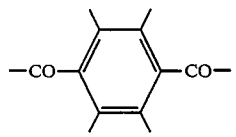

and C$_6$—H of the pyridine ring) 7.31 (5H, s,

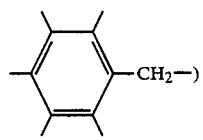

6.62 (1H, d, J=2 Hz, C$_3$—H of the pyridine ring) 6.44–6.14 (2H, m, C$_{1'}$—H and C$_{5}$—H of the pyridine ring) 4.52 (2H, d,

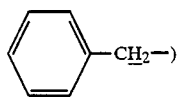

4.30–4.00 (6H, m, C$_{3'.4'.5'}$—H and —NHCH$_2$COOCH$_3$) 3.78 (3H, s, —COOC$\underline{H}_3$) 2.76–1.92 (5H, m, C$_{2'}$—H and COC$\underline{H}_3$).

EXAMPLE 66

Preparation of 5'-O-acetyl-3'-O-benzyl-3-[4-[5-chloro-1,2-dihydro-2-oxo-1-(2-tetrahydrofuranyl)-4-pyridyloxycarbonyl]benzoyl]-2'-deoxy-5-fluorouridine The general procedure of Example 58 was followed using terephthaloyl chloride in place of isophthaloyl chloride and using 5-chloro-4-hydroxy-1-(2-tetrahydrofuranyl)-2(1H)-pyridone in place of 4-hydroxy-2(1H)-pyridone, thereby producing the title compound as a powder in a yield of 38%.

$^1$H-NMR (DMSO-d$_6$)δ: 8.50–8.20 (5H, m, C$_6$—H and

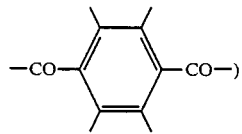

7.93 (1H, s, C$_6$—H of the pyridine ring) 7.34 (5H, s,

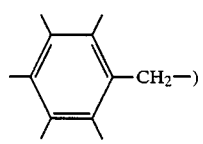

6.66 (1H, s, C$_3$—H of the pyridine ring) 6.20–6.10 (2H, m, C$_{1'}$—H and

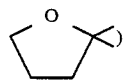

4.55–3.70 (8H, m, C$_{3'.4'.5'}$—H,

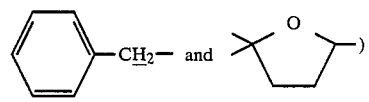

2.60–1.80 (9H, m, C$_{2'}$—H,

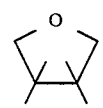

and COC$\underline{H}_3$).

EXAMPLE 67

Preparation of 3-benzoyl-3'-O-benzyl-5'-O-[3-(5-chloro-4-hydroxy-2-pyridyloxycarbonyl)benzoyl]-2'-deoxy-5-fluorouridine The general procedure of Example 59 was followed using 3-benzoyl-3'-O-benzyl-2'-deoxy-5-fluorouridine in place of 5'-O-acetyl-3'-O-benzyl-2'-deoxy-5-fluorouridine, thereby producing the title compound as a powder in a yield of 15%.

$^1$H-NMR (CDCl$_3$)δ: 8.73–7.34 (11H, m, C$_6$—H,

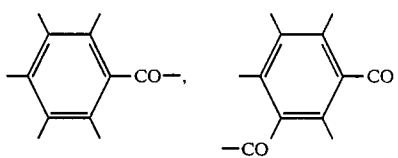

and C$_6$—H of the pyridine ring) 7.28 (5H, s,

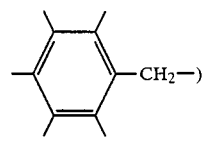

6.77 (1H, s, C$_3$—H of the pyridine ring) 6.21 (1H, t, J=7 Hz, C$_{1'}$—H) 4.70–4.20 (6H, m, C$_{3'.4'.5'}$—H and

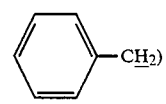

2.60–2.13 (2H, m, C$_{2'}$—H).

EXAMPLE 68

Preparation of 3-benzoyl-3'-O-benzyl-5'-O-[3-[5-chloro-1,2-dihydro-2-oxo-1-(2-tetrahydrofuranyl)-4-pyridyloxycarbonyl]benzoyl]-2'-deoxy-5-fluorouridine The general procedure of Example 58 was followed using 3-benzoyl-3'-O-benzyl-2'-deoxy-5-fluorouridine in place of 5'-O-acetyl-3'-O-benzyl-2'-deoxy-5-fluorouridine and using 5-chloro-4-hydroxy-1-(2-tetrahydrofuranyl)-2(1H)-pyridone in place of 4-hydroxy-2(1H)-pyridone, thereby producing the title compound as a powder in a yield of 46%.

$^1$H-NMR (CDCl$_3$)δ: 8.77–7.34 (11H, m, C$_6$—H,

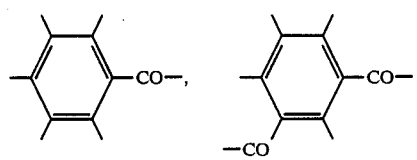

and C$_6$—H of the pyridine ring) 7.26 (5H, s,

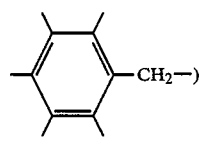

6.57(1H, s, C$_3$—H of the pyridine ring) 6.21–6.06 (2H, m, C$_1'$—H and

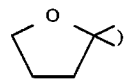

4.53 (2H, s,

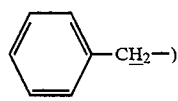

4.53–4.02 (6H, m, C$_{3',4',5'}$—H and

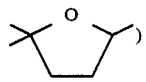

2.55–1.96 (6H, m, C$_{2'}$—H and

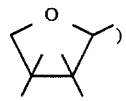

EXAMPLE 69

Preparation of 5'-O-acetyl-3'-O-benzyl-2'-deoxy-3-[3-(1,2-dihydro-2-oxo-1-phthalidyl-4-pyridyloxycarbonyl)benzoyl]-5-fluorouridine The general procedure of Example 58 was followed using 4-hydroxy-1-phthalidyl-2(1H)-pyridone in place of 4-hydroxy-2(1H)-pyridone, thereby producing the title compound in a yield of 19%.

$^1$H-NMR (CDCl$_3$)δ: 8.60–7.57 (10H, m, C$_6$—H,

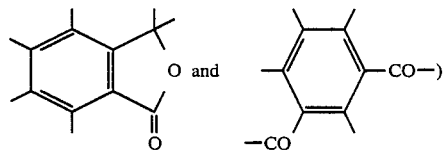

7.32 (5H, s,

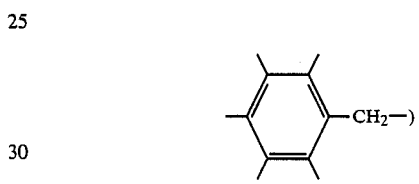

6.90 (1H, d, J=8 Hz, C$_6$—H of the pyridine ring) 6.60 (1H, d, J=2 Hz, C$_3$—H of the pyridine ring) 6.28–6.04 (2H, m, C$_1'$—H and C$_5$—H of the pyridine ring) 4.51 (2H, s,

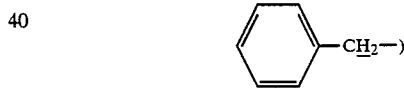

4.28–4.06 (4H, m, C$_{3',4',5'}$—H) 2.60–2.01 (5H, m, C$_{2'}$—H and COC$\underline{H}_3$).

EXAMPLE 70

Preparation of 5'-O-acetyl-3'-O-benzyl-3-(3-carbomethoxybenzoyl)-2'-deoxy-5-fluorouridine The general procedure of Example 58 was followed using methanol in place of 4-hydroxy-2(1H)-pyridone, thereby giving the title compound as a powder in a yield of 69%.

$^1$H-NMR (CDCl$_3$)δ: 8.54–7.47 (5H, m, C$_6$—H and

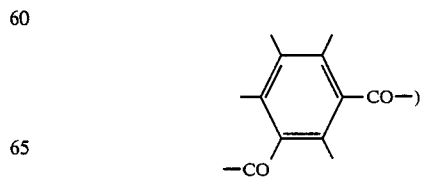

7.28 (5H, s, 6.20 (1H, t, J=6 Hz, C$_{1'}$—H) 4.50 (2H, s,

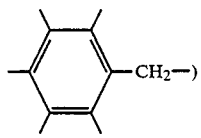

4.48–4.13 (4H, m, C$_{3'.4'.5'}$—H) 3.89 (3H, s, —COOCH$_3$) 2.50–1.93 (5H, m, C$_{2'}$—H and COCH$_3$).

EXAMPLE 71

Preparation of 5'-O-acetyl-3'-O-benzyl-3-[3-(1-benzyloxymethyl-5-chloro-1,2-dihydro-2-oxo-4-pyridyloxycarbonyl)benzoyl]-2'-deoxy-5-fluorouridine The general procedure of Example 58 was followed using 1-benzyloxymethyl-5-chloro-4-hydroxy2(1H)-pyridone in place of 4-hydroxy-2(1H)-pyridone, thereby producing the title compound as a powder in a yield of 34%.

$^1$H-NMR(CDCl$_3$)δ: 8.65–7.58 (6H, m, C$_3$—H,

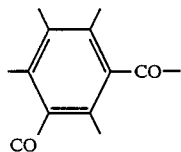

and C$_6$—H of the pyridine ring 7.34 (10H, s,

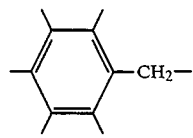

×2) 6.64 (1H, s, C$_3$—H of the pyridine ring) 6.22 (1H, t, J=7 Hz, C$_{1'}$—H) 5.42 (2H, s, —NCH$_2$O—) 4.66 (2H, s,

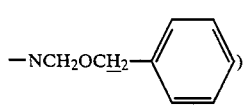

4.53 (2H, s, C$_3$,

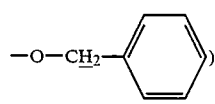

4.30–4.03 (4H, m, C$_{3'.4'.5'}$—H) 2.77–1.97 (5H, m, C$_{2'}$—H and COCH$_3$).

EXAMPLE 72

Preparation of 5'-O-acetyl-3-[3-(2-acetoxy-5-chloro-4-pyridyloxycarbonyl)benzoyl]-3'-O-benzyl-2'-deoxy-5-fluorouridine To a solution of 2.00 g of 5'-O-acetyl-3'-O-benzyl-2'-deoxy-5-fluorouridine in 100 ml of dry dioxane were added 1.60 g of isophthaloyl chloride and 1.47 ml of triethylamine, and the mixture was refluxed for 30 minutes. Then 4.40 ml of triethylamine was further added and the mixture was refluxed for 50 minutes. The salt formed was filtered off and the filtrate was concentrated under reduced pressure. The concentrate was dissolved in 100 ml of acetonitrile. To the solution were added 3.66 ml of triethylamine and 1.19 g of 2-acetoxy-5-chloro-4-hydroxypyridine, and the resulting mixture was stirred at room temperature for 1.5 hours. The solvent was distilled off and the residue was subjected to a silica gel column chromatography. The fractions corresponding to the title compound were collected and evaporated to dryness, giving 2.83 g of the title compound as a powder in a yield 77%.

$^1$H-NMR(CDCl$_3$)δ: 8.68 (6H, m, C$_6$—H, C$_6$—H of the pyridine ring and

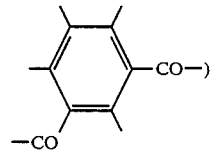

7.30 (5H, s,

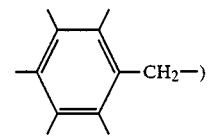

7.27 (1H, s, C$_3$—H of the pyridine ring) 6.20 (1H, t, J=6 Hz, C$_{1'}$—H) 4.51 (2H, d,

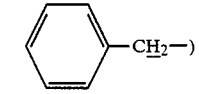

4.25–4.07 (4H, m, C$_{3'.4'.5'}$—H) 2.60–2.20 (5H, m, C$_{2'}$—H and —COCH$_3$ on the pyridine ring) 2.09 (3H, s, —COCH$_3$ at the 5'-position).

EXAMPLE 73

Preparation of 5'-O-acetyl-3-[3-(4-benzoyloxy-5-chloro-2-pyridyloxycarbonyl)benzoyl]-3'-O-benzyl-2'-deoxy-5-fluorouridine To a solution of 0.60 g of 5'-O-acetyl-3'-O-benzyl-2'-deoxy-5-fluorouridine in 30 ml of dry dioxane were added 0.42 g of isophthaloyl chloride and 1.11 ml of triethylamine, and the mixture was refluxed for 2 hours. Then 0.60 g of 4-benzoyloxy-5-chloro-2(1H)-pyridone and 1.11 ml of triethylamine were added and the resulting mixture was refluxed for 1 hour. The precipitate thus formed was filtered off, and the filtrate was concentrated. The residue was placed on a silica gel column and eluted with 40% ethyl acetate-benzene, giving 0.45 g of the title compound in a yield of 37%.

$^1$H-NMR(CDCl$_3$)δ: 8.66–7.28 (17H, m, phenyl—H, C$_6$—H and C$_{3,6}$—H of the pyridine ring) 6.19 (1H, t, J=6 Hz, C$_{1'}$—H) 4.49 (2H, s,

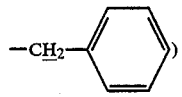

4.27–4.01 (4H, m, C$_{3',4',5'}$—H) 2.6614 1.90 (5H, m, C$_{2'}$—H and COCH$_3$).

EXAMPLE 74

Preparation of 5'-O-acetyl-3-[3-(4-acetyloxy-5-chloro-2-pyridyloxycarbonyl)benzoyl]-3'-O-benzyl-2'-deoxy-5-fluorouridine The general procedure of Example 73 was followed using 4-acetoxy-5-chloro-2(1H)-pyridone in place of 4-benzoyloxy-5-chloro-2(1H)-pyridone, thereby producing the title compound in a yield of 51%.

$^1$H-NMR (CDCl$_3$)δ: 8.65–7.17 (12H, m, phenyl—H, C$_6$—H and C$_{3,6}$—H of the pyridine ring) 6.19 (1H, t, J=6 Hz, C$_{1'}$—H) 4.49 (2H, s,

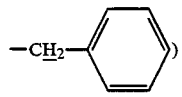

4.26–4.12 (4H, m, C$_{3',4',5'}$—H) 2.55–2.07 (8H, m, C$_{2'}$—H and COCH$_3$×2).

EXAMPLE 75

Preparation of 5'-O-acetyl-3-[3-(4-benzoyloxy-2-pyridyloxycarbonyl)-benzoyl]-3'-O-benzyl-2'-deoxy-5-fluorouridine The general procedure of Example 73 was followed using 4-benzoyloxy-2(1H)-pyridone in place of 4-benzoyloxy-5-chloro-2(1H)-pyridone, thereby producing the title compound in a yield of 55%.

$^1$H-NMR(CDCl$_3$)δ: 8.66–7.25 (18H, m, phenyl—H, C$_6$—H and C$_{3,5,6}$—H of the pyridine ring) 6.21 (1H, t, J=6 Hz, C$_{1'}$—H) 4.51 (2H, s,

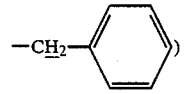

4.29–4.07 (4H, m, C$_{3',4',5'}$—H) 2.76–1.98 (5H, m, COCH$_3$ and C$_{2'}$—H).

EXAMPLE 76

Preparation of 5'-O-acetyl-3-[3-(2-benzoyloxy-4-pyridyloxycarbonyl)-benzoyl]-3'-O-benzyl-2'-deoxy-5-fluorouridine The general procedure of Example 73 was followed using 2-benzoyloxy-4-hydroxypyridine in place of 4-benzoyloxy-5-chloro-2(1H)-pyridone, thereby producing the title compound in a yield of 42%.

$^1$H-NMR(CDCl$_3$)δ: 8.66–7.23 (18H, m, phenyl—H, C$_6$—H and C$_{3,5,6}$—H of the pyridine ring) 6.22 (1H, t, J=6 Hz, C$_{1'}$—H) 4.52 (2H, s,

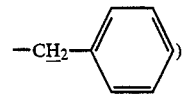

4.30–4.06 (4H, m, C$_{3',4',5'}$—H) 2.72–2.04 (5H, m, C$_{2'}$—H and COCH$_3$).

EXAMPLE 77

Preparation of 5'-O-acetyl-3-[3-[2-(2-methylbenzoyloxy)-4-pyridyloxycarbonyl]benzoyl]-3'-O-benzyl-2'-deoxy-5-fluorouridine The general procedure of Example 73 was followed using 2-(2-methylbenzoyloxy)-4-hydroxypyridine in place of 4-benzoyloxy-5-chloro-2(1H)-pyridone, thereby producing the title compound in a yield of 31%.

$^1$H-NMR(CDCl$_3$)δ: 8.66–7.20 (17H, m, phenyl—H, C$_6$—H and C$_{3,5,6}$—H of the pyridine ring) 6.21 (1H, t, J=6 Hz, C$_{1'}$—H) 4.51 (2H, s,

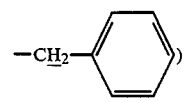

4.28–4.07 (4H, m, C$_{3',4',5'}$—H) 2.68–2.02 (8H, m, C$_{2'}$—H,

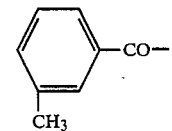

and COCH$_3$).

EXAMPLE 78

Preparation of 5'-O-acetyl-3'-O-benzyl-3-[3-(5-chloro-2-ethoxycarbonyloxy-4-pyridyloxycarbonyl)benzoyl]-2'-deoxy-5-fluorouridine The general procedure of Example 73 was followed using 5-chloro-2-ethoxycarbonyloxy-4-hydroxypyridine in place of 4-benzoyloxy-5-chloro-2(1H)-pyridone, thereby producing the title compound in a yield of 52%.

$^1$H-NMR(CDCl$_3$)δ: 8.66–7.26 (12H, m, phenyl—H, C$_6$—H and C$_{3,6}$—H of the pyridine ring) 6.22 (1H, t, J=6 Hz, C$_{1'}$—H) 4.53–4.08 (8H, m,

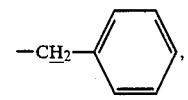

—O—CH$_2$CH$_3$ and C$_{3',4',5'}$—H) 2.75–2.11 (5H, m, C$_{2'}$—H and COCH$_3$) 1.40 (3H, t, J=7 Hz, —OCH$_2$CH$_3$).

EXAMPLE 79

Preparation of 5′-O-acetyl-3-[3-(4-benzoyloxy-5-chloro-2-pyridyloxycarbonyl)benzoyl]-3′-O-(4-chlorobenzyl)-2′-deoxy-5-fluorouridine The general procedure of Example 73 was followed using 5′-O-acetyl-3′-O-(4-chlorobenzyl)-2′-deoxy-5-fluorouridine in place of 5′-O-acetyl-3′-O-benzyl-2′-deoxy-5-fluorouridine, thereby producing the title compound in a yield of 50%.

$^1$H-NMR(CDCl$_3$)δ: 8.65–7.22 (16H, m, phenyl—H, C$_6$—H and C$_{3,6}$—H of the pyridine ring) 6.18 (1H, t, J=6 Hz, C$_{1'}$—H) 4.44 (2H, s,

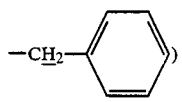

4.27–4.11 (4H, m, C$_{3',4',5'}$—H) 2.70–2.00 (5H, m, COCH$_3$ and C$_{2'}$—H).

EXAMPLE λ

Preparation of 5′-O-acetyl-3-[3-(2-acetoxy-5-chloro-4-pyridyloxycarbonyl)benzoyl]-3′-O-(4-chlorobenzyl)-2′-deoxy-5-fluorouridine The general procedure of Example 73 was followed using 5′-O-acetyl-3′-O-(4-chlorobenzyl)-2′-deoxy-5-fluorouridine in place of 5′-O-acetyl-3′-O-benzyl-2′-deoxy-5-fluorouridine and using 2-acetoxy-5-chloro-4-hydroxypyridine in place of 4-benzoyloxy-5-chloro-2(1H)-pyridone, thereby producing the title compound in a yield of 43%.

$^1$H-NMR(CDCl$_3$)δ: 8.67–7.24 (11H, m, phenyl—H, C$_6$—H and C$_{3,6}$—H of the pyridine ring) 6.20 (1H, t, J=6 Hz, C$_{1'}$—H) 4.47 (2H, s,

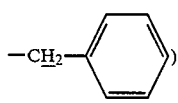

4.30–4.08 (4H, m, C$_{3',4',5'}$—H) 2.62–2.11 (8H, m, C$_{2'}$—H and COCH$_3$×2).

EXAMPLE 81

Preparation of 5′-O-acetyl-3-[3-(4-acetoxy-5-chloro-2-pyridyloxycarbonyl)benzoyl]-3′-O-(4-chlorobenzyl)-2′-deoxy-5-fluorouridine The general procedure of Example 73 was followed using 5′-O-acetyl-3′-O-(4-chlorobenzyl)-2′-deoxy-5-fluorouridine in place of 5′-O-acetyl-3′-O-benzyl-2′-deoxy-5-fluorouridine and using 4-acetoxy-5-chloro-2(1H)-pyridone in place of 4-benzoyloxy-5-chloro-2(1H)-pyridone, thereby producing the title compound in a yield of 52%.

$^1$H-NMR(CDCl$_3$)δ: 8.65–7.18 (11H, m, phenyl—H, C$_6$—H and C$_{3,6}$—H of the pyridine ring) 6.18 (1H, t, J=6 Hz, C$_{1'}$—H) 4.46 (2H, s,

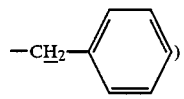

4.28–4.07 (4H, m, C$_{3',4',5'}$—H) 2.54–2.09 (8H, m, C$_{2'}$—H and COCH$_3$×2).

EXAMPLE 82

Preparation of 5′-O-acetyl-3-[3-(2-benzoyloxy-5-chloro-4-pyridyloxycarbonyl)benzoyl]-3′-O-(4-chlorobenzyl)-2′-deoxy-5-fluorouridine The general procedure of Example 73 was followed using 5′-O-acetyl-3′-O-(4-chlorobenzyl)-2′-deoxy-5-fluorouridine in place of 5′-O-acetyl-3′-O-benzyl-2′-deoxy-5-fluorourdine and using 2-benzoyloxy-5-chloro-4-hydroxypyridine in place of 4-benzoyloxy-5-chloro-2(1H)-pyridone, thereby producing the title compound in a yield of 53%.

$^1$H-NMR(CDCl$_3$)δ: 8.68–7.26 (16H, m, phenyl—H, C$_6$—H and C$_{3,6}$—H of the pyridine ring) 6.20 (1H, t, J=6 Hz, C$_{1'}$—H) 4.46 (2H, s,

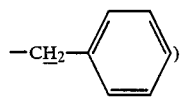

4.30–4.08 (4H, m, C$_{3',4',5'}$—H) 2.73–2.05 (5H, m, C$_{2'}$—H and COCH$_3$).

EXAMPLE 83

Preparation of 5′-O-acetyl-3-[5-(2-acetoxy-5-chloro-4-pyridyloxycarbonyl)-3-pyridylcarbonyl]-3′-O-benzyl-2′-deoxy-5-fluorouridine To a solution of 1.00 g of 5′-O-acetyl-3′-O-benzyl-2′-deoxy-5-fluorouridine in 50 ml of dry dioxane were added 3.26 ml of triethylamine and 0.80 g of pyridine-3,5-dicarbonyl chloride, and the mixture was refluxed for 1 hour. The precipitate thus formed was filtered off, and the filtrate was concentrated under reduced pressure. The concentrate was dissolved in 50 ml of acetonitrile. To the solution were added 1.83 ml of triethylamine and 0.59 g of 2-acetoxy-5-chloro-4-hydroxypyridine, and the resulting mixture was stirred at room temperature for 2.5 hours. The solvent was evaporated off under reduced pressure and the residue was placed on a silica gel column and eluted with chloroform, giving 0.22 g of the title compound in a yield of 12%.

$^1$H-NMR(CDCl$_3$)δ: 9.57–8.88 (3H, m,

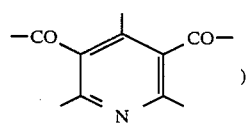

8.47 (1H, s,

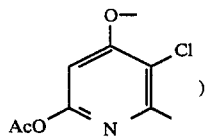

7.83 (1H, d, J=6 Hz, C$_6$—H) 7.30 (5H, s, phenyl—H) 7.27 (1H, s,

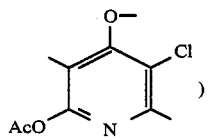

6.19 (1H, t, J=6 Hz, C$_{1'}$—H) 4.51 (2H, s,

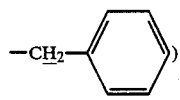

4.28–4.12 (4H, m, C$_{3',4',5'}$—H) 2.38–2.09 (8H, m, C$_{2'}$—H and COCH$_3$×2).

EXAMPLE 84

Preparation of 5'-O-acetyl-3'-O-benzyl-3-[4-(5-chloro-4-hydroxy-2-pyridyloxycarbonyl)benzoyl]-2'-deoxy-5-fluorouridine To a solution of 1.00 g of 5'-O-acetyl-3'-O-benzyl-2'-deoxy-5-fluorouridine in 50 ml of dry dioxane were added 2.88 ml of triethylamine and 0.80 g of terephthaloyl chloride, and the mixture was refluxed for 1.5 hours. The solvent was distilled off, and the residue was dissolved in 50 ml of acetonitrile. To the solution were added 1.53 g of 2,4-bis(trimethylsilyloxy)-5-chloropyridine, and the mixture was stirred overnight at room temperature. The solvent was distilled off, and the residue was placed on a silica gel column and eluted with 0.5% ethanol-chloroform, giving 0.18 g of the title compound in a yield of 10%.

$^1$H-NMR(CDCl$_3$)δ: 8.25 (1H, s, C$_6$—H of the pyridine ring) 8.17–7.93 (4H, m,

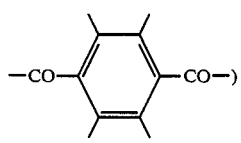

7.80 (1H, d, J=6 Hz, C$_6$—H) 7.28 (5H, s,

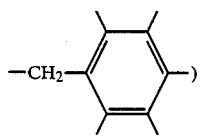

6.79 (1H, s, C$_3$—H of the pyridine ring) 6.20 (1H, t, J=6 Hz, C$_{1'}$—H) 4.51 (2H, s,

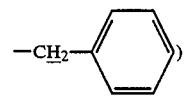

4.44–4.09 (4H, m, C$_{3',4',5'}$—H) 2.75–2.10 (5H, m, C$_{2'}$—H and COCH$_3$).

EXAMPLE 85

Preparation of 3-[3-(4-acetoxy-5-chloro-2-pyridyloxycarbonyl)benzoyl]-3'-O-benzyl-5-fluoro-5'-O-nicotinoyluridine The general procedure of Example 73 was followed using 3'-O-benzyl-2'-deoxy-5-fluoro-5'-O-nicotinoyluridine in place of 5'-O-acetyl-3'-O-benzyl-2'-deoxy-5-fluorouridine and using 4-acetoxy-5-chloro-2(1H)-pyridone in place of 4-benzoyloxy-5-chloro-2(1H)-pyridone, thereby producing the title compound in a yield of 41%.

H-NMR(CDCl$_3$)δ: 9.21–7.29 (15H, m, phenyl—H,

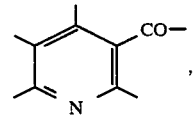

C$_6$—H and

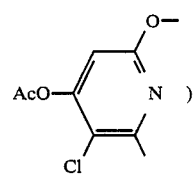

7.18 (1H, s,

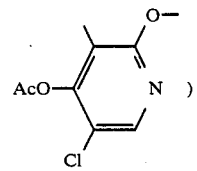

6.18 (1H, t, J=6 Hz, C$_{1'}$—H) 4.60–4.19 (6H, m,

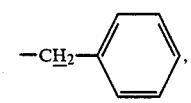

C$_{3',4',5'}$—H) 2.8–2.03 (5H, m, C$_{2'}$—H and COCH$_3$).

EXAMPLE 86

Preparation of 3-[3-(4-acetoxy-5-chloro-2-pyridyloxycarbonyl)benzoyl]-3'-O-benzyl-2'-deoxy-5-fluoro-5'-O-(3,4-methylenedioxybenzoyl)uridine The general procedure of Example 73 was followed using 3'-O-benzyl-2'-deoxy-5-fluoro-5'-O-(3,4-methylenedioxybenzoyl)uridine in place of 5'-O-acetyl-3'-O-benzyl-2'-deoxy-5-fluorouridine and using 4- acetoxy-5-chloro-2(1H)-pyridone in place of 4-benzoyloxy-5-chloro-2(1H)-pyridone, thereby producing the title compound in a yield of 42%.

¹H-NMR(CDCl₃)δ: 8.65–8.17 and 7.79–7.52 (7H, m,

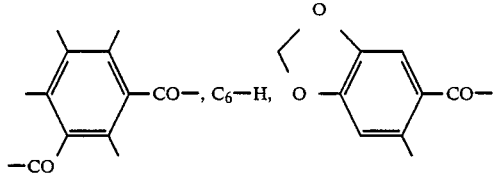

and C₆—H of the pyridine ring) 7.39 (1H, d, J=2 Hz,

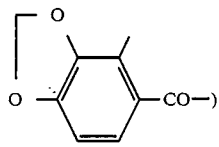

7.30 (5H, s,

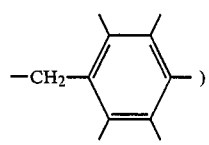

7.25 (1H, s, C₃—H of the pyridine ring) 6.84 (1H, d, J=8 Hz,

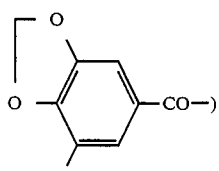

6.20 (1H, t, J=6 Hz, C₁,—H) 6.03 (2H, s, —OCH₂O—) 4.55–4.12 (6H, m, C₃′.₄′.₅′—H and

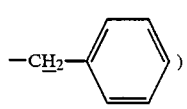

2.70–2.51 and 2.25–2.02 (2H, m, C₂′—H) 2.38 (3H, s, COCH₃).

EXAMPLE 87

Preparation of 3-[3-(4-acetoxy-5-chloro-2-pyridyloxycarbonyl)benzoyl]-3′-O-benzyl-5′-O-(4-chlorobenzoyl)-2′-deoxy-5-fluorouridine The general procedure of Example 73 was followed using 3′-O-benzyl-5′-O-(4-chlorobenzoyl)-2′-deoxy-5-fluorouridine in place of 5′-O-acetyl-3′-O-benzyl-2′-deoxy-5-fluorouridine and using 4-acetoxy-5-chloro-2(1H)-pyridone in place of 4-benzoyloxy-5-chloro-2(1H)-pyridone, thereby producing the title compound in a yield of 61%.

¹H-NMR(CDCl₃)δ: 8.64–7.17 (16H, m, phenyl-H, C₆—H and C₃.₆—H of the pyridine ring) 6.19 (1H, t, J=6 Hz, C₁′—H) 4.55–4.18 (6H, m, C₃′.hd 4′.₅′—H and

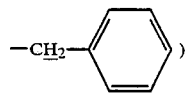

2.62–2.13 (5H, m, C₂′—H and —COCH₃).

EXAMPLE 88

Preparation of 3′-O-benzyl-2′-deoxy-5-fluoro-5′-O-(3,4-methylenedioxybenzoyl)uridine The general procedure of Example 26 was followed, thereby producing the title compound in a yield of 72%. M.p. 169°–171° C.

¹H-NMR(CDCl₃)δ: 9.72 (1H, bs, —NH—, disappeared by addition of D₂O) 7.71–7.52 (2H, m, C₆—H and

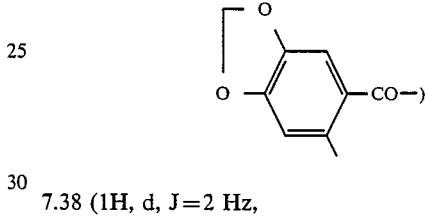

7.38 (1H, d, J=2 Hz,

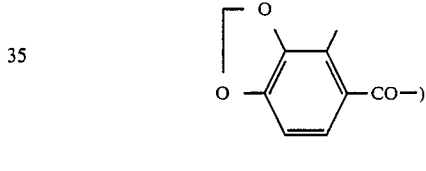

7.32 (5H, s,

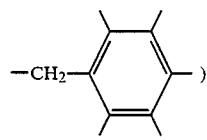

6.83 (1H, d, J=8 Hz,

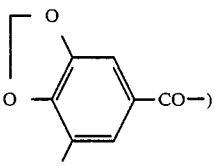

6.23 (1H, t, J=6 Hz, C₁′—H) 6.03 (2H, s, —OCH₂O—) 4.57–4.14 (6H, m,

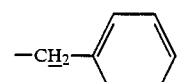

and C₃′.₄′.₅′—H) 2.75–2.49 and 2.19–1.89 (2H, m, C₂′—H).

EXAMPLE 89

Preparation of 3'-O-benzyl-5'-O-(4-chlorobenzoyl)-2'-deoxy-5-fluorouridine

The general procedure of Example 26 was followed, thereby producing the title compound in a yield of 53%.

$^1$H-NMR(DMSO-d$_6$)$\delta$: 11.9 (1H, bs, —NH—, disappeared by addition of D$_2$O) 7.95 (2H, d, J=9 Hz,

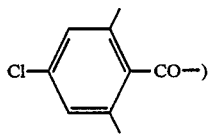

7.92 (1H, d, J=6 Hz, C$_6$—H) 7.59 (2H, d, J=9 Hz,

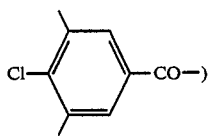

7.33 (5H, s,

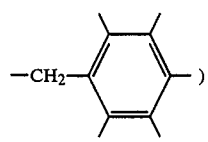

6.15 (1H, t, J=6 Hz, C$_{1'}$—H) 4.58–4.31 (6H, m, C$_{3'.4'.5'}$—H and

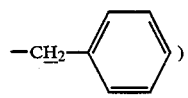

2.42–2.31 (2H, m, C$_{2'}$—H).

EXAMPLE 90

Preparation of 3'-O-(3-chlorobenzyl)-2'-deoxy-5-fluorouridine

A 2.00 g quantity of potassium hydroxide was dissolved in a mixture of 75 ml of water and 40 ml of dioxane. To the solution were added 1.00 g of 2'-deoxy-5-fluorouridine and 2.50 g of 3-chlorobenzyl chloride, and the resulting mixture was stirred at 45° C. for 3 days. After the reaction, the same subsequent procedure as in Examples 4 and 5 was carried out, and the residue was placed on a silica gel column to conduct a gradient elution with chloroform and mixtures of methanol (up to 2%) and chloroform, thereby producing 0.21 g of the title compound in a yield of 14%.

M.p. 153°–155° C.

EXAMPLE 91

Preparation of 3'-O-(2-chlorobenzyl)-2'-deoxy-5-fluorouridine

A 3.75 g quantity of potassium hydroxide was dissolved in a mixture of 150 ml of water and 40 ml of dioxane. To the solution were added 1.00 g of 2'-deoxy-5-fluorouridine and 10 ml of 2-chlorobenzyl chloride, and the resulting mixture was stirred at 30° C. for 3 days. After the reaction, the same subsequent procedure as in Examples 4 and 5 was carried out, and the residue was placed on a silica gel column and eluted with 2% methanol-chloroform, thereby producing 0.34 g of the title compound in a yield of 23%.

M.p. 78°–80° C.

EXAMPLE 92

Preparation of 2'-deoxy-5-fluoro-3'-O-(4-fluorobenzyl)uridine

A 7.5 g quantity of potassium hydroxide was dissolved in a mixture of 300 ml of water and 80 ml of dioxane. To the solution were added 2.00 g of 2'-deoxy-5-fluorouridine and 4.9 ml of 4-fluorobenzyl chloride, and the resulting mixture was stirred at 35° C. for 2 days. After the reaction, the same subsequent procedure as in Examples 4 and 5 was carried out, and the residue was placed on a silica gel column and eluted with 2% methanol-chloroform, thereby producing 0.57 g of the title compound in a yield of 20%.

M.p. 130°–131° C.

EXAMPLE 93

Preparation of 2'-deoxy-5-fluoro-3'-O-(1-naphthylmethyl)uridine

The general procedures of Examples 4 and 5 were followed using 1.3 g of potassium hydroxide, 1.00 g of 2'-deoxy-5-fluorouridine and 2.7 g of 1-naphthylmethyl bromide, thereby producing 0.28 g of the title compound in a yield of 18%.

M.p. 159°–160° c.

EXAMPLE 94

Preparation of 5'-O-acetyl-3-O-benzoyl-3'-O-(4-chlorobenzyl)-2'-deoxy-5-fluorouridine To a solution of 0.25 g of 3'-O-(4-chlorobenzyl)-5'-O-acetyl-2'-deoxy-5-fluorouridine in 30 ml of dioxane were added 0.26 g of benzoyl chloride and 0.51 ml of triethylamine, and the mixture was stirred at 90° C. for 2 hours. The reaction mixture was concentrated and the residue was dissolved in 50 ml of ethyl acetate. The solution was washed three times with a saturated aqueous solution of sodium hydrogen carbonate and dried over anhydrous sodium sulfate. The ethyl acetate was distilled off, and the residue was placed on a silica gel column and eluted with chloroform, thereby producing 0.29 g of the title compound in a yield of 92%.

NMR(CDCl$_3$)$\delta$: 7.98–7.87 (2H, m,

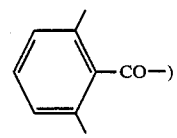

7.77 (1H, d, J=6 Hz, H$_6$) 7.69–7.32 (3H, m,

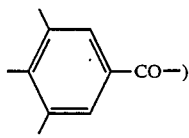

7.27 (4H, d, J=3 Hz, phenyl—H) 6.21 (1H, t, J=4 Hz, H$_{1'}$) 4.90 (2H, d, J=1 Hz,

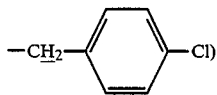

4.32–4.03 (4H, m, H$_{3'}$, H$_{4'}$, H$_{5'}$) 2.72–1.96 (5H, m, H$_2$ and CH$_3$CO—).

EXAMPLE 95

Preparation of 5'-O-acetyl-3-(4-chlorobenzoyl)-3'-O-(4-chlorobenzyl)-2'-deoxy-5-fluorouridine To a solution of 0.30 g of 3'-O-(4-chlorobenzyl)-5'-O-acetyl-2'-deoxy-5-fluorouridine in 30 ml of dioxane were added 0.38 g of 4-chlorobenzoyl chloride and 0.61 ml of triethylamine, and the mixture was stirred at 40° C. for 3 hours. The insolubles were removed by filtration, and the residue was dissolved in 50 ml of ethyl acetate. The solution was washed with water and dried. The ethyl acetate was distilled off, and the residue was placed on a silica gel column and eluted with chloroform-n-hexane (3:2), thereby producing 0.33 g of the title compound in a yield of 82%.

NMR(CDCl$_3$)δ: 7.86 (2H, d, J=9 Hz,

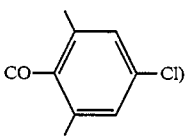

7.77 (1H, d, J=7 Hz, H$_6$) 7.48 (2H, d, J=9 Hz,

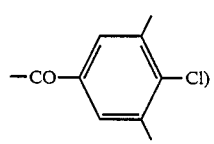

7.27 (4H, d, J=4 Hz,

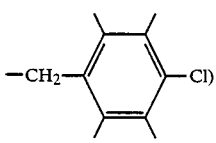

6.20 (1H, t, J=6 Hz, H$_{1'}$) 4.49 (2H, s,

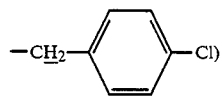

4.32–4.03 (4H, m, H$_{3'}$.H$_{4'}$.H$_{5'}$) 2.75–1.95 (5H, m, H$_{2'}$ and CH$_3$CO—).

EXAMPLE 96

Preparation of 5'-O-acetyl-3-(4-n-propoxybenzoyl)-3'-O-(4-chlorobenzyl)-2'-deoxy-5-fluorouridine To a solution of 0.30 g of 3'-O-(4-chlorobenzyl)-5'-O-acetyl-2'-deoxy-5-fluorouridine in 30 ml of dioxane were added 0.44 g of 4-n-propoxybenzoyl chloride and 0.61 ml of triethylamine, and the mixture was stirred at 70° C. for 3 hours. The insolubles were removed by filtration, and the residue was dissolved in ethyl acetate. The solution was washed with water and dried. The ethyl acetate was distilled off, and the residue was placed on a silica gel column and eluted with chloroform-petroleum ether (1:1), thereby producing 0.15 g of the title compound in a yield of 36%.

NMR(CDCl$_3$)δ: 7.87 (2H, d, J=9 Hz,

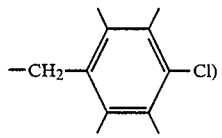

7.74 (1H, d, J=6 Hz, H$_6$) 7.27 (4H, d, J=3 Hz, 6.21 (1H, t, J=4 Hz, H$_{1'}$) 4.49 (2H, s, 4.31–3.93 (6H, m, H$_{3'}$.H$_{4'}$.H$_{5'}$ and —O—CH$_2$CH$_2$CH$_3$) 2.72–1.65 (7H, m, H$_2$, CH$_3$CO— and —O—CH$_2$CH$_2$CH$_3$) 1.04 (3H, t, J=7 Hz, —OCH$_2$CH$_2$CH$_3$).

EXAMPLE 97

Preparation of 3-benzoyl-3'-O-(4-chlorobenzyl)-2'-deoxy-5-fluorouridine

The general procedure of Example 41 was followed using 0.50 g of 3'-O-(4-chlorobenzyl)-2'-deoxy-5-fluorouridine, thereby producing 0.46 g of the title compound as a powder in a yield of 72%.

M.p.-(powder).

NMR(CDCl$_3$)δ: 8.19 (1H, d, J=6 Hz, H$_6$) 7.90 (2H, bd, J=7 Hz,

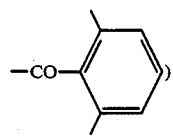

7.65–7.35 (3H, m,

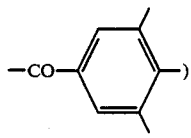

7.24 (4H, s,

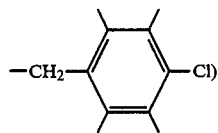

6.24 (1H, t, J=6 Hz, H$_{1'}$) 4.42 (2H, s,

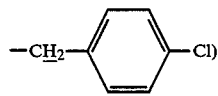

4.24–4.15 (2H, m, H$_{3'}$, H$_{4'}$) 3.95–3.60 (2H, m, H$_{5'}$) 2.59–1.98 (2H, m, H$_{2'}$).

EXAMPLE 98

Preparation of 3-benzoyl-5'-O-benzoyl-3'-O-(4-chlorobenzyl)-2'-deoxy-5-fluorouridine A 0.23 ml quantity of benzoyl chloride was added to a solution of 0.25 g of 3'-O-(4-chlorobenzyl)-2'-deoxy-5-fluorouridine in pyridine. The mixture was stirred at room temperature for 2 hours. The solvent was distilled off. To the residue were added ethyl acetate and water to separate the ethyl acetate layer. The ethyl acetate layer was dried over anhydrous sodium sulfate and concentrated. The concentrate was subjected to silica gel column chromatography using chloroform as an eluent, giving 0.27 g of the title compound in a yield of 70%.

NMR(CDCl$_3$)δ: 8.05–7.85 (4H, m,

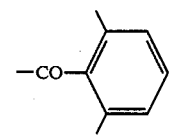

x 2) 7.71 (1H, d, J=6 Hz, H$_6$) 7.63–7.32 (6H, m,

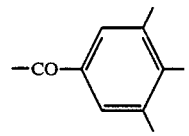

x 2) 7.25 (4H, s,

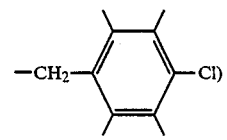

6.21 (1H, t, J=4 Hz, H$_{1'}$) 4.63–4.20 (6H, m, H$_{3'}$, H$_{4'}$, H$_{5'}$ and

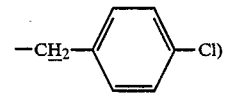

2.77–2.02 (2H, m, H$_{2'}$).

EXAMPLE 99

Preparation of 3'-O-benzyl-2'-deoxy-5-fluoro-3-nicotinoyl-5'-O-nicotinoyluridine A 0.40 g quantity of nicotinoyl chloride hydrochloride and 1.0 ml of triethylamine were added to a solution of 0.50 g of 3'-O-benzyl-2'-deoxy-5-fluorouridine in 40 ml of dioxane. The mixture was refluxed for 6 hours. The solvent was distilled off and the residue was subjected to silica gel column chromatography using 1% methanol-chloroform as an eluent, giving 0.23 g of the title compound in a yield of 29%.

NMR(DMSO-d$_6$)δ: 9.27 and 9.11 (each 1H, d,

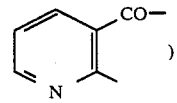

8.97–8.81 (2H, m,

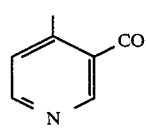

x 2) 8.57–8.16 (3H, m, H$_6$ and

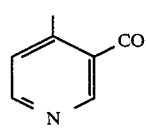

x 2) 7.73–7.50 (2H, m,

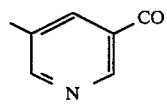

x 2) 7.32 (5H, s,

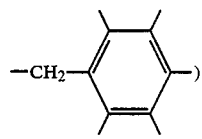

6.10 (1H, m, J=6 Hz, H$_{1'}$) 4.59 (2H, s,

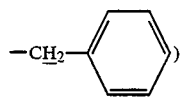

4.54–4.33 (4H, m, H$_{3'}$, H$_{4'}$, H$_{5'}$) 2.37–2.20 (2H, m, H$_{2'}$).

EXAMPLE 100

Preparation of 3-[3-(4-acetoxy-5-chloro-2-pyridyloxycarbonyl)benzoyl]-3'-O-benzyl-5-fluoro-2'-deoxy-5'-o-(1-naphthoyl)uridine The general procedure of Example 73 was followed using 0.50 g of 3'-O-benzyl-2'-deoxy-5-fluoro-5'-O-(1-naphthoyl)uridine, thereby producing 0.05 g of the title compound as a powder in a yield of 6%.

NMR(CDCl$_3$)δ: 8.89–7.36 (13H, m,

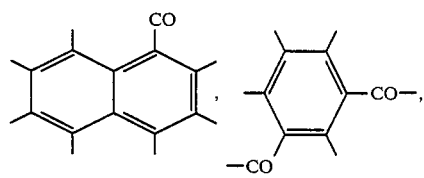

H$_6$ and H$_6$ of the pyridine ring) 7.30 (5H, s,

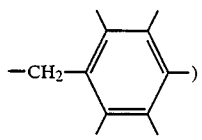

7.16 (1H, s, H$_3$ of the pyridine ring) 6.24 (1H, t, J=6 Hz, H$_{1'}$) 4.70–4.24 (6H, m, H$_{3'}$, H$_{4'}$, H$_{5'}$ and

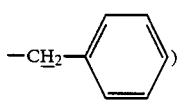

2.75–2.03 (5H, m, H$_{2'}$ and CH$_3$CO—).

EXAMPLE 101

Preparation of 3-[3-(4-acetoxy-5-chloro-2-pyridyloxycarbonyl)benzoyl]-3'-O-benzyl-2'-deoxy-5-fluorouridine Trimethylchlorosilane (1.50 ml) and 4.20 ml of triethylamine were added to a solution of 1.00 g of 3'-O-benzyl-2'-deoxy-5-fluorouridine in 30 ml of dried dioxane. The mixture was stirred at room temperature for 20 minutes. The precipitate obtained was separated by filtration and the filtrate was concentrated. The concentrate was dissolved in 30 ml of dried dioxane. To the solution were added 724 mg of isophthaloyl chloride and 2.47 ml of triethylamine and the mixture stirred at 100° C. for 45 minutes.

The reaction mixture was cooled to room temperature and 0.84 g of 4-acetyloxy-5-chloro-2-pyridone was added to the reaction mixture. The resulting mixture was stirred at room temperature for 2 hours. The precipitate obtained was removed by filtration, the filtrate was concentrated, the concentrate was dissolved in 50 ml of ethyl acetate, and the solution was washed with 30 ml of a saturated aqueous solution of sodium chloride three times (3×30 ml). The ethyl acetate layer was dried over anhydrous sodium sulfate and concentrated. To the concentrate were added 50 ml of methanol and 1.0 ml of acetic acid. The mixture was stirred at room temperature for 16 hours. The solvent was distilled off and the residue was subjected to silica gel column chromatography using as an eluent 1% acetone-chloroform, giving 0.74 g of the title compound in a yield of 38%.

NMR(CDCl$_3$)δ: 8.66–8.18 (3H, m,

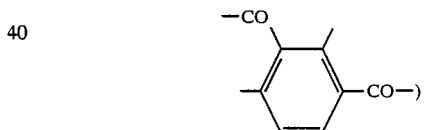

8.45 (1H, s, H$_6$ of the pyridine ring) 8.11 (1H, d, H$_6$, J=7 Hz) 7.68 (1H, t,

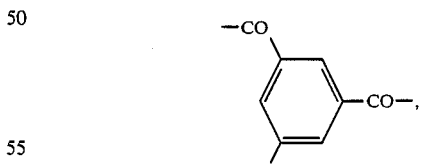

J=8 Hz) 7.31 (5H, s,

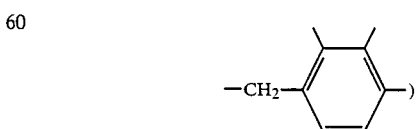

7.18 (1H, s, H$_3$ of the pyridine ring) 6.24 (1H, t, H$_{1'}$, J=4 Hz) 4.52 (1H, d,

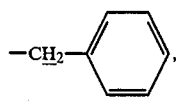

J=1 Hz) 4.29–4.11 (2H, m, $H_{3'}$, $H_{4'}$) 4.04–3.67 (2H, m, $H_{5'}$) 2.57–2.04 (2H, m, $H_{2'}$) 2.39 (3H, s, C$\underline{H}_3$CO—).

EXAMPLE 102

Preparation of 3'-O-benzyl-3-[3-(5-chloro-1,2-dihydro-2-oxo-pyridyloxycarbonyl)benzoyl]-2'-deoxy-5-fluorouridine Silylation and introduction of isophthaloyl group were conducted using 0.50 g of 3'-O-benzyl-2'-deoxy-5-fluorouridine in the same manner as in Example 101. The insolubles were removed by filtration. The solvent was distilled off and the residue was dissolved in 100 ml of pyridine. To the solution was added 0.35 g of 5-chloro-4-hydroxy-2-pyridone. The mixture was left to stand at room temperature overnight. The pyridine was distilled off and the residue was subjected to silica gel column chromatography to conduct gradient elution using chloroform and mixtures of methanol (up to 4%) and chloroform, giving 0.23 g of the title compound in a yield of 25%.

NMR(DMSO-$d_6$)δ: 12.04 (1H, bs, —NH—) 8.62–8.26 (4H, m, $H_6$ and

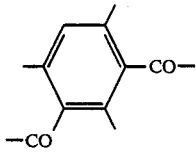

7.92–7.74 (2H, m,

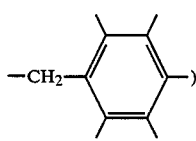

and $H_6$ of the pyridine ring) 7.33 (5H, s,

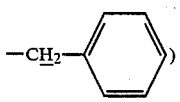

6.63 (1H, s, $H_3$ of the pyridine ring) 6.11 (1H, t, J=6 Hz, $H_{1'}$) 5.29 (1H, t, J=5 Hz, 5'—OH) 4.54 (2H, s,

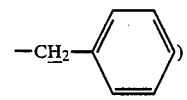

4.35–4.08 (2H, m, $H_{3'}$, $H_{4'}$) 3.70–3.61 (2H, m, $H_{5'}$) 2.51–2.08 (2H, m, $H_{2'}$).

EXAMPLE 103

Preparation of 3-[3-(4-benzoyloxy-5-chloro-2-pyridyloxycarbonyl)-benzoyl]-3'-O-benzyl-2'-deoxy-5-fluorouridine The general procedure of Example 101 was followed using 0.50 g of 3'-O-benzyl-2'-deoxy-5-fluorouridine, thereby producing 0.29 g of the title compound as a powder in a yield of 27%.

NMR(CDCl$_3$)δ: 8.68–8.13 (7H, m,

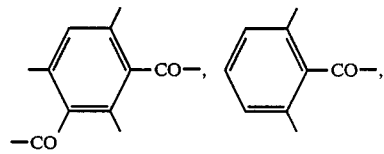

$H_6$ and $H_6$ of the pyridine ring) 7.81–7.42 (4H, m,

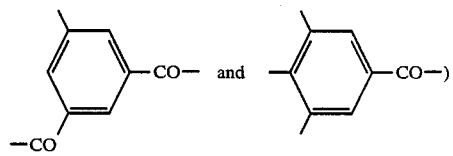

7.39 (1H, s, $H_3$ of the pyridine ring) 7.30 (5H, s,

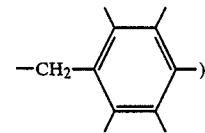

6.21 (1H, t, J=4 Hz, $H_{1'}$) 4.55 (2H, d, J=1 Hz,

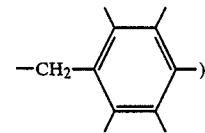

4.46–4.12 (2H, m, $H_{3'}$, $H_{4'}$) 4.03–3.66 (2H, m, $H_{5'}$) 2.67–2.07 (2H, m, $H_{2'}$).

EXAMPLE 104

Preparation of 3'-O-benzyl-3-[3-(5-chloro-4-hydroxy-2-pyridyloxycarbonyl)benzoyl]-2'-deoxy-5-fluorouridine Silylation and introduction of isophthaloyl group were conducted using 0.50 g of 3'-O-benzyl-2'-deoxy-5-fluorouridine in the same manner as in Example 101. The insolubles were removed by filtration and the solvent was distilled off. The residue was dissolved in 50 ml of dichloromethane. To the solution were added 0.57 g of 2,4-bis(trimethylsilyloxy)-5-chloropyridine and 0.10 ml of stannic chloride. The mixture was stirred at room temperature for 6 hours. The reaction mixture was neutralized with triethylamine and concentrated. The concentrate was extracted with ethyl acetate, and the extract was washed with water, dried and concentrated. The concentrate was suspended in 40 ml of methanol and the suspension was stirred at room temperature overnight. The solvent was distilled off and the residue was subjected to silica gel column chromatography using as an eluent 1% methanol-chloroform, giving 0.19 g of the title compound as a powder in a yield of 21%.

NMR (CDCl$_3$)δ: 8.58–8.16 (4H, m, H$_6$ of the pyridine ring,

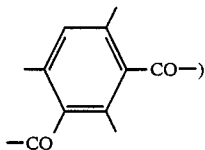

8.05 (1H, d, J=6 Hz, H$_6$) 7.62 (1H, t, J=8 Hz,

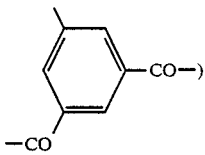

7.29 (5H, s, phenyl—H) 6.78 (1H, s, H$_3$ of the pyridine ring) 6.19 (1H, t, J=6 Hz, H$_{1'}$) 4.49 (2H, s,

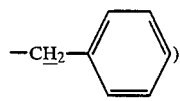

4.32–3.78 (4H, m, H$_{3'}$, H$_{4'}$, H$_{5'}$) 2.49–2.09 (2H, m, H$_{2'}$).

EXAMPLE 105

Preparation of 3-[3-(4-benzoyloxy-5-chloro-2-pyridyloxycarbonyl)-benzoyl]-3'-O-(4-chlorobenzyl)-2'-deoxy-5-fluorouridine The same reaction as in Example 101 was repeated using 3'-O-(4-chlorobenzyl)-2'-deoxy-5-fluorouridine and 4-benzoyloxy-5-chloro-2-pyridone.

A reaction for removing the silyl group was conducted by dissolving the residue of the reaction mixture in 5 ml of chloroform, adding 10 ml of methanol to the solution and leaving the mixture to stand at room temperature for 16 hours. The solvent was distilled off and the residue was subjected to silica gel column chromatography using as an eluent 1% acetone-chloroform, giving 0.24 g of the title compound as a powder in a yield of 24%.

NMR (CDCl$_3$)δ: 8.67–8.17 (6H, m,

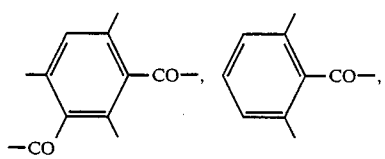

and H$_6$ of the pyridine ring) 8.11 (1H, d, H$_6$, J=6 Hz) 7.78–7.43 (4H, m,

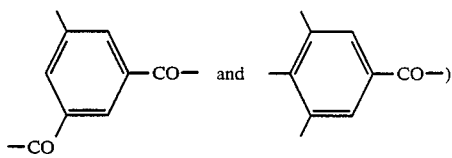

7.39 (1H, s, H$_3$ of the pyridine ring) 7.26 (4H, d,

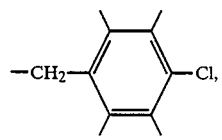

J=2 Hz) 6.24 (1H, t, J=4 Hz, H$_{1'}$) 4.48 (2H, s,

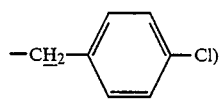

4.36–4.15 (2H, m, H$_{3'}$, H$_{5'}$) 4.10–3.73 (2H, m, H$_{5'}$) 2.70–2.10 (2H, m, H$_{2'}$).

EXAMPLE 106

Preparation of 3'-O-benzyl-3-[3-(5-chloro-4-dimethylaminobenzoyloxy-2-pyridyloxycarbonyl)benzoyl]-2'-deoxy-5-fluorouridine The general procedure of Example 101 was followed using 1.00 g of 3'-O-benzyl-2'-deoxy-5-fluorouridine, thereby producing 0.48 g of the title compound as a powder in a yield of 21%.

NMR (CDCl$_3$)δ: 8.69–8.46 (4H, m, H$_6$ of the pyridine ring,

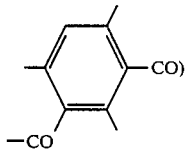

8.00–7.76 (4H, m, H$_6$,

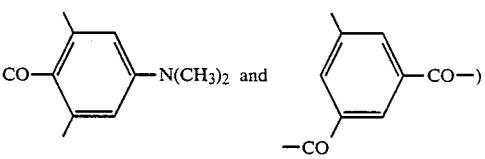

7.73 (1H, s, H$_3$ of the pyridine ring) 7.32 (5H, s,

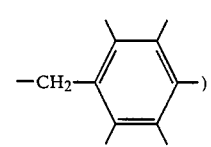

6.82 (2H, d, J=9 Hz,

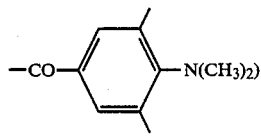

6.12 (1H, t, J=7 Hz, H$_{1'}$) 5.30 (1H, t, J=5 Hz, 5'—OH) 4.53 (2H, s,

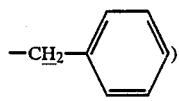

4.42–3.63 (4H, m, H$_{3'}$, H$_{4'}$, H$_{5'}$) 3.07 (6H, s, —N(C$\underline{H}_3$)$_2$) 2.56–2.20 (2H, m, H$_{2'}$).

EXAMPLE 107

Preparation of 3-[3-(4-acetoxy-2-pyridyloxycarbonyl)benzoyl]-5'-O-acetyl-3'-O-benzyl-2'-deoxy-5-fluorouridine The general procedure of Example 73 was followed, thereby producing the title compound in a yield of 46%.

NMR (CDCl$_3$)δ: 8.66–8.11 (4H, m, H$_6$ of the pyridine ring,

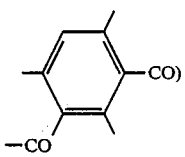

7.80 (1H, d, J=6 Hz, H$_6$) 7.68 (1H, t, J=8 Hz,

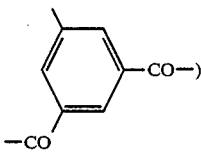

7.31 (5H, s, phenyl—H) 7.22–7.09 (2H, m, H$_3$ and H$_5$ of the pyridine ring) 6.20 (1H, t, J=6 Hz, H$_{1'}$) 4.52 and 4.50 (each 1H, s,

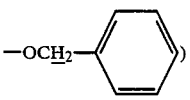

4.44–4.08 (4H, m, H$_{3'}$, H$_{4'}$, H$_{5'}$) 2.69–2.02 (8H, m, H$_{2'}$ and C$\underline{H}_3$CO— x 2)

EXAMPLE 108

Preparation of 5'-O-acetyl-3'-O-benzyl-3-[3-(5-chloro-1,2-dihydro-2-oxo-4-pyridyloxycarbonyl)benzoyl]-2'-deoxy-5-fluorouridine Isophthaloyl chloride (0.40 g) and 1.0 ml of triethylamine were added to a solution of 0.50 g of 5'-O-acetyl-3'-O-benzyl-2'-deoxy-5-fluorouridine in 50 ml of dioxane. The mixture was refluxed for 1 hour. After the mixture was left to stand for cooling, the insolubles were removed by filtration and the filtrate was concentrated. The concentrate was dissolved in 100 ml of pyridine. To the solution was added 0.38 g of 5-chloro-4-hydroxy-2-pyridone. The mixture was stirred at room temperature overnight. The solvent was distilled off and the residue was subjected to silica gel column chromatography using as an eluent 2% methanol-chloroform, giving 0.23 g of the title compound in a yield of 27%.

NMR (DMSO-d$_6$)δ: 12.00 (1H, bs, —NH—) 8.67–7.88 (6H, m, H$_6$,

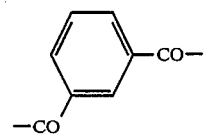

and H$_6$ of the pyridine ring) 7.33 (5H, s,

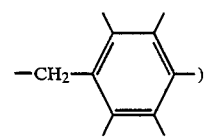

6.63 (1H, s, H$_3$ of the pyridine ring) 6.10 (1H, t, J=6 Hz, H$_{1'}$) 4.54 (2H, s,

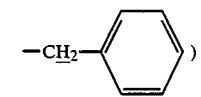

4.24 (4H, bs, H$_{3'}$, H$_{4'}$, H$_{5'}$) 2.46–2.01 (5H, m, H$_{2'}$ and CH$_3$CO—).

EXAMPLE 109

Preparation of 5'-O-acetyl-3'-O-benzyl-3-[3-(5-chloro-4-n-hexanoyloxy-2-pyridyloxycarbonyl)benzoyl]-2'-deoxy-5-fluorouridine The general procedure of Example 73 was followed, thereby producing the title compound as a powder in a yield of 75%.

NMR (CDCl$_3$)δ: 8.63–8.06 (4H, m,

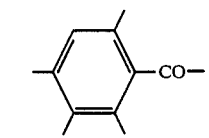

and H$_6$ of the pyridine ring) 7.83–7.60 (2H, m,

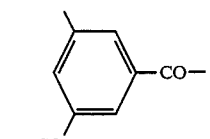

and H₆) 7.31 (5H, s,

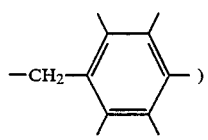

7.18 (1H, s, H₃ of the pyridine ring) 6.21 (1H, t, J=6 Hz, H₁·) 4.52 (2H, s,

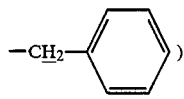

4.44–4.09 (4H, m, H₃·, H₄·, H₅·) 2.65 (2H, t, J=7 Hz, —COCH₂CH₂—) 2.22–0.93 (14H, m, COCH₃—, H₂· and —COCH₂(CH₂)₃CH₃).

EXAMPLE 110

Preparation of 5'-O-acetyl-3'-O-benzyl-3-[3-(5-chloro-4-octadecanoyloxy-2-pyridyloxycarbonyl)benzoyl]-2'-deoxy-5-fluorouridine The general procedure of Example 73 was followed, thereby producing the title compound as a powder in a yield of 17%. ;p NMR (CDCl₃)δ: 8.60–8.05 (4H, m,

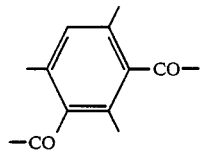

and H₆ of the pyridine ring) 7.82–7.57 (2H, m,

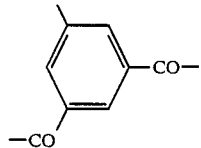

and H₆) 7.31 (5H, s,

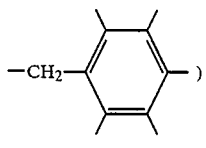

7.18 (1H, s, H₃ of the pyridine ring) 6.19 (1H, t, J=6 Hz, H₁·) 4.52 (2H, s,

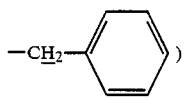

4.30–4.10 (4H, m, H₃·, H₄·, H₅·) 2.67 (2H, t, J=7 Hz, —COCH₂CH₂—) 2.58–2.05 (5H, m, COCH₃— and H₂·)

1.26 (30H, bs, —COCH₂(CH₂)₁₅CH₃) 0.88 (3H, t, J=7 Hz, —CH₂CH₃).

EXAMPLE 111

Preparation of 5'-O-acetyl-3'-O-benzyl-3-[3-[5-chloro-4-(2-furoyloxy)-2-pyridyloxycarbonyl]benzoyl]-2'-deoxy-5-fluorouridine The general procedure of Example 73 was followed, thereby producing the title compound in a yield of 57%. NMR (CDCl₃)δ: 8.66–8.21 (5H, m,

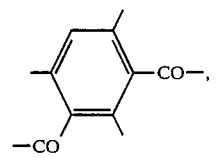

H₆ of the pyridine ring and H₅ of the furan ring) 7.84–7.69 (2H, m,

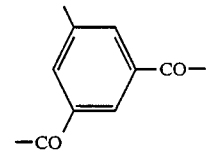

and H₆) 7.49 (1H, dd, J₃,₄=4 Hz, J₃,₅=1 Hz, H₃ of the furan ring) 7.36 (1H, s, H₃ of the pyridine ring) 7.31 (5H, s,

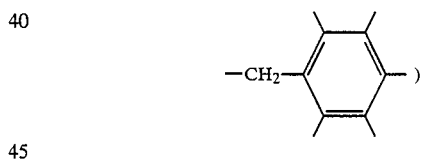

6.64 (1H, dd, J₃,₄=4 Hz, J₄,₅=2 Hz, H₄ of the furan ring) 6.21 (1H, t, J=6 Hz, H₁·) 4.53 and 4.51 (each 1H, s,

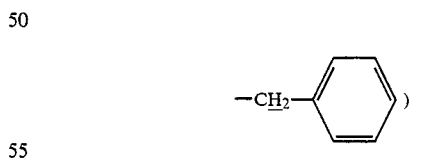

4.30–4.09 (4H, m, H₃·, H₄·, H₅·) 2.58–2.09 (5H, m, H₂· and CH₃CO—).

EXAMPLE 112

Preparation of 5'-O-acetyl-3'-O-benzyl-3-[3-[5-chloro-4-(2-thenoyloxy)-2-pyridyloxycarbonyl]benzoyl]-2'-deoxy-5-fluorouridine The general procedure of Example 73 was followed, thereby producing the title compound in a yield of 59%. NMR (CDCl₃)δ: 8.65–7.58 (8H, m,

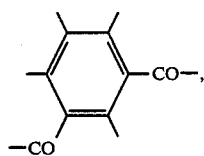

H₆ of the pyridine ring, H₃ of the thiophene ring, H₅ of the thiophene ring and H₆) 7.38 (1H, s, H₃ of the pyridine ring) 7.30–7.15 (6H, m,

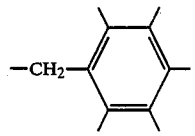

and H₄ of the thiophene ring) 6.21 (1H, t, J=6 Hz, H₁′) 4.52 and 4.50 (each 1H, s,

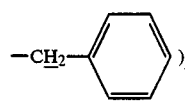

4.28–4.09 (4H, m, H₃′, H₄′, H₅′) 2.72–2.05 (5H, m, H₂′ and C$\underline{H}$₃CO—).

EXAMPLE 113

Preparation of 5′-O-acetyl-3′-O-benzyl-3-[3-[5-chloro-4-(3,4,5-trimethoxybenzoyloxy)-2-pyridyloxycarbonyl]benzoyl]-2′-deoxy-5-fluorouridine The general procedure of Example 73 was followed, thereby producing the title compound as a powder in a yield of 71%.

NMR (CDCl₃)δ: 8.67–8.18 (4H, m,

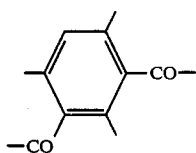

and H₆ of the pyridine ring) 7.84–7.60 (2H, m,

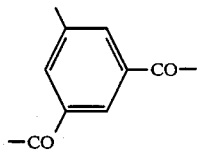

and H₆) 7.47 (2H, s,

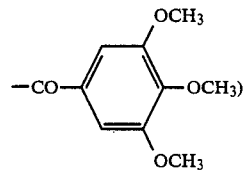

7.38 (1H, s, H₃ of the pyridine ring) 7.31 (5H, s,

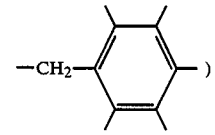

6.21 (1H, t, J=6 Hz, H₁′) 4.53 and 4.50 (each 1H, s,

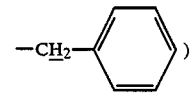

4.29–4.08 (4H, m, H₃′, H₄′, H₅′) 3.96 and 3.93 (9H, each s, —OCH₃ x 3) 2.50–2.05 (5H, m, H₂′ and C$\underline{H}$₃CO—).

EXAMPLE 114

Preparation of 2′-deoxy-5-fluoro-3′-O-(4-carboxybenzyl)uridine [R²=R³=H, R¹=4-carboxybenzyl group]

Potassium hydroxide (4.30 g) and 1.70 g of 4-methoxycarbonylbenzyl bromide was added to a solution of 3.00 g of 2′-deoxy-5-fluoro-5′-O-trityluridine in 200 ml of dioxane. The mixture was stirred at room temperature for a day. The reaction mixture was concentrated under a reduced pressure. To the concentrate was added 200 ml of water and the mixture was stirred at room temperature for 15 minutes. The reaction mixture was rendered acidic with acetic acid, and extracted with ethyl acetate. The organic layer was dried over magnesium sulfate and concentrated under a reduced pressure. The concentrate was dissolved in 50 ml of a 80% aqueous solution of acetic acid. The solution was heated to 100° C. for 2 hours. The solvent was distilled off and the residue was applied to silica gel column chromatography using 3% methanol-chloroform as an eluent, affording 650 mg of the title compound in a yield of 28%.

¹H-NMR (DMSO-d₆)δ: 11.83 (1H, bs, N₃—H, disappeared by addition of D₂O) 8.19 (1H, d, J=7 Hz, C₆—H) 7.94 (2H, d, J=8 Hz,

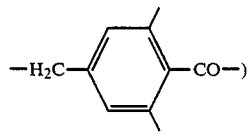

7.46 (2H, d, J=8 Hz,

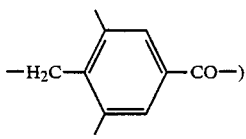

6.14 (1H, t, J=6 Hz, $C_{1'}$—H) 5.20 (1H, bs, $C_{5'}$—OH, disappeared by addition of $D_2O$) 4.63 (2H, s,

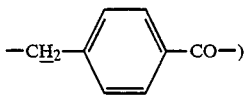

4.22–3.64 (4H, m, $C_{3'.4'.5'}$—H) 2.35–2.04 (2H, m, $C_{2'}$—H).

EXAMPLE 115

Preparation of 2'-deoxy-3'-O-benzyl-5-fluorouridine [$R^1=C_6H_5CH_2$, $R^2=R^3=H$]

In 50 ml of dioxane was dissolved 10 g of 2'-deoxy-5'-O-trityl-5-fluorouridine. To the solution were added 2.9 ml of benzyl bromide and 14.6 g of particles of potassium hydroxide. The mixture was stirred at room temperature for 1 hour. Thereto was added 40 ml of water. The mixture was adjusted to a pH of about 3 to about 4 and extracted with ethyl acetate. The ethyl acetate layer was washed with an aqueous solution of sodium chloride and dried over anhydrous sodium sulfate. The sodium sulfate was separated by filtration and the solvent was distilled off, giving as an intermediate 16.0 g of 2'-deoxy-3'-O-benzyl-5'-O-trityl-5-fluorouridine.

The compound thus obtained was dissolved in 80 ml of a 80% solution of acetic acid to undergo reaction at 50° to 60° C. for 2 hours. The reaction mixture was cooled with ice for 1 hour and 5.1 g of trityl alcohol was removed by filtration. The mother liquor was concentrated and ethanol was added to the concentrate. The mixture was stirred and the crystals thus precipitated were separated by filtration and dried, giving 5.3 g of the title compound in a yield of 75.7%.

M.p. 138°–139° C.

The analysis by $^1$H-NMR showed that the compound obtained above was identical with the compound prepared in Example 2.

EXAMPLE 116

Preparation of 2'-deoxy-3'-O-benzyl-5-fluorouridine [$R^1=C_6H_5CH_2$, $R^2=R^3=H$]

The general procedure of Example 115 was followed using 2'-deoxy-5'-O-(diphenyl-p-methoxphenyl)methyl-5-fluorouridine, thereby producing the title compound in a yield of 63%. M.p. 138°–139° C.

The analysis by $^1$H-NMR showed that the compound obtained above was identical with the compound prepared in Example 115.

EXAMPLE 117

Preparation of 2'-deoxy-3'-O-benzyl-5-fluorouridine [$R^1=C_6H_5CH_2$, $R^2=R^3=H$]

A 10 g quantity of 2'-deoxy-5'-O-trityl-5-fluorouridine was dissolved in 100 ml of dioxane. To the solution were added 2.9 ml of benzyl chloride, 6.9 g of particles of potassium hydroxide and 3.56 g of sodium iodide. The mixture was stirred at 40° C. for 4 hours, and 2.9 ml of benzyl chloride and 1.15 g of potassium hydroxide were added and stirred for 1 hour. Thereto was added water to dissolve the potassium hydroxide in water. The solution was adjusted to a pH of about 3 with acetic acid and extracted with ethylene dichloride. The extract was washed with water and the ethylene dichloride layer was dried over anhydrous sodium sulfate. The sodium sulfate was separated by filtration and the solvent was distilled off, giving 8 g of 2'-deoxy-3'-O-benzyl-5'-O-trityl-5-fluorouridine as an oil.

The compound thus obtained was dissolved in 80 ml of a 80% solution of acetic acid to undergo reaction at 50° to 60° C. for 2 hours. The reaction mixture was cooled with ice for 1 hour. The trityl alcohol was separated by filtration and the filtrate was concentrated. The concentrate was recrystallized from ethanol, giving a first crop of crystals of the title compound in a yield of 70.6%.

The ethanol mother liquor was concentrated and the concentrate was recrystallized from a small amount of ethanol, affording a second crop of crystals of the title compound in a yield of 15.9%. Overall yield 86.5%

M.p. 138°–139° C.

The analysis by $^1$H-NMR showed that the product was identical with the compound prepared in Example 115.

EXAMPLE 118

Preparation of 2'-deoxy-3'-O-benzyl-5-fluorouridine [$R^1=C_6H_5CH_2$, $R^2=R^3=H$]

In 50 ml of dioxane was dissolved 10 g of 2'-deoxy-5'-O-trityl-5-fluorouridine. To the solution were added 2.9 ml of benzyl bromide and 14.6 g of particles of potassium hydroxide. The mixture was stirred at room temperature for 1 hour. The solvent was distilled off and the residue was dissolved in 80 ml of a 80% solution of acetic acid to undergo reaction at 50° to 60° C. for 2 hours. The reaction mixture was cooled with ice for 1 hour, the trityl alcohol was separated by filtration and the mother liquor was concentrated. To the concentrate was added ethanol and the mixture was stirred. The crystals precipitated were separated by filtration and dried, affording 5.0 g of the title compound in a yield of 72%.

M.p. 138°–139° C.

The analysis by $^1$H-NMR showed that the compound thus prepared was identical with the compound obtained in Example 115.

EXAMPLES 119 TO 147

The general procedure of Example 115 was followed, thereby producing compounds identical with those prepared in Examples 1, 3 to 25, 90 to 93 and 114, respectively.

EXAMPLES 148 TO 176

The general procedure of Example 117 was followed, thereby producing compounds identical with those prepared in Examples 1, 3 to 25, 90 to 93 and 114, respectively.

EXAMPLE 177

Preparation of 3'-O-benzyl-2'-deoxy-5-fluoro-5'-O-stearoyluridine

The title compound was prepared as an oil by carrying out the same reaction and subsequent treatment as in Example 26. Yield 78%.

$^1$H-NMR(CDCl$_3$)δ: 7.65 (1H, d, J=6 Hz, C$_6$—H) 7.32 (5H, s, phenyl—H) 6.23 (1H, t, J=6 Hz, C$_{1'}$—H) 4.54 (2H, d, J=2 Hz, —CH$_2$—⟨phenyl⟩)

4.29–4.01 (4H, m, C$_{3'.4'.5'}$—H) 2.33–1.83 (4H, m, C$_{2'}$—H and —OCOCH$_2$—) 1.25 (30H, bs, —(CH$_2$)$_{15}$—) 0.88 (3H, t, —CH$_3$).

EXAMPLE 178

Preparation of 5'-O-cyclohexanoyl-2'-deoxy-3'-O-(2,4-dichlorobenzyl)-5-fluorouridine The title compound was prepared as an oil by carrying out the same reaction and subsequent treatment as in Example 26. Yield 77%.

$^1$H-NMR(CDCl$_3$)δ: 9.50 (1H, b, NH) 7.67 (1H, d, J=6 Hz, C$_6$—H) 7.40–7.16 (3H, m, phenyl—H) 6.25 (1H, t, J=6 Hz, C$_{1'}$—H) 4.58 (2H, s, —CH$_2$—⟨phenyl⟩)

4.37–4.08 (4H, m, C$_{3'.4'.5'}$—H) 2.77–2.51 and 2.48–1.04 (13H, m, C$_{2'}$—and cyclohexyl—H).

EXAMPLE 179

Preparation of 2'-deoxy-5-fluoro-3'-O-(4-methoxybenzyl)-5'-O-(2-thenoyl)uridine

The title compound was prepared as a powder by carrying out the same reaction and subsequent treatment as in Example 26. Yield 91%.

$^1$H-NMR(CDCl$_3$)δ: 9.20 (1H, bs, NH) 7.82 (1H, dd, J$_{4,5}$=4 Hz, J$_{3,5}$=2 Hz,

⟨thienyl-S⟩)

7.63 (1H, d, J=6 Hz, C$_6$—H) 7.59 (1H, dd, J$_{3,4}$=5 Hz, J$_{4,5}$=4 Hz,

⟨thienyl-S⟩)

7.29–7.08 (3H, m,

⟨thienyl-S⟩ and —CH$_2$—⟨phenyl⟩—OCH$_3$)

6.87 (2H, d, J=9 Hz,

—CH$_2$—⟨phenyl⟩—OCH$_3$)

6.25 (1H, t, J=6 Hz, C$_{1'}$—H) 4.56–4.10 (6H, m, C$_{3'.4'.5'}$—H and

—CH$_2$—⟨phenyl⟩—OCH$_3$)

3.78 (3H, s, —OCH$_3$) 2.74–2.48 and 2.22–1.78 (2H, m, C$_{2'}$—H).

EXAMPLE 180

Preparation of 2'-deoxy-5-fluoro-3'-(3-methylbenzyl)-5'-O-(2-furoyl)uridine

The title compound was prepared as a powder by carrying out the same reaction and subsequent treatment as in Example 26. Yield 85%.

$^1$H-NMR(CDCl$_3$)δ: 9.14 (1H, bs, NH) 7.93 (1H, d, J=6 Hz, C$_6$—H) 7.58 (1H, bs,

⟨furanyl-O⟩)

7.29–7.10 (5H, m, furanyl—H,

⟨furanyl-O⟩)

6.55 (1H, dd, J$_{3,4}$=4 Hz, J$_{4,5}$=2 Hz,

⟨furanyl-O⟩)

6.35 (1H, t, J=6 Hz, C$_{1'}$—H) 4.77–4.10 (6H, m, C$_{3'.4'.5'}$—H and —CH$_2$ 2.71–2.44 and 2.34–1.97 (5H, m, C$_{2'}$—H and CH$_3$).

EXAMPLE 181

Preparation of 3'-O-benzyl-5'-O-crotonoyl-2'-deoxy-5-fluorouridine

The title compound was prepared as a powder in a yield of 75% by carrying out the same reaction and treatment as in Example 54.

$^1$H-NMR(CDCl$_3$)δ: 8.63 (1H, bs, NH) 7.67 (1H, d, J=6 Hz, C$_6$—H) 7.32 (5H, s, phenyl—H) 7.14–6.89 (1H, m, —CH=CHCH$_3$) 6.24 (1H, t, J=6 Hz, C$_{1'}$—H) 5.84 (1H, dd, J$_{\alpha,\beta}$=16 Hz, J$_{\alpha,\gamma}$=2 Hz, —CH=CHCH$_3$) 4.54 (2H, s,

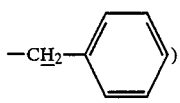

4.42–4.05 (4H, m, C$_{3'.4'.5'}$—H) 2.73–2.44 and 2.20–2.02 (2H, m, C$_{2'}$—H) 1.90 (3H, dd, J$_{\beta,\gamma}$=7 Hz, J$_{\alpha,\gamma}$=2 Hz, —CH=CHCH$_3$).

EXAMPLE 182

Preparation of 3'-(2-bromobenzyl)-2'-deoxy-5'-O-ethoxyacetyl-5-fluorouridine A 1.24 g quantity of DCC was added to a solution of 1 g of 3'-(2-bromobenzyl)-2'-deoxy-5-fluorouridine and 0.63 g of ethoxy acetate in 10 ml of pyridine. The mixture was stirred at room temperature for 24 hours. The insolubles were separated by filtration and the filtrate was concentrated. The concentrate was purified with isopropanol-ether, giving 1.06 g of the title compound as a powder in a yield of 80%.

$^1$H-NMR(CDCl$_3$)δ: 9.49 (1H, bs, NH) 7.74 (1H, d, J=6 Hz, C$_6$—H) 7.60–7.06 (4H, m, phenyl—H) 6.34 (1H, t, J=6 Hz, C$_{1'}$—H) 4.60 (2H, s,

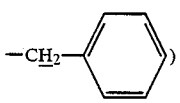

4.39–4.13 (6H, m, C$_{3'.4'.5'}$—H and —COCH$_2$O—) 3.59 (2H, q, J=7 Hz, —OCH$_2$CH$_3$) 2.73–2.48, 2.31–2.00 (2H, m, C$_{2'}$—H) 1.22 (3H, t, J=7 Hz, —OCH$_2$CH$_3$).

EXAMPLE 183

Preparation of 2'-deoxy-5-fluoro-3'-O-(2,4,6-trimethylbenzyl)uridine

A 1.66 g quantity of 2,4,6-trimethylbenzyl chloride was added to a solution of 4.00 g of 2'-deoxy-5-fluoro-5'-O-trityluridine, 2.30 g of potassium hydroxide and 1.47 g of sodium iodide in 50 ml of dried dioxane. The mixture was stirred at 60° C. for 3 hours. The solvent was distilled off, and ethyl acetate and water were added to the residue. The ethyl acetate layer was washed with water and dried over anhydrous sodium sulfate. The ethyl acetate was distilled off and the residue was dissolved in 50 ml of a 80% solution of acetic acid. The resulting solution was left to stand at 70° C. for 2 hours. The reaction mixture was concentrated and water was added to the concentrate. The mixture was rendered weakly basic with an aqueous solution of sodium hydroxide and washed with ether. The aqueous layer was made weakly acidic with a 6N solution of hydrochloric acid and extracted with ethyl acetate. The ethyl acetate layer was washed with water, dried over anhydrous sodium sulfate and concentrated. Ether was added to the concentrate to deposit solids and the solids were recrystallized from ethanol, giving 1.69 g of the title compound in a yield of 55%.

M.p. 179°–181° C. $^1$H-NMR(DMSO)-d$_6$)δ: 11.82 (1H, bs, NH) 8.20 (1H, d, J=7 Hz, C$_6$—H) 6.83 (2H, s,

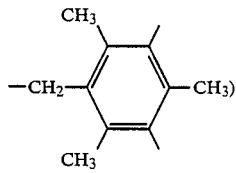

6.07 (1H, bt, J=6 Hz, C$_{1'}$—H) 5.19 (1H, bt, J=5 Hz, 5'—OH) 4.47 (2H, s,

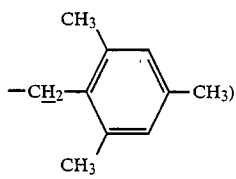

4.20–4.10 (1H, m, C$_{3'}$—H) 4.02–3.91 (1H, m, C$_{4'}$—H) 3.69–3.57 (2H, m, C$_{5'}$—H) 2.29–2.12 (11H, m, CH$_3$×3 and C$_{2'}$—H).

EXAMPLE 184

Preparation of 2'-deoxy-3-[3-[6-(2,4-dichlorobenzoyloxy)-2-pyridyloxycarbonyl]benzoyl]-5-fluoro-3'-O-(3-methylbenzyl)-5'-O-(2-furoyl)uridine.

The title compound was prepared as a powder by carrying out the same reaction and subsequent treatment as in Example 73. Yield 24%.

$^1$H-NMR(CDCl$_3$)δ: 8.66 (1H, t, J=2 Hz,

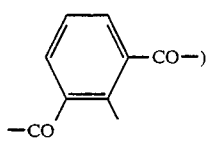

8.50 and 8.26 (2H, each dt, J=8 Hz, J=2 Hz,

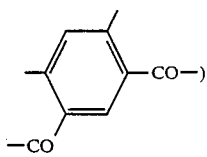

8.14–7.92 (3H, m,

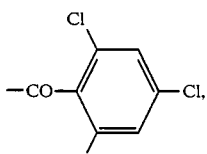

$C_6$—H, $C_4$—H of the pyridine ring) 7.69 (1H, t, J=8 Hz,

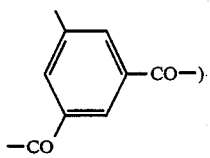

7.60 (1H, bs, $C_5$—H of furanyl 7.53 (1H, d, J=2 Hz,

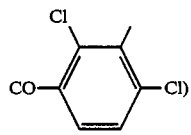

7.36 (1H, dd, J=8 Hz, J=2 Hz,

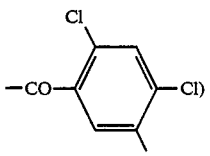

7.30–7.11 (7H, m,

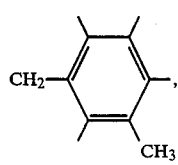

$C_{3,5}$—H of the pyridine ring and $C_3$—H of furanyl) 6.55 (1H, dd, J=4 Hz, J=2 Hz, $C_4$—H of furanyl) 6.34 (1H, t, J=6 Hz, $C_{1'}$—H) 4.75–4.15 (6H, m, $C_{3'.4'.5'}$—H and

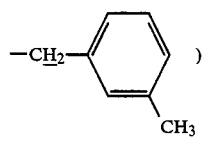

2.77–2.01 (5H, $C_{2'}$—H and $CH_3$).

EXAMPLE 185

Preparation of 5'-O-cyclohexanoyl-2'-deoxy-3'-O-(2,4-dichlorobenzyl)-5-fluoro-3-[3-[3-cyano-6-(3-methylbenzoyloxy)-2-pyridyloxycarbonyl]benzoyl]uridine The title compound was prepared as a powder by carrying out the same reaction and subsequent treatment as in Example 73. Yield 13%.

$^1$H-NMR(CDCl$_3$)δ: 8.66 (1H, t, J=2 Hz,

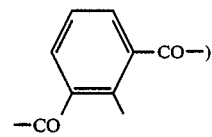

8.52 and 8.35–8.18 (3H, m,

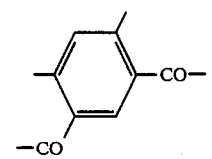

and $C_4$—H of the pyridine ring) 8.04–7.92 (2H, m,

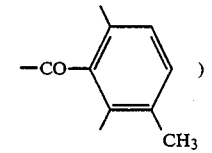

7.86–7.65 (2H, m, $C_6$—H and

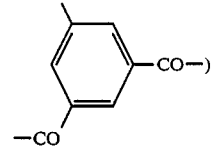

7.49–7.16 (6H, m, $C_5$—H of the pyridine ring,

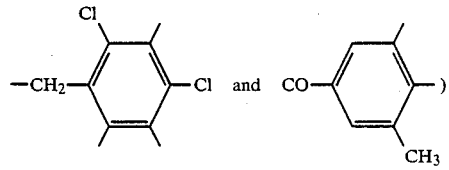

6.22 (1H, t, J=6 Hz, $C_{1'}$—H) 4.55 (2H, s,

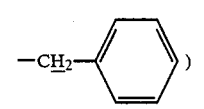

4.42–4.09 (4H, m, $C_{3'.4'.5'}$—H) 2.85–1.10 (16H, m, $C_{2'}$—H, $CH_3$, cyclohexyl).

EXAMPLE 186

Preparation of 3'-O-benzyl-3-[3-(5-chloro-1,2-dihydro-1-ethoxymethyl-2-oxo-4-pyridyloxycarbonyl)benzoyl]-2'-deoxy-5-fluorouridine The title compound was prepared as a powder by carrying out the same reaction and subsequent treatment as in Example 101. Yield 49%.

$^1$H-NMR(CDCl$_3$)δ: 8.67–8.19 (4H, m, $C_6$—H and 7.77–7.61 (2H, m, 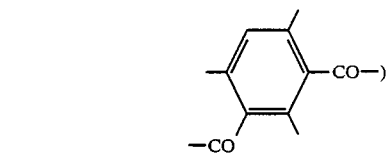

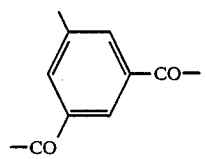

and C$_6$—H of the pyridine ring) 7.30 (5H, s,

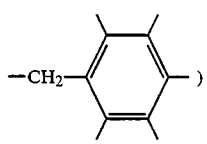

6.66 (1H, s, C$_3$—H of the pyridine ring) 6.20 (1H, t, J=6 Hz, C$_{1'}$—H) 5.34 (2H, s, N—C$\underline{H}_2$O—) 4.52 (2H, s,

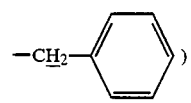

4.32–3.81 (4H, m, C$_{3'.4'.5'}$—H) 3.64 (2H, q, J=7 Hz, —OC$\underline{H}_2$CH$_3$) 3.10 (1H, bs, 5'—OH) 2.52–2.19 (2H, m, C$_{2'}$—$\overline{H}$) 1.24 (3H, t, J=7 Hz, OCH$_2$C$\underline{H}_3$).

EXAMPLE 187

Preparation of
3-[3-(6-benzoyloxy-3-chloro-2-pyridyloxycarbonyl)-benzoyl]-3'-O-benzyl-2'-deoxy-5-fluorouridine The title compound was prepared as a powder by carrying out the same reaction and subsequent treatment as in Example 101. Yield 39%.

$^1$H-NMR(CDCl$_3$)δ: 8.71–8.10 (6H, m, C$_6$—H and

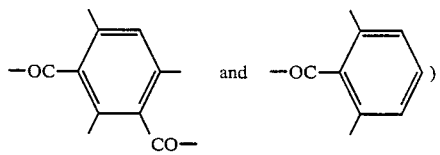

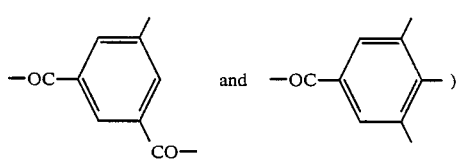

7.28 (5H, s,

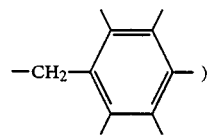

7.25 (1H, d, J=8 Hz, C$_5$—H of the pyridine ring) 6.23 (1H, t, J=6 Hz, C$_{1'}$—H) 4.48 (2H, s,

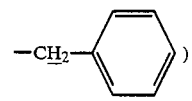

4.26–3.66 (4H, m, C$_{3'.4'.5'}$—H) 3.07 (1H, bs, C$_{5'}$—OH) 2.52–2.12 (2H, m, C$_{2'}$—H).

EXAMPLE 188

Preparation of
3-[3-(6-benzoyloxy-3-chloro-2-pyridyloxycarbonyl)-benzoyl]-3'-O-(4-chloro-benzyl)-2'-deoxy-5-fluorouridine The title compound was prepared as a powder by carrying out the same reaction and subsequent treatment as in Example 101. Yield 45%. $^1$H-NMR(CDCl$_3$)δ: 8.69–8.11 (6H, m, C$_6$—H and

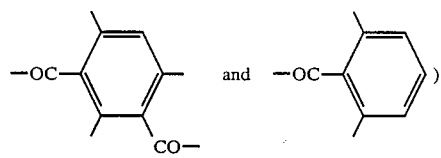

7.98 (1H, d, J=8 Hz, C$_4$—H of the pyridine ring) 7.76–7.39 (4H, m,

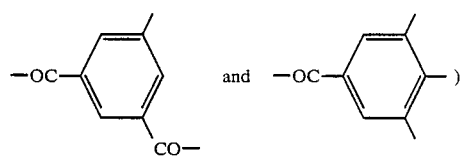

7.30–7.11 (5H, m,

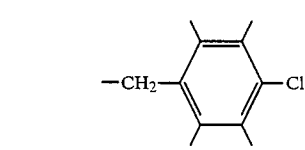

and C$_5$—H of the pyridine ring) 6.22 (1H, t, J=6 Hz, C$_{1'}$—H) 4.42 (2H, s,

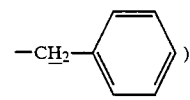

4.23–3.75 (4H, m, C$_{3'.4'.5'}$—H) 3.06 (1H, bs, C$_{5'}$—OH) 2.66–2.02 (2H, m, C$_{2'}$—H).

EXAMPLE 189

Preparation of
3-[4-(6-benzoyloxy-3-cyano-2-pyridyloxycarbonyl)-3-furoyl]-3'-O-benzyl-2'-deoxy-5-fluorouridine The title compound was prepared as a powder by carrying out the same reaction and subsequent treatment as in Example 101. Yield 31%.

$^1$H-NMR(CDCl$_3$)δ: 8.35 (2H, s,

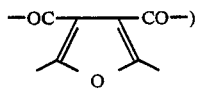

8.18–7.94 (4H, m, C$_6$—H, C$_4$—H of the pyridine ring and

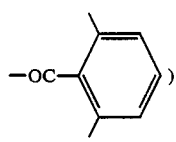

7.63–7.38 (4H, m, C$_5$—H of the pyridine ring and

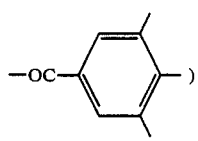

7.25 (5H, s,

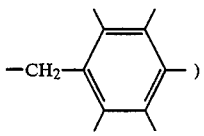

6.12 (1H, t, J=6 Hz, C$_{1'}$—H) 4.39 and 4.37 (each 1H, s,

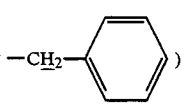

4.25–3.55 (4H, m, C$_{3'.4'.5'}$—H) 2.78 (1H, bs, C$_{5'}$—OH) 2.60–2.11 (2H, m, C$_{2'}$—H).

EXAMPLE 190

Preparation of
3-[3-(6-benzoyloxy-3-cyano-2-pyridyloxycarbonyl)benzoyl]-3'-O-benzyl-2'-deoxy-5-fluorourine The title compound was prepared as a powder by carrying out the same reaction and subsequent treatment as in Example 101. Yield 33%.

$^1$H-NMR(CDCl$_3$)δ: 8.71–8.12 (7H, m, C$_6$—H), C$_4$—H of the pyridine ring and

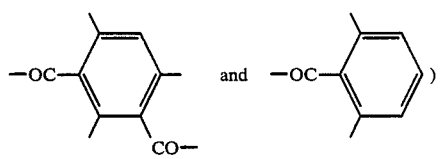

7.78–7.37 (5H, m, C$_5$—H of the pyridine ring and

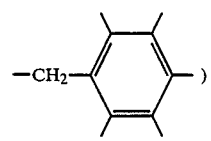

7.29 (5H, s,

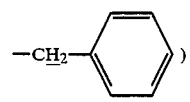

6.23 (1H, t, J=6 Hz, C$_{1'}$—H) 4.49 (2H, s, 4.29–3.66 (4H, m, C$_{3'.4'.5'}$—H) 3.47 (1H, bs, C$_{5'}$—OH) 2.68–2.19 (2H, m, C$_{2'}$—H).

EXAMPLE 191

Preparation of
3-[3-(6-benzoyloxy-3-cyano-2-pyridyloxycarbonyl)benzoyl]-3'-O-(2-chlorobenzyl)-2'-deoxy-5-fluorouridine The title compound was prepared as a powder by carrying out the same reaction and subsequent treatment as an Example 101. Yield 43%.

$^1$H-NMR(CDCl$_3$)δ: 8.72–8.12 (7H, m,

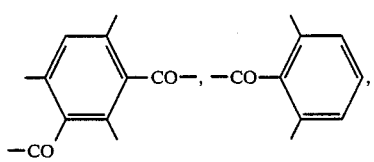

C$_6$—H, C$_4$—H of the pyridine ring) 7.78–7.15 (9H, m,

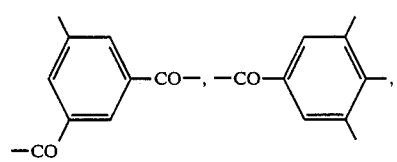

and C₅—H of the pyridine ring) 6.26 (1H, bt, J=6 Hz, C₁′—H) 4.57 (2H, s,

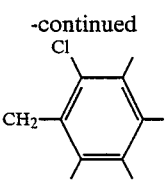

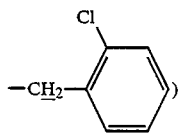

4.33–4.17 (2H, m, C₃′.₄′—H) 4.01–3.71 (2H, m, C₅′—H) 2.86 (1H, bs, 5′—OH) 2.68–2.14 (2H, m, C₂′—H).

EXAMPLE 192

Preparation of 3-[3-(6-benzoyloxy-3-cyano-2-pyridyloxycarbonyl)benzoyl]-2′-deoxy-5-fluoro-3′-O-(4-fluorobenzyl)uridine The title compound was prepared as a powder by carrying out the same reaction and subsequent treatment as in Example 101. Yield 57%.

¹H-NMR(CDCl₃)δ: 8.70–8.10 (7H, m,

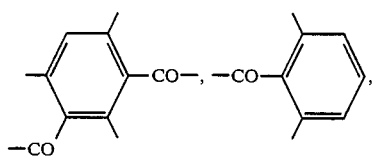

C₆—H, C₄—H of the pyridine ring) 7.79–6.89 (6H, m,

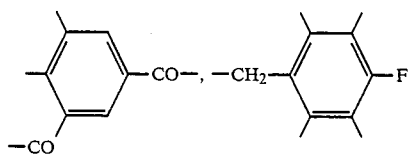

and C₅—H of the pyridine ring) 6.22 (1H, bt, J=6 Hz, C₁′—H) 4.45 (2H, s,

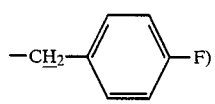

4.31–4.10 (2H, m, C₃′.₄′—H) 4.00–3.63 (2H, m, C₅′—H) 2.80–2.00 (3H, m, 5′—OH, C₂′—H).

EXAMPLE 193

Preparation of 3-[3-(6-benzoyloxy-3-chloro-2-pyridyloxycarbonyl)-benzoyl]-2′-deoxy-5-fluoro-3′-O-(2,4,6-tri-methylbenzyl)uridine The title compound was prepared as a powder by carrying out the same reaction and subsequent treatment as in Example 101. Yield 47%.

¹H—NMR(CDCl₃) δ: 8.67–8.12 (6H, m,

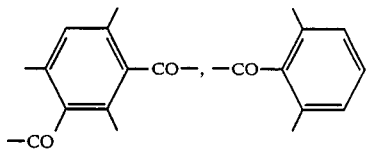

and C₆—H) 7.97 (1H, d, J=8 Hz, C₄—H of the pyridine ring) 7.77–7.37 (4H, m,

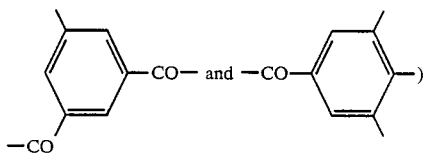

7.25 (1H, d, J=8 Hz, C₅—H of the pyridine ring) 6.82 (2H, s,

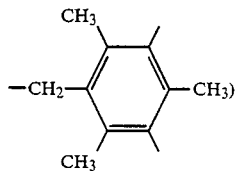

6.27 (1H, bt, J=6 Hz, C₁′—H) 4.48 (2H, s,

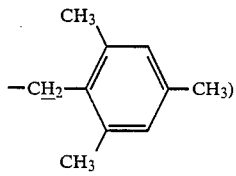

4.27–4.02 (2H, m, C₃′.₄′—H) 4.00–3.71 (2H, m, C₅′—H) 2.72–2.05 (12H, m, 5′—OH, C₂′—H, CH₃×3)

EXAMPLE 194

Preparation of 3′-O-benzyl-2′-deoxy-5-fluoro-3-[3-(1,6-dihydroxy-6-oxo-2-pyridyloxy)benzoyl]uridine The title compound was prepared as a powder by carrying out the same reaction and subsequent treatment as in Example 104. Yield 33%.

¹H—NMR(DMSO-d₆) δ: 11.45 (1H, bs, NH) 8.66–8.44 (4H, m,

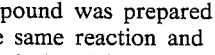

and C₄—H of the pyridone ring) 7.94–7.73 (2H, m,

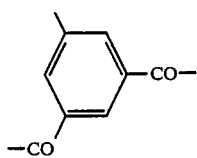

and C<sub>6</sub>—H) 7.33 (5H, s, phenyl—H) 6.81 and 6.64 (2H, each d, J=8 Hz, C<sub>3,5</sub>—H of the pyridone ring) 6.11 (1H, t, J=7 Hz, C<sub>1'</sub>—H) 5.29 (1H, t, J=6 Hz, 5'—OH) 4.54 (2H, s,

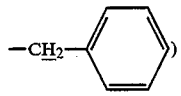

4.29–4.10 (2H, m, C<sub>3'.4'</sub>—H) 3.74–3.63 (2H, m, C<sub>5'</sub>—H) 2.45–2.23 (2H, m, C<sub>2'</sub>—H).

EXAMPLE 195

Preparation of 3-[3-(1,2-dihydro-2-oxo-4-pyridyloxycarbonyl)benzoyl]-5-fluoro-1-(2-tetrahydrofuranyl)uracil A 1.00 g quantity of isophthaloyl chloride and 0.70 ml of triethylamine were added to a solution of 1.00 g of 5-fluoro-1-(2-tetrahydrofuranyl)uracil in 30 ml of dried dioxane. The mixture was refluxed for 2 hours. Thereto added was 1.00 ml of triethylamine and the mixture was refluxed for 2 hours. Thereto further added was 0.60 g of 4-hydroxy-2(1H)-pyridone and the mixture was refluxed for 3 hours. The solvent was distilled off and 30 ml of ethyl acetate and 30 ml of water were added to the residue. The insolubles were removed by filtration. The ethyl acetate layer was separated, dried over anhydrous sodium sulfate and concentrated. The concentrate was subjected to silica gel column chromatography to conduct gradient elution using chloroform and mixtures of methyl (up to 2%) and chloroform. The fractions corresponding to the title compound were collected and concentrated, giving 0.40 g of a powder in a yield of 18%.

<sup>1</sup>H—NMR(DMSO-d<sub>6</sub>)δ: 11.74 (1H, bs, —NH—, disappeared by addition of D<sub>2</sub>O) 8.63–8.41 (3H, m, C<sub>2.4.6</sub>—H of the benzoyl ring) 8.14 (1H, d, J=7 Hz, C<sub>6</sub>—H) 7.84 (1H, t, J=8 Hz, C<sub>3</sub>—H of the benzoyl ring) 7.51 (1H, d, J=8 Hz, C<sub>6</sub>—H of the pyridine ring) 6.34–6.26 (2H, m, C<sub>3,5</sub>—H of the pyridine ring) 5.93 (1H, t, J=4 Hz, C<sub>1'</sub>—H) 4.41–4.20 and 3.92–3.72 (each 1H, m, C<sub>4'</sub>—H) 2.27–1.92 (4H, m, C<sub>2'.3'</sub>—H).

EXAMPLE 196

Preparation of 3-[4-(1,2-dihydro-2-oxo-4-pyridyloxycarbonyl)benzoyl]-5-fluoro-1-(2-tetrahydrofuranyl)uracil The title compound was prepared in the same manner as in Example 195.

<sup>1</sup>H—NMR(DMSO-d<sub>6</sub>) δ: 11.73 (1H, bs, —NH—, disappeared by addition of D<sub>2</sub>O) 8.28 (4H, s, phenyl—H) 8.14 (1H, d, J=7 Hz, C<sub>6</sub>—H) 7.52 (1H, d, J=8 Hz, C<sub>6</sub>—H of the pyridine ring) 6.33–6.25 (2H, m, C<sub>3,5</sub>—H of the pyridine ring) 5.92 (1H, bt, J=4 Hz, C<sub>1'</sub>—H) 4.49–4.26 and 4.03–3.77 (each 1H, m, C<sub>4'</sub>—H).

EXAMPLE 197

Preparation of 3-[3-(4-benzoyloxy-5-chloro-2-pyridyloxycarbonyl)-benzoyl]-2'-deoxy-3',5'-di-O-acetyl-5-fluorouridine The title compound was prepared in the same manner as in Example 195.

<sup>1</sup>H—NMR(CDCl<sub>3</sub>) δ: 8.68–8.17 (6H, m,

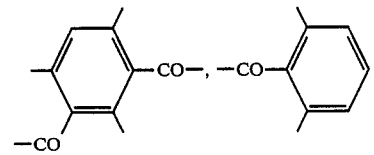

and C<sub>6</sub>—H of the pyridine ring) 7.79–7.44 (5H, m,

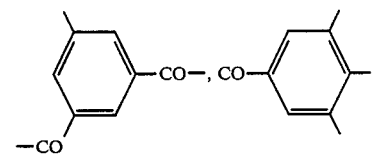

and C<sub>6</sub>—H) 7.39 (1H, s, C<sub>3</sub>—H of the pyridine ring) 6.27 (1H, t, J=8 Hz, C<sub>1'</sub>—H) 5.29–5.17 (1H, m, C<sub>3'</sub>—H) 4.51–4.28 (3H, m, C<sub>4'.5'</sub>—H) 2.70–2.08 (8H, m, C<sub>2'</sub>—H and COCH<sub>3</sub>×2).

EXAMPLE 198

Preparation of 3-[3-(2-benzoyloxy-5-chloro-4-pyridyloxycarbonyl)-benzoyl]-5-fluoro-1-(2-tetrahydrofuranyl)uracil The title compound was prepared in the same manner as in Example 195.

<sup>1</sup>H—NMR(CDCl<sub>3</sub>) δ: 8.69–8.16 (6H, m,

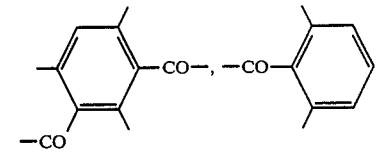

and C<sub>6</sub>—H of the pyridine ring) 7.81–7.45 (5H, m,

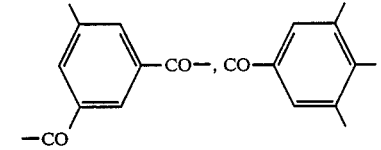

and C<sub>6</sub>—H) 7.41 (1H, s, C<sub>3</sub>—H of the pyridine ring) 6.00–5.90 (1 m, C<sub>1'</sub>—H) 4.42–3.87 (2H, m, C<sub>4'</sub>—H) 2.55–1.89 (4H, m, C<sub>2'.3'</sub>—H).

EXAMPLE 199

Preparation of 3-[3-(4-benzoyloxy-5-chloro-2-pyridyloxycarbonyl)-benzoyl]-5-fluoro-1-(2 -tetrahydrofuranyl)uracil The title compound was prepared in the same manner as in Example 195.

<sup>1</sup>H—NMR(CDCl<sub>3</sub>) δ: 8.66–8.17 (6H, m,

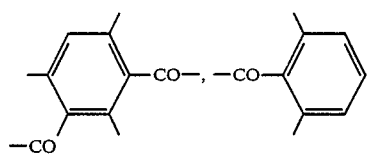

and C$_6$—H of the pyridine ring) 7.79–7.41 (5H, m,

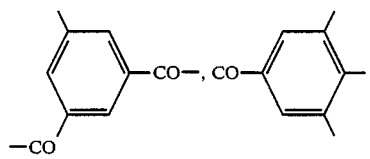

and C$_6$—H) 7.38 (1H, s, C$_3$—H of the pyridine ring) 6.02–5.90 (1m, C$_{1'}$—H) 4.45–3.87 (2H, m, C$_{4'}$—H) 2.55–1.89 (4H, m, C$_{2',3'}$—H).

EXAMPLE 200

Preparation of 3-[3-(2-acetoxy-5-chloro-4-pyridyloxycarbonyl)benzoyl]-5-fluoro-1-(2-tetrahydrofuranyl)uracil A 5.53 ml quantity of triethylamine and 1.52 g of isophthaloyl chloride were added to a solution of 1.00 g of 1-(2-tetrahydrofuranyl)-5-fluorouracil in 50 ml of dried dioxane. The mixture was refluxed for 1 hour. The reaction mixture was filtered and the filtrate was concentrated. The concentrate was dissolved in 50 ml of acetonitrile. To the solution were added 3.46 ml of triethylamine and 1.40 g of 2-acetoxy-5-chloro-4-hydroxypyridine. The mixture was stirred at room temperature for 2 hours. The reaction mixture was filtered and concentrated. The concentrate was purified by silica gel column chromatography using chloroform as an eluent, giving 530 mg of the title compound in a yield of 20%.

$^1$H—NMR(CDCl$_3$) δ: 8.68–8.22 (3H, m,

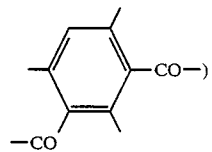

8.47 (1H, s, C$_6$—H of the pyridine ring) 7.72 (1H, t, J=8 Hz,

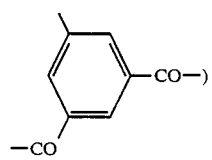

7.54 (1H, d, J=6 Hz, C$_6$—H) 7.27 (1H, s, C$_3$—H of the pyridine ring) 5.98–5.90 (1m, C$_{1'}$—H) 4.29–4.04 (2H, m, C$_{4'}$—H) 2.35 (3H, s, COCH$_3$) 2.43–1.89 (4H, m, C$_{2',3'}$—H).

EXAMPLAE 201

Preparation of 3-[3-(2-acetoxy-5-chloro-4-pyridyloxycarbonyl)benzoyl]-5'-deoxy-2',3'-di-O-acetyl-5-fluorouridine The title compound was prepared in the same manner as in Example 200.

$^1$H—NMR(CDCl$_3$) δ: 8.75–8.21 (4H, m,

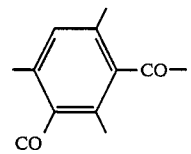

and C$_6$—H of the pyridine ring) 7.73 (1H, t, J=8 Hz,

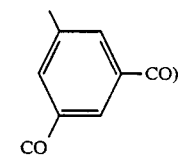

7.48 (1H, d, J=6 Hz, C$_6$—H) 7.26 (1H, s, C$_3$—H of the pyridine ring) 5.93 (1H, d, J=5 Hz, C$_{1'}$—H) 5.31 (1H, t, J=6 Hz, C$_{2'}$—H) 5.03 (1H, t, J=6 Hz, C$_{3'}$—H) 4.38–4.12 (1H, m, C$_{4'}$—H) 2.35 (3H, s, COCH$_3$ on the pyridine ring) 2.10 and 2.01 (each 3H, s, COCH$_3$) 1.46 (3H, d, J=6 Hz, C$_{5'}$—H).

EXAMPLE 202

Preparation of 3-[3-(4-benzoyloxy-5-chloro-2-pyridyloxycarbonyl)-benzoyl]-5-fluoro-2',3',5'-tri-O-acetyluridine The title compound was prepared in the same manner as in Example 200.

$^1$H—NMR(CDCl$_3$) δ: 8.75–8.18 (6H, m,

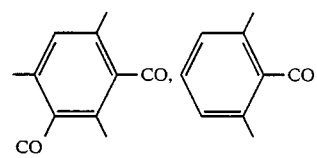

and C$_6$—H of the pyridine ring) 7.79–7.43 (5H, m,

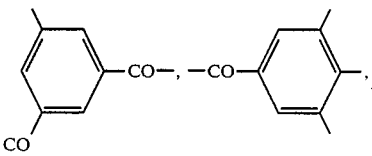

C$_6$—H) 7.39 (1H, s, C$_3$—H of the pyridine ring) 6.12–6.05 (1H, m, C$_{1'}$—H) 5.34–5.29 (2H, m, C$_{2',3'}$—H) 4.38 (3H, bs, C$_{4',5'}$—H) 2.18, 2.11, and 2.03 (each 3H, s, COCH$_3$).

EXAMPLE 203

Preparation of 3-[3-(4-acetoxy-5-chloro-2-pyridyloxycarbonyl)benzoyl]-5-fluoro-1-(2-tetrahydrofuranyl)uracil The title compound was prepared in the same manner as in Example 200.

$^1$H—NMR(CDCl$_3$) δ: 8.65–8.19 (4H, m,

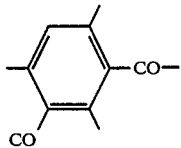

and C$_6$—H of the pyridine ring) 7.70 (1H, t, J=8 Hz,

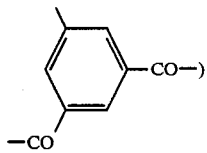

7.53 (1H, d, J=6 Hz, C$_6$—H) 7.18 (1H, s, C$_3$—H of the pyridine ring) 6.02–5.90 (1H, m, C$_{1'}$—H) 4.45—3.87 (2H, m, C$_{4'}$—H) 2.44–1.90 (7H, m, COCH$_3$ and C$_{2',3'}$—H).

EXAMPLE 204

Preparation of 5-fluoro-3-[3-[2-(2-methylbenzoyloxy)-4-pyridyloxycarbonyl]benzoyl]-1-(2-tetrahydrofuranyl)uracil The title compound was prepared in the same manner as in Example 200.

$^1$H—NMR(CDCl$_3$) δ: 8.67–7.21 (12H, m, phenyl—H, H of the pyridine ring and C$_6$—H) 6.00–5.90 (1H, m, C$_{1'}$—H) 4.40–3.90 (2H, m, C$_{4'}$—H) 2.69 (3H, s, CH$_3$) 2.60–1.95 (4H, m, C$_{2',3'}$—H).

EXAMPLE 205

Preparation of 3-[3-(2-benzoyloxy-4-pyridyloxycarbonyl)benzoyl]-5-fluoro-1-(2-tetrahydrofuranyl)uracil The title compound was prepared in the same manner as in Example 200.

$^1$H—NMR(CDCl$_3$) δ: 8.67–8.18 (6H, m,

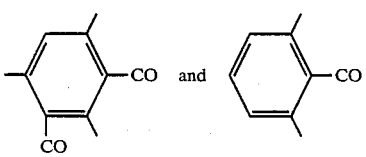

and C$_6$—H of the pyridine ring) 7.79–7.40 (5H, m,

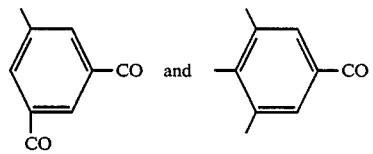

and C$_6$—H) 7.34–7.23 (2H, m, C$_{3,5}$—H of the pyridine ring) 6.00–5.90 (1H, m, C$_{1'}$—H) 4.45–3.87 (2H, m, C$_{4'}$—H) 2.55–1.89 (4H, m, C$_{2',3'}$—H).

EXAMPLE 206

Preparation of 3-[3-(1-benzyloxymethyl-5-chloro-1,2-dihydro-2-oxo-4-pyridyloxycarbonyl)benzoyl]-5-fluoro-1-(2-tetrahydrofuranyl)uracil The title compound was prepared in the same manner as in Example 200.

$^1$H—NMR(CDCl$_3$) δ: 8.65–8.21 (3H, m,

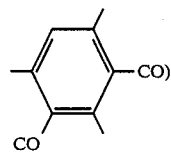

7.79–7.51 (3H, m,

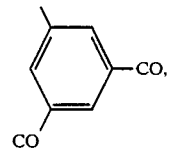

C$_6$—H, and C$_6$—H of the pyridine ring) 7.34 (5H, s, —CH$_2$) 6.65 (1H, s, C$_3$—H of the pyridine ring) 5.98–5.91 (1H, m, C$_{1'}$—H) 5.42 (2H, s, NCH$_2$O—) 4.66 (2H, s,

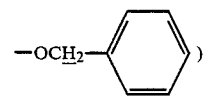

)

4.27–3.89 (2H, m, C$_{4'}$—H) 2.57–1.90 (4H, m, C$_{2',3'}$—H).

EXAMPLE 207

Preparation of 3-[3-[5-chloro-1,2-dihydro-2-oxo-1-(2-tetrahydrofuranyl)-4-pyridyloxycarbonyl]benzoyl]-5-fluoro-1-(2-tetrahydrofuranyl)uracil The title compound was prepared in the same manner as in Example 200.

$^1$H—NMR(CDCl$_3$)δ: 8.92–8.20 (3H, m, 7.79–7.54 (3H, m,

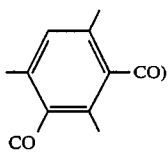

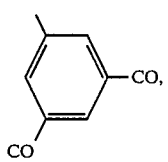

$C_6$—H and $C_6$—H of the pyridine ring) 6.58 (1H, s, $C_3$—H of the pyridine ring) 6.18–5.91 (2H, m, $C_{1'}$—H of the furanyl group×2) 4.33–3.87 (4H, m, $C_{4'}$—H of the furanyl group×2) 2.67–1.78 (8H, m, $C_{2',3'}$—H of the furanyl group×2).

EXAMPLE 208

Preparation of 3-[3-(4-benzoyloxy-5-chloro-2-pyridyloxycarbonyl)-benzoyl]-2'-deoxy-3',5'-di-O-benzyl-5-fluorouridine The title compound was prepared in the same manner as in Example 200.

$^1$H—NMR(CDCl$_3$) δ: 8.66–8.11 (7H, m,

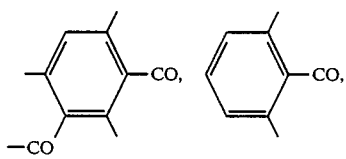

$C_6$—H, $C_6$—H of the pyridine ring) 7.75–7.30 (15H, m,

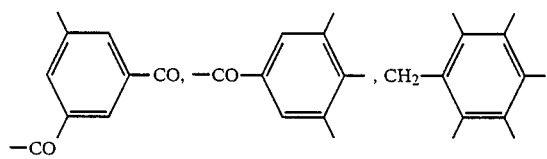

×2 and $C_3$—H of the pyridine ring) 6.31 (1H, bt, J=7 Hz, $C_{1'}$—H) 4.56 (2H, s,

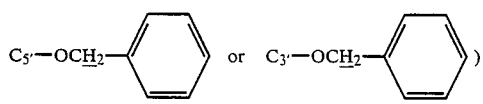

4.50 (2H, d, J=2 Hz,

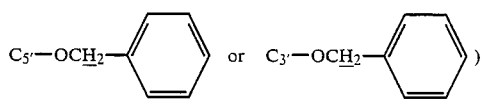

4.28–4.22 (2H, m, $C_{3'}$—H, $C_{4'}$—H) 3.91–3.52 (2H, m, $C_{5'}$—H) 2.66–2.04 (2H, m, $C_{2'}$—H).

EXAMPLE 209

Preparation of 3-[3-(4-benzoyloxy-5-chloro-2-pyridyloxycarbonyl)-benzoyl]-2'-deoxy-3',5'-di-O-(4-chlorobenzyl)-5-fluorouridine The title compound was prepared in the same manner as in Example 200.

$^1$H—NMR(CDCl$_3$) δ: 8.64–8.17 (6H, m, and $C_6$—H of the pyridine ring) 8.07 (1H, d, J=6 Hz, $C_6$—H) 7.77–7.13 (13H, m, ×2 and $C_3$—H of the pyridine ring) 6.29 (1H, bt, J=7 Hz, $C_{1'}$—H) 4.52 (2H, s, 4.45 (2H, d, J=2 Hz, 4.24–4.18 (2H, m, $C_{3'}$—H, $C_{4'}$—H) 3.90–3.51 (2H, m, $C_{5'}$—H) 2.67–2.03 (2H, m, $C_{2'}$—H).

EXAMPLE 210

Preparation of 5-fluoro-3-[3-[4-(2-naphthoyloxy)-2-pyridyloxycarbonyl]benzoyl]-1-(2-tetrahydrofuranyl)uracil The title compound was prepared in the same manner as in Example 200.

$^1$H—NMR(CDCl$_3$) δ: 8.75–7.20 (15H, m, naphthyl—H, phenyl—H, H of the pyridine ring and $C_6$—H) 5.97–5.90 (1H, m, $C_{1'}$—H) 4.52–3.85 (2H, m, $C_{4'}$—H) 2.52–1.78 (4H, m, $C_{2',3'}$—H).

EXAMPLE 211

Preparation of
3-[3-[3-chloro-6-(4-fluorobenzoyloxy)-2-pyridyloxycarbonyl]benzoyl]-5-fluoro-1-(2-tetrahydrofuranyl)uracil The title compound was prepared in the same manner as in Example 200.

$^1$H—NMR(CDCl$_3$) δ: 8.67–8.13 (5H, m,

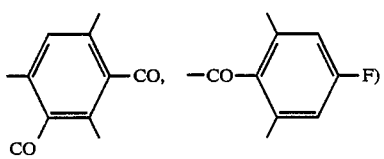

8.00 (1H, d, J=8 Hz, C$_4$—H of the pyridine ring) 7.70 (1H, t, J=8 Hz,

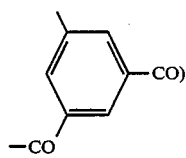

7.54 (1H, d, J=6 Hz, C$_6$—H) 7.31–7.07 (3H, m,

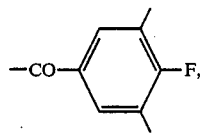

C$_5$—H of the pyridine ring) 5.97–5.89 (1H, m, C$_{1'}$—H) 4.34–3.84 (2H, m, C$_{4'}$—H) 2.47–1.86 (4H, m, C$_{2'}$—H, C$_{3'}$—H).

EXAMPLE 212

Preparation of
3-[3-(6-benzoyloxy-3-cyano-2-pyridyloxycarbonyl)benzoyl]-5-fluoro-1-(2-tetrahydrofuranyl)uracil The title compound was prepared in the same manner as in Example 200.

$^1$H-NMR(CDCl$_3$)δ: 8.69–8.12 (6H, m,

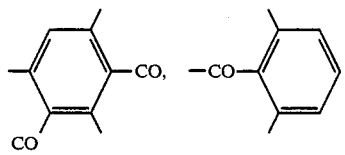

and C$_4$—H of the pyridine ring) 7.79–7.38 (6H, m,

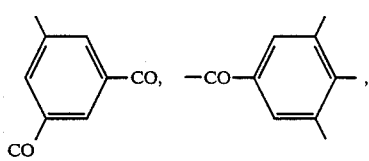

C$_6$—H, C$_5$—H of the pyridine ring) 5.96–5.87 (1H, m, C$_{1'}$—H) 4.30–3.80 (2H, m, C$_{4'}$—H) 2.50–1.85 (4H, m, C$_{2'}$—H, C$_{3'}$—H).

EXAMPLE 213

Preparation of
3-[3-[3-cyano-6-(3,4,5-trimethoxybenzoyloxy)-2-pyridyloxycarbonyl]benzoyl]-5-fluoro-1-(2-tetrahydrofuranyl)uracil The title compound was prepared in the same manner as in Example 200.

$^1$H-NMR(CDCl$_3$)δ: 8.69–8.21 (4H, m,

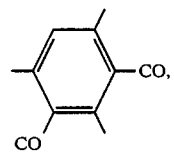

C$_4$—H of the pyridine ring) 7.73 (1H, t, J=8 Hz,

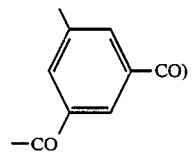

7.54 (1H, d, J=6 Hz, C$_6$—H) 7.44 (2H, s,

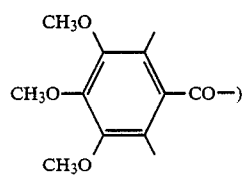

7.42 (1H, d, J=8 Hz, C$_4$—H of the pyridine ring) 5.97–5.90 (1H, m, C$_{1'}$—H) 4.34–3.81 (11H, m, C$_{4'}$—H and

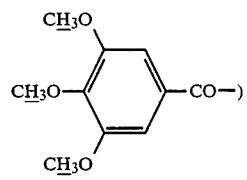

2.50–1.87 (4H, m, C$_{2'}$—H, C$_{3'}$—H).

EXAMPLE 214

Preparation of
3-[3-[3-cyano-6-(2-furoyloxy)-2-pyridyloxycarbonyl]-benzoyl]-5-fluoro-1-(2-tetrahydrofuranyl)uracil The title compound was prepared in the same manner as in Example 200.

$^1$H-NMR(CDCl$_3$)δ: 8.68–8.20 (4H, m,

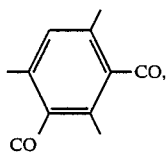

$C_4$—H of the pyridine ring) 7.81–7.40 (5H, m,

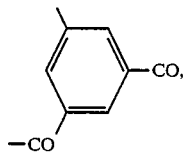

$C_6$—H, $C_5$—H of the pyridine ring and

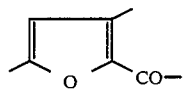

6.61 (1H, dd, J=2 Hz, J=4 Hz,

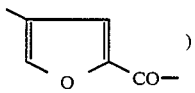

)

5.98–5.88 (1H, m, $C_{1'}$—H) 4.27–3.84 (2H, m, $C_{4'}$—H) 2.36–1.86 (4H, m, $C_{2'}$—H, $C_{3'}$—H).

EXAMPLE 215

Preparation of
3-[4-(6-benzoyloxy-3-cyano-2-pyridyloxycarbonyl)-3-furoyl]-5-fluoro-1-(2-tetrahydrofuranyl)uracil The title compound was prepared in the same manner as in Example 200.

$^1$H-NMR(CDCl$_3$)δ: 8.39 (2H, s,

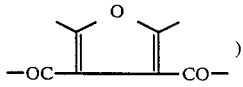
)

8.25–8.11 (3H, m,

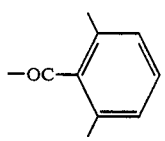

and $C_4$—H of the pyridine ring) 7.69–7.22 (5H, m,

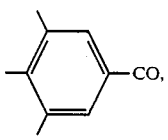

$C_6$—H and $C_5$—H of the pyridine ring) 5.92–5.82 (1H, m, $C_{1'}$—H) 4.22–3.71 (2H, m, $C_{4'}$—H) 2.33–1.68 (4H, m, $C_{2'}$—H, $C_{3'}$—H).

EXAMPLE 216

Preparation of
3-[3-(6-benzoyloxy-3-cyano-2-pyridyloxycarbonyl)benzoyl]-5'-deoxy-2',3'-di—O—acetyl-5-fluorouridine The title compound was prepared in the same manner as in Example 200.

$^1$H-NMR(CDCl$_3$)δ: 8.77–8.14 (6H, m,

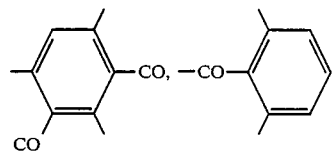

and $C_6$—H of the pyridine ring) 7.80–7.39 (6H, m,

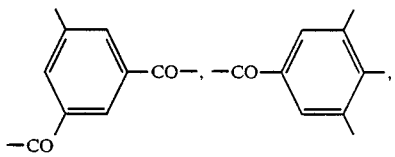

$C_5$—H of the pyridine ring, $C_6$—H) 5.96 (1H, dd, J=1 Hz and J=5 Hz, $C_{1'}$—H) 5.32 (1H, t, J=6 Hz, $C_{2'}$—H) 5.03 (1H, t, J=6 Hz, $C_{3'}$—H) 4.30–4.18 (1H, m, $C_{4'}$—H) 2.09 (3H, s, $C_{2'}$—OCO$\underline{C}H_3$ or $C_{3'}$—OCO$\underline{C}H_3$) 2.00 (3H, s, $C_{2'}$—OCO$\underline{C}H_3$ or $C_{4'}$—OCO$\underline{C}H_3$) 1.46 (3H, d, J=6 Hz, $C_{5'}$—H).

EXAMPLE 217

Preparation of
3-[3-[3-cyano-6-(2-thenoyloxy)-2-pyridyloxycarbonyl]-benzoyl]-5-fluoro-1-(2-tetrahydrofuranyl)uracil The title compound was prepared in the same manner as in Example 200.

$^1$H-NMR(CDCl$_3$)δ: 8.66–8.18 (4H, m,

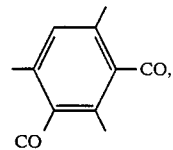

$C_4$—H of the pyridine ring) 8.03 (1H, dd, J=1 Hz, J=4 Hz,

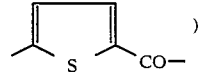
)

7.81–7.64 (2H, m,

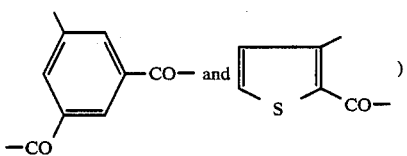

7.53 (1H, d, J=6 Hz, C<sub>6</sub>—H) 7.44 (1H, d, J=8 Hz, C<sub>5</sub>—H of the pyridine ring) 7.26–7.14 (1H, m,

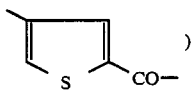

6.00–5.90 (1H, m, $C_{1'}$—H) 4.28–3.87 (2H, m, $C_{4'}$—H) 2.50–1.89 (4H, m, $C_{2'}$—H, $C_{3'}$—H).

EXAMPLE 218

Preparation of 3-[3-[3-cyano-6-(2,4-dichlorobenzoyloxy)-2-pyridyloxycarbonyl]benzoyl]-5-fluoro-1-(2-tetrahydrofuranyl)uracil The title compound was prepared in the same manner as in Example 200.

$^1$H-NMR(CDCl$_3$)δ: 8.67–8.21 (4H, m,

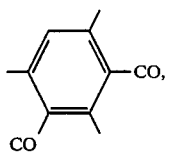

C<sub>4</sub>—H of the pyridine ring) 8.09 (1H, d, J=9 Hz,

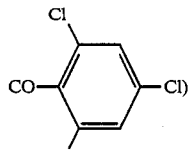

7.73 (1H, t, J=8 Hz,

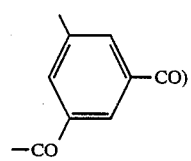

7.57–7.33 (4H, m, C<sub>6</sub>—H, C<sub>5</sub>—H of the pyridine ring and

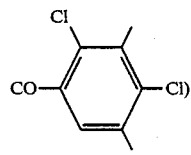

6.01–5.90 (1H, m, $C_{1'}$—H 4.35–3.82 (2H, m, $C_{4'}$—H) 2.50–1.80 (4H, m, $C_{2'}$—H, $C_{3'}$—H).

EXAMPLE 219

Preparation of 3-[5-(6-benzoyloxy-3-cyano-2-pyridyloxycarbonyl)-3-nicotinoyl]-5-fluoro-1-(2-tetrahydrofuranyl)uracil The title compound was prepared in the same manner as in Example 200.

$^1$H-NMR(CDCl$_3$)δ: 9.57–8.84 (3H, m,

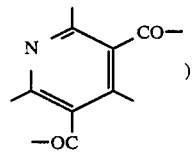

8.27 (1H, d, J=8 Hz,

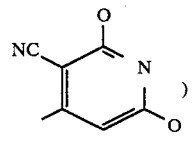

8.25–8.12 (2H, m,

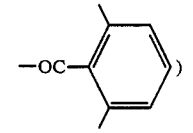

7.70–7.42 (4H, m, C<sub>6</sub>—H and

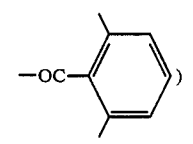

7.40 (1H, d, J=8 Hz,

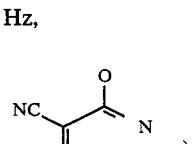

5.94–5.88 (1H, m, $C_{1'}$—H) 4.34–3.71 (2H, m, $C_{4'}$—H) 2.50–1.88 (4H, m, $C_{2'}$—H, $C_{3'}$—H).

EXAMPLE 220

Preparation of 3-[3-(1,2-dihydro-2-oxo-6-pyridyloxycarbonyl)benzoyl]-5-fluoro-1-(2-tetrahydrofuranyl)uracil Isophthaloyl chloride (1.50 g) and 6.0 ml of triethylamine were added to a solution of 1.00 g of 5-fluoro-1-(2-tetrahydrofuranyl)uracil in 50 ml of dioxane. The mixture was refluxed for 1.5 hours. The resulting precipitate was removed by filtration and the filtrate was concentrated. To the concentrate was added 50 ml of methylene chloride and thereto added was 10 ml of a solution of 1.50 g of 2,6-bis(trimethylsilyloxy)pyridine in methylene chloride. The mixture was left to stand at room temperature for 3 hours. The solvent was distilled off and the residue was subjected to silica gel column chromatography using as an eluent 2% methanol-chloroform, giving 0.30 g of the title compound in a yield of 14%.

$^1$H-NMR(CDCl$_3$)δ: 8.66–8.19 (3H, m,

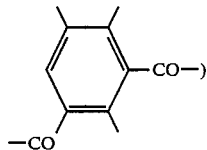

7.83–7.62 (2H, m,

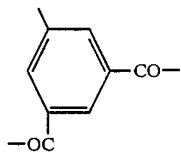

and C$_4$—H of the pyridine ring) 7.52 (1H, d, J=6 Hz, C$_6$—H) 6.77 and 6.68 (each 1H, d, J=8 Hz, C$_{3.5}$—H of the pyridine ring) 5.99–5.92 (1H, m, C$_{1'}$—H) 4.30–3.88 (2H, m, C$_{4'}$—H) 2.44–1.89 (4H, m, C$_{2'.3'}$—H).

EXAMPLE 221

Preparation of 3-[3-(5-chloro-4-hydroxy-2-pyridyloxycarbonyl)benzoyl]-2'-deoxy-3',5'-di-O-acetyl-5-fluorouridine The title compound was prepared in the sae manner as in Example 220.

$^1$H-NMR(CDCl$_3$)δ: 8.57–8.16 (4H, m,

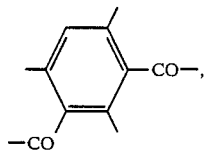

C$_6$—H of the pyridine ring) 7.80–7.53 (2H, m,

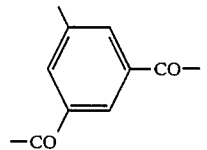

and C$_6$—H) 6.76 (1H, s, C$_3$—H of the pyridine ring) 6.19 (1H, bt, J=7 Hz, C$_{1'}$—H) 5.23–5.16 (1H, m, C$_{3'}$—H) 4.32–4.24 (3H, m, C$_{4'}$—H, C$_{5'}$—H) 2.60–1.85 (8H, m, C$_{2'}$—H, COCH$_3$×2).

EXAMPLE 222

Preparation of 3-[3-(6-benzoyloxy-3-cyano-2-pyridyloxycarbonyl)benzoyl]-3'—O—benzyl-2'-deoxy-5-fluorouridine Triethylamine (2.88 ml) and 1.01 g of isophthaloyl chloride were added to a solution of 1.00 g of 6-benzoyloxy-3-cyano-2-hydroxypyridine in 50 ml of dioxane. The mixture was stirred at room temperature for 1.5 hours.

Aside from the above procedure, 2.88 ml of triethylamine and 0.69 ml of trimethylsilyl chloride were added to a solution of 1.40 g of 3'—O—benzyl-2'-deoxy-5-fluorouridine in 50 ml of dioxane. The mixture was stirred at room temperature for 1 hour. The reaction mixture was filtered and concentrated. The concentrate was added to the reaction mixture prepared above and the resulting mixture was stirred at 80° C. for 30 minutes. The reaction mixture was filtered and concentrated. The residue was dissolved in 20 ml of acetone. Thereto was added 5 ml of water. The mixture was stirred at 75° C. for 1 hour. The acetone was distilled off and the residue was extracted with 50 ml of ethyl acetate. The organic layer was washed with water, dried over magnesium sulfate and concentrated. The concentrate was subjected to florisil column chromatography using as an eluent benzene-ethyl acetate (4:1), giving 80 mg of the title compound in a yield of 3%.

Analysis by thin layer chromatography and liquid chromatography showed that the compound obtained was identical with the compound prepared in Example 190.

EXAMPLE 223

Preparation of 2'-deoxy-5-fluoro-3'-O-(4-methoxycarbonylbenzyl)uridine

The general procedure of Example 114 was followed, thereby producing the title compound.

M.P. 169°–170° C.

$^1$H-NMR (CDCl$_3$)δ: 9.85 (1H, bs, N$_3$—H) 8.04–7.94 (3H, m, C$_6$—H and

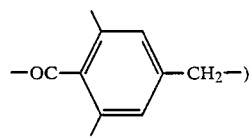

7.37 (2H, d, J=8 Hz,

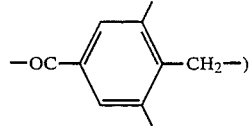

6.24 (1H, t, J=6 Hz, C$_1$, —H) 4.58 (2H, s, 3'—O—CH$_2$—) 4.31–3.70 (7H, m, C$_{3'.4'.5'}$—H and —COCH$_3$) 3.19 (1H, bs, C$_{5'}$—OH) 2.66–2.04 (2H, m, C$_{2'}$—H).

EXAMPLE 224

Preparation of 2'-deoxy-3'—O—cinnamyl-5-fluorouridine

The general procedure of Example 114 was followed, thereby producing the title compound in a yield of 23%.

$^1$H-NMR(DMSO-d$_6$)δ: 11.75 (1H, bs, N$_3$—H) 8.20 (1H, d, J=7 Hz, C$_6$—H) 7.53–7.24 (5H, m,

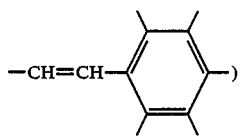

6.64 (1H, d, J=16 Hz,

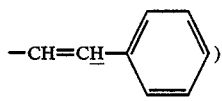

6.47–6.08 (2H, m, C$_{1'}$—H and

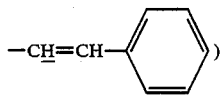

5.20 (1H, bs, C$_{5'}$—OH) 4.17 (2H, d, J=5 Hz, C$_{3'}$—O—C$\underline{H}_2$—) 4.20–4.03 (2H, m, C$_{3',4'}$—H) 3.74–3.59 (2H, m, C$_{5'}$—H) 2.34–2.21 (2H, m, C$_{2'}$—H).

EXAMPLE 225

Preparation of 2'-deoxy-3'—O—(4-dimethylaminobenzyl)-5-fluorouridine

A 0.86 ml quantity of pyridine and 1.19 ml of phosphorus tribromide were added to a solution of 1.60 g of 4-dimethylaminobenzyl alcohol in 20 ml of benzene, and the mixture was stirred at 80° C. for 1 hour. The reaction mixture was concentrated and the concentrate was dissolved in 50 ml of a 2:1 mixture of water and acetonitrile. The resulting mixture was adjusted to a pH of 11 by addition of potassium hydroxide. Thereto was added 1.00 g of 2'-deoxy-5-fluorouridine and the mixture was stirred at room temperature for 2 days.

The reaction mixture was poured into ice water and extracted with ethyl acetate. The organic layer was dried over magnesium sulfate and concentrated. The concentrate was placed on silica gel column and eluted with 1% methanol-chloroform, thereby giving 70 mg of the title compound in a yield of 5%.

$^1$H-NMR (DMSO-d$_6$)δ: 11.98 (1H, bs, N$_3$—H) 8.18 (1H, d, J=7 Hz, C$_6$—H) 7.15 (2H, d, J=9 HZ,

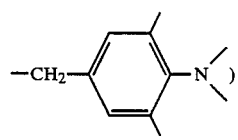

6.69 (2H, d, J=9 Hz,

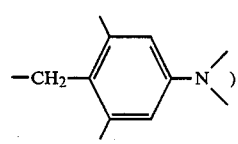

6.09 (1H, t, J=6 Hz, C$_{1'}$—H) 5.18 (1H, bs, C$_{5'}$—OH) 4.38 (2H, s,

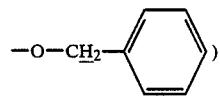

4.18–3.96 (2H, m, C$_{3',4'}$—H) 3.70–3.58 (2H, m, C$_{5'}$—H) 2.88 (6H, s, C$\underline{H}_3$×2) 2.28–2.09 (2H, m, C$_{2'}$—H).

EXAMPLE 226

Preparation of 2'-deoxy-5-fluoro-3'—O—(3-phenylpropyl)uridine

To a solution of 500 mg of the 2'-deoxy-3'—O—cinnamyl-5-fluoro-5'—O—trityluridine prepared as the intermediate in Example 224 in 30 ml of methanol was added 50 mg of 5% palladium-carbon, and the catalytic reduction was conducted at room temperature for 1 hour.

The reaction mixture was filtered and concentrated. The concentrate was dissolved in 20 ml of 80% acetic acid and the solution was stirred at 65° C. for 2 hours. The reaction mixture was concentrated, and the concentrate was placed on a silica gel column and eluted with 1% methanol-chloroform, thereby giving 190 mg of the title compound in a yield of 63%.

$^1$H-NMR (DMSO-d$_6$)δ: 11.80 (1H, bs, N$_3$—H) 8.19 (1H, d, J=7 Hz, C$_6$—H) 7.22 (5H, s,

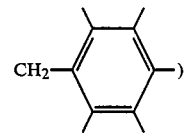

6.12 (1H, t, J=6 Hz, C$_{1'}$—H) 5.18 (1H, t, J=5 Hz, C$_{5'}$—OH) 4.06–3.93 (2H, m, C$_{3',4'}$—H) 3.66–3.62 (2H, m, C$_{5'}$—H) 3.41 (2H, t, J=6 Hz, C$_{3'}$—O—C$\underline{H}_2$—) 2.72–1.66 (6H, m, C$_{2'}$—H and

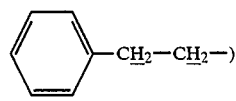

EXAMPLE 227

Preparation of 3-[3-(3-cyano-6-benzoyloxy-2-pyridyloxycarbonyl)benzoyl]-1-ethoxymethyl-5-fluorouracil The title compound was prepared following the general procedure of Example 200. Yield 25%.
M. P. 162°–164° C.
$^1$H-NMR (CDCl$_3$)δ: 8.66–8.14 (6H, m,

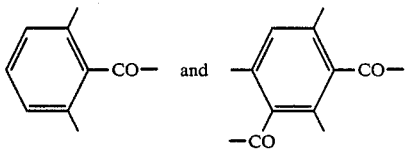

and C4—H of the pyridine ring) 7.82-7.33 (6H, m, C6—H and

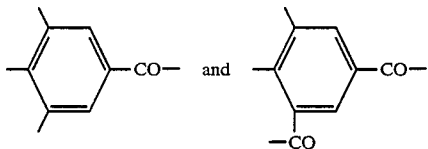

and C5—H of the pyridine ring) 5.15 (2H, s, N—CH2) 3.62 (2H, q, J—7 Hz, —CH2CH3) 1.22 (3H, t, J—7 Hz, —CH3).

EXAMPLE 228

Preparation of 3-[3-[3-cyano-6-(4-chlorobenzoyloxy)-2-pyridyloxycarbonyl]benzoyl]-1-ethoxymethyl-5-fluorouracil The title compound was prepared following the general procedure of Example 200. Yield 18%.

M.p. 156°–158° C.

$^1$H-NMR (CDCl$_3$) δ: 8.66–8.08 (6H, m,

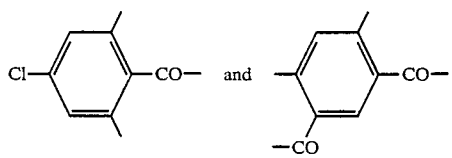

and C4—H of the pyridine ring) 7.74 (1H, t, J=8 Hz,

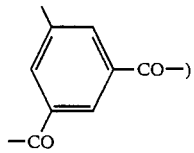

7.57-7.39 (5H, m,

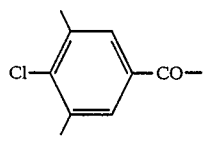

and C6—H, and C5—H of the pyridine ring) 5.16 (2H, s, N—CH2) 3.63 (2H, q, J=7 Hz, —CH2CH3) 1.23 (3H, t, J=7 Hz, —CH3).

EXAMPLE 229

Preparation of 3-[3-[3-cyano-6-(2,4-dichlorobenzoyloxy)-2-pyridyloxycarbonyl]benzoyl]-1-ethoxymethyl-5-fluorouracil The title compound was prepared following the general procedure of Example 200. Yield 12%.

M.p. 140°–142° C.

$^1$H-NMR (CDCl$_3$) δ: 8.66–8.21 (4H, m,

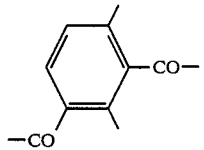

and C4—H of the pyridine ring) 8.09 (1H, d, J=8 Hz,

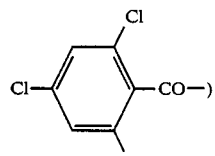

7.74 (1H, t, J=8 Hz,

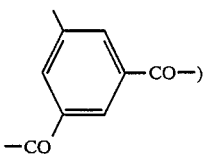

7.58–7.33 (4H, m,

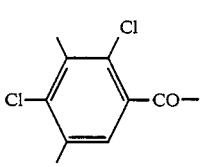

and C6—H and C5—H of the pyridine ring) 5.16 (2H, s, N—CH2) 3.63 (2H, q, J=7 Hz, —CH2CH3) 1.22 (3H, t, J=7 Hz, —CH3).

EXAMPLE 230

Preparation of 3-[4-(3-cyano-6-benzoyloxy-2-pyridyloxycarbonyl)benzoyl]-1-ethoxymethyl-5-fluorouracil The title compound was prepared following the general procedure of Example 200. Yield 24%.

Form: powder.

$^1$H-NMR (CDCl$_3$) δ: 8.39–8.02 (7H, m,

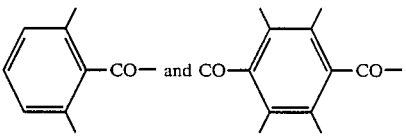

and C4—H of the pyridine ring) 7.67-7.39 (5H, m,

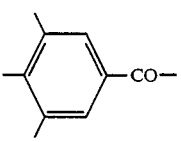

and C6—H and C5—H of the pyridine ring) 5.14 (2H, s, N—CH2) 3.61 (2H, q, J=7 Hz, —CH2CH3) 1.22 (3H, t, J=7 Hz, CH3).

EXAMPLE 231

Preparation of 3-[4-(3-cyano-6-furoyloxy-2-pyridyloxycarbonyl)-3-furoyl]-1-(2-tetrahydrofuranyl)-5-fluorouracil The title compound was prepared following the general procedure of Example 200. Yield 17%.

Form: powder $^1$H-NMR (CDCl3)δ: 8.41 and 8.38 (each 1H, d, J=2 Hz,

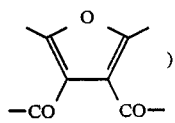

8.20 (1H, d, J=8 Hz, C4—H of the pyridine ring) 7.74-7.72 (1H, m,

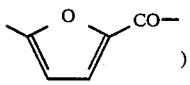

7.49-7.20 (3H, m, C6—H and C5—H of

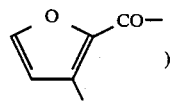

the pyridine ring and 6.64 (1H, dd, J=4 Hz, 2 Hz,

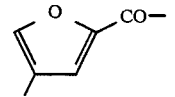

5.92-5.83 (1H, m, C1'—H) 4.28-3.57 (2H, m, C4'—H) 2.38-1.67 (4H, m, C2', 3'—H).

EXAMPLE 232

Preparation of 3-[4-(4-acetoxy-5-chloro-2-pyridyloxycarbonyl)-3-furoyl]-1-(2-tetrahydrofuranyl)-5-fluorouracil The title compound was prepared following the general procedure of Example 200. Yield 18%.

Form: powder.

$^1$H-NMR (CDCl3) δ: 8.39-8.38 (2H, m, C6—H of the pyridine ring and

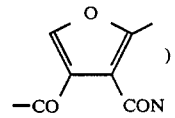

8.29 (1H, d, J=2 Hz,

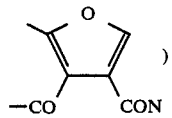

7.38 (1H, d, J=6 Hz, C6—H) 7.02 (1H, s, C3—H of the pyridine ring) 5.92-5.81 (1H, m, C1'—H) 4.24-3.80 (2H, m, C4'—H) 2.38-1.68 (7H, m, COCH3 and C2',3'—H).

EXAMPLE 233

Preparation of 3-[4-(3-cyano-6-thenoyloxy-2-pyridyloxycarbonyl)-3-furoyl]-1-(2-tetrahydrofuranyl)-5-fluorouracil The title compound was prepared following the general procedure of Example 200. Yield 27%.

Form: powder.

$^1$H-NMR (CDCl3) δ: 8.41 and 8.37 (each 1H, d, J=2 Hz,

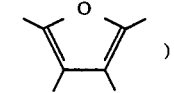

8.19 (1H, d, J=8 Hz, C4—H of the pyridine ring) 8.03 (1H, dd, J=4 Hz, 1 Hz, C5—H of the thiophene ring) 7.76 (1H, dd, J=5 Hz, 1 Hz, C3—H of the thiophene ring) 7.40 (1H, d, J=8 Hz, C5—H of the pyridine ring) 7.37 (1H, d, J=6 Hz, C6—H). 7.21 (1H, d, J=4 Hz, 1 Hz, C4—H of the thiophene ring) 5.94-5.83 (1H, m, C1'—H) 4.26-3.75 (2H, m, C4'—H) 2.44-1.72 (4H, m, C2', 3'—H).

EXAMPLE 234

Preparation of 3-[3-(5-cyano-6-hydroxy-2-pyridyloxycarbonyl)benzoyl]-1-ethoxymethyl-5-fluorouracil The title compound was prepared in the same manner as in Example 221.

$^1$H-NMR (CD3COCD3) δ: 8.59-8.24 (3H, m,

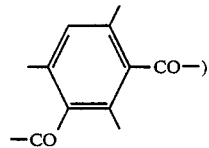

8.14 (1H, d, J=8 Hz, C4—H of the pyridine ring) 7.95 (1H, d, J=6 Hz, C6—H) 7.80-7.64 (1H, m,

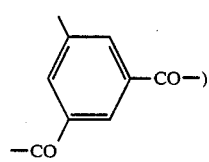

6.89 (1H, d, J=8 Hz, C3—H of the pyridine ring) 5.09 (2H, s, N—CH2) 3.53 (2H, q, J=7 Hz, —CH2CH3) 1.05 (3H, t, J=7 Hz, —CH3).

PHARMACOLOGICAL TEST I (a) Sarcoma-180 subcultured in an ascites of ICR mice was diluted with a physiological saline solution and subcutaneously transplated into the backs of ICR mice in an amount of $2\times10^7$ each. Twenty-four hours after the transplantation, a test compound suspended in a 5% solution of gum arabic was orally administered to each of mice once a day for 7 consecutive days.

The solid tumor was extirpated from under the dorsal skin of mice on the 10th day after the transplantation to measure the weight of the tumor. There was determined the ratio (T/C) of the weight of tumor (T) cut out from the group of mice treated with the test compound to the weight of tumor (C) from the group of mice not treated therewith. The 50% tumor inhibition dose ($ED_{50}$ value) in which T/C is 0.5 was determined from the dose-response curve of dosage and the ratio (T/C). Table 1 shows the results.

TABLE 1

| No. | Test compound (formula (1a)) $R^1$ | $R^2$ | $R^3$ | $ED_{50}$ (mg/kg) |
|---|---|---|---|---|
| 1 | C₆H₅–CH₂– | H | H | 8 |
| 2 | 2-F-C₆H₄–CH₂– | H | H | 8 |
| 3 | 3-F-C₆H₄–CH₂– | H | H | 8 |
| 4 | 3-Br-C₆H₄–CH₂– | H | H | 8 |
| 5 | 4-Br-C₆H₄–CH₂– | H | H | 1 |
| 6 | 4-Cl-C₆H₄–CH₂– | H | H | 1 |
| 7 | 3,4-Cl₂-C₆H₃–CH₂– | H | H | 3 |
| 8 | 3,4-(OCH₂O)-C₆H₃–CH₂– | H | H | 8 |
| 9 | C₆H₅–CH₂– | CH₃CO– | H | 5 |
| 10 | C₆H₅–CH₂– | 3-CH₃-C₆H₄–CO– | H | 5 |

TABLE 1-continued

| No. | R¹ | R² | R³ | ED$_{50}$ (mg/kg) |
|---|---|---|---|---|
| 11 | " | naphthyl-CO— | H | 6 |
| 12 | 4-Cl-C₆H₄-CH₂— | CH₃CO— | H | 1 |
| 13 | C₆H₅-CH₂— | C₆H₅-OCO— | H | 5 |
| 14 | " | H | C₆H₅-CO— | 5 |
| 15 | " | H | tetrahydrofuran-2-yl | 5 |
| 16 | C₆H₅-CH₂— | H | 4-C₃H₇O-C₆H₄-CO— | 7 |
| 17 | " | H | C₆H₅-OCO— | 7 |
| 18 | " | H | 3,4,5-(CH₃O)₃-C₆H₂-CO— | 7 |
| 19 | " | C₆H₅-CO— | C₆H₅-CO— | 5 |
| 20 | " | CH₃CO | " | 4 |
| 21 | " | naphthyl-CO— | naphthyl-CO— | 6 |
| 22 | " | CH₃CO— | 4-CH₃-C₆H₄-CO— | 5 |

TABLE 1-continued
| No. | R¹ | R² | R³ | ED$_{50}$ (mg/kg) |
|---|---|---|---|---|
| 23 | " | " |  CH$_3$O—⌬—CO— | 5 |
| 24 | 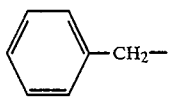 ⌬—CH$_2$— | CH$_3$CO— | 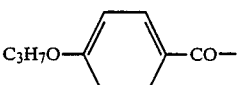 C$_3$H$_7$O—⌬—CO— | 6 |
| 25 | " | 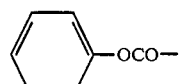 ⌬—OCO— | 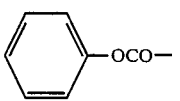 ⌬—OCO— | 4 |
| 26 | H | 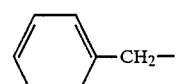 ⌬—CH$_2$— | H | 10 |
| 27 | H | 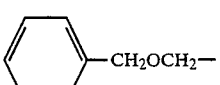 ⌬—CH$_2$OCH$_2$— | 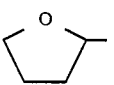 | 7 |
| 28 | 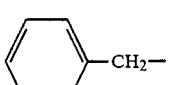 ⌬—CH$_2$— | CH$_3$CO— | 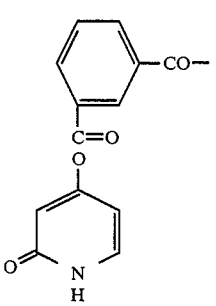 | 0.7 |
| 29 | 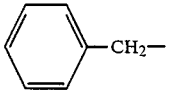 ⌬—CH$_2$— | CH$_3$CO— | 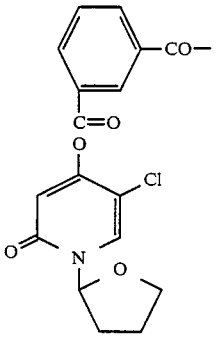 | 4.0 |
| 30 | " | " | 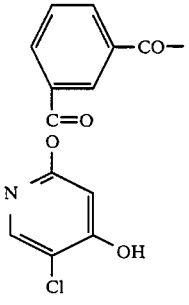 | 0.6 |

TABLE 1-continued
| No. | R¹ | R² | R³ | $ED_{50}$ (mg/kg) |
|---|---|---|---|---|
| 31 | " | 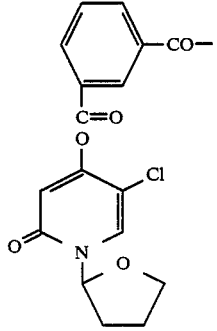 | 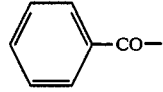 | 5.0 |
| 32 | 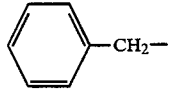 | CH₃CO— | 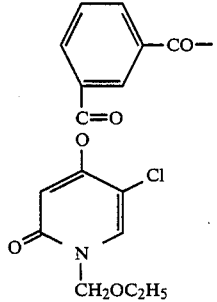 | 3.0 |
| 33 | " | " | 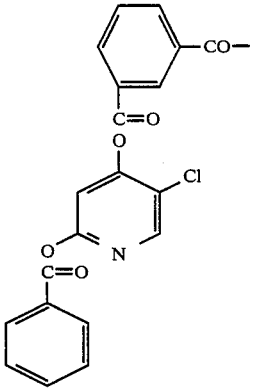 | 0.8 |
| 34 | " | 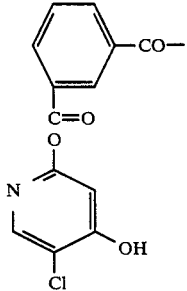 | 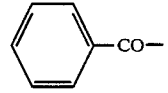 | 4.0 |

TABLE 1-continued
| No. | R¹ | R² | R³ | ED$_{50}$ (mg/kg) |
|---|---|---|---|---|
| 35 |  | CH$_3$CO— | 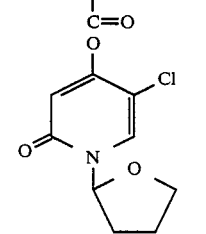 | 4.0 |
| 36 | " | " | 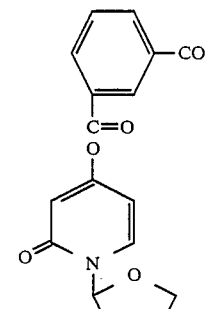 | 6.0 |
| 37 | " | " | 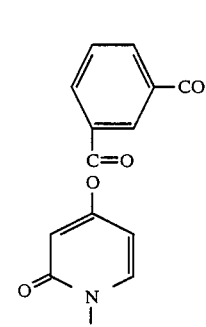 | 2.0 |
| 38 |  | CH$_3$CO— | 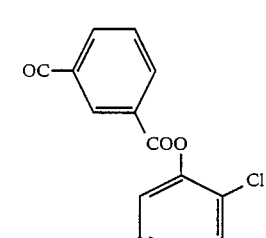 | 0.7 |
| 39 |  | CH$_3$CO— | 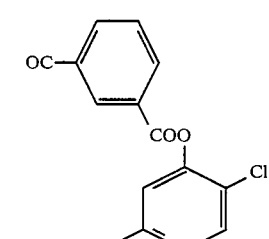 | 3.0 |

TABLE 1-continued

| | Test compound (formula (1a)) | | | $ED_{50}$ |
|---|---|---|---|---|
| No. | $R^1$ | $R^2$ | $R^3$ | (mg/kg) |
| 40 | $C_6H_5CH_2-$ | $CH_3CO-$ | 3-benzoyloxy-benzoyloxy at 2-position, benzoyloxy at 5-position of pyridine | 0.7 |
| 41 | $C_6H_5CH_2-$ | $CH_3CO-$ | 3-benzoyloxy-benzoyloxy at 2-position, benzoyloxy at 4-position, Cl at 5-position of pyridine | 0.7 |
| 42 | $C_6H_5CH_2-$ | $CH_3CO-$ | 3-benzoyloxy-benzoyloxy at 4-position, benzoyloxy at 2-position of pyridine | 0.7 |
| 43 | $C_6H_5CH_2-$ | $CH_3CO-$ | 3-benzoyloxy-benzoyloxy at 2-position, acetoxy at 4-position, Cl at 5-position of pyridine | 0.7 |
| 44 | $C_6H_5CH_2-$ | $CH_3CO-$ | 3-benzoyloxy-pyridyl-carbonyloxy at 4-position, Cl at 5-position, acetoxy at 2-position of pyridine | 0.8 |

TABLE 1-continued
| | Test compound (formula (1a)) | | | ED$_{50}$ |
|---|---|---|---|---|
| No. | R$^1$ | R$^2$ | R$^3$ | (mg/kg) |
| 45 | 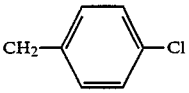 | CH$_3$CO— | 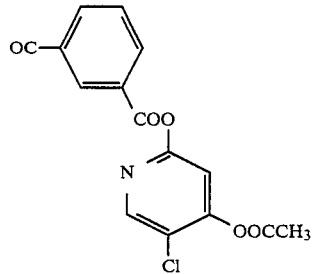 | 0.7 |
| 46 | 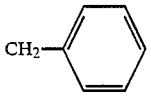 | CH$_3$CO— | 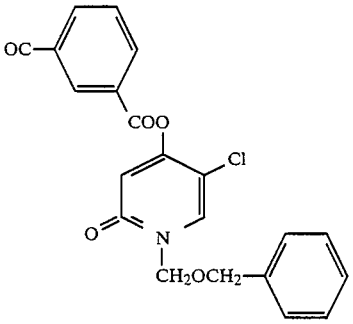 | 2.0 |
| 47 | 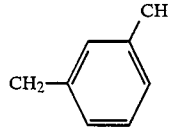 | 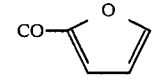 | H | 3 |
| 48 | 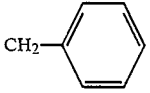 | H | 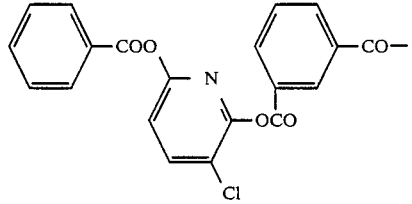 | 0.4 |
| 49 | 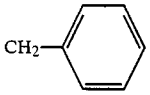 | H | 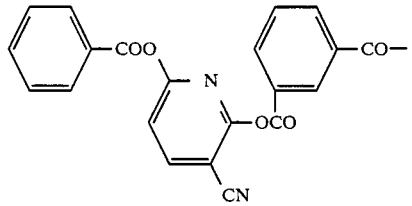 | 0.4 |
| 50 | 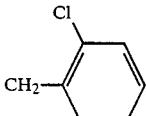 | H | 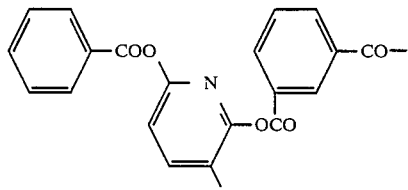 | 1 |

TABLE 1-continued

| No. | R¹ | R² | R³ | ED$_{50}$ (mg/kg) |
|---|---|---|---|---|
| 51 | 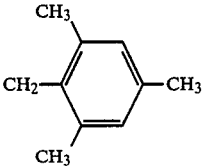 | H | 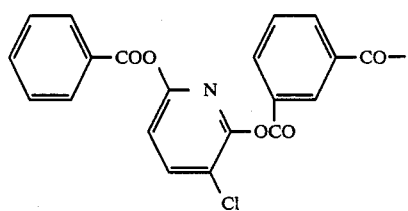 | 8 |
| 52 | 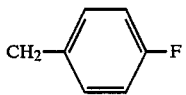 | H | 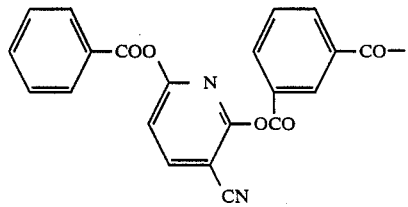 | 0.5 |
| 53 (control) | H | H | H | 23 |
| 54 (control) | 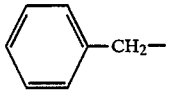 | 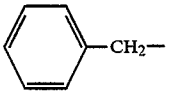 | H | 15 |

(b) The ED$_{50}$ value was determined in the same manner as in (a) with the exception of using the test compounds shown below in Table 2.

Table 2 below lists the results together with the value obtained by using as a control an anti-cancer preparation containing 5-fluoro-1-(2-tetrahydrofuranyl)uracil and uracil in a ratio by weight of 1 to 4.

TABLE 2

| Test Compound | ED$_{50}$ (mg/kg) |
|---|---|
| Compound of Example 195 | 10 |
| Compound of Example 197 | 7 |
| Compound of Example 198 | 25 |
| Compound of Example 199 | 18 |
| Compound of Example 201 | 12 |
| Compound of Example 202 | 22 |
| Compound of Example 207 | 28 |
| Compound of Example 208 | 5 |
| Compound of Example 214 | 18 |
| Compound of Example 227 | 5 |
| Control | 30 |

PHARMACOLOGICAL TEST II (acute toxicity)

The compounds of the present invention prepared in Examples 2 and 54 were each orally administered to 5-week-old ICR male mice (8 mice in each group) to check the mice for the symptoms, change of weight and mortality by observing the mice for 14 consecutive days after the administration of the compounds. The LD$_{50}$ value was determined from the mortality by the Litchfield-Wilcoxon method with the results shown below in Table 3.

TABLE 3

| Test Compound | LD$_{50}$ (mg/kg) |
|---|---|
| Compound of Example 2 | Over 1000 |
| Compound of Example 54 | Over 1000 |

PREPARATION EXAMPLE 1

| Compound of Example 54 | 50 mg |
|---|---|
| Lactose | 97 mg |
| Crystalline cellulose | 50 mg |
| Magnesium stearate | 3 mg |

Capsules (200 mg each) were prepared which each had the foregoing composition.

PREPARATION EXAMPLE 2

| Compound of Example 54 | 10 mg |
|---|---|
| Lactose | 184 mg |
| Crystalline cellulose | 100 mg |
| Magnesium stearate | 6 mg |

Capsules (300 mg each) were prepared which each had the foregoing composition.

PREPARATION OF EXAMPLE 3

| Compound of Example 54 | 10 mg |
|---|---|
| Lactose | 240 mg |
| Corn starch | 340 mg |
| Hydroxypropyl cellulose | 10 mg |

Granules (600 mg each wrapper) were prepared which each had the foregoing composition.

PREPARATION EXAMPLE 4

| Compound of Example 54 | 10 mg |
|---|---|
| Macrogol 300 | 500 mg |
| Distilled water for injection | (Suitable amount) |

An injection solution (5 ml per ampoule) was prepared which had the foregoing composition.

PREPARATION EXAMPLE 5

A thousand tablets for oral administration were prepared which each contained 10 mg of the compound obtained in Example 54 and which each had the following composition.

| | |
|---|---|
| Compound of Example 54 | 10 g |
| Lactose (Japanese Pharmacopeia) | 45 g |
| Corn starch (Japanese Pharmacopeia) | 25 g |
| Crystalline cellulose (Japanese Pharmacopeia) | 25 g |
| Methyl cellulose (Japanese Pharmacopeia) | 1.5 g |
| Magnesium stearate (Japanese Pharmacopeia) | 1 g |

The compound of Example 54, lactose, corn starch and crystalline cellulose were thoroughly mixed and the mixture was granulated with a 5% aqueous solution of methyl cellulose. The granules thus obtained were passed through a 200-mesh sieve and carefully dried. The dry granules were passed through 200-mesh sieve and mixed with magnesium stearate. The mixture was pressed into tablets.

PREPARATION EXAMPLE 6

| | |
|---|---|
| Compound of Example 197 | 0.025 mg |
| Starch | 132 mg |
| Magnesium stearate | 18 mg |
| Lactose | 50 mg |
| Total | About 200 mg |

Tablets were prepared in a conventional manner which each had the foregoing composition.

PREPARATION EXAMPLE 7

| | |
|---|---|
| Compound of Example 196 | 0.25 mg |
| Starch | 130 mg |
| Magnesium stearate | 20 mg |
| Lactose | 50 mg |
| Total | About 200 mg |

Tablets were prepared in a conventional manner which each had the foregoing composition.

PREPARATION EXAMPLE 8

| | |
|---|---|
| Compound of Example 195 | 12.5 mg |
| Polyethylene glycol (molecular weight: 4000) | 0.3 g |
| Sodium chloride | 0.9 g |
| Polyoxyethylene sorbitan monooleate | 0.4 g |
| Sodium methabisulfite | 0.1 g |
| Methylparaben | 0.18 g |
| Propylparaben | 0.02 g |
| Distilled water for injection | 100 ml |

In the distilled water were dissolved with stirring at 80° C. the parabens, sodium methabisulfite, and sodium chloride. The resulting solution was cooled to 40° C. In the solution were dissolved the compound of this invention, polyethylene glycol and polyoxyethylene sorbitan monooleate in this order. To the solution was added the distilled water to adjust the amount to the desired level. Then the mixture was passed through filter paper for sterilization and placed into ampoules in an amount of 1 ml per ampoule to obtain an injection preparation.

What is claimed is:

1. A compound represented by the formula

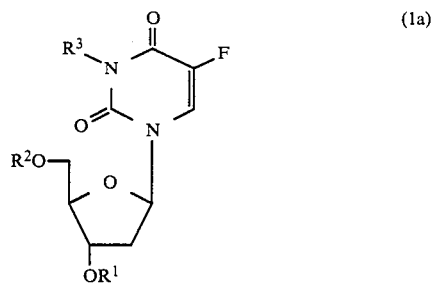

(1a)

wherein one of $R^1$ and $R^2$ is phenyl-lower alkyl group which may have a substituent selected from the group consisting of lower alkyl group, lower alkoxy group, halogen atom, carboxyl group, lower alkoxycarbonyl group and di(lower alkyl)amino group on the phenyl ring, phenyl-loer alkyl group having lower alkylenedioxy or phenyl group as the substituent on the phenyl ring, phenyl-lower alkenyl group or naphthyl-lower alkyl group; the other of $R^1$ and $R^2$ is hydrogn atom or acyl group; and $R^3$ is hydrogen atom, acyl group or tetrahydrofuranyl group; with the proviso that at least one of $R^1$ and $R^3$ or at least one of $R_2$ and $R_3$ is an acyl group represented by the formula

(Y)

wherein $R^x$ is a pyridyl group optionally having 1 to 4 substituents selected from the group consisting of hydroxy group, oxo group, halogen atom, amino group, carboxyl group, cyano group, nitro group, carbamoyl group, lower alkylcarbamoyl group, carboxy-lower alkylcarbamoyl group, phenyl-carbamoyl which may be substituted with 1 to 3 substituents selected from the group consisting of halogen atom, lower alkoxy group and lower alkyl group on the phenyl ring, lower alkoxycarbonyl-lower alkyl-carbamoyl group, lower alkyl group, lower alkenyl group, lower alkoxycarbonyl group, tetrahydrofuranyl group, tetrahydropyranyl group, lower alkoxy-lower alkyl group, lower alkylthio-lower alkyl group, phenyl-lower alkoxy-lower alkyl group, phthalidyl group and acyloxy group, and Y is arylene group selected from the group consisting of phenylene, naphthylene, pyridinediyl, pyrazinediyl, furandiyl and 4-pyridon-1-lower alkyl-diyl.

2. A compound as defined in claim 1 wherein the acyl group represented by $R^1$, $R^2$ and $R^3$ is selected from the group consisting of:

(i) $C_1$–$C_{20}$ alkanoyl groups which may have a substituent selected from the group consisting of halogen atom, hydroxy group, lower alkoxy group, aryloxy group, substituted or unsubstituted aryl group, phenyl-lower alkoxycarbonyl group and lower alkylcarbamoyl group, (ii) arylcarbonyl groups which may be substituted with lower alkylenedioxy group or with 1 to 3 substituents selected from the group consisting of halogen atom, lower alkyl group, lower alkoxy group, carboxy group, lower alkoxycarbonyl group, nitro group, cyano group, phenyl-lower alkoxycarbonyl group, hydroxy group, guanidyl group, phenyl-lower alkoxy group, amino group and amino group substituted with lower alkyl group,
(iii) 5- or 6-membered unsaturated hetero ring-carbonyl groups having nitrogen atom, sulfur atom or oxygen atom as the hetero atom,
(iv) carbonic acid ester residue such as aryloxycarbonyl groups, straight or branched-chain or cyclic alkoxycarbonyl groups,
(v) substituted or unsubstituted cycloalkylcarbonyl groups,
(vi) lower alkenyl (or lower alkynyl)carbonyl groups,
(vii) lower alkenyl (or lower alkynyl)oxycarbonyl groups, and
(viii) pyridyloxycarbonylarylenecarbonyl groups represented by the formula

(Y)

wherein $R^x$ is pyridyl group which may be substituted with 1 to 4 substituents selected from the group consisting of hydroxy group, oxo group, halogen atom, amino group, carboxy group, cyano group, nitro group, carbamoyl group, lower alkylcarbamoyl group, carboxylower alkylcarbamoyl group, lower alkoxycarbonyllower alkylcarbamoyl group, phenyl carbamoyl group which may be substituted with 1 to 3 substituents selected from the group consisting of halogen atom, lower alkoxy group and lower alkyl group on the phenyl ring, lower alkyl group, lower alkenyl group, lower alkoxycarbonyl group, tetrahydrofuranyl group, tetrahydropyranyl group, lower alkoxy-lower alkyl group, lower alkylthio-lower alkyl group, phenyl-lower alkoxy-lower alkyl group, phthalidyl group and acyloxy group having acyl defined above under the items (i) to (vii) in the acyl moiety, and Y is defined as in claim 1.

3. A compound as defined in claim 2 wherein $R^1$ is phenyl-lower alkyl group which may have a substituent selected from the group consisting of lower alkyl group, lower alkoxy group, halogen atom, carboxyl group, lower alkoxycarbonyl group and di(lower alkyl)amino group on the phenyl ring, phenyl-lower alkyl group having lower alkylenedioxy or phenyl group as the substituent on the phenyl ring, phenyl-lower alkenyl group or naphthyl-lower alkyl group.

4. A compound as defined in claim 2 wherein $R^2$ is phenyl-lower alkyl group optionally having substituent selected from the group consisting of lower alkyl group, lower alkoxy group, halogen atom, carboxyl group, lower alkoxycarbonyl group and di(lower alkyl)amino group on the phenyl ring, phenyl-lower alkyl group having lower alkylenedioxy or phenyl group as the substituent on the phenyl ring, phenyl-lower alkenyl group or naphthyl-lower alkyl group.

5. A compound as defined in claim 3 wherein $R^3$ is an acyl group selected from the group consisting of those defined above under the items (i) to (viii).

6. A compound as defined in claim 3 wherein $R^3$ is hydrogen atom or tetrahydrofuranyl group.

7. A compound as defined in claim 4 wherein $R^3$ is an acyl group represented by the formula

(Y)

wherein $R^x$ and Y are as defined above.

8. A compound as defined in claim 5 wherein $R^3$ is an acyl group selected from the group consisting of those defined above under the items (i) to (vii).

9. A compound as defined in claim 8 wherein $R^2$ is an acyl group represented by the formula

(Y)

wherein $R^x$ and Y are as defined above.

10. A compound as defined in claim 9 wherein $R^1$ is benzyl group which may have a substituent selected from the group consisting of lower alkyl group, lower alkoxy group, halogen atom, carboxyl group, lower alkoxycarbonyl group and di(lower alkyl)amino group on the phenyl ring, or benzyl group having lower alkylenedioxy or phenyl group as the substituent on the phenyl ring.

11. A compound as defined in claim 5 wherein $R^3$ is an acyl group represented by the formula

(Y)

wherein $R^x$ and Y are as defined above.

12. A compound as defined in claim 11 wherein $R^2$ is hydrogen atom.

13. A compound as defined in claim 11 wherein $R^2$ is an acyl group selected from the group consisting of those defined above under the items (i) to (vii).

14. A compound represented by the formula

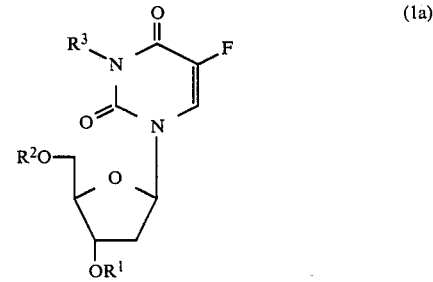

(Ia)

wherein one of $R^1$ and $R^2$ is phenyl-lower alkyl which may be substituted by a substituent selected from the group consisting of lower alkyl group, halogen atom, carboxyl group, lower alkoxycarbonyl group and di(lower alkyl)amino group on the phenyl ring, phenyl-lower alkyl group having lower alkylene dioxy or phenyl group as the substituent on the phenyl ring, phenyl lower alkenyl group or naphthyl-lower alkyl group; the other of $R^1$ and $R^2$ is hydrogen atom or acyl group; and $R^3$ is hydrogen atom, acyl group or tetrahydrofuranyl group; with the proviso that at least one of $R^1$ and $R^3$ or at least one of $R_2$ and $R_3$ is an acyl group represented by the formula

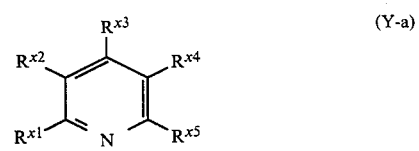

(Y-a)

wherein $R^{x1}$ is hydroxy or acyloxy; $R^x$ and $R^{x4}$ are each hydrogen, halogen, amino, carboxyl, carbamoyl, cyano, nitro, lower alkyl, lower alkenyl or lower alkoxycarbonyl; $R^{x3}$ and $R^{x5}$ are each hydrogen, hydroxy or acyloxy; when at least one of $R^{x1}$, $R^{x3}$ and $R^{x5}$ is free hydroxy, the structure of 1-position on the pyridine ring can be

due to keto-enol tautomerism, said hydrogen attached to the nitrogen may be substituted with a substituent selected from the group consisting of lower alkyl, tretrahydrofuranyl, tetrahydropyranyl, lower alkoxy-lower alkyl, phthalidyl, carbamoyl, lower alkoxycarbonyl-lower alkylcarbamoyl, phenyl-lower alkoxy-lower alkyl, phenyl-carbamoyl which may have 1 to 3 substituents selected from the group consisting of halogen, lower alkoxy and lower alkyl on the phenyl ring, lower alkylcarbamoyl, carboxy-lower alkylcarbamoyl, lower alkylthio-lower alkyl and lower alkenyl, provided that at least one of $R^{x1}$, $R^{x3}$ and $R^{x5}$ represents hydroxy group and that the hydrogen of one hydroxy group represented by $R^{x1}$, $R^{x3}$ or $R^{x5}$ is substituted with a group

wherein Y is an arylene group selected from the group consisting of phenylene, naphthylene, pyridinediyl, pyrazinediyl, furandiyl and 4-pyridon-1-lower alkyldiyl.

15. A compound as defined in claim 14 wherein the group

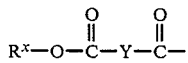

is a group represented by the formula

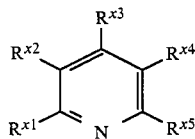

wherein $R^{x1}$ is hydroxy or acyloxy; $R^{x2}$ and $R^{x4}$ are each hydrogen, halogen, amino, carboxyl, carbamoyl, cyano, nitro, lower alkyl, lower alkenyl or lower alkoxycarbonyl; $R^{x3}$ and $R^{x5}$ are each hydrogen, hydroxy or acyloxy, provided that at least one of $R^{x1}$, $R^{x3}$ and $R^{x5}$ represents hydroxy group and that the hydrogen of one hydroxyl group represented by $R^{x1}$, $R^{x3}$ or $R^{x5}$ is substituted with a group

wherein Y is as defined above.

16. A compound as defined in claim 15 wherein $R^{x1}$ is hydroxy, benzoyloxy, $C_1-C_6$ alkanoyloxy or furoyloxy, $R^{x2}$ is hydrogen atom, one of $R^{x3}$ and $R^{x5}$ is hydrogen atom and the other of $R^{x3}$ and $R^{x5}$ is hydroxy, benzoyloxy, $C_1-C_6$ alkanoyloxy or furoyloxy, and $R^{x4}$ is cyano group or halogen atom, provided that at least one of $R^{x1}$, $R^{x3}$ and $R^{x5}$ is hydroxy and that the hydrogen of one hydroxyl group represented by $R^{x1}$, $R^{x3}$ or $R^{x5}$ is substituted with a group

wherein Y is as defined above; and $R^1$ is benzyl group which may have a substituent selected from the group consisting of lower alkyl group, lower alkoxy group, halogen atom, carboxyl group, lower alkoxycarbonyl group and di(lower alkyl)amino group on the phenyl ring, or benzyl group having lower alkylenedioxy or phenyl group as the substituent on the phenyl ring.

17. A compound as defined in claim 16 wherein $R^1$ is benzyl group which may be substituted with halogen atom.

18. A compound as defined in claim 1 which is 3-[3-(6-benzoyloxy-3-cyano-2-pyridyloxycarbonyl)benzoyl]-3'-O-benzyl-2'-deoxy-5-fluorouridine.

19. A compound as defined in claim 1 which is selected from the group consisting of 3-[4-(6-benzoyloxy-3-cyano-2-pyridyloxycarbonyl)-3-furoyl]-3'-O-benzyl-2'-deoxy-5-fluorouridine, 3-[3-(6-benzoyloxy-3-cyano-2-pyridyloxycarbonyl)benzoyl]-3'-O-benzyl-2'-deoxy-5'-O-acetyl-5-fluorouridine, 3-[3-(6-benzoyloxy-3-cyano-2-pyridyloxycarbonyl)benzoyl]-3'-O-(p-fluorobenzyl)-2'-deoxy-5-fluorouridine and 3-[3-(6-benzoyloxy-3-cyano-2-pyridyloxycarbonyl)benzoyl]-3'-O-(o-chlorobenzyl)-2'-deoxy-5-fluorouridine.

20. A compound as defined in claim 1 which is selected from the group consisting of 3-[3-(6-benzoyloxy-3-chloro-2-pyridyloxycarbonyl)benzoyl]-3'-O-(p-chlorobenzyl)-2'-deoxy-5-fluorouridine, 3-[3-(6-benzoyloxy-3-chloro-2-pyridyloxycarbonyl)benzoyl]-3'-O-benzyl-2'-deoxy-5-fluorouridine, 3-[3-(4-benzoyloxy-5-chloro-2-pyridyloxycarbonyl)benzoyl]-3'-O-benzyl-2'-deoxy-5-fluorouridine, 3-[3-(4-acetyloxy-5-chloro-2-pyridyloxycarbonyl)benzoyl]-3'-O-benzyl-2'-deoxy-5-fluorouridine and 3-[3-(4-furoyloxy-5-chloro-2-pyridyloxycarbonyl)benzoyl]-3'-O-benzyl-2'-deoxy-5-fluorouridine.

* * * * *